(12) United States Patent
Ahmad et al.

(10) Patent No.: US 10,226,201 B2
(45) Date of Patent: *Mar. 12, 2019

(54) FLOW REGULATION DEVICE FOR BREATH ANALYSIS AND RELATED METHOD

(71) Applicant: Invoy Holdings, LLC, Aliso Viejo, CA (US)

(72) Inventors: Lubna M. Ahmad, Chandler, AZ (US); Zachary Smith, Phoenix, AZ (US); Salman A. Ahmad, Chandler, AZ (US)

(73) Assignee: Invoy Holdings, LLC, Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,870

(22) Filed: Oct. 31, 2016

(65) Prior Publication Data

US 2017/0119279 A1    May 4, 2017

Related U.S. Application Data

(60) Provisional application No. 62/247,778, filed on Oct. 29, 2015, provisional application No. 62/396,240, filed on Sep. 19, 2016.

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *A61B 5/087* (2013.01); *A61B 5/0823* (2013.01);
(Continued)

(58) Field of Classification Search
CPC .......... A61B 5/082; A61B 5/087; A61B 5/097
See application file for complete search history.

(56) References Cited

U.S. PATENT DOCUMENTS

| 4,147,514 A | 4/1979 | Magers et al. |
| 4,844,867 A | 7/1989 | Bather |

(Continued)

FOREIGN PATENT DOCUMENTS

| EP | 1 524 522 | 4/2005 |
| WO | WO 03/039367 | 5/2003 |

(Continued)

OTHER PUBLICATIONS

U.S. Appl. No. 13/052,963, filed Mar. 21, 2011, Ahmad et al.
(Continued)

*Primary Examiner* — Puya Agahi
(74) *Attorney, Agent, or Firm* — Knobbe, Martens, Olson & Bear, LLP

(57) ABSTRACT

A breath capture device for determining the concentration of acetone in a breath sample from a user. In some embodiments, the device includes a controller programmed to use stored data to control flow of a breath sample into an analysis chamber as the user exhales into a port. In other embodiments, the device includes a switch responsive to an action by the user that is operable between a first orientation in which breath entering the port preferentially travels through a second flow path and a second orientation in which breath entering the port preferentially travels through a first flow path. In still other embodiments, the device includes a flow regulator both responsive to user action and operable from a first position in which breath entering a port preferentially travels through a second flow path to a second position in which breath entering the port preferentially travels through a first flow path.

25 Claims, 73 Drawing Sheets

(51) Int. Cl.
*A61B 5/087* (2006.01)
*A61B 5/091* (2006.01)
*A61B 5/083* (2006.01)
*A61B 10/00* (2006.01)
*A61B 5/01* (2006.01)

(52) U.S. Cl.
CPC ............ *A61B 5/0878* (2013.01); *A61B 10/00* (2013.01); *A61B 5/01* (2013.01); *A61B 5/0803* (2013.01); *A61B 5/0833* (2013.01); *A61B 5/0836* (2013.01); *A61B 5/091* (2013.01); *A61B 2010/0087* (2013.01)

(56) References Cited

U.S. PATENT DOCUMENTS

| | | |
|---|---|---|
| 4,931,404 A | 6/1990 | Kundu |
| 4,970,172 A | 11/1990 | Kundu |
| 5,071,769 A | 12/1991 | Kundu et al. |
| 5,174,959 A | 12/1992 | Kundu et al. |
| 5,465,728 A | 11/1995 | Phillips |
| 5,834,626 A | 11/1998 | De Castro et al. |
| 6,010,459 A | 1/2000 | Silkoff et al. |
| 6,067,989 A | 5/2000 | Katzman |
| 6,190,858 B1 | 2/2001 | Persaud |
| 6,206,837 B1 | 3/2001 | Brugnoli |
| 6,221,026 B1 | 4/2001 | Phillips |
| 6,234,006 B1 | 5/2001 | Sunshine et al. |
| 6,254,547 B1 | 7/2001 | Phillips |
| 6,454,723 B1 | 9/2002 | Montagnino |
| 6,540,691 B1 | 4/2003 | Phillips |
| 6,582,376 B2 | 6/2003 | Baghdassarian |
| 6,599,253 B1 | 7/2003 | Baum et al. |
| 6,607,387 B2 | 8/2003 | Mault |
| 6,609,068 B2 | 8/2003 | Cranley et al. |
| 6,629,934 B2 | 10/2003 | Mault et al. |
| 6,658,915 B2 | 12/2003 | Sunshine et al. |
| 6,723,056 B1 | 4/2004 | Alving et al. |
| 6,726,637 B2 | 4/2004 | Phillips |
| 6,841,391 B2 | 1/2005 | Lewis et al. |
| 6,981,947 B2 | 1/2006 | Melker |
| 7,052,854 B2 | 5/2006 | Melker et al. |
| 7,104,963 B2 | 9/2006 | Melker et al. |
| 7,220,387 B2 | 5/2007 | Flaherty et al. |
| 7,300,408 B2 | 11/2007 | Hancock et al. |
| 7,364,551 B2 | 4/2008 | Allen et al. |
| 7,533,558 B2 | 5/2009 | Flaherty et al. |
| 7,794,994 B2 | 9/2010 | Cranley et al. |
| 7,837,936 B1 | 11/2010 | Martin |
| 7,920,998 B2 | 4/2011 | Brown |
| 7,976,467 B2 | 7/2011 | Young et al. |
| 8,021,308 B2 | 9/2011 | Carlson et al. |
| 8,036,708 B2 | 10/2011 | Oozeki |
| 8,286,088 B2 | 10/2012 | Shaffer et al. |
| 8,287,454 B2 | 10/2012 | Wolpert et al. |
| 8,342,178 B2 | 1/2013 | Hengstenberg et al. |
| 8,399,837 B2 | 3/2013 | Robbins et al. |
| 8,514,086 B2 | 8/2013 | Harper et al. |
| 8,545,415 B2 | 10/2013 | West |
| 8,680,974 B2 | 3/2014 | Meiertoberens et al. |
| 8,722,417 B2 | 5/2014 | Ahmad |
| 8,816,862 B2 | 8/2014 | Harper et al. |
| 8,848,189 B2 | 9/2014 | Atkin et al. |
| 8,871,521 B2 | 10/2014 | Akers |
| 8,917,184 B2 | 12/2014 | Smith et al. |
| 9,170,225 B2 | 10/2015 | Dutta et al. |
| 9,173,595 B2 | 11/2015 | Böhm et al. |
| 9,299,238 B1 | 3/2016 | Ahmad et al. |
| 9,486,169 B1 | 11/2016 | Ahmad |
| 9,636,044 B2 | 5/2017 | Ahmad et al. |
| 2003/0208133 A1 | 11/2003 | Mault |
| 2004/0018114 A1 | 1/2004 | Wang et al. |
| 2004/0097820 A1 | 5/2004 | Bradley et al. |
| 2005/0137491 A1* | 6/2005 | Paz .................. A61B 5/097 600/543 |
| 2005/0177056 A1* | 8/2005 | Giron ............... A61M 16/0666 600/543 |
| 2005/0177057 A1* | 8/2005 | Friedman .............. A61B 5/097 600/543 |
| 2007/0245810 A1 | 10/2007 | Carter et al. |
| 2007/0258894 A1 | 11/2007 | Melker et al. |
| 2008/0008666 A1 | 1/2008 | Phillips |
| 2008/0053194 A1 | 3/2008 | Ahmad |
| 2008/0056946 A1 | 3/2008 | Ahmad |
| 2008/0234553 A1 | 9/2008 | Urman et al. |
| 2009/0054799 A1 | 2/2009 | Vrtis et al. |
| 2009/0187111 A1 | 7/2009 | Reilly, Jr. et al. |
| 2010/0301197 A1 | 12/2010 | Boyle |
| 2011/0028091 A1 | 2/2011 | Higgins et al. |
| 2011/0098590 A1 | 4/2011 | Garbutt et al. |
| 2012/0029376 A1 | 2/2012 | Meng et al. |
| 2012/0071737 A1 | 3/2012 | Landini et al. |
| 2012/0130265 A1 | 5/2012 | Cha et al. |
| 2012/0295595 A1 | 11/2012 | Gibori et al. |
| 2013/0231711 A1 | 9/2013 | Kaib |
| 2013/0253358 A1 | 9/2013 | Phillips |
| 2014/0194703 A1 | 7/2014 | Wondka et al. |
| 2014/0276100 A1* | 9/2014 | Satterfield ............ A61B 5/082 600/476 |
| 2014/0366610 A1 | 12/2014 | Rodriguez |
| 2015/0073233 A1 | 3/2015 | Rich et al. |
| 2015/0168307 A1 | 6/2015 | Kück et al. |
| 2015/0265184 A1 | 9/2015 | Wondka et al. |
| 2015/0289782 A1 | 10/2015 | Peverall et al. |
| 2016/0022946 A1 | 1/2016 | Sislian et al. |
| 2016/0146779 A1 | 5/2016 | Gallagher et al. |
| 2016/0150995 A1 | 6/2016 | Ratto et al. |
| 2016/0345910 A1 | 12/2016 | Ahmad et al. |
| 2017/0119280 A1 | 5/2017 | Ahmad et al. |

FOREIGN PATENT DOCUMENTS

| | | |
|---|---|---|
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2015/134390 | 9/2015 |

OTHER PUBLICATIONS

U.S. Appl. No. 15/340,811, filed Nov. 1, 2016, Ahmad et al.
Ahmad, L. et al., "Design of a Breath Ketone Sensor for Obesity Management", Poster Presentation, Fall Meeting of the Biomedical Engineering Society, 2004, in 3 pages.
Barnett, D. et al., "Breath acetone and blood sugar measurements in diabetes", Clinical Science, vol. 37 (1969), in 1 page.
"CMS Operator Guide", CMS Operator Training 0108, dated April 19, 2002, in 10 pages. URL: http://www.buydraegertubes.com/ds/cms-ops-guide.pdf
Crofford, O. et al., "Acetone in Breath and Blood", Transactions of the American Clinical and Climatological Association, vol. 88 (1977), in 12 pages.
Diskin, A. et al., "Time variation of ammonia, acetone, isoprene and ethanol in breath: a quantitative SIFT-MS study over 30 days", Physiological Measurement, vol. 24 (2003), in 13 pages.
Dräger CMS Production Information (document properties of document indicate that the document was created on December 1, 2008), in 4 pages. URL: http://www.draeger.com/sites/assets/PublishingImages/Products/cin_chip_measurement_system/US/cms-ds-pi-9044337-en-us.pdf
DrägerTubes & Accuro Pump Production Information (document properties of document indicate that the document was created on November 11, 2008), in 4 pages. URL: http://www.draeger.com/sites/assets/PublishingImages/Products/cin_accuro/US/081209-pi-DetectorTubes-22-10-2008-en.9df
Dubowski, K. et al., "Response of Breath-Alcohol Analyzers to Acetone: Further Studies", Journal of Analytical Toxicology, vol. 8, Sep./Oct. 1984, in 4 pages.
Gervais, T. et al., "Mass transport and surface reactions in microfluidic systems", Chemical Engineering Science, vol. 61 (2006), in 20 pages.

(56) References Cited

OTHER PUBLICATIONS

Ketonix US, "Ketonix 2015 Blue Specifications", 2015, in 2 pages. URL:https://www.ketonix.com/index.php/product-2/ketonix-2015-blue Ketonix, "Ketonix data for Michel Lundell", 2015, in 1 page. URL: https://www.ketonix.com.

Khan, A. et al. "Evaluation of a bedside blood ketone sensor: the effects of acidosis, hyperglycaemia and acetoacetate on sensor performance", Diabetic Medicine, vol. 21 (2004), in 5 pages.

Kundu, S. et al., "Breath Acetone Analyzer: Diagnostic Tool to Monitor Dietary Fat Loss", Clinical Chemistry, vol. 39 (1993), in 6 pages.

Kundu, S. K. et al., "Novel Solid-Phase Assay of Ketone Bodies in Urine", Clinical Chemistry, vol. 37 (1991), in 5 pages.

Kupari, M. et al., "Breath Acetone in Congestive Heart Failure", The American Journal of Cardiology, vol. 76, Nov. 15, 1995, in 3 pages.

Landini, B. et al., "Breath Acetone Concentration Measured Using a Palm-Size Enzymatic Sensor System", IEEE Sensors Journal, vol. 9, Dec. 2009, in 6 pages.

Landini, B. et al., "Effect of Exhalation Variables on the Current Response of an Enzymatic Breath Acetone Sensing Device", IEEE Sensor Journal, vol. 10, Jan. 2010, in 6 pages.

Likhodii, S., et al., "Breath Acetone as a Measure of Systemic Ketosis Assessed in a Rat Model of the Ketogenic Diet", Clinical Chemistry, vol. 48 (2002), in 6 pages.

Loken, S. C., "Breath Acetone and Ketone Metabolism in Obese and Diabetic Mice", Diabetes, vol. 25 (1976), in 1 page.

"Figaro Gas Sensor TGS 822", Figaro Engineering Inc., Mar. 1987, in 10 pages.

"MiniMed 530G System User Guide", Medtronic MiniMed, Inc., 2012, in 312 pages.

Musa-Veloso, K. et al., "Breath acetone is a reliable indicator of ketosis in adults consuming ketoqenic meals", The American Journal of Clinical Nutrition, vol. 76 (2002), in 6 pages.

Schwarz, K., et al., "Breath acetone—aspects of normal physiology related to age and gender as determined in a PTR-MS study", Journal of Breath Research, vol. 3 (2009), in 9 pages.

Wang, L. et al., "Nanosensor Device for Breath Acetone Detection", Sensor Letters, vol. 8 (2010), in 4 pages.

Wang, L., "Tailored synthesis and characterization of selective metabolite-detecting nanoprobes for handheld bireath analysis", Dissertation Ph. D. Thesis, Stony Brook University, Dec. 2008, in 127 pages.

Yoon, S. et al., "Active control of the depletion boundary layers in microfluidic electrochemical reactors", Lab on a Chip, vol. 6 (2006), in 9 pages.

\* cited by examiner

FIG. 3
① Select an analyte.
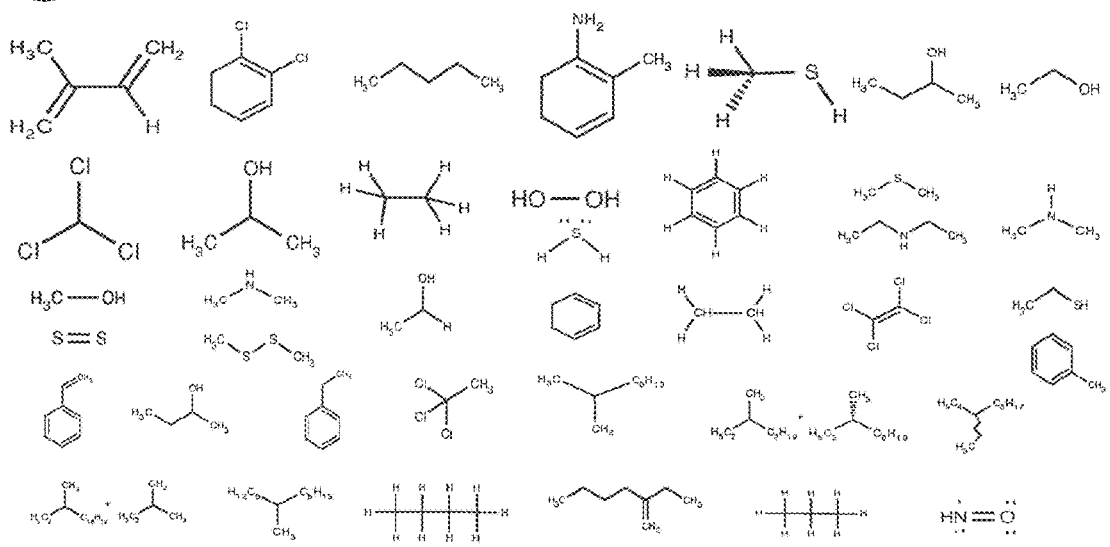
② Select a breath profile.
For clinically recommended breath profiles for the selected analyte, please click here.
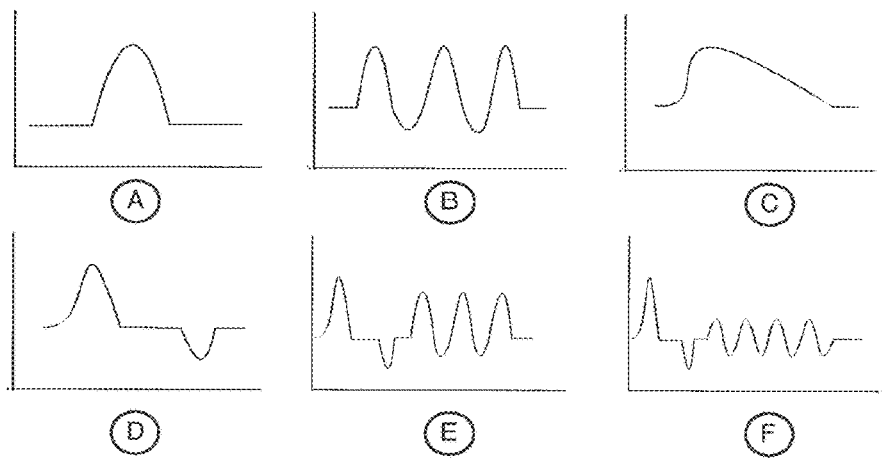
③ Add another analyte-breath profile combination?
Yes    No Sample Algorithm to Create an Order for the Breath Profiles to Appear on the Display:

Ranking = (Criticality x 3) + (Difficulty x 2)

| Analyte Being Measured | Analyte 1 | Analyte 2 | Analyte 3 |
|---|---|---|---|
| Difficulty to Perform (3 = high, 1 = low) | 2 | 3 | 1 |
| Criticality for Physician Intervention | 3 | 1 | 2 |
| Ranking = Criticality x 3 + Difficulty x 2 | 13 | 9 | 8 |
| Order (based on which Ranking is highest) | $1^{st}$ | $2^{nd}$ | $3^{rd}$ |

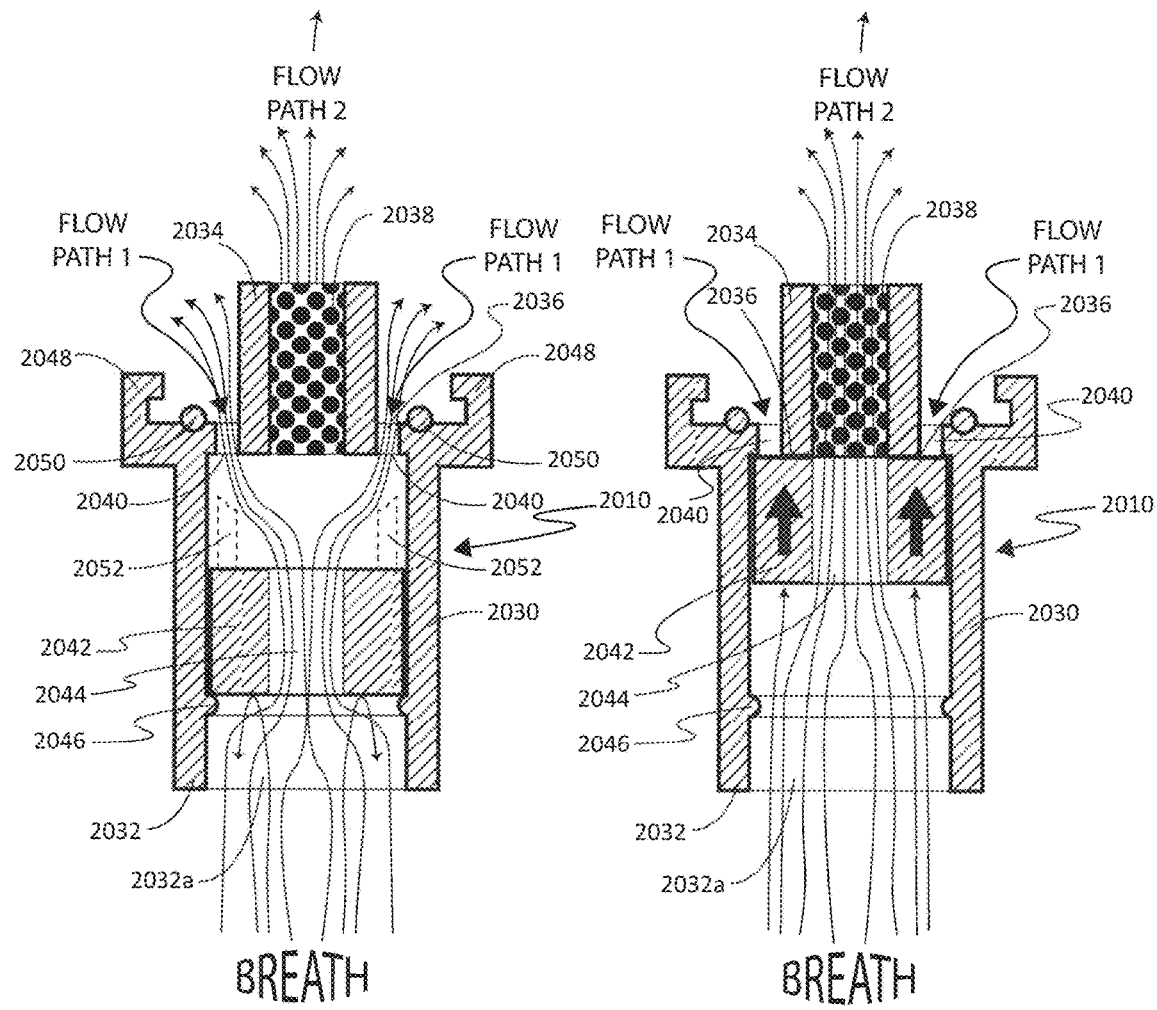

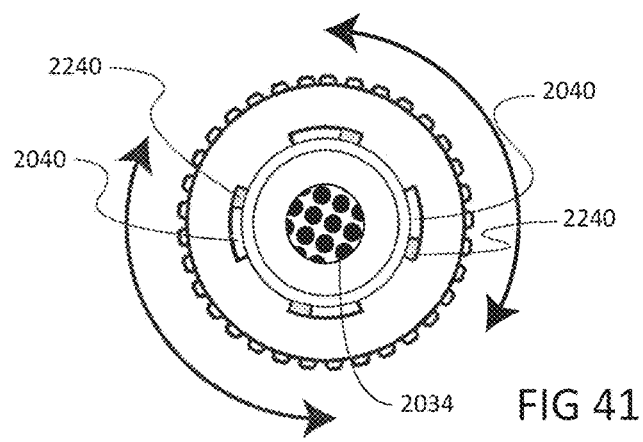
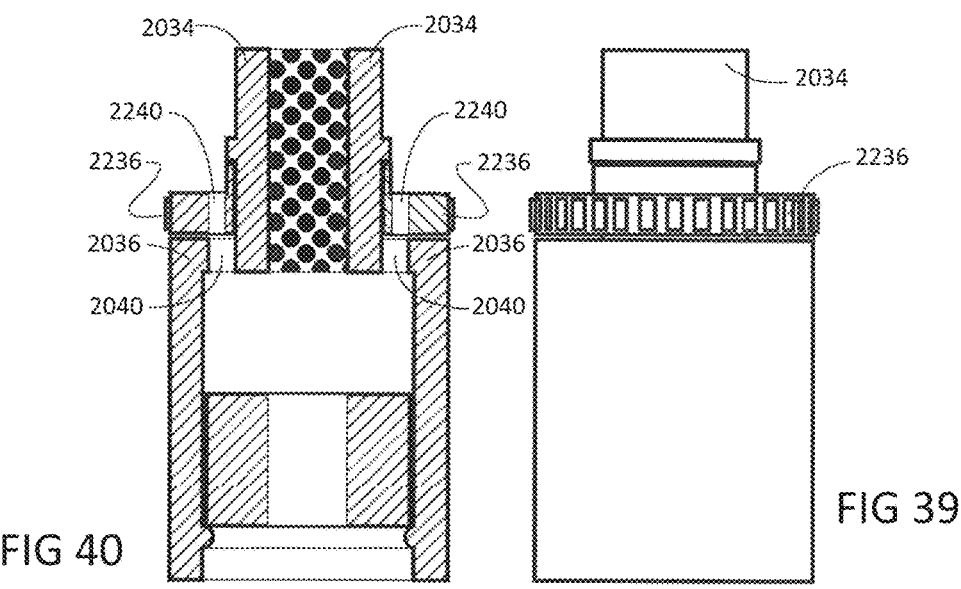
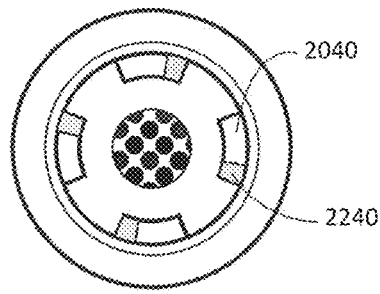

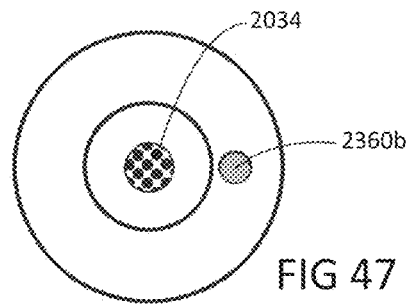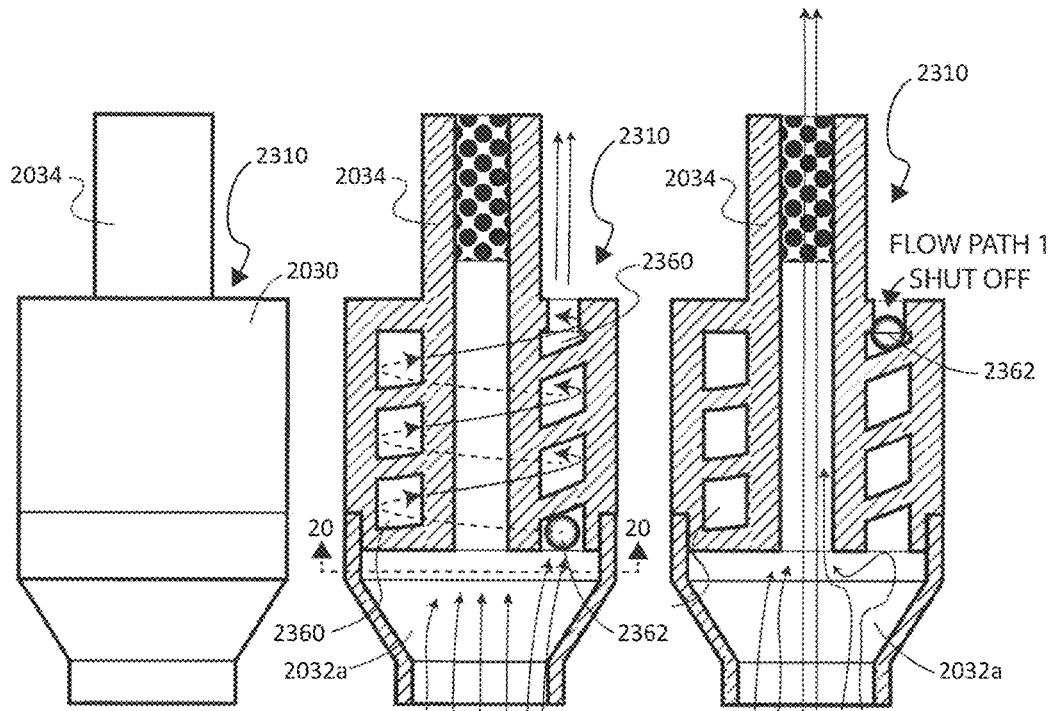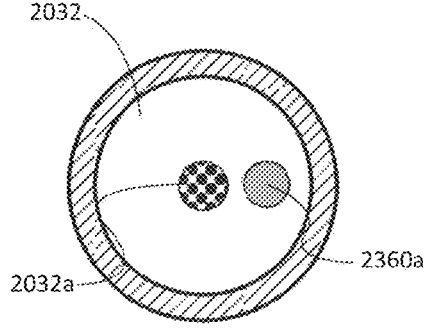
FIG 47
FIG 43
FIG 44
FIG 45
FIG 46

Partial Pressures of Respiratory Gases as They Enter and Leave the Lungs (at Sea Level)

| | Atmospheric Air* (mm Hg) | | Humidified Air (mm Hg) | | Alveolar Air (mm Hg) | | Expired Air (mm Hg) | |
|---|---|---|---|---|---|---|---|---|
| $N_2$ | 597.0 | (78.62%) | 563.4 | (74.09%) | 569.0 | (74.9%) | 566.0 | (74.5%) |
| $O_2$ | 159.0 | (20.84%) | 149.3 | (19.67%) | 104.0 | (13.6%) | 120.0 | (15.7%) |
| $CO_2$ | 0.3 | (0.04%) | 0.3 | (0.04%) | 40.0 | (5.3%) | 27.0 | (3.6%) |
| $H_2O$ | 3.7 | (0.50%) | 47.0 | (6.20%) | 47.0 | (6.2%) | 47.0 | (6.2%) |
| Total | 760.0 | (100.0%) | 760.0 | (100.0%) | 760.0 | (100.0%) | 760.0 | (100.0%) |

FIG 59

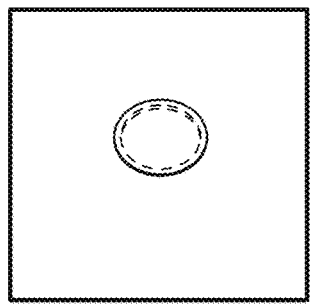
FIG. 64A
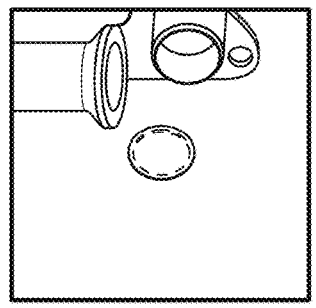
FIG. 64B
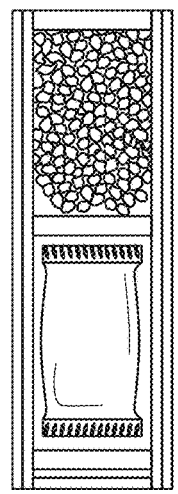
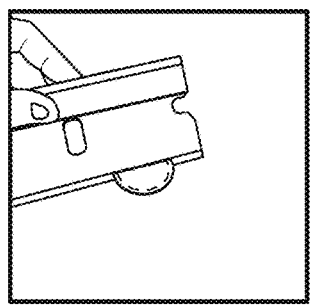
FIG. 64C
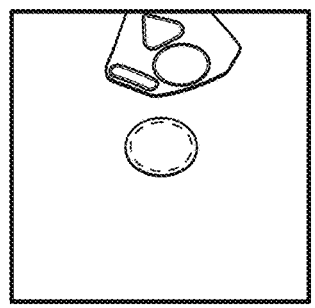
FIG. 64D
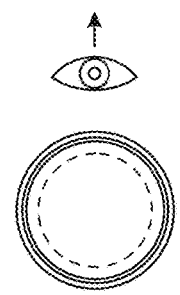
FIG. 64E
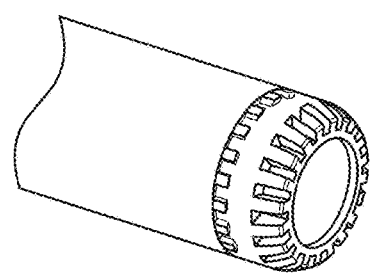
FIG. 64F

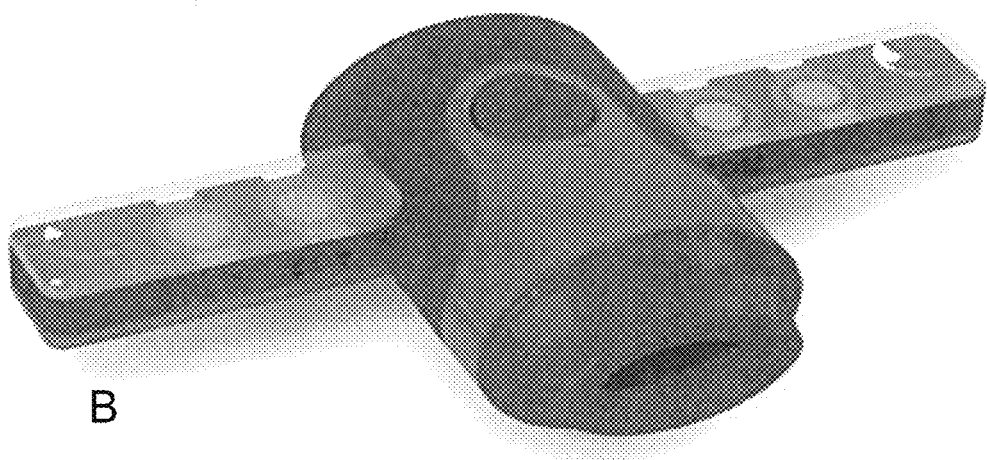
B
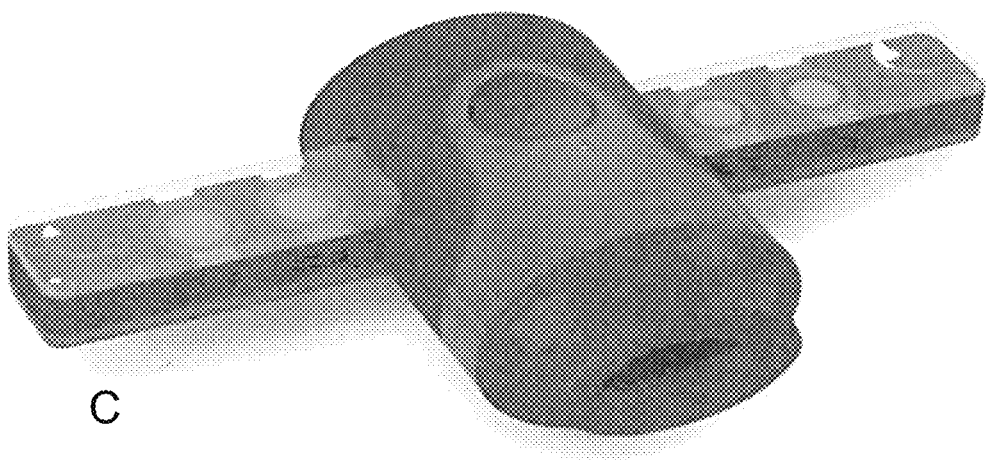
C
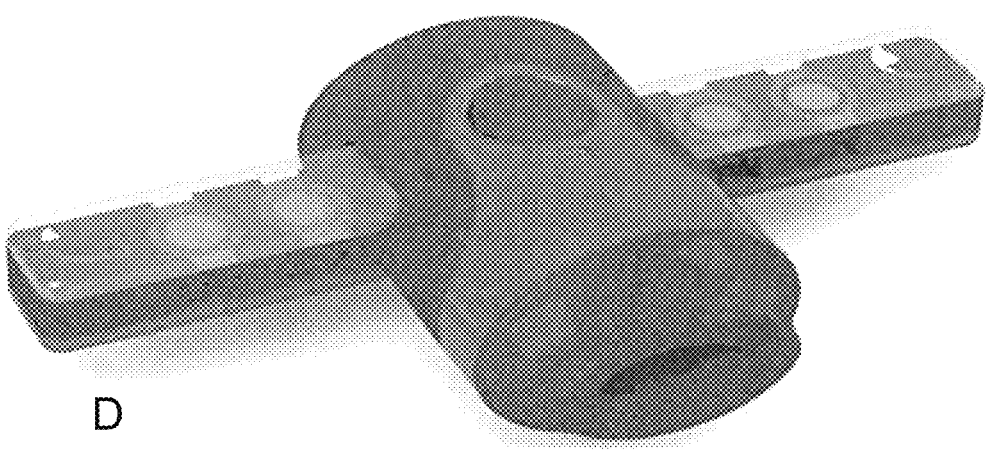
D
FIG 67

FLOW REGULATION DEVICE FOR BREATH ANALYSIS AND RELATED METHOD

INCORPORATION BY REFERENCE TO ANY PRIORITY APPLICATIONS

This application claims the benefit of U.S. Provisional Application Nos. 62/247,778, filed Oct. 29, 2015, and 62/396,240, filed Sep. 19, 2016, which are hereby incorporated herein by reference in their entirety. Any and all applications for which a foreign or domestic priority claim is identified in the Application Data Sheet as filed with the present application are hereby incorporated by reference under 37 CFR 1.57.

BACKGROUND

Field of the Invention

The present invention relates to apparatuses, systems, and methods for sensing or measuring chemical components or constituents (e.g., analytes) in the breath of a patient or "subject," and preferably endogenous analytes in breath, and correspondingly, to devices and methods for regulating the flow of the breath sample during the pre-measurement capture process and/or during such sensing or measurement.

Description of the Related Art

The importance or benefits of measuring the presence or concentration of chemical constituents in the body to aid in assessing a patient or subject's physiological or pathophysiological state is well known in the medical and diagnostic communities. Standard approaches to chemically-based diagnostic screening and analysis typically involve blood tests and urine tests.

Blood tests of course require that blood be drawn. Patients associate this procedure with pain, a factor that can have adverse implications for patient compliance in home-based assessments. In clinical settings, the need to draw blood typically requires trained personnel to draw the blood, carefully and properly label it, handle it and the like. It is typically necessary to transport the sample to a laboratory, often off site, for analysis. Given the logistics and economics, the lab analysis usually is carried out in bulk on large numbers of samples, thus requiring bulk handling and logistics considerations and introducing delay into the time required to obtain results. It is then typically necessary for follow-up analysis by the physician or clinician to assess the lab results and further communicate with the patient. In large part because of these logistics and delays, it is usually necessary for the patient or subject to return for a follow up visit, thus taking additional clinical time and causing additional expense.

Urine tests involve similar drawbacks. Such tests can be messy, unsanitary, and introduce issues with respect to labeling, handling and contamination avoidance. They also usually involve lab analysis, with associated delays and expense. As with blood, urine tests, it is typically necessary to transport the samples to an off-site laboratory for analysis. Given the logistics, the lab analysis usually is carried out in bulk on large numbers of samples, thus again involving delay and expense.

There are many instances in which it is desirable to sense the presence and/or quantity or concentration of an analyte in a gas. "Analyte" as the term is used herein is used broadly to mean the chemical component or constituent that is sought to be sensed using devices and methods according to various aspects of the invention. An analyte may be or comprise an element, compound or other molecule, an ion or molecular fragment, or other substance that may be contained within a fluid. In some instances, embodiments and methods, there may be more than one analyte present, and an objective is to sense multiple analytes. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like. "Sense" and "sensing" as the terms are used herein are used broadly to mean detecting the presence of one or more analytes, or to measure the amount or concentration of the one or more analytes.

The use of breath as a source of chemical analysis can overcome many of these drawbacks. The presence of these analytes in breath and their associated correlations with physiological or pathophysiological states offer the substantial theoretical or potential benefit of providing information about the underlying or correlated physiological or pathophysiological state of the subject, in some cases enabling one to screen, diagnose and/or treat a patient or subject easily and cost effectively. Breath analysis can avoid painful invasive techniques such as with blood tests, and messy and cumbersome techniques such as urine analysis. Moreover, in many applications test results can be obtained promptly, e.g., during a single typical patient exam or office visit, and cost effectively.

As is well known in the field of pulmonology, breath, and particularly breath exhalations, comprise a range of chemical components, or analytes. An "analyte" is a chemical component or constituent that is a candidate for sensing, detection or measurement. Breath composition varies somewhat from subject to subject, and within a given subject, from time to time, depending on such factors as physical condition (e.g., weight, body composition), diet (e.g., general diet, recent intake of food, liquids, etc.), exertion level (e.g., resting metabolic rate versus under stress or exercise), and pathology (e.g., diseased state). Approximately 200 to 300 analytes can be found in human breath.

Certain breath analytes have been correlated with specific physiological or pathophysiological states. Such correlations are particularly useful for "endogenous" analytes (i.e., those that are produced by the body), as opposed to "exogenous" analytes (i.e., those that are present in breath strictly as a result of inhalation, ingestion or consumption and subsequent exhalation by the subject). Examples are set forth in Table 1.

TABLE 1

| Candidate Analyte | Illustrative Pathophysiology/Physical State |
|---|---|
| Acetone | Lipid metabolism (e.g., epilepsy management, nutritional monitoring, weight loss therapy, early warning of diabetic ketoacidosis), environmental monitoring, acetone toxicity, congestive heart failure, malnutrition, exercise, management of eating disorders |

TABLE 1-continued

| Candidate Analyte | Illustrative Pathophysiology/Physical State |
|---|---|
| Ethanol | Alcohol toxicity, bacterial growth |
| Acetaldehyde | |
| Ammonia | Liver or renal failure, protein metabolism, dialysis monitoring, early detection of chronic kidney disease, acute kidney disease detection and management |
| Oxygen and Carbon Dioxide | Resting metabolic rate, respiratory quotient, oxygen uptake |
| Isoprene | Lung injury, cholesterol synthesis, smoking damage |
| Pentane | Lipid peroxidation (breast cancer, transplant rejection), oxidative tissue damage, asthma, smoking damage, chronic obstructive pulmonary disease ("COPD") |
| Ethane | Smoking damage, lipid peroxidation, asthma, COPD |
| Alkanes | Lung disease, cancer metabolic markers |
| Benzene | Cancer metabolic monitors |
| Carbon-13 | *H. pylori* infection |
| Methanol | Ingestion, bacterial flora |
| Leukotrienes | Present in breath condensate, cancer markers |
| Hydrogen peroxide | Present in breath condensate |
| Isoprostane | Present in breath condensate, cancer markers |
| Peroxynitrite | Present in breath condensate |
| Cytokines | Present in breath condensate |
| Glycans | Glucose measurement, metabolic anomalies (e.g., collected from cellular debris) |
| Carbon monoxide | Inflammation in airway (asthma, bronchiesctasis), lung disease |
| Chloroform | |
| Dichlorobenzene | Compromised pulmonary function |
| Trimethyl amine | Uremia |
| Dimethyl amine | Uremia |
| Diethyl amine | Intestinal bacteria |
| Methanethiol | Intestinal bacteria |
| Methylethylketone | Lipid metabolism |
| O-toluidine | Cancer marker |
| Pentane sulfides | Lipid peroxidation |
| Hydrogen sulfide | Dental disease, ovulation |
| Sulfated hydrocarbon | Cirrhosis |
| Cannabis | Drug concentration |
| G-HBA | Drug testing |
| Nitric oxide | Inflammation, lung disease |
| Propane | Protein oxidation, lung disease |
| Butane | Protein oxidation, lung disease |
| Other Ketones (other than acetone) | Lipid metabolism |
| Ethyl mercaptane | Cirrhosis |
| Dimethyl sulfide | Cirrhosis |
| Dimethyl disulfide | Cirrhosis |
| Carbon disulfide | Schizophrenia |
| 3-heptanone | Propionic acidaemia |
| 7-methyl tridecane | Lung cancer |
| Nonane | Breast cancer |
| 5-methyl tridecane | Breast cancer |
| 3-methyl undecane | Breast cancer |
| 6-methyl pentadecane | Breast cancer |
| 3-methyl propanone | Breast cancer |
| 3-methyl nonadecane | Breast cancer |
| 4-methyl dodecane | Breast cancer |
| 2-methyl octane | Breast cancer |
| Trichloroethane | |
| 2-butanone | |
| Ethyl benzene | |
| Xylene (M, P, O) | |
| Styrene | |
| Tetrachloroethene | |
| Toluene | |
| Ethylene | |
| Hydrogen | |

The inherent relative advantage of breath analysis over other techniques, together with the relatively wide array of analytes and analyte correlations, illustrate that the potential benefits breath analysis offers are substantial.

Notwithstanding these potential benefits, however, with the exception of breath ethanol devices used for law enforcement, there has been a paucity of breath analyzers on the commercial market, particularly in medically-related applications. This lack of commercialization is attributable in large measure to the relatively substantial technical and practical challenges associated with the technology. Principal among them is the requirement for sensitivity. Analytes of interest, particularly endogenous analytes, often are present in extremely low concentrations, e.g., of only parts per million ("ppm") or parts per billion ("ppb"). In addition, the requirements for discrimination or selectivity is of critical concern. As noted herein above, breath typically includes a large number, sometimes hundreds, of chemical components in a complex matrix. Breath also usually has considerable moisture content. Chemical sensing regimes conducive for breath ammonia measurement, for example, are preferably sensitive to 50 ppb in the presence of 3 to 6% water vapor with 3 to 5% carbon dioxide. Successfully and reliably sensing a particular analyte in such a heterogeneous and chemically-reactive environment presents substantial challenges.

Most publicly-known breath analysis devices and methods involve using a single breath, and more specifically a single exhalation, as the breath sample to identify or measure a single analyte. The sample is collected and analyzed to determine whether the analyte is present, and in some cases, to measure its concentration. The breath analysis system introduced by Abbott Laboratories, e.g., in U.S. Pat. Nos. 4,970,172, 5,071,769, and 5,174,959, provides an illustrative example. There, Abbott used a single exhalation from a patient to detect the presence of acetone to obtain information about fat metabolism.

Notwithstanding the potential benefits of breath analysis, particularly portable breath analysis devices for home or field use, commercial offerings of such devices have been available only recently, and the accuracy and reliability in such settings have left much room for improvement. Practical breath analysis devices must operate accurately and reliably in the context of their use, e.g., in patient homes, clinics, etc., in varying environments, (temperatures, humidity, etc.), with various types of patients, over the life of the devices.

The use of multiple breaths is substantially lesser known and studied. Published reports generally have been limited to the determination of the production rate of carbon dioxide and the consumption rate of oxygen. This technique was developed due to the presence of these two analytes (oxygen and carbon dioxide) in the ambient atmosphere.

These approaches have been limited and relatively deficient, however, for example, in that the breath sample or samples are collected in bulk, so that the analyte of interest is mixed in with other constituents. This often dilutes the analyte and increases the difficulty of discriminating the desired analyte. These approaches also limit the flexibility of the breath analysis to undertake more specialized or complex analyses.

Additionally, such approaches are relatively deficient because the instrumentation used for single breath analysis usually is different from and sometimes inadequate for multiple breath analyte measurement.

Yet another challenge to breath analysis involves the fluid mechanical properties of the breath sample as it travels through the measurement device.

There is considerable advantage in providing breath analysis devices that can accurately and reliably sense or measure breath analytes in a clinical or patient home setting. Thus, there is a need for small or portable, cost effective devices and components.

In many instances, there is a need or it is desirable to make the analysis for an analyte in the field, or otherwise to make such assessment without a requirement for expensive and cumbersome support equipment such as would be available in a hospital, laboratory or test facility. It is often desirable to do so in some cases with a largely self-contained device, preferably portable, and often preferably easy to use. It also is necessary or desirable in some instances to have the capability to sense the analyte in the fluid stream in real time or near real time. In addition, and as a general matter, it is highly desirable to accomplish such sensing accurately and reliably.

The background matrix of breath presents numerous challenges to sensing systems, which necessitate complex processing steps and which further preclude system integration into a form factor suitable for portable usage by layman end-users. For example, breath contains high levels of humidity and moisture, which may interfere with the sensor or cause condensation within the portable device, amongst other concerns. Also, the flow rate or pressure of breath as it is collected from a user typically varies quite considerably. Flow rate variations are known to impact, often significantly, the response of chemical sensors. Breath, especially when directly collected from a user, is typically at or near core body temperature, which may be considerably different than the ambient temperature. Additionally, body temperature may vary from user to user or from day to day, even for a single user. Devising a breath analyzer thus is a non-trivial task, made all the more difficult to extent one tries to design and portable and field-amenable device.

Notably, the measurement of endogenous analytes in breath presents different challenges and requires different techniques and devices than the measurement of exogenous analytes. Endogenous analytes are those that are produced by the body, excluding the lumen of the gastrointestinal tract, whereas exogenous analytes are those that are present in breath as a result of the outside influence or as a result of user consumption. However, many analytes are produced endogenously and can also be exogenously introduced. For example, ammonia is produced endogenously through the metabolism of amino acids, but can also be introduced exogenously from the environment such as ammonia-containing household cleaning supplies. The term "endogenous" is used according to its common meaning within the field. Endogenous analytes are produced by natural or unnatural means within the human body, its tissues or organs, typically excluding the lumen of the gastrointestinal tract.

There are a number of significant challenges to measuring endogenous analytes in breath. Endogenous analytes typically have significantly lower concentrations in the breath, often on the order of parts per million ("ppm"), parts per billion ("ppb"), or less. Additionally, measurement of endogenous analytes requires discrimination of the analyte in a complex matrix of background gases. Instead of typical atmospheric gas composition (e.g., primarily nitrogen), exhaled breath has high humidity content and larger carbon dioxide concentration. This leads to unique challenges in chemical sensitivity, selectivity and stability. For example, chemistries conducive for breath ammonia measurement are preferably sensitive to 50 ppb in the presence of 3 to 6% water vapor with 3 to 5% carbon dioxide.

Because of the historical difficulty in even detecting endogenous breath analytes, other challenges have not been extensively investigated. Examples of such challenges include: (a) correlating the analytes to health or disease states, (b) measuring these analytes given characteristics of human exhalation, e.g., flow rate and expiratory pressure, (c) measuring these analytes sensitively and selectively, and (d) doing all these in a portable, cost effective package that can be implemented in medical or home settings.

Colorimetric devices are one method for measuring a reaction involving a breath analyte. Colorimetric approaches to endogenous breath analysis have historically been plagued with lengthy response times, and expensive components. Often such analysis has to be performed in a laboratory. Thus there remains a need for a breath analyzer that can measure endogenous breath components present in relatively low concentrations, such as acetone, accurately and quickly, without a long wait period for results, in addition to being inexpensive and useable by the layperson. It is also preferable if the breath analyzer is capable of measuring multiple analytes.

SUMMARY

To address these limitations and advance the art, in accordance with some embodiments, an apparatus is provided for sensing at least one endogenous analyte from a breath sample comprising at least one substantially contemporaneous breath of a patient. The apparatus comprises a breath input portion that receives the breath sample, and an analysis portion in fluid communication with the breath input portion. The analysis portion comprises a sensor. The breath sample is directed by the breath input portion to the analysis portion and to the sensor. The apparatus also comprises a processor operatively coupled to the sensor that: (a) segregates the breath sample into a breath profile comprising the at least one breath, each breath comprising a plurality of segments, each of the segments of a given breath corresponding to an anatomical region of the patient that is non-identical to the anatomical regions for others of the segments, (b) selects at least one but less than all of the breath profile segments of each of the breaths of the breath profile to thereby select at least one but less than all of the corresponding anatomical regions, (c) analyzes the selected at least one breath profile segments for the at least one endogenous analyte to obtain information about the analyte, and (d) generates a signal representative of the information.

In a related but independent embodiment, a method is provided for sensing at least one endogenous analyte from a breath sample comprising at least one substantially contemporaneous breath of a patient, the method comprises providing an apparatus that comprises a breath input portion and an analysis portion, inputting the breath sample into the breath input portion and directing the breath sample to the analysis portion, and using the apparatus to segregate the breath sample into a breath profile comprising the at least one breaths. Each of the at least one breaths comprises a plurality of segments, and each of the segments of a given breath corresponds to an anatomical region of the patient that is non-identical to the anatomical regions for others of the segments. The method also comprises using the apparatus to select at least one but less than all of the breath profile segments of each of the breaths of the breath profile to thereby select at least one but less than all of the corresponding anatomical regions, analyzing the selected at least one breath profile segments for the at least one endogenous analyte to obtain information about the analyte, and generating a signal in the apparatus representative of the information.

To address these limitations and advance the art, a breath flow regulation device is provided that separates the breath sample into an analytical portion (e.g., the portion of interest and with which the analyte measurement will be made) and a residual portion (e.g., portions of the breath sample other than the analytical portion. This separation can be achieved using a breath flow regulation device, used in conjunction with a breath analysis device, e.g., as a separate but cooperative apparatus or as an integrated part of the breath analysis device. The flow regulation device divides the breath sample into respective analytical and residual portions and, directly or indirectly, is used to provide the analytical portion to the breath analysis device, where the analytical portion is analyzed to sense the presence of or provide quantitative information (e.g., the concentration) of the analyte or analytes in that portion of the breath sample.

In some embodiments, the breath flow regulation device comprises a flow channel for receiving the breath sample from the user. The flow channel comprises a first flow path and a second flow path separate from the first flow path. The regulation device also comprises a valve in fluid communication with the flow channel that directs an analytical portion of the breath sample into the second flow path and diverts a residual portion of the breath sample into the first flow segment. The breath analysis device receives the analytical portion of the breath sample, directly or indirectly, from the second flow path and senses the analyte.

Multiple other embodiments are disclosed. They include, for example, a device that comprises a moveable piston to regulate the flow path, and a device that comprises a ball valve for flow regulation. Related methods also are provided.

In accordance with some embodiments, a system is provided for sensing an analyte in breath of a user. The system comprises a base; a breath input operatively coupled to the base that receives the breath; a cartridge coupled to the base and in fluid communication with the breath input to receive the breath, wherein the cartridge comprises an interactant subsystem that is selected to undergo a reaction with the analyte when the analyte is present in the breath and to undergo an optical change corresponding to the reaction; and an optical subsystem coupled to the base and configured to sense the optical change, wherein the optical subsystem generates an output comprising information about the analyte in response to the optical detection.

In accordance with one embodiment, a method is provided for measuring an analyte in a breath sample using a disposable cartridge. The method includes directing flow of the breath sample to a first flow path with a first flow property in the disposable cartridge; directing flow of the breath sample to a second flow path with a second flow property; altering the first flow property and/or the second flow property so that the breath sample flow increases in the first flow path compared to the second flow path; and measuring a value indicative of the concentration of an analyte from a portion of the breath sample obtained from the second flow path. The method may include a first flow property that is flow resistance. The method may include determining flow resistance by the output of a mass flow sensor.

In accordance with another embodiment, a method is provided for measuring an analyte in a breath sample using a disposable cartridge. The method includes directing flow of the breath sample to a first flow path with a first characteristic; changing the first characteristic after a first time interval; measuring a value indicative of the concentration of an analyte from a portion of the breath sample obtained from the first flow path after the first time interval.

In accordance with another embodiment, a method is provided for measuring an analyte in a breath sample using a disposable cartridge. The method includes directing flow of the breath sample to a first flow path at a first flow rate; changing the first flow rate at a first time; measuring a value indicative of the concentration of an analyte from a portion of the breath sample obtained from the first flow path after the first time interval. The method may include indicating a change in the user flow rate.

In accordance with another embodiment, a method is provided for sensing an analyte in breath using a disposable cartridge. The method includes directing an alveolar breath sample through a first flow path, the first flow path comprising a porous disk and beads with affinity for the analyte; wherein the first flow path has a static dimension; directing the alveolar breath sample through a reactant in a reaction zone in a second flow path within the cartridge, wherein the reaction zone has an optical characteristic that is at a reference level; facilitating a change in the optical characteristic of the reaction zone relative to the reference level; and detecting the change in the optical characteristic to sense the analyte in the breath.

In accordance with another embodiment, a method is provided for measuring an analyte in a breath sample using a disposable cartridge. The method includes providing a cartridge with a flow path consisting of a resistance that allows user breath to flow through without use of a pump; obtaining a deep lung sample of breath; directing the deep lung sample through the cartridge; sensing the analyte in the deep lung sample to generate a sensor response; displaying an output indicative of the concentration of the analyte based on the sensor response.

In accordance with another embodiment, a method is provided for measuring an analyte in a breath sample using a disposable cartridge. The method includes directing flow of the breath sample to a first flow path in the disposable cartridge; directing flow of the breath sample to a second flow path; diverting the flow of the breath to either the first flow path or the second first flow path based on a characteristic of the breath sample, wherein the characteristic is capable of distinguishing the expired airway phase of a breath sample from the alveolar phase of the breath sample; and measuring a value indicative of the concentration of an analyte from an alveolar portion of the breath sample.

In accordance with another embodiment, a device is provided for isolating a desired fraction of exhaled air. The device comprises: (a) a housing, (b) an influent port on the housing for receiving a volume of exhaled air, and (c) an air fractionator in the housing and in air flow communication with the influent port. The fractionator is configured to divide the volume of exhaled air into a first fraction having a predetermined volume, a second desired fraction having a predetermined volume, and a third fraction. The device isolates the second fraction for breath analysis.

Preferably but optionally, the first fraction has a volume of at least about 300 $cm^3$. The first fraction preferably has a volume within the range of from about 450-550 $cm^3$. The second fraction preferably has a volume within the range of from about 150-250 $cm^3$. The device may further comprise an effluent port on the housing configured to vent the first fraction through the effluent port. Optionally but preferably, the device further comprises a sample port on the housing that is configured to deliver the second desired fraction through the sample port.

The breath input optionally may comprise a mouthpiece and an attachment for attaching a non-human breath container in which the breath is contained. An example of a non-human breath container includes a bag, such as a Tedlar® bag. The cartridge preferably is detachably coupled to the base. The cartridge also optionally but preferably comprises a handle, and also preferably a light shielding device. More specifically, in some instances there is a concern that components of the cartridge, for example, such as chemical components, may be adversely affected by ambient light. Accordingly, in some embodiments and methods, the base of the system comprises an exterior surface that forms an interior and shields the interior from ambient light, wherein the exterior surface comprises an aperture; and the cartridge comprises a shroud that substantially conforms to the aperture to shield ambient light from entering the aperture when the cartridge is coupled to the base.

In certain embodiments, the base is configured to accept breath from a plurality of breath inputs. The base may further be configured to accept variable volumes of breath and/or remove unneeded volume of breath. In some instances, it is necessary or desirable to undertake a multiple-stage reaction system. Accordingly, in some embodiments and methods, the interactant subsystem comprises a first interactant that is selected to undergo a first reaction with the analyte when the analyte is present in the breath and to generate a first intermediate; and a second interactant that is selected to undergo a second reaction with the first intermediate and to cause the optical change corresponding to the second reaction. In an illustrative example, the first interactant comprises a primary amine coupled to a first substrate a substantially in the absence of a tertiary amine; and the second interactant comprises the tertiary amine.

The optical subsystem can be configured to sense the optical change in a number of ways and according to a number of different criteria. It may be configured, for example, to sense the optical change at a predetermined time after the breath is inputted into the breath input. In some embodiments, the system may further comprise a flow sensor that senses a characteristic of the breath as the breath moves in the system; and the optical subsystem is configured to sense the optical change in response to the flow sensor.

The system also may and preferably does comprise a processor that performs various roles in the system. One of those roles may comprise using process information, such as the identification of one or more specific analytes that the system is configured to sense, information relating to the analyte, such as expected concentration ranges, states, reactivities, temperature and/or pressure dependencies, partial pressure and other vapor state information, and the like, flow characteristics such as fluid temperature, pressure, humidity, mass or volume flow rate, etc., each measured statically or dynamically over time. The process information also may comprise information relating to the cartridge, for example, such as the type of cartridge, the analyte or analytes it is configured to sense, its capacity, its permeability or flow characteristics, its expected response times, at the like. The process information also may comprise information relating to the breath input, for example, such as the breath temperature, pressure, humidity, expected constituents, and the like. In such systems and methods, the optical subsystem can be configured to sense the optical change in response to the processor, and in response to one more of such on the process-based information.

In some system embodiments and methods, a flow facilitator also is provided, and may be coupled to the base. The flow facilitator facilitates the flow of the breath into the cartridge and into contact with the interactant subsystem.

In accordance with another embodiment, a method is provided for sensing an analyte in breath of a user. The method comprises providing a cartridge comprising a cavity that comprises an interactant subsystem that is selected to undergo a reaction with the analyte when the analyte is present in the breath and to undergo an optical change corresponding to the reaction. The method also comprises providing a flow path for the breath that comprises a breath input and the cavity of a cartridge, and disposing an optical sensor in fixed relation relative to the cavity. In addition, the method comprises moving the breath through the flow path, causing the optical sensor to detect the optical change as the breath is moved through the flow path, and outputting an output that comprises information about the analyte in response to the optical detection.

In some implementations of this method, the providing of the flow path comprises providing a mouthpiece in the flow path; and the moving of the breath through the flow path comprises causing the user to exhale into the flow path through the mouthpiece. In addition or alternatively, the providing of the flow path also may comprise providing a non-human breath container in the flow path; and the moving of the breath through the flow path may comprise causing the breath to flow from the non-human breath container into the flow path.

In some implementations of the method, the cartridge is detachably coupled to the base. The method also optionally comprises shielding the interactant from ambient light as the breath is moved through the cavity.

In some implementations of the method wherein the interactant comprises a first interactant that is selected to undergo a first reaction with the analyte when the analyte is present in the breath and to generate a first intermediate; and a second interactant that is selected to undergo a second reaction with the first intermediate and to cause the optical change corresponding to the second reaction. In some implementations, the first interactant comprises a primary amine coupled to a first substrate a substantially in the absence of a tertiary amine; and the second interactant comprises the tertiary amine.

In some implementations, the causing of the optical sensor to detect the optical change comprises sensing the optical change at a predetermined time after the breath is initially moved through the flow path. Alternatively or in addition, the method may comprise sensing a characteristic of the breath as the breath moves in the flow path; and the causing of the optical sensor to detect the optical change may comprise sensing the optical change in response to the sensing of the characteristic. The causing of the optical sensor to detect the optical change also may comprise sensing the optical change in response to process information, such as the process information summarized herein above.

In some implementations of the method, the moving of the breath through the flow path comprises facilitating the flow of the breath into the cavity and into contact with the interactant subsystem.

In accordance with another embodiment, a system is provided for sensing an analyte in breath of a user. This system can be used, for example, where it is necessary or desirable to use multiple steps in processing the analyte or analytes, for example, to facilitate sensing. The system comprises a base; a breath input operatively coupled to the base that receives the breath; and a cartridge coupled to the base and in fluid communication with the breath input to receive the breath. The cartridge comprises a first interactant that is selected to undergo a first reaction with the analyte when the analyte is present in the breath to generate a first intermediate. The system further comprises a dispensing device coupled to the base that dispenses a second interactant that is selected to undergo a second reaction with the first intermediate wherein an optical change corresponding to the reaction is generated. The system further comprises an optical subsystem coupled to the base and configured to sense the optical change, wherein the optical subsystem generates an output comprising information about the analyte in response to the optical detection.

The breath input may comprise a mouthpiece, an attachment for attaching a non-human breath container in which the breath is contained, for example such as a bag, or both.

The cartridge is detachably coupled to the base. It preferably but optionally comprises a handle.

Particularly where internal system components such as the interactant are light-sensitive, the base may comprise an exterior surface that forms an interior and shields the interior from ambient light, wherein the exterior surface comprises an aperture; and the cartridge may comprises a shroud that substantially conforms to the aperture to shield ambient light from entering the aperture when the cartridge is coupled to the base.

The interactant subsystem preferably comprises a first interactant that is selected to undergo a first reaction with the analyte when the analyte is present in the breath and to generate a first intermediate; and a second interactant that is selected to undergo a second reaction with the first intermediate and to cause the optical change corresponding to the second reaction. In some embodiments, the first interactant may comprise a primary amine coupled to a first substrate substantially in the absence of a tertiary amine; and the second interactant may comprise the tertiary amine.

The interactant subsystem may, in certain embodiments, comprise sodium nitroprusside, dinitrophenylhydrazine, sodium dichromate, pararosaniline, bromophenol blue, dischloroisocyanourate, sodium salicylate, sodium dichromate, crystal violet, benzyl mercaptan, or combinations thereof.

In some embodiments, the interactant subsystem is configured to measure endogenous levels of analytes in breath, where such levels may be 5 ppm or less.

As with embodiments and options described herein above, the dispensing device may be configured to dispense the second interactant at a predetermined time after the breath is inputted into the breath input. Alternatively or in addition, the system may comprise a flow sensor that senses a characteristic of the breath as the breath moves in the system; and the dispensing device may be configured to dispense the second interactant in response to the flow sensor.

Also as explained with respect to other embodiments and methods described herein above, the system may further comprise a processor that comprises process information, e.g., such as that described herein above; and the dispensing device may be configured to dispense the second interactant in response to the processor based on the process information.

The optical subsystem according to this embodiment also may comprise the components and features as described herein above, and/or a flow facilitator as described more fully herein above.

In accordance with another embodiment, a system is provided for sensing an analyte in breath of a user, wherein the system comprises a base; a breath input operatively coupled to the base that receives the breath; a cartridge detachably coupled to the base and in fluid communication with the breath input to receive the breath; and a sensing subsystem coupled to the base, wherein the base comprises an exterior surface that forms an interior and shields the interior from ambient light, and wherein the exterior surface comprises an aperture, and this aspect of the invention comprises the further improvement of a shroud coupled to the cartridge that substantially conforms to the aperture to shield ambient light from entering the aperture when the cartridge is coupled to the base.

In accordance with still another aspect of the invention, a system is provided for sensing a plurality of analytes in breath of a user. The system may comprise a base; a breath input operatively coupled to the base that receives the breath; a plurality of cartridges coupled to the base and in fluid communication with the breath input to receive the breath, wherein each of the cartridges comprises a corresponding interactant subsystem that is unique with regard to others of the cartridges and is selected to undergo a corresponding reaction with a corresponding one of the analytes when the corresponding analyte is present in the breath to form a corresponding product state; and a sensing subsystem coupled to the base and configured to sense the product states and to generate an output comprising information about the plurality of analytes.

In accordance with still another aspect of the invention, a method is provided for sensing a plurality of analytes in breath of a user. The method comprises providing a plurality of cartridges coupled to a base and in fluid communication with the breath input to receive the breath, wherein each of the cartridges comprises a corresponding interactant subsystem that is unique with regard to others of the cartridges and is selected to undergo a corresponding reaction with a corresponding one of the analytes when the corresponding analyte is present in the breath to form a corresponding product state; and causing a sensing subsystem coupled to the base and configured to sense the product states to sense the product states and to generate an output comprising information about the plurality of analytes.

In accordance with another aspect of the invention, a system is provided for sensing an analyte in breath of a patient. The system comprises a cartridge comprising a first container, a fluid container, and a reaction volume in fluid communication with the first container and the fluid container, the first container containing a first interactant and the fluid container containing a fluid, wherein the fluid container has an initial fluid level and a space above the initial fluid level. The system also comprises a base comprising a flow path for flow of the breath within the base, a breath input receiver in fluid communication with the flow path that receives the breath and directs the breath into the flow path, a cartridge housing that detachably receives the cartridge into the base so that the reaction volume is in fluid communication with the flow path, a dispensing device that creates a hole in the fluid container below the initial fluid level and that moderates pressure in the space above the initial fluid level so that the fluid flows out of the liquid container and into the reaction volume, thereby facilitating an optical change in the reaction volume in relation to at least one of a presence and a concentration of the analyte, and an optical subsystem that senses the optical change and generates an output comprising information about the analyte in response to the optical change. The dispenser preferably comprises an elongated member, for example, such as a needle, pin, rod and the like. It may comprise a solid member, or it may comprise a fluid channel.

In some embodiments, the dispensing device and related function involves dispensing the liquid in the liquid container. To accomplish this, a hole is created in the liquid container below the initial level of the liquid, preferably well below this level and more preferably at the bottom of the liquid container or otherwise so that the maximum amount of liquid is obtained from the container. The dispensing function also involves moderating the pressure in the space above the initial fluid level as the fluid moves out of the liquid container so that the fluid moves out of the liquid container and into the reaction volume. This preferably is accomplished by piercing or otherwise creating an opening in the space above the liquid so that gas can enter the space to equalize the pressure, to avoid creating a negative pressure or vacuum in the space, and to thereby permit the liquid to flow or otherwise move out the hole in the liquid container below the initial liquid level. Thus, preferably the elongated member is outside the liquid container to a deployed position in which the elongated member has created the hole in the fluid container below the initial fluid level and has moderated the pressure in the space above the initial fluid level so that the fluid flows out of the liquid container and into the reaction volume. The elongated member may comprise, for example, a needle, pin, rod and the like.

In accordance with another aspect of the invention, a method is provided for sensing an analyte in breath of a patient. The method comprises providing a cartridge comprising a first container, a fluid container, and a reaction volume in fluid communication with the first container and the fluid container. The first container contains a first interactant and the fluid container contains a fluid. The fluid container has an initial fluid level and a space above the initial fluid level. The method also comprises providing a base comprising a flow path for flow of the breath within the base, a breath input receiver in fluid communication with the flow path, cartridge housing, a dispensing device, and an optical subsystem. The method further comprises inserting the cartridge into the cartridge housing of the base so that the reaction volume is in fluid communication with the flow path, and causing the breath to flow in the flow path and into the reaction volume. After the breath has flowed through the reaction volume, the method comprises using the dispensing device to create a hole in the fluid container below the initial fluid level and moderating pressure in the space above the initial fluid level so that the fluid flows out of the liquid container and into the reaction volume, thereby facilitating an optical change in the reaction volume in relation to at least one of a presence and a concentration of the analyte. In addition, the method comprises sensing the optical change and generating an output comprising information about the analyte in response to the optical change.

In accordance with still another aspect of the invention, a system is provided for sensing an analyte in breath of a patient. The system comprises a cartridge comprising a reaction volume and a shroud that is opaque to ambient light. It further comprises a base comprising a flow path for flow of the breath within the base, a breath input receiver in fluid communication with the flow path that receives the breath and directs the breath into the flow path and through the reaction volume, wherein flow of the breath through the reaction volume facilitates an optical change to the reaction volume in relation to at least one of a presence and a concentration of the analyte, a cartridge housing that detachably receives the cartridge into the base so that the reaction volume is in fluid communication with the flow path, wherein the shroud of the cartridge mates with the cartridge housing of the base to block ambient light from impinging on the reaction volume, and an optical subsystem that senses the optical change and generates an output comprising information about the analyte in response to the optical change.

In accordance with one aspect of the invention, a system is provided for sensing an analyte in a breath sample. The system comprises a breath bag, a cartridge and a base. The breath bag contains the breath sample comprising a mouthpiece fixedly disposed on the breath bag. The cartridge comprises an interactant that reacts with the analyte and generates a change in an optical characteristic relative to a reference. The base comprises a flow path, a breath bag receiver for detachably receiving and retaining the mouthpiece of the breath bag in fluid communication with the flow path and a cartridge receiver that detachably receives and retains the cartridge in the base, such that the base engages the cartridge so that the interactant is in fluid communication with the flow path. The base further comprises a flow handling system in fluid communication with the flow path, an optical subsystem for sensing the change in the optical characteristic, a processor operatively coupled to the flow handling system and the optical subsystem, and a user interface operatively coupled to the processor and comprising a start command. Upon user selection of the start command, the processor is configured to automatically regulate the flow handling system to move the breath sample in the flow path and to contact the breath sample and the interactant. Upon the occurrence of a predetermined process parameter, the processor is configured to perform the following actions: (a) to automatically regulate the optical subsystem to sense the change in the optical characteristic, (b) to correlate the sensing of the optical system with information about the analyte in the breath sample, and (c) to output the information about the analyte in the breath sample to the user interface.

In certain embodiments, the mouthpiece is fixedly disposed at a corner of the breath bag. The breath bag receiver preferably is configured to fluidically connect the breath bag with the flow handling system and is configured to retain the breath sample in the breath bag until the processor causes the flow handling system to move the breath sample through the flow path.

In certain embodiments, the optical subsystem comprises only a single optical sensor. A low cost system may also function without the use of light pipes and the single optical sensor may be positioned within 1" or preferably ¼" of the disposable cartridge.

In certain embodiments, the cartridge further comprises an optical sensing zone, and, wherein the optical subsystem comprises an optical detector that is fixedly positioned with regards to the optical sensing zone. The cartridge may further comprises a cartridge identifier, and further wherein the optical detector generates a signal with information about this cartridge identifier.

The optical subsystem is preferably designed so that it senses through the optical sensing zone of the cartridge, but the cartridge does not physically move. A stationary cartridge provides certain advantages for the flow handling system as well.

In certain configurations, the cartridge comprises beads with a mesh size smaller than 100. In other configurations, the cartridge comprises beads with a mesh size between 270 and 100. An application utilizing these beads is sensing acetone for certain purposes. The cartridge may comprise a flow path. The flow path may be substantially linear. In one embodiment, the interactant is specific for an endogenous analyte. Preferably, the interactant is useful over a physiological range of interest. The cartridge may comprise at least one liquid reagent and at least one dry reagent. The predetermined process parameter may be at least one of: (a) elapsed time from a start command, (b) elapsed time from pump initiation, (c) elapsed time from flow initiation, (d) elapsed time at a predetermined pressure, and (e) volume of the breath sample through the flow path is greater than 350 ml. The optical subsystem may comprise a camera. The processor may be configured to do at least one of: (a) activate an optical detector, (b) activate an illuminator, and (c) obtain an image from a camera and store the image in memory.

In certain embodiments, the base is configured to receive a plurality of cartridges, each having a different cartridge type, and, wherein the processor is configured to regulate the flow handling system and to regulate the optical subsystem according to different parameters, wherein these parameters vary depending on the cartridge type. The plurality of cartridges may comprise interactants that are specific for the analyte, but different ranges thereof. Also, the plurality of cartridges may comprise interactants that are specific for a plurality of analytes.

Certain embodiments of the cartridge comprise a cartridge identifier, and further wherein the base is configured to recognize the cartridge identifier. The cartridge identifier may be a standard barcode, but may also be the color of the liquid container or the color of the handle of the cartridge.

The base may be configured to recognize the cartridge identifier using at least one of (a) a barcode scanner, (b) a magnetic scanner, (c) a chip, (d) a pin set, and (e) a mirror configuration. Also, the cartridge identifier may comprise information about the interactant and wherein the processor uses this information to determine information about the analyte. The information is at least one of (a) batch lot, (b) expiration date, (c) chemical variability, (d) analyte identifier, and (e) serial number.

The interactant may generate an intended change in an optical characteristic and an unintended change in an optical characteristic, and further wherein the processor is configured to separate the intended change from the unintended change. The unintended change may be caused by at least one of (a) bubbles, (b) a second analyte in the breath sample, (c) packing anomalies, (d) particle size void space, (e) liquid reagent concentration changes, (f) cartridge recognition, (g) packing anomalies, (h) subsystem failure, and (i) device failure.

Certain cartridges contain an optical sensing zone. For these cartridges, the optical subsystem is able to sense a change in optical characteristic in two spatial dimensions within the optical sensing zone. The optical sensing zone may have an inlet and an outlet corresponding to the direction of the flow path. Here, the processor determines if the cartridge is saturated by comparing the change in the optical characteristic at the inlet and the outlet and determining that they are approximately the same. Another approach would be to measure the gradient of the optical characteristic along the axis of the flow path. In certain configurations, the change in optical characteristic has greater than three levels.

In certain embodiments, the breath bag further comprises an outlet. The full breath sample may be directed through the mouthpiece and a portion is directed from the outlet. The outlet may be configured to close when the breath sample is no longer being input through the mouthpiece. The outlet may also be configured to close when the breath bag depresses against a spring.

In one configuration, the breath bag receiver is on the top portion of the base. In another, the breath bag receiver is configured to accept the breath bag without moving the base. In yet another embodiment, the cartridge receiver is configured to accept the cartridge without moving the base. The cartridge may be designed such that a portion of it remains outside the base at all times during the sensing process.

In certain embodiments, the breath bag may attach to the breath bag receiver via a face seal flange with a spring loaded snap fit. The breath bag may mate with the interior of the base.

The cartridge may be comprised of an inlet aperture and an outlet aperture, wherein the base comprises a dispensing device, and further wherein the dispensing device delivers the breath sample through the inlet aperture using an elongated member.

In accordance with an aspect of the invention, a cartridge is provided for use with a breath analysis system comprising an optical subsystem for sensing an analyte in a breath sample. The cartridge comprises a housing, a flow path, an interactant, an optical sensing zone. The flow path may begin at an inlet aperture and end at an outlet aperture. The interactant region comprises interactant beads. The optical sensing zone is within view of the optical subsystem. The breath sample is delivered to the interactant region and generates a change in an optical characteristic that is sensed by the optical subsystem through the optical sensing zone.

In one cartridge embodiment, the housing is comprised essentially of plastic. The housing may also be manufactured from a single material and parts of that single material were extruded from it. The housing may not held together using mechanical parts.

The aspect ratio of the cross sectional area along the axis of flow of the breath sample through the interactant region may be between 1 and 10. The cross sectional area may be between 1 and 10 $mm^2$. In certain embodiments, the length of the interactant region is less than 0.25".

In some embodiments, a cartridge may comprise a liquid container. The liquid container may be essentially opaque and the housing is not opaque. The liquid container, for certain applications, contains between 25 and 150 microliters of liquid reagent.

In systems described herein, the analyte may be acetone, ammonia or carbon dioxide.

The base may be configured to receive a plurality of cartridges, wherein the cartridges contain interactants for at least two of: acetone, ammonia and carbon dioxide.

In accordance with another aspect of the invention, a cartridge is provided for use with a breath analysis system comprising an optical subsystem for sensing an analyte in a breath sample. The cartridge comprises (a) a housing, (b) a flow path disposed in the housing for directing flow of the breath sample, the flow path comprising an inlet aperture and an outlet aperture, (c) an interactant region in fluid communication with the flow path that comprises interactant that, when contacted by the analyte in the breath sample, generate a change in an optical characteristic of the interactant region, and (d) an optical sensing zone in operative communication with the interactant region and the optical subsystem so that, when the breath sample is directed through the flow path and the analyte in the breath sample contacts that interactant and generates the change in the optical characteristic, the change in the optical characteristic is sensed by the optical subsystem at the optical sensing zone.

In accordance with another aspect of invention, a cartridge is provided for use with a breath analysis system for sensing an analyte in a breath sample. The cartridge comprises an interactant region that comprises an interactant that reacts with the analyte in the breath sample, an inverted cup, inverted with respect to local gravity, wherein the cup comprises a liquid and a bottom portion, a biasing device that biases the inverted cup so that the bottom portion creates a liquid seal to retain the liquid in the inverted cup, and an actuation receiver responsive to the breath analysis system so that the actuation receiver interacts with the biasing device to break the liquid seal and release the liquid from the inverted cup in response to the breath analysis system.

In accordance with another aspect of the invention, a breath analysis system is provided for a user to analyze an analyte in breath. The system comprises a cartridge comprising a liquid chamber comprising a liquid and a reactive bead chamber, and a base unit comprising an actuator, wherein the actuator is configured to release the liquid without interaction with the user.

In accordance with still another aspect of the invention, a breath analysis system is provided for use by a user to analyze an analyte in breath. The system comprises a base unit comprising a cartridge receiver and an actuator, and a cartridge detachably disposed in the cartridge receiver of the base unit. The cartridge comprises an interactant region that comprises an interactant, an inverted cup, inverted with respect to local gravity, wherein the cup comprises a liquid and a bottom portion, a biasing device that biases the inverted cup so that the bottom portion creates a liquid seal to retain the liquid in the inverted cup, an actuation receiver operatively coupled to the actuator so that, in response to the actuator, the actuation receiver interacts with the biasing device to break the liquid seal and release the liquid from the inverted cup. This breaking of the liquid seal is achieved without interaction with the user other than user activation of the breath analysis test.

In accordance with another aspect of the invention, a method is provided for producing a cartridge for use in sensing an analyte in a breath sample. The method comprises providing a housing that comprises a flow path comprising an upstream direction and a downstream direction. The housing comprises a first chamber, a second chamber positioned in the downstream direction relative to the first chamber, and a housing outlet positioned in the downstream direction relative to the second chamber. The method further comprises disposing an interactant in the first chamber, disposing a first porous barrier material between the first chamber and the second chamber, which first porous barrier material retains the interactant in the first chamber but allows passage of the breath sample, disposing a breath sample conditioning material in the second chamber, disposing a second porous barrier material at a downstream end of the second chamber; and immobilizing the second porous barrier material by disposing a plurality of notched protrusions in the housing at the second porous barrier material. The disposing of the plurality of the notched protrusions preferably comprises using heat to form the notched protrusions.

According to another aspect of the invention, a cartridge is provided for use with a breath analysis system comprising an optical subsystem for sensing an analyte in a breath sample. The cartridge comprises a housing comprising an exterior surface having an exterior surface dimension. It also comprises a first chamber disposed in the housing and comprising a first chamber surface having a first chamber dimension. The first chamber comprises an interactant that interacts with the analyte in the breath sample. The housing exterior surface dimension at the first chamber comprises a first housing exterior surface dimension. A first chamber wall thickness is defined by the first housing exterior surface dimension minus the first chamber dimension, and the first chamber wall thickness is uniform throughout the first chamber surface. The cartridge also comprises a second chamber disposed in the housing and comprising a second chamber surface having a second chamber dimension. The second chamber comprises a breath sample conditioner. The housing exterior surface dimension at the second chamber comprises a second housing exterior surface dimension. A second chamber wall thickness is defined by the second housing exterior surface dimension minus the second chamber dimension, and the second chamber wall thickness is uniform throughout the second chamber surface. The first housing exterior surface dimension differs from the second housing exterior surface dimension, and the first chamber wall thickness is the same as the second chamber wall thickness.

In accordance with another aspect of the invention, a breath analysis system is provided that comprises a disposable system component comprising at least one of a cartridge and a breath bag. The system also includes a base unit that comprises a disposable system component receiving port configured to detachably receive and affix the disposable system component to the base; and a gasket disposed between the disposable system component and the disposable receiving port to create an air-tight seal.

In addition, related methods for the foregoing inventions are also provided herein.

The present invention according to one aspect comprises a method of determining the concentration of an analyte of interest in breath. The method comprises the steps of obtaining a disposable cartridge comprising a reaction chamber, a liquid chamber, and a window to permit determination of a color intensity in the reaction chamber. The method also comprises directing a volume of breath into the cartridge, and initiating a sequence whereby liquid is released from the liquid container into the reaction chamber to cause a reaction which produces a change in the intensity of a color viewable through the window. The intensity of the color corresponds to the concentration of the analyte of interest. The reaction progresses through a kinetic phase and eventually reaching equilibrium. The sequence additionally comprises the step of measuring the intensity of the color at a point in the kinetic phase, to determine the concentration of the analyte of interest in breath.

In some implementations of the method, the analyte comprises acetone. In others, it may comprise ammonia, isoprene or other endogenous analytes.

The reaction optionally but preferably is with an amine, more preferably wherein the amine is bound to a surface, a silica gel surface, the surface of a plurality of silica gel beads, or a combination of two or more of these. Where silica gel beads are employed, the silica gel beads have a size distribution between 270 and 100 mesh. In some implementations of the method, the silica gel beads have a volume of no more than about 1.0 ml. Other chemistry substrates can also be used such as sodium silicate derivates, and silica/quartz wool. For example, a 4"×1" strip of silica wool can put in a solution of 1.6 ml APTES+3.2 ml propanol+3.2 ml sulfuric acid. Solution is heated to 80° C. for 2 hours and then 110° C. for 1 hour. The resulting formulation is silica wool conjugated with primary amine. Also, in addition to beads, these substrates can have different geometries, such as planar, sheets, etc.

The liquid released from the liquid container optionally but preferably comprises a nitroprusside solution. In some method implementations, prior to the release of liquid step, the reaction chamber comprises an alkaline environment. Optionally but preferably, no more than about 1 ml of liquid is released from the liquid container, and in some implementations of the method no more than about 0.5 ml of liquid is released from the liquid container.

The method optionally but preferably comprises a step of removing water vapor from the volume of breath.

The step of measuring the intensity of the color preferably is accomplished within six minutes following the initiating step, and more preferably within four minutes following the initiating step. The step of measuring the intensity of the color also preferably is accomplished using a camera. The method may comprise using the camera to view information carried by the cartridge in addition to the color intensity.

The method may comprise using the camera to view both color intensity as well as a bar code. Similarly, it may comprise using the camera to view both color intensity as well as an indication of expiration date.

The present invention according to one aspect comprises a disposable cartridge for indicating the concentration of an analyte of interest in breath. The disposable cartridge comprises a housing, having a side wall and a longitudinal axis, and a reaction chamber in the housing. The disposable cartridge also comprises an optically transparent window in the side wall for viewing contents of the reaction chamber, wherein the window has a height measured in the direction of the longitudinal axis. The disposable cartridge further comprises a liquid chamber in the housing. The cartridge is configured to display a color that extends along the entire height of the window following the transfer of liquid from the liquid chamber into the reaction chamber. The intensity of the color corresponds to a concentration of the analyte of interest in the reaction chamber.

The disposable cartridge may further comprise an actuator for opening the valve and releasing liquid from the liquid chamber into the reaction chamber. The cartridge also may comprise an opening in the side wall for providing access to the actuator, wherein the actuator may be laterally displaceable.

The liquid chamber may be defined within a container having an open end, and the cartridge may further comprise a cover on the open end, for enclosing liquid. In such method implementations, the open end and the cover optionally may separate to release liquid in response to displacement of the actuator. The liquid optionally but preferably comprises a nitroprusside solution. The disposable cartridge in such method implementations may comprise a primary amine in the reaction chamber. The window of the disposable cartridge optionally but preferably has a height of no more than about 7 mm, and more preferably a height of no more than about 4 mm. The disposable cartridge also comprises particles in the reaction chamber. Such particles optionally but preferably have a size of no more than about 200 microns, and in some implementations a size of no more than about 120 microns. The actuator optionally but preferably is isolated from contents of the liquid chamber throughout operation of the cartridge. The particles in the reaction chamber in some implementations have a volume of no more than about 0.5 ml, and in some implementations their volume is no more than about 0.1 ml. In some implementations, no more than about 0.2 ml of nitroprusside solution is disposed in the liquid chamber. The disposable cartridge in preferably is configured to produce a color change corresponding to a concentration of the analyte of interest in no more than about 6 minutes.

In accordance with one aspect of the invention, an analyzer is provided for sensing an analyte in breath of a patient. The analyzer comprises a base, a breath input port on the base for removable coupling to a source of breath, a cartridge receiving cavity on the base for removably receiving a disposable cartridge having an optically transparent window and a reaction volume, and a flow path disposed in the base. The flow path is configured to place the breath input port into communication with the reaction volume when the cartridge is installed in the cartridge receiving cavity. The analyzer further comprises an optical subsystem in the base that senses an optical change in the reaction volume through the window. A pump is disposed in the base and configured to pump breath from the source of breath to the reaction volume during a measurement cycle when the source of breath is coupled to the breath input port, and to pump atmospheric air through the flow path during a flush cycle.

Optionally but preferably, the pump is programmed to deliver air through the flow path at a first flow rate during the measurement cycle, and at a second, different flow rate during the flush cycle. The second flow rate during the flush cycle preferably is greater than the first flow rate during the flush cycle, and more preferably the first flow rate during the measurement cycle is lower than the second flow rate during the flush cycle. In some embodiments, the first flow rate during the measurement cycle is in the range of about 150 to 750 ml per minute. In other embodiments, the first flow rate during the measurement cycle extends at the upper end to about 300 ml/min, about 500 ml/min, about 1 L/min, about 2 L/min, about 5 L/min, or any other flow rate that is helpful or necessary to the systems and methods as disclosed herein. In yet other embodiments, the first flow rate during the measurement cycle is about 330 ml per minute, and the second flow rate during the flush cycle is at least about 300 ml per minute. These flow rates should not be understood as limiting. The second flow rate during the flush cycle, for example, may extend to about 1000 ml per minute, but in various applications and embodiments may be about 500 ml/min, about 1.5 L/min, about 2 L/min, about 4 L/min, about 10 L/min, or any other flow rate that is helpful or necessary to the systems and methods as disclosed herein.

The pump may be programmed to turn off after a predetermined flush cycle duration. That predetermined flush cycle duration preferably is at least about 30 seconds, but in various applications and embodiments, for example, may be at least about 5 sec, 15 sec, 30 sec, or and 60 sec.

The optical subsystem preferably comprises a camera oriented so that the optically transparent window is within a field of view of the camera when the cartridge is installed in the cartridge receiving cavity. The camera may be configured to capture an image of the contents of the reaction volume through the window and also capture an image of information on the cartridge adjacent the window when the cartridge is installed in the cartridge receiving cavity.

The analyzer preferably is configured to initiate the flush cycle following removal of the source of breath from the breath input port. It also preferably is configured to generate a baseline flow rate during the flush cycle, and to increase the flush cycle flow rate in response to a determination by the optical subsystem that the analyte is present in a concentration which is greater than a preset threshold.

In some embodiments of the analyzer, the analyte is acetone and the preset threshold is about 40 ppm, although that threshold in variants of this embodiment may be about 20 ppm, 30 ppm, 60 ppm, or 100 ppm.

In accordance with one aspect of the invention, a method is provided for extending an effective working range of an analyzer for measuring an analyte in a breath sample. The method comprises initiating a reaction in the analyzer that produces an optically discernable reaction product having an optical property that is indicative of a concentration of the analyte in the breath sample. The method also comprises taking a first reading of the optical property at a first time, and comparing the first reading to a reference. If the comparison of the first reading to the reference has a first state, the method comprises determining the concentration using the first reading. If the comparison of the first reading to the reference has a second state different from the first state, the method comprises taking a second reading of the optical property at a second time and determining the concentration of the analyte using the second reading.

The determining of the concentration using the first reading may be conducted using a first calibration data set, a lookup table, a calibration curve, or a combination of these.

Similarly, the determining of the concentration using the second reading may be conducted using a second calibration data set, a lookup table, a calibration curve, or some combination of these.

The method preferably but optionally comprises displaying the concentration. The optical property preferably comprises intensity, but this is not necessarily limiting. In some embodiments, the first calibration data set calibrates the analyzer to measure the analyte over a working range of from about 0 to 10 ppm of the analyte, and the second calibration data set calibrates the analyzer to measure the analyte over a working range of from about 0 to 20 ppm of the analyte. These are not, however, necessarily limiting. In related embodiments, the first calibration data set calibrates the analyzer to measure the analyte over a working range of from about 0 to 20 ppm of the analyte. In similarly related embodiments, the first calibration data set calibrates the analyzer to measure the analyte over a working range of from about 0 to 120 ppm of the analyte. In other related embodiments, the first calibration data set calibrates the analyzer to measure the analyte over a first working range of less than about 20 ppm and the second calibration data set extends the first working range by at least about 100%. In certain embodiments, the analyzer has an effective working range equal to the sum of at least a first working range and a second working range, wherein the second working range is at least 100% of the first working range. In others, the second working range is at least 300% of the first working range.

In accordance with another aspect of the invention, a method is provided for measurement of an analyte in a breath sample using a breath analysis device. The method comprises initiating a reaction that produces an optically discernable reaction product having an optical property that is indicative of the concentration of the analyte in the breath sample, taking a first reading of the optical property at a first time, and comparing the first reading to a reference. If the comparison of the first reading to the reference has a first state, the method comprises determining the concentration using the first reading. If the comparison of the first reading to the reference has a second state, the method comprises adjusting a process parameter of the breath analysis device and taking a second reading of the optical property at a second time subsequent to the adjusting of the process parameter, and using the second reading to obtain the concentration of the analyte using a calibration process. The method also preferably comprises displaying the concentration of the analyte.

The adjusting of the process parameter may comprise changing a pump speed, adjusting a duration of pump operation, avoiding the process parameter to avoid saturation of the reaction, or some combination of these. The optical property comprises intensity. In some implementations of the method, the taking of the second reading is commenced within about six minutes following the initiating of the reaction. In some method implementations, the initiating of the reaction comprises releasing a nitroprusside solution into a reaction volume. In such implementations, for example, the displaying of the concentration of the analyte comprises displaying a concentration of acetone within a range of from about 0 ppm to about 120 ppm.

In some embodiments, a breath capture device for determining the concentration of acetone in a breath sample from a user includes an influent flow port, a first flow path coupled to the influent flow port, the first flow path comprising a chamber, a second flow path coupled to the influent flow port, an indicator responsive to a signal, and a switch configured to be responsive to an action by the user that is operable between a first orientation in which breath entering the influent port travels through the second flow path and a second orientation in which breath entering the influent port travels through the first flow path.

In some embodiments, the signal is generated by a sensor that measures a property of the breath sample of the user. In some embodiments, the property of the breath sample of the user is a pressure. In other embodiments, the signal is related to at least one of a flow rate and a volume. In other embodiments, the signal is related to a duration of time. In some embodiments, the property of the breath sample of the user is a temperature of the breath sample. In other embodiments, the switch comprises at least one of an electronically driven solenoid and a mechanically driven valve.

In some embodiments, a breath capture device for determining the concentration of an analyte in a breath sample from a user includes an influent flow port, a flow path coupled to the influent flow port, the flow path comprising a chamber, a first sensor configured to determine a value indicative of the concentration of the analyte in a breath sample, a second sensor configured to determine a flow exhalation property related to the breath sample, a memory configured to store the value and the flow exhalation property, and a controller programmed to analyze the value and the flow exhalation property to determine the validity of the value.

In some embodiments, the flow exhalation property is indicative of a cough. In other embodiments, the flow exhalation property is indicative of at least one of a suboptimal breathing flow and an irregular breathing flow. In other embodiments, the flow exhalation property is indicative of a delayed exhalation. In other embodiments, the flow exhalation property is indicative of a lack of total lung capacity. In other embodiments, the flow exhalation property is indicative of the user not being at rest. In some embodiments, the flow exhalation property comprises at least one of time, volume, flow rate, temperature, carbon dioxide concentration, and oxygen concentration.

In some embodiments, a breath capture device includes an influent flow port, a first flow path coupled to the influent flow port, the first flow path comprising a chamber, a second flow path coupled to the influent flow port, and a flow regulator configured to be responsive to user action that is operable from a first position in which breath entering the influent port preferentially travels through the second flow path to a second position in which breath entering the influent port preferentially travels through the first flow path.

In some embodiments, the breath capture device includes a dial coupled to the flow regulator. In some embodiments, the breath capture device includes a valve coupled to the flow regulator. In some embodiments, the flow regulator is configured to be controlled by a mobile device. In some embodiments, the flow regulator has a first position in a first spatial orientation and a second position in a second spatial orientation. In some embodiments, the flow regulator further comprises a flow restrictor.

In some embodiments, a breath capture device for collecting a breath sample from a user includes an influent flow port, a flow path coupled to the influent flow port, the flow path comprising a chamber, a memory configured to store data based on at least one characteristic of the user, the data generated before the user exhales the breath sample into the device, and a controller programmed to use the data stored in the memory to control the flow of a portion of the breath sample into the chamber as the user exhales the breath sample into the influent flow port.

In some embodiments, the characteristic is a duration of time for the user to exhale. In other embodiments, the characteristic is an age of the user. In other embodiments, the characteristic is a height of the user. In other embodiments, the characteristic is a lung capacity of the user. In other embodiments, the characteristic is a sex of the user. In some embodiments, the controller is programmed to control the flow of air through a valve. In other embodiments, the controller is programmed to use an output of a sensor that senses a characteristic of the breath sample to control the flow of breath. In other embodiments, the controller is programmed to generate the data by monitoring at least one exhalation of the user prior to the user exhaling the breath sample In some embodiments, a portable breath analysis device includes a breath input port fluidly coupled to a valve, a first conduit that extends downstream to an exhaust portion of the device, a second conduit that extends downstream to a capture chamber, and a controller programmed to actuate the valve during exhalation of a breath sample to cause a first portion of the breath sample to be routed through the first conduit and out of the device and to cause a second portion of the breath sample to be routed through the second conduit into the capture chamber. In some of these embodiments, the controller is programmed to implement a process that includes, during a first exhalation by a user, recording data regarding at least one exhalation characteristic of the user, and during a second exhalation by the user, actuating the valve at a point in time that is dependent upon the recorded data regarding the at least one exhalation characteristic of the user.

In some embodiments, the first exhalation is performed while the device is in a device configuration mode in which the device does not capture a portion of a breath sample in the capture chamber. In some embodiments, the data regarding the at least one exhalation characteristic comprises an exhalation duration time. In some embodiments, the device further includes a flow sensor, and the data regarding the at least one exhalation characteristic comprises a total exhalation volume. In some embodiments, actuating the valve comprises measuring a flow volume during the second exhalation, and actuating the valve when the flow volume reaches a selected fraction of the total exhalation volume. In some embodiments, the point in time is selected such that the valve is actuated during an alveolar portion of the second exhalation. In some embodiments, the controller is programmed to select the point in time based on user exhalation characteristic data captured over a plurality of exhalations. In other embodiments, the controller is programmed to initiate valve actuation a selected time interval before a desired actuation point to account for valve actuation delay. In some embodiments, the capture chamber is a reaction chamber that includes a reactant. In some embodiments, the device is a disposable cartridge that is configured for post-capture insertion into an analysis device that measures a color change occurring within the reaction chamber.

In some embodiments, a method of breath sample capture includes during a first exhalation by a user, recording, in a memory, data regarding at least one exhalation characteristic of the user, and during a second exhalation by the user of a breath sample into a breath capture device, by a programmed controller of the breath capture device, actuating a valve of the breath capture device at a point in time that is dependent upon the recorded data regarding the at least one exhalation characteristic of the user, wherein the valve is initially in a state that causes exhaled breath to be vented from the breath capture device, and wherein the actuation of the valve causes a remaining portion of the breath sample to be routed to a capture chamber of the breath capture device.

In some embodiments, the first exhalation is into the breath capture device, and the breath capture device measures the at least one exhalation characteristic. In some embodiments, the first exhalation is into a user profiling device that is separate from the breath capture device.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 3 is a flow chart demonstrating a method for operating a breath analysis device using multiple breath profiles.

FIG. 27 shows a side cutaway view of a breath flow regulation device according to an embodiment of the invention, wherein the device is in an initial or open position and directs breath flow through a Flow Path 1.

FIG. 28 shows a side cutaway view of the regulation device of FIG. 27, wherein the device is in a position that diverts flow from Flow Path 1 to a Flow Path 2.

FIG. 39 shows a side external view of a regulation device according to another embodiment of the invention.

FIG. 40 shows a side cutaway view of the regulation device of FIG. 39.

FIG. 41 shows a top view of the regulation device of FIGS. 39 and 40.

FIG. 42 shows a bottom view of the regulation device of FIGS. 39-41.

FIG. 43 shows a side external view of a regulation device according to another embodiment of the invention that comprises a ball valve.

FIG. 44 shows a side cutaway view of the regulation device of FIG. 43, in which the ball valve is in an initial or open position.

FIG. 45 is a side cutaway view of the regulation device of FIGS. 43-44, in which the ball valve is in a closed position that directs breath flow into a Flow Path 2.

FIG. 46 is a cross-sectional cutaway view of the device of FIGS. 43-45 taken from the cutaway shown by the dashed line and in the direction indicated by the arrows in FIG. 44.

FIG. 47 is a top view of the device of FIGS. 43-45.

FIG. 51A shows a first design with a first flow channel design. FIG. 51B shows a second design with a second flow channel design.

FIG. 54A shows a side view of the cartridge with a partially packed reactive chamber. FIG. 54B shows a top view of the cartridge with a partially packed reactive chamber.

FIG. 56A shows a cross-sectional view of the breath analysis device of FIG. 53 with a hammer pivoted to an initial upward position. FIG. 56B shows a cross-sectional view of the breath analysis device of FIG. 53 with the hammer pivoted to a downward position.

FIG. 59 shows the partial pressure of respiratory gases as they enter and leave the lungs.

FIG. 60D is a cross-sectional cutaway view of the device of FIG. 60C taken from the cutaway shown by the dashed line D-D. FIG. 60E is a cross-sectional cutaway view of the device of FIG. 60C taken from the cutaway shown by the dashed line E-E. FIG. 60G is a cross-sectional cutaway view of the device of FIG. 60F taken from the cutaway shown by the dashed line G-G.

FIG. 63A shows a cross-sectional view of the cartridge. FIG. 63B is a cross-sectional cutaway view of the device of FIG. 63A taken from the cutaway shown by the dashed line B-B. FIG. 63C is a view of the cartridge from the exterior. The breath sample is first exposed to an optional desiccant, then to an ampoule (which is initially sealed) and then to a reactive bead chamber. In this embodiment, the color change is monitored perpendicular to the flow of the breath sample (instead of parallel to it).

FIGS. 64A-F show the assembly of a miniature reactive chamber that can work with the cartridge design shown in FIG. 63.

FIG. 65A shows a mobile device, a mouthpiece loaded with a multiple-use cartridge, and a base unit. FIG. 65B shows an embodiment of a base unit. FIG. 65C shows an embodiment of an integrated mouthpiece FIG. 66A is an embodiment of a single-use cartridge. FIG. 66B is an embodiment of a multiple-use cartridge. FIG. 66C shown an exploded view of an embodiment of a multiple-use cartridge.

FIGS. 67A-D show various embodiments of an integrated mouthpiece mating with a multiple-use cartridge. FIG. 67A shows an example of a multiple-use cartridge mating with an integrated mouthpiece. FIGS. 67B-D show an integrated mouthpiece with an LED that is in different stages of illumination for purposes of providing the user with guidance on generating an appropriate breath profile.

FIG. 68A shows an embodiment of a single-use cartridge mating with a base unit. FIG. 68B shows an embodiment of a multiple-use cartridge mating with a base unit.

DETAILED DESCRIPTION OF SPECIFIC EMBODIMENTS

Figure 1:
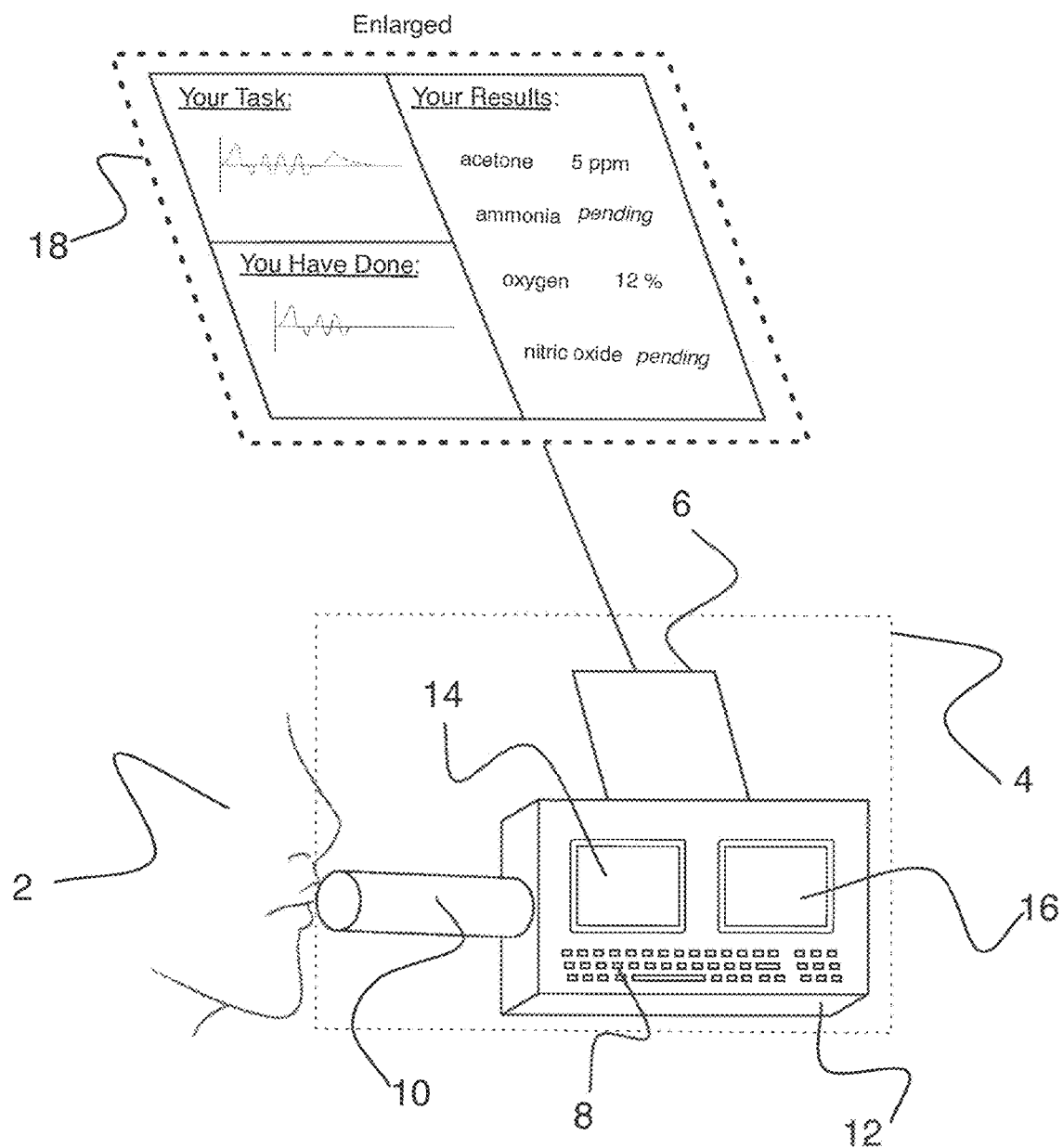
FIG. 1 is a breath analysis device that comprises feedback to the user regarding compliance with a breath profile.

Reference will now be made in detail to the embodiments and methods of the invention as described herein below and as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

In accordance with one aspect of the invention, an apparatus is provided for obtaining information about an endogenous volatile organic analyte from a breath sample of a patient.

The apparatus according to this aspect of the invention comprises a breath input that receives the breath sample, and an analyzing system in fluid communication with the breath input. The analyzing system segregates the breath sample into a breath profile comprising at least one breath, each of the at least one breaths comprising a plurality of segments, each of the segments of a given breath corresponding to an anatomical region of the patient that is non-identical to the anatomical regions for others of the segments. The analyzing system also analyzes at least one but less than all of the breath profile segments of each of the breaths of the breath profile to sense the analyte within the anatomical region or regions corresponding to the at least one breath profile segments to obtain the information about the analyte, and generates a signal representative of the information.

In a related but independent aspect of the invention, a method is provided for sensing an endogenous volatile organic analyte from a breath sample of a patient. The method comprises providing an apparatus that comprises a breath input portion and an analysis portion, and inputting the breath sample into the breath input portion and directing the breath sample to the analysis portion. The breath sample comprises a breath profile comprising at least one breath, wherein each of the at least one breaths comprises a plurality of segments. Each of the segments of a given breath corresponds to an anatomical region of the patient that is non-identical to the anatomical regions for others of the segments. The method further comprises analyzing at least one but less than all of the breath profile segments of each of the breaths of the breath profile to sense the analyte within the anatomical region or regions corresponding to the at least one breath profile segments to obtain information about the analyte, and generating a signal in the apparatus representative of the information.

To illustrate these aspects of the invention, an embodiment of an apparatus (4) for sensing an analyte from a breath sample is shown in FIG. 1, which illustrates the functional components of apparatus (4). In this embodiment, apparatus (4) is a portable device suitable for field use, or in the home of a patient or subject, and thus is not confined to use in a laboratory setting. Apparatus (4) comprises a housing, with a breath input portion in the form of a mouthpiece extending from an end of the housing. The breath input portion according to this and other aspects of the invention as described herein is not necessarily limited to a mouthpiece and may comprise, for example, a connector for indirect breath sample inputs such as a Tedlar® bag attachment, a hose or pipe connector, or the like. As shown in FIG. 1, the breath input portion further comprises an input conduit that extends the mouthpiece internally into the housing.

Additionally, because the apparatus may be configured to measure a single or a plurality of breaths, the breath input may be modifiable. In some instances, it may be a mouthpiece for a single exhalation, but in other cases, it may be a tube designed for re-breathing. An apparatus that is capable of using both should be "smart" and capable of modifying its operating protocols using limited user input.

In some embodiments and methods according to the invention, means are included for measuring or controlling certain gas properties or conditions and flow characteristics as breath is inputted into and passes through the apparatus. Examples of gas properties or conditions may comprise pressure, temperature, humidity, viscosity, and concentration. Examples of flow characteristics comprise mass or volume flow rate, gas velocity (average or as a function of location, velocity profiles, etc.), turbulence, pulsation, and pressure differential. Such parameters facilitate analysis of the phenomenology underlying the breath analysis, enable more sophisticated designs and analyses, and can provide feedback to the user if the subject failed to perform the measurement correctly. They also provide information, signals, triggers and the like for distinguishing between conditions and for switching gas flow, sensor activation and the like, as more fully explained and described herein. Devices or components used to provide these measurements may be essentially any device that can detect or measure the desired parameter, and may include those known in the corresponding metrology fields. Examples would include pressure transducers, flow meters, temperature measurement devices, and the like. In this embodiment, i.e., apparatus (4), breath sample input flow velocity is measured as the subject inhales or exhales into the mouthpiece by a bi-directional pneumotachometer disposed in conduit.

Optionally but preferably, apparatus and methods according to these aspects of the invention comprise at least one fluid conditioner for appropriately conditioning the breath sample as it enters the breath input and is directed to the analyzing portion. The fluid conditioner may condition the sample, for example, by heating it, cooling it, removing or reducing moisture, restricting the flow rate (e.g., variable or fixed rate of attenuation), converting between laminar and turbulent flow, dampening pressure pulsation, removing or filtering interferent substances, and the like, including combinations of these. As implemented in the illustrative embodiment shown in FIG. 1, apparatus (4) comprises a fluid conditioner coupled to the mouthpiece.

Devices and methods according to its various aspects segregate breath samples into a plurality of segments. Preferably, each of these breath profile segments correspond to an anatomical region of the patient that is non-identical to the anatomical regions for others of the segments.

Figure 2:
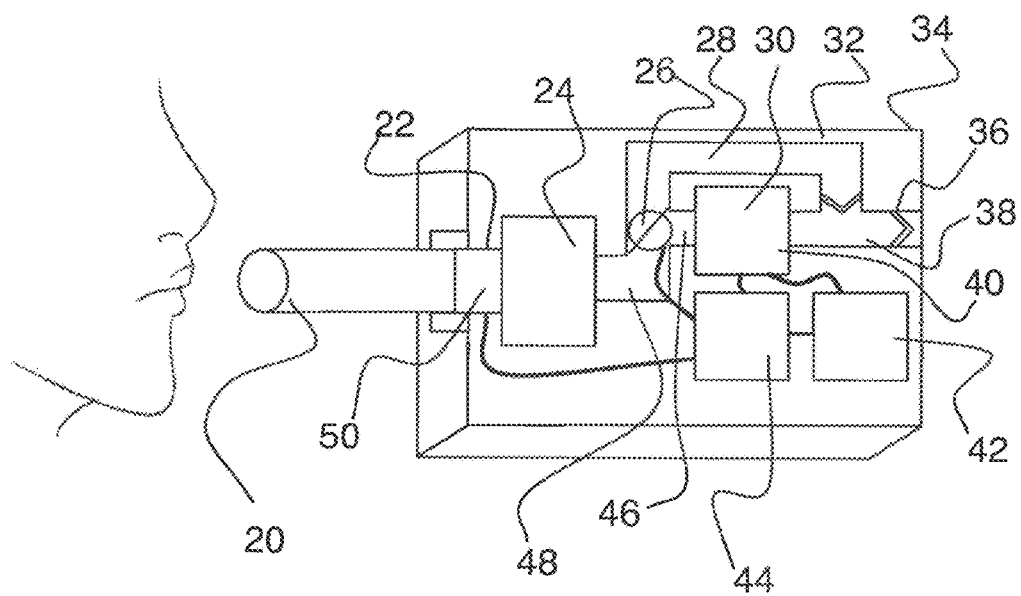
FIG. 2 is an embodiment of a breath analysis device.

In the embodiment shown in FIG. 2, apparatus (4) comprises a relatively simple valving subsystem that selectively switches the breath sample flow into the analyzing portion. More specifically, a conduit extends from the output of fluid conditioner. A valving device is disposed in the flow path of the conduit. The valving device in this embodiment comprises a directional valve that alternatively or selectively directs flow to a first conduit or a second conduit. When the valving device is in a first open position, it directs flow to the first conduit but prevents flow to the second conduit. When in a second open position, valving device directs flow to the second conduit but prevents flow to the first conduit. The valving device also can assume a closed position in which flow is prevented to either the first conduit or the second conduit.

It will be appreciated that considerably more sophisticated and complex segregating subsystems can be used for physically segregating the breath sample, illustrative examples of which are provided herein below. In addition or alternatively, segmentation of the breath sample can be performed by other means, such as the use of stationary analysis on segments of the gas flow as the gas passes a given point or region, or such segmentation can be achieved or aided using software. Software-based segmentation preferably utilizes real-time sensors or sensors configured to take samples at multiple points during the measurement process. For example, a real-time oxygen measurement can be made alongside a trend of accumulated flow. The average oxygen reading within the first 25% of lung volume can be compared against the average oxygen reading in the last 25%.

Apparatus (4) also comprises an analysis portion that in this embodiment comprises a reaction vessel or cavity 30 fluidically coupled to and in fluid communication with the first conduit to receive the breath sample from the mouthpiece and fluid conditioner when valving device is in the first open position. Analysis portion further comprises a sensor disposed at or within reaction vessel so that fluid entering the analysis portion contacts a second sensor and interacts with its reactive component or components.

Various sensor designs may be used in conjunction with this implementation. Examples include nanoparticle, enzyme-based, thermoelectric, quartz crystal microbalance, optical, colorimetric, metal oxide, semiconductor, magnetoelastic, and gravimetric sensors. Specific yet merely illustrative examples of such sensors include those disclosed in U.S. Pat. No. 6,609,068 and U.S. patent application Ser.

Nos. 11/656,338, 13/052,963, and 61/593,862, each of which is hereby incorporated herein by express reference as if fully set forth herein.

These sensors may operate continuously, sense the analyte at multiple points during a single analysis session, or may simply sense the analyte at one given point in time. For continuous or multiple point analysis, the system preferably would be configured with a "replenishable" or regenerating sensor, or it may require use of multiple disposable components.

An exit or exhaust conduit is disposed at an end of a reaction cavity to direct fluids out of the reaction cavity and externally of the housing. A one-way valve is disposed in the exhaust conduit so that flow is permitted out of the reaction cavity but not back into it. A bypass conduit is fluidically coupled to the exhaust conduit internally with respect to the valve so that, when the valving device is in its second open position, fluids directed through the conduit are passed to the exhaust conduit and exhausted from the housing.

Apparatus (4) further comprises a processor disposed within the housing. The processor in this embodiment comprises a microprocessor or microcontroller appropriately configured and programmed to carry out the functions as described herein, in addition to standard housekeeping, testing and other functions known to those in the art. The processor is operatively coupled to the sensor to receive signals from the sensor as inputs. The processor is operatively coupled to a pneumotachometer to receive the signal output from the pneumotachometer as an input.

In other embodiments, the processor also is operatively coupled to segmentation means, e.g., a valving device, so that the processor can both control the position or state of the device and monitor its position. Other examples of segmentation means are a switch that the user toggles that sets the amount or position of the breath that is analyzed.

A power supply is disposed in the housing and is operatively coupled to the processor, the sensor and the valving device to provide necessary power to those devices.

Apparatus (4) may output the information gleaned from the breath analysis using any one or combination of output forms or formats. In this specific embodiment, apparatus (4) comprises a display disposed on the exterior of the housing and operatively coupled to the processor. The processor is configured and programmed to output the sensed information to the user. This is not, however, limiting. The output also may comprise a wired or, more preferably, a wireless data link with another device, such as a centralized database from which a care giver, such as a physician, family member, watch service or the like can monitor the output.

The display may and preferably does include feedback for the patient on the type of breath profile sought for analysis. The feedback may include a trace that describes the flow rate of exhalation and provide user with guidance on how to maintain the optimal flow characteristics.

An implementation of the method according to this aspect of the invention will now be described with respect to the embodiment identified herein as apparatus (4). It should be noted and appreciated, however, that the method according to this aspect is not limited to this specific apparatus, and may be practiced or implemented with other hardware configurations. The actual hardware configurations of apparatus (4) also are illustrative, and may be modified in their details to facilitate such factors or objectives as space use efficiency, thermal controls, manufacturability, cost efficiency, and the like. The electrical components, for example, may be reconfigured to achieve space or power savings, optical components may be substituted, and the like.

In accordance with aspects of the invention, a breath sample is inputted into the breath input portion of the apparatus and directed to the analysis portion. "Breath" as used herein is used according to its broad but common meaning in the field and includes any gas generated by the respiratory system of the body. For example, breath may be gas in the nasal passages, gas in the bronchial space, gas in the alveolar space, etc. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like.

Breath may include a single exhalation or it may include a plurality of exhalations. Multiple exhalations can take many forms, including re-breathing and non-rebreathing, which are described herein.

In the analysis portion, the breath sample or a portion thereof is analyzed to sense one or more analytes. As mentioned herein above, the term "analyte" is used broadly herein to mean a chemical component or constituent that is sought to be sensed or measured. An analyte may be or comprise an element, compound or other molecule, an ion or molecular fragment, or other substance that may be contained within a fluid. In some instances, embodiments and methods, there may be more than one analyte present, and an objective is to sense multiple analytes.

In some embodiments and method implementations, the analyte or analytes of interest are endogenous analytes, although this is not necessarily limiting. The analysis of endogenous analytes in breath presents different challenges and requires different techniques and devices than the measurement of exogenous analytes. As explained herein above, "endogenous" analytes are those that are produced by the body, whereas "exogenous" analytes are those that are present in breath as a strict result of the outside influence or as a result of user consumption. However, many analytes are produced endogenously and can also be exogenously introduced. For example, ammonia is produced endogenously through the metabolism of amino acids, but can also be introduced exogenously from the environment such as ammonia-containing household cleaning supplies. Endogenous analytes are produced by natural or unnatural means within the human body, its tissues or organs, typically excluding the lumen of the gastrointestinal tract.

Volatile organic compounds or analytes comprise a particularly interesting and useful class of analytes that have significant utility for medical diagnostic purposes, and which are well suited for analysis using various aspects of the invention. The term "volatile organic compound" or "volatile analyte" is used according to its general meaning within the field to include such analytes as small molecules present in human breath. While the term "organic" implies carbon containing, we do not intend for the term to be limited in this manner. In other words, we view analytes such as nitric oxide to fall within the definition of a volatile organic compound or a volatile analyte.

Additionally, endogenous analytes for which various aspects of the invention may be particular well suited and useful include, for example, ammonia and nitric oxide. Ammonia is produced and present in human breath as a result of biological processes such as protein metabolism. Nitric oxide is generally present in the upper airway as a result of tissue inflammation and can serve as an indicator of asthmatic conditions and the like.

"Sense" and "sensing" as the terms are used in this document are used broadly to mean detecting the presence of one or more analytes, or to measure the amount or concentration of the one or more analytes. "Sense" and "analyze" are used interchangeably herein.

characteristics vary significantly from user to user. A summary of a select few characteristics, relevant to the instant disclosure, is provided in Table 2, below:

TABLE 1

Characteristics of Breathing

| Characteristic | Abbreviation | Definition |
|---|---|---|
| Vital Capacity | VC | Volume of air (L) pushing out of the lungs during normal breathing. This is typically 80% of an individual's total lung capacity. |
| Residual Volume | RV | Volume of air (L) remaining within the lungs after a full exhalation. |
| Forced Vital Capacity | FVC | Volume of air (L) that can be exhaled with maximum force and speed, following a normal expiration. This is typically expelled into a spirometer. |
| Forced Expiratory Volume | FEV | Volume of air (L) delivered through a spirometer during an FVC exhalation. FEVs are recorded at times t = 0.5, 1.0, 2.0, and 3.0 seconds. FEV-1 (FEV at t = 1 second) normally constitutes 70% of the FVC. |
| Forced Expiratory Flow 25-75% | FEF 25-75 | Average flow rate of the center part of the FEV recording. Calculated using time (s) at which an individual reaches 25% and 75% of their vital capacity. |
| Maximal Voluntary Ventilation | MVV | Average air flow (L/s) recorded as an individual breaths as deeply and as rapidly as they can for 15 seconds. This is an indicator of respiratory muscle strength and endurance. |

"Characterize" as used herein is used according to its broad but common meaning within the field and includes obtaining information about the analyte. For example, characterizing the analyte may involve identifying the presence of the analyte, completely or partially determining its chemical makeup (e.g., sequencing a nucleic acid), isolating, determining certain characteristics of the analyte, ascertaining or estimating its concentration, reactivity, and the like. Characteristics that may be important include, but are not limited to, size, charge, the presence of certain functional groups, etc. Size, for instance and in certain implementations, may be determined by gel electrophoresis. Other manners of identifying an analyte may be used as well.

These aspects of the invention further comprise using the apparatus to segregate the breath sample into a breath profile comprising the at least one breaths, wherein each of the at least one breaths comprises a plurality of segments, and each of the segments of a given breath correspond to an anatomical region of the patient that is non-identical to the anatomical regions for others of the segments.

A "breath profile" is a specific depiction of breath with certain characteristics, such as the duration of the breath, the volume of the breath used, the volume of breath discarded, the number of breaths, the number of exhalations, the number of inhalations, the length of time between inhalations and exhalations, etc. A breath profile may be a single exhalation, but it may also be multiple exhalations separated by a certain period of time. A breath profile may be a natural exhalation, but it may also be a forced expiration or an expiration that is controlled (by the patient directly or by a patient assist device) in terms of flow rate. Accordingly, there are a number of different breath profiles that may exist either naturally or because a patient is instructed to breathe according to the profile.

A few observations regarding respiratory physiology will help to underscore the significance of different breath profiles and the challenges associated with characterizing an analyte specific to (e.g., present in higher concentrations) in one portion or segment of a breath profile. First, breathing Normal values for the above-listed parameters generally vary based on age, gender, and height. Examples of these values can be obtained from different models, such as the European Respiratory Society 1993 (ERS'93) Model, the Pogar '79 Model, the Third National Health and Nutrition Examination Survey (NHANES III) Model, and the Global Lung Quanjer (GLI-2012) Model. Normal values are 80-100% of the predicted values from models like NHANES III Model as described above (in other words, there is some 20% variance within the population).

Variations among users of a breath analysis device may include patient size, lung capacity, lung strength, etc. These can cause variations in results even for users with the same concentration of analyte in the lungs or upper airways. The differing properties of the exhalations provided by various users affect the fluid mechanical properties of the breath sample as it travels through the device. Given the sensitive nature of the sensors typically involved, variations in pressure, flow rate and the like can affect results. Larger users or those with greater lung strength can exhale into a breath analysis device with sufficient flow volume or velocity that the sensor is overwhelmed or otherwise is unable to make an accurate measurement because the device may not capture the appropriate portion of the breath where detecting the analyte of interest is optimized.

Further or alternative variation from normal values can occur due to many factors, including, but not limited to, obstructive or restrictive breathing. Obstructive breathing may be caused by cystic fibrosis, asthma, bronchiectasis, bronchitis, emphysema or more generally chronic obstructive pulmonary disease (COPD). Restrictive breathing may be caused by heart disease, pregnancy, lung fibrosis, pneumonia, pneumothorax, and pleural effusion. By contrast to the approximately 20% variation in normal values, abnormal values can be substantially less with "mild" dysfunction being 60-79% of normal, "moderate" being 40-59% of normal, and "severe" being below 40% of normal.

Additionally, different anatomical regions of the lungs or airway spaces have been associated with the production or presence of different gaseous compounds of analytical significance. Of importance is the distinction between the upper airways (nose, pharynx, trachea, 'dead space' airways) and the alveolar airspace. In general, metabolic gas exchange does not occur in the dead space airways and thus volatile substances originating in systemic blood are not sourced from the dead space airways. Rather, gaseous substances reflecting the local physiology of the dead space airways themselves (e.g., nitric oxide due to local inflammation or increased carbon dioxide due to *H. pylori* infection of the gut) will be present in higher concentrations in the dead space airways in comparison to the alveolar airspace. For these reasons, it is useful to demarcate the anatomical regions of the airways in order to link the physiological sources of the various analytes of interest to optimum breath profiles for sampling. See FIGS. 4 and 5. It is interesting to note that the volume of air inspired routinely by a patient in a state of normal, quiet respiration ("tidal volume") is only slightly more than the volume of the upper airways. Although direct gas exchange with the alveoli is not occurring with each normal breath, diffusion of the gases over the remaining distance takes place rapidly, within less than 1 second (Guyton and Hall, 1996, pg. 484).

Tidal volume is the portion of breath displaced in normal inhalations and exhalations when no extra effort is applied (e.g., sitting still, at rest, breathing normally without extra depth). Under normal circumstances, the tidal volume comprises a portion of dead-space, mixed air (including a mixture of dead-space and alveolar air), and alveolar air. The dead-space is air from at least one of the trachea, nasal cavity, and mouth. The mixed air includes some breath sourced from the deeper regions of the lung, including, for example, the alveoli, but it also contains some breath sourced from the dead-space. The final segment, alveolar air, is sourced substantially entirely from the deeper segments of the lungs, including the alveoli—this, third and final segment is generally appropriate for analyzing as an alveolar breath sample. Tidal volume varies considerably based on age, sex, and size (e.g., height). As he or she grows, the tidal volume changes considerably. Table 3, generated using the ERS Model, shows the tidal volume as a function of height and age for a representative male and female individual. This data may be better understood in view of FIG. 58 and its accompanying explanation, presented elsewhere herein.

Figure 58:
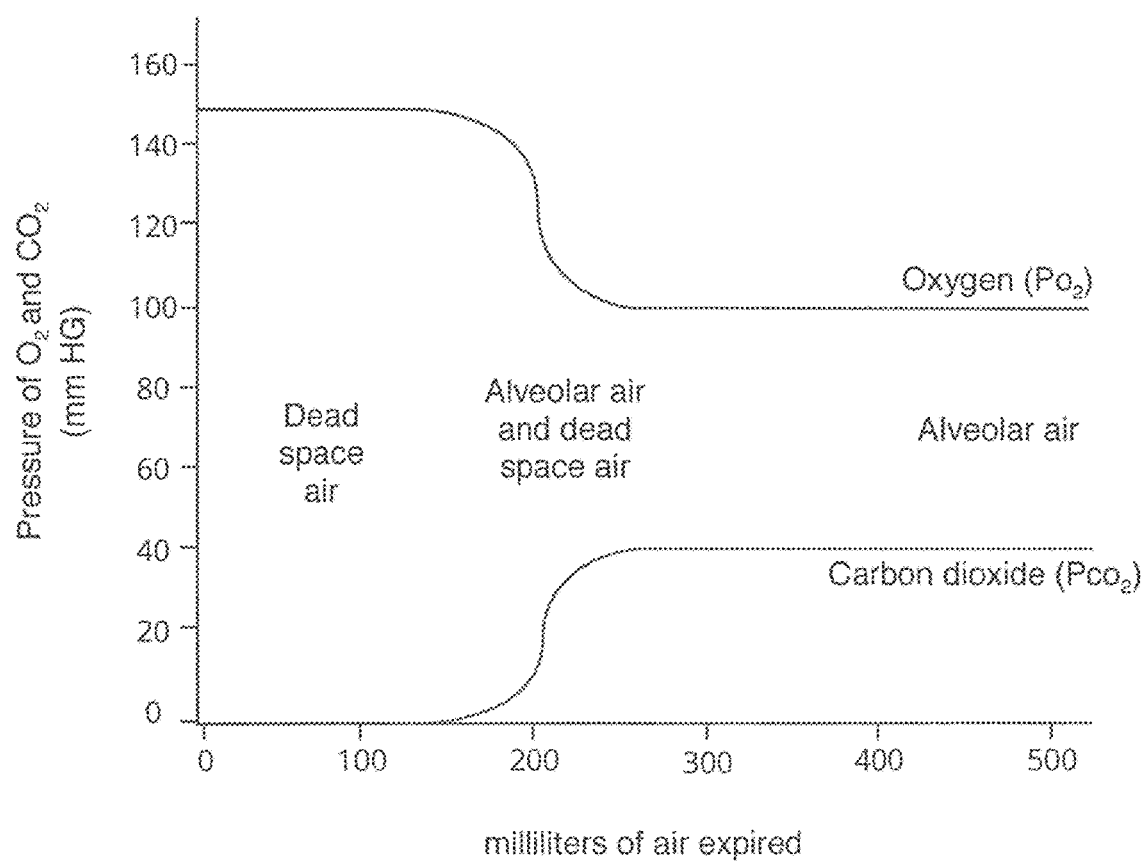
FIG. 58 shows the oxygen and carbon dioxide pressures as a function of volume of expired air.
Figure 60:
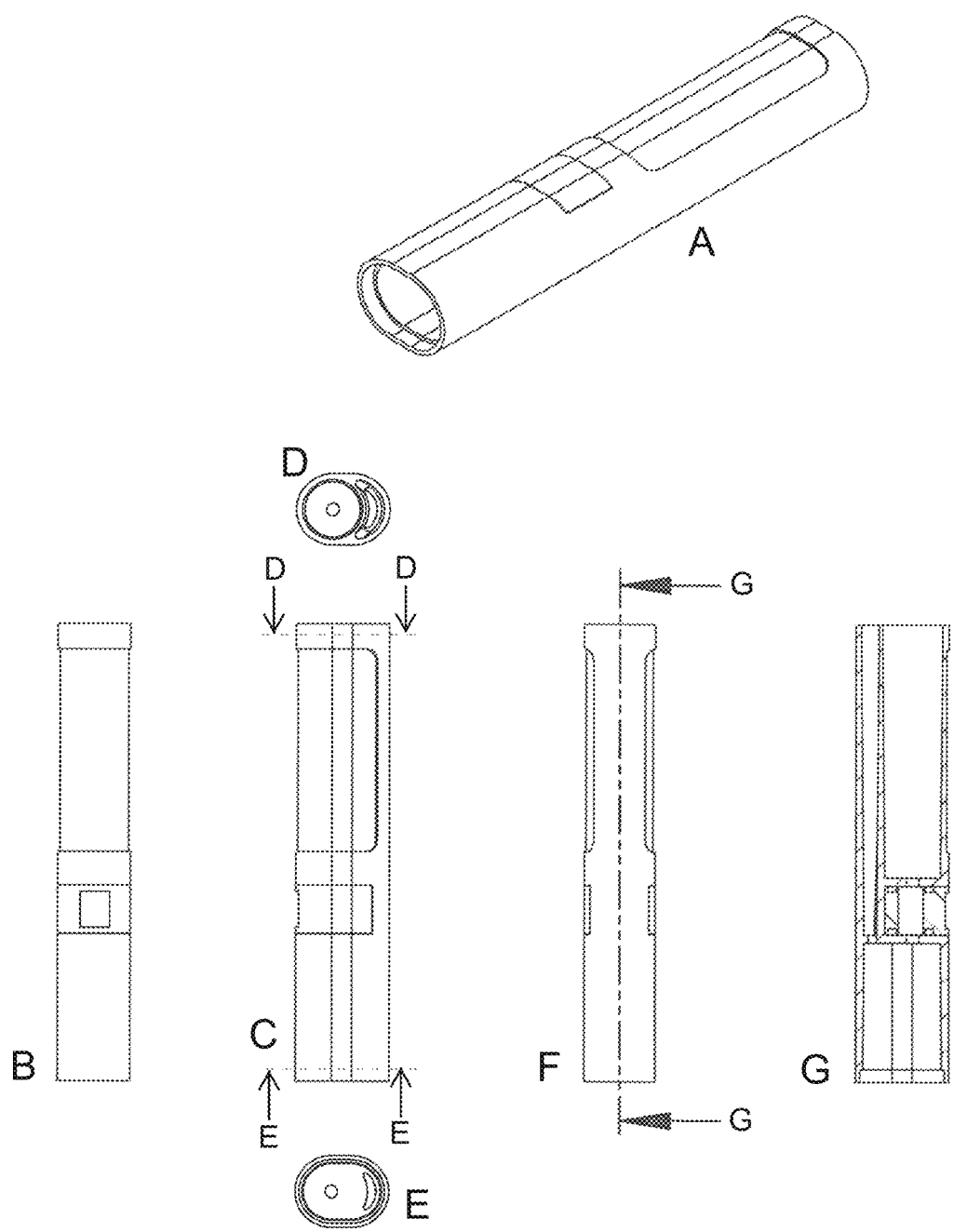
FIGS. 60A-G show various views of another cartridge embodiment that utilizes a clear viewing window that is detachably coupled to the remainder of the body of the cartridge. In this embodiment, a seal is made with two o-rings. The two o-rings press to channels on each side of the clear insert.
Figure 61:
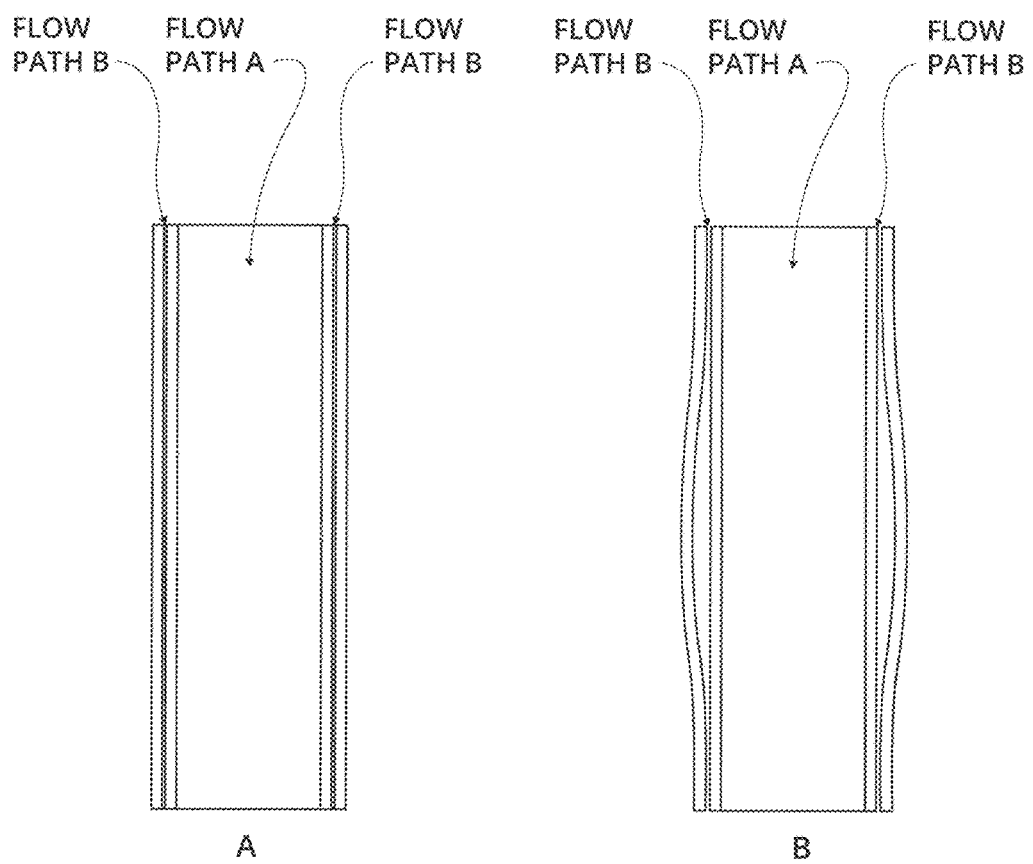
FIGS. 61A-B show another cartridge embodiment that utilizes a concentric design where Flow Path B surrounds Flow Path A. Optionally, but preferably, the cartridge housing is flexible such that when a breath sample is delivered, the housing shape is altered to accommodate the volume.
Figure 62:
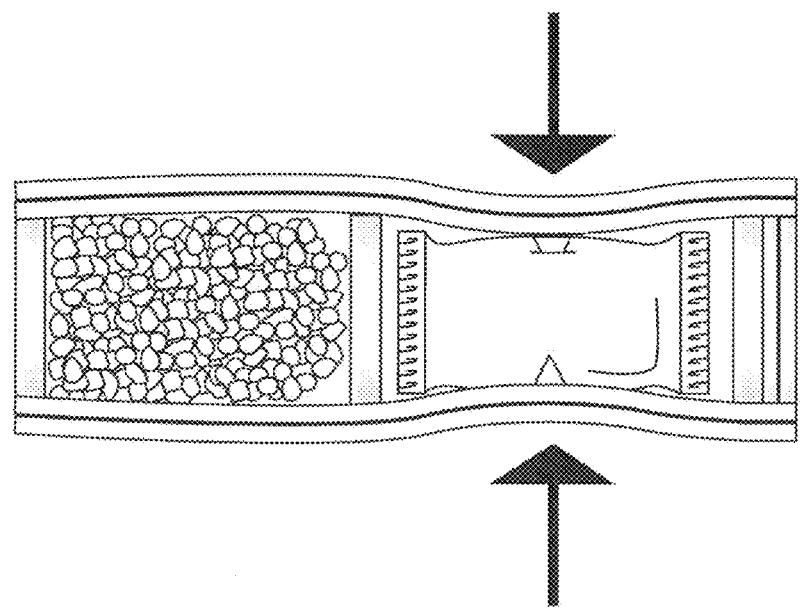
FIG. 62 shows a cartridge embodiment with flexible housing, such that a "bending" motion of the cartridge results in the piercing of an ampoule.

As can be seen, for example, from Table 3 and FIG. 58, the average adult male has a tidal volume measuring about 500 ml and the average adult female has a tidal volume measuring about 400 ml. The following, simplistic and estimated relationships have been used successfully by some groups: dead-space=0-150 ml; mixed air=151-300 ml; and alveolar air=301+ml. However, as males and females have statistically significantly different tidal volumes, percentages may be useful in some applications. As a broad generalization, for example, the dead-space segment of an adult breath can be considered to be about the first 20-30% of their tidal volume and the alveolar segment of an adult breath can be considered to be about the last 30-40% of their tidal volume, but of course this can vary considerably given the various anatomical and other differences described herein.

TABLE 3

Tidal Volume for a Representative Person Over Time

| Age | Height | Tidal Volume (ml) of Female | Tidal Volume (ml) of Male |
|---|---|---|---|
| 5 | 3'7" = 43 inches~110 cm | 157 | 147 |
| 11 | 4'5" = 53 inches~135 cm | 278 | 287 |
| 15 | 5'5" = 65 inches~165 cm | 424 | 454 |
| 25 | 5'7" = 67 inches~170 cm | 449 | 571 |
| 31 | 5'7" = 67 inches~170 cm | 439 | 555 |
| 35 | 5'7" = 67 inches~170 cm | 431 | 545 |
| 41 | 5'7" = 67 inches~170 cm | 421 | 530 |
| 51 | 5'7" = 67 inches~170 cm | 403 | 504 |
| 61 | 5'7" = 67 inches~170 cm | 385 | 478 |
| 71 | 5'7" = 67 inches~170 cm | 367 | 452 |
| 81 | 5'7" = 67 inches~170 cm | 379 | 426 |

Using the same ERS '93 model, for a given age (31), across different heights, the vital capacity differs.

TABLE 4

Vital Capacity of Persons Having Various Heights

| Height | Female Adult | Male Adult |
|---|---|---|
| 5'1" = 61 inches~155 cm | 3.12 L | 3.73 L |
| 5'3" = 63 inches~160 cm | 3.34 L | 4.02 L |
| 5'7" = 67 inches~170 cm | 3.78 L | 4.59 L |
| 5'9" = 69 inches~175 cm | 4.00 L | 4.88 L |
| 5'11" = 71 inches~180 cm | 4.23 L | 5.17 L |
| 6'3" = 75 inches~190 cm | 4.67 L | 5.75 L |

These models are heavily influenced assuming "normal" anatomical respiratory characteristics. However, as described above, these values can change from individual to individual based on smoking status, pulmonary disease, and illness (e.g., a flu that makes it hard to exhale), among other factors.

Volume that is Vented by the Device

Variability between patients, as explained above, highlights the importance of adjusting the "vented" or "flushed" gas sample depending on the individual user. On one hand, it would seem best to just vent the 750 mL sample to ensure that an alveolar sample is captured across all people. However, this would exclude pediatrics. Moreover, the differences between adult men in their late 20s and adult women in their 70s is significant: tidal volume of 571 mL v. 367 mL and FVC of 4.70 L v. 2.85 L (It is important to note that forced vital capacity assumes little to no flow resistance, which the user would experience if blowing through chemical reagents, a sensor or a valving system).

As such, in one embodiment disclosed herein, a device vents a range of between about 100 mL to 750 mL of exhaled breath in increments of about 50 mL. In other embodiments, the device vents a range of between 100 mL to 750 mL of exhaled breath in increments of 100 mL. In yet other embodiments, which may find highest applicability to adult patients, a device vents a range of between 300 mL to 750 mL of exhaled breath in increments of 50 mL or increments of 100 mL. In a pediatric only embodiment, a device vents a range of between 50 mL to 100 mL in increments of either 10 or 25 mL. Young pediatric or neonatal use for applications such as DKA management or indication of renal failures would be smaller.

The Trigger for Change by the Device

The trigger to change or "vent" different fractions may be based on one or more variables other than volume, including, for example flow rate and time or just time as a proxy for volume. As an example, assuming that about 30% of tidal volume is dead space, an adult male may have approximately 150 mL of dead space volume that needs to be exhaled before expelling a deep alveolar lung sample (containing about 300 mL). This dead space can be evacuated in about 3 seconds under normal exhalation rates. The device can manipulate the time that a vent is opened for to ensure that only about 3 seconds worth of air (i.e., dead space) is evacuated before carrying the deep lung sample through to a disposable for analysis. Alternatively, an elderly female may have approximately 200 mL of dead space to expel before receiving a deep lung sample, as dead space capacity increases with age. This user may require that the dead space be evacuated in about 6 seconds before receiving a useable sample. The device can also manipulate the opening and closing of the vent to allow a longer time for dead space evacuation. Additional examples of systems and methods for venting, exhausting, segmenting, or fractionating a breath are provided elsewhere herein.

Figure 4:
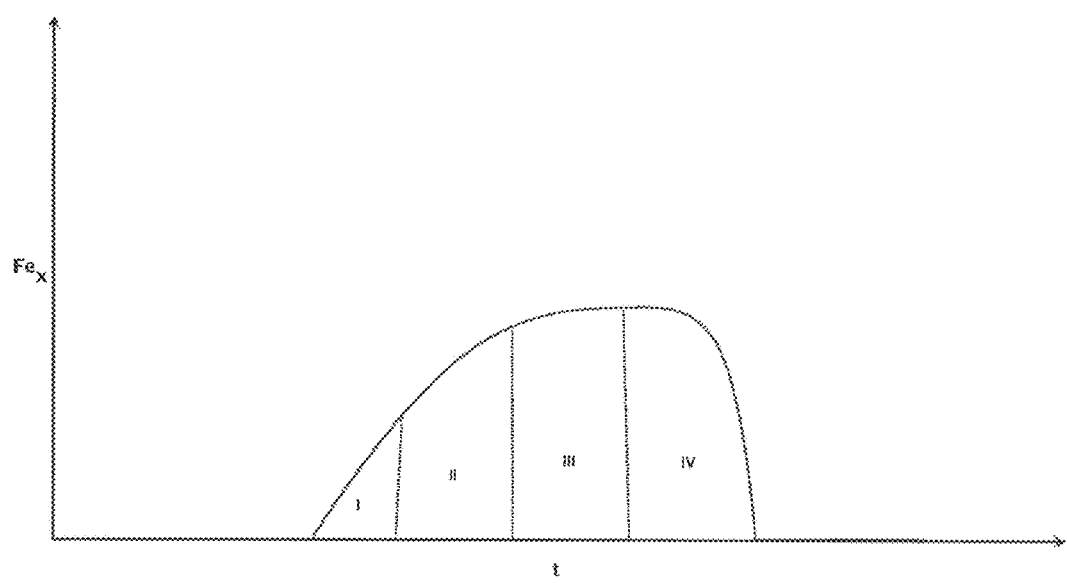
FIG. 4 shows a depiction of an exhalation as a function of time.
Figure 5:
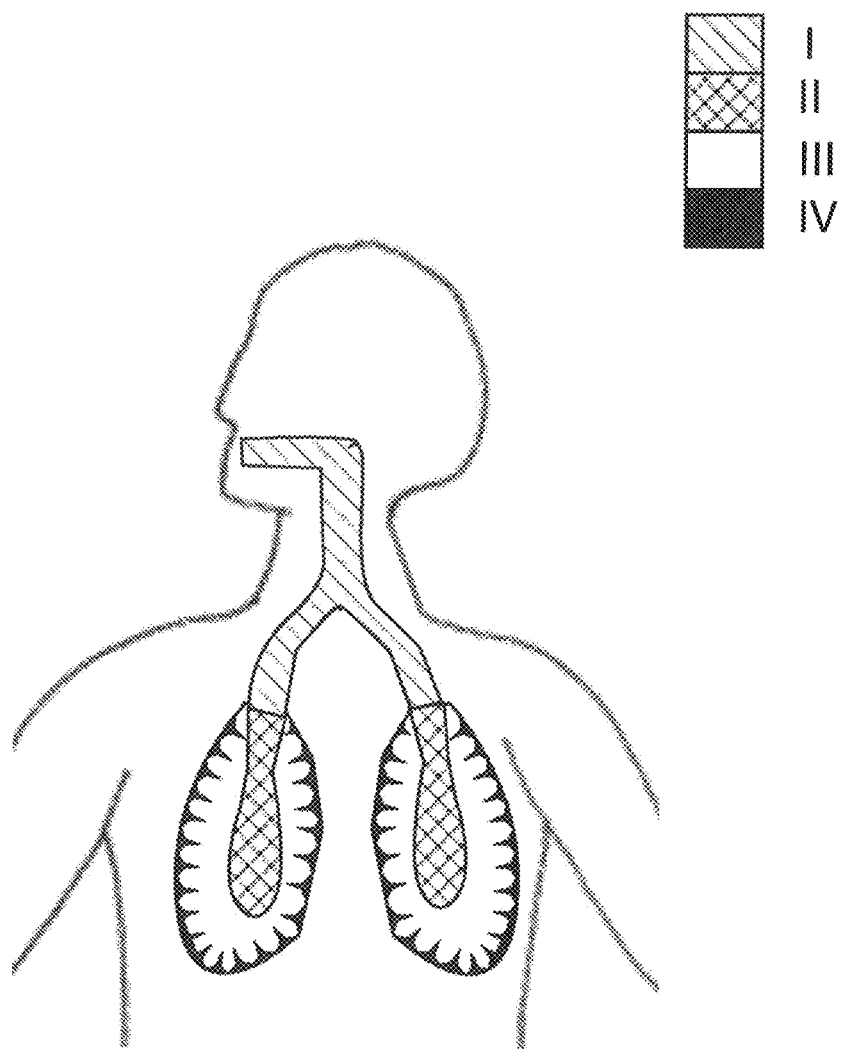
FIG. 5 shows the lung space of a representative patient.

In some cases, it may be useful to demarcate the anatomical regions of the airways in order to link the physiological sources of the various analytes of interest to optimum breath profiles for sampling. In FIG. 4, some portions of breath exhalation are labelled. In FIG. 4, some portions of breath exhalation are labelled. FIG. 4 depicts a plot of an increasing concentration of substance X as it is exhaled from the lungs over time. As time increases, the region sourcing substance X will also change, with the deepest regions sourcing the substance last. In this example, very little of substance X, if any, is associated with region I, corresponding to the upper airways. There is no sharp distinction between these regions as far as gas concentrations are concerned, as significant mixing takes place between regions due to the fast diffusion times of gases. FIG. 4 shows an illustration of possible lung regions. In general, as the lung gases are emptied, the regions will be emptied in numerical order. By the same token, these regions will also fill in numerical order, and thus the significance extends to both inhalations as well as exhalations. A given breath profile will consist of a specification for both.

Figure 6:
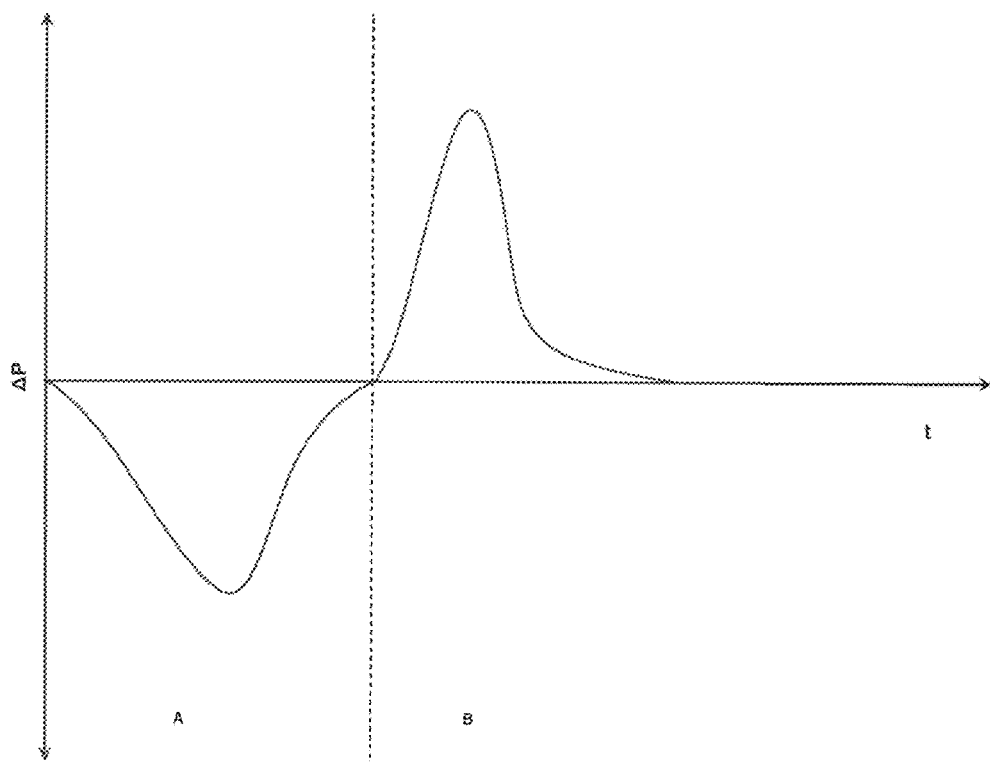
FIG. 6 is an example of a breath profile.

In a simple case, a specific breath profile might consist of two stages. See FIG. 6. In this case, the profile is divided into stages A and B. In the figure, the x-axis denotes time and the y-axis shows the pressure differential as could be measured with a pneumotachometer. In this example (and in the examples which follow), negative pressure differentials correspond to inhalations, whereas positive deflections correspond to exhalations. In this example of a specific breath profile, a deep inhalation is immediately followed with a strong exhalation. The specification could include further requirements such as "inspire as much as is possible and as quickly as is possible" and "exhale as much as is possible, and as fast as is possible."

Figure 7:
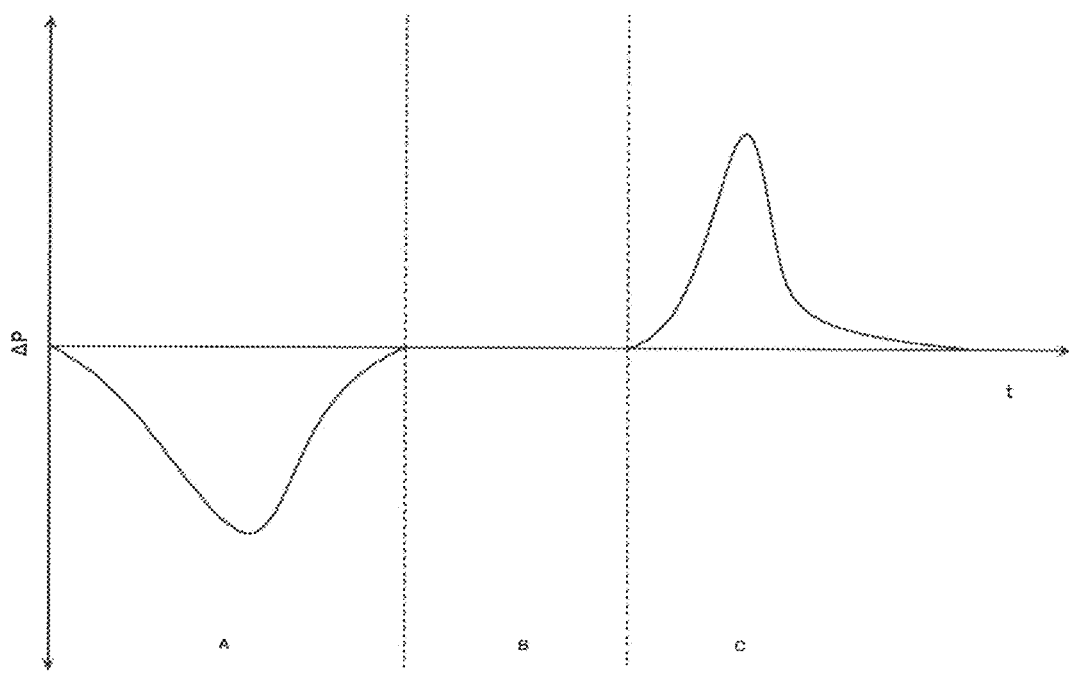
FIG. 7 is another example of a breath profile.

A slightly more complex breath profile might consist of three stages A, B, and C. See FIG. 7. In this example, a deep inhalation is followed by a rest period of a given duration during which no breathing takes place. A final region shows a strong exhalation.

Figure 8:
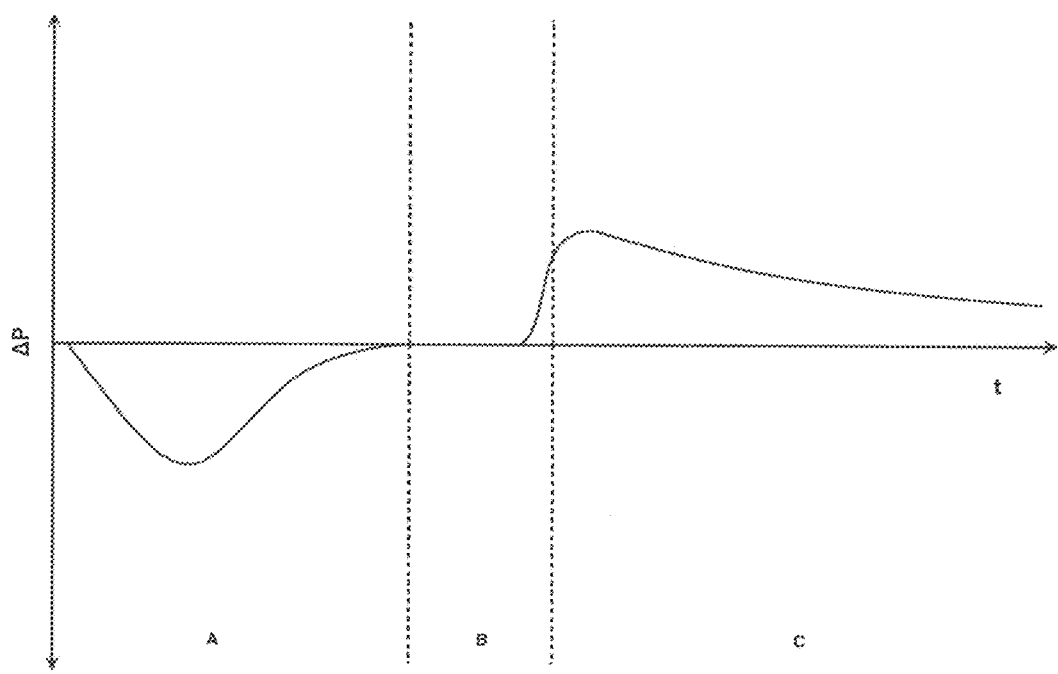
FIG. 8 is another example of a breath profile.

FIG. 8 shows another possibility. In this example, the breath profile is again composed of three stages A, B, and C. Stage C, however, differs from the previous example in that the exhalation is steady with sub-maximal exertion. A steady, sub-maximal exhalation may be created by a conscientious blower or by the design of the sampling equipment (intentional or otherwise).

The ability to selectively sample the gases from the various regions of the airways provides analytical benefit. If all the exhaled gases are expired into a single collection bag, for instance, then the gases obtained from lung regions that are not sourcing the analyte of interest will serve only to dilute the final concentration of the analyte of interest in the bag. One approach is to sample only from the region of interest in the case of a collection bag.

Figure 9:
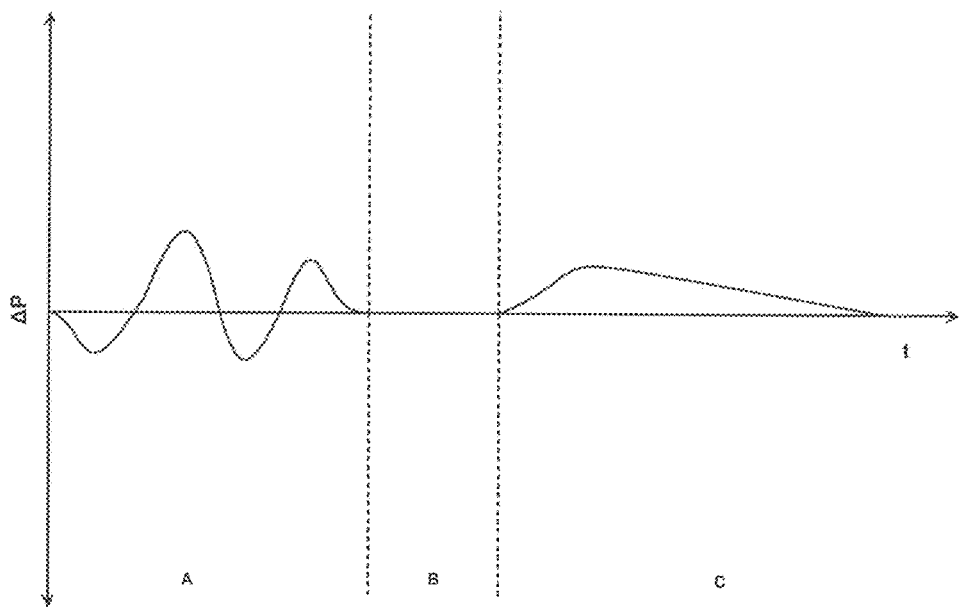
FIG. 9 is another example of a breath profile.

Sampling from a region of interest can be done with specific breath profiles. This fractionated sampling can be accomplished by conscientious users or it may be accomplished through instrument design. Conscientious users might breathe the first portion of exhaled air into a bag (or discard it entirely), and then collect the second portion. A simple way of doing this would be to breathe for some period of time, and then, after a normal exhalation, wait for 10 seconds and then expire the remaining air in the lungs. An example of such a profile is shown in FIG. 9.

Figure 10:
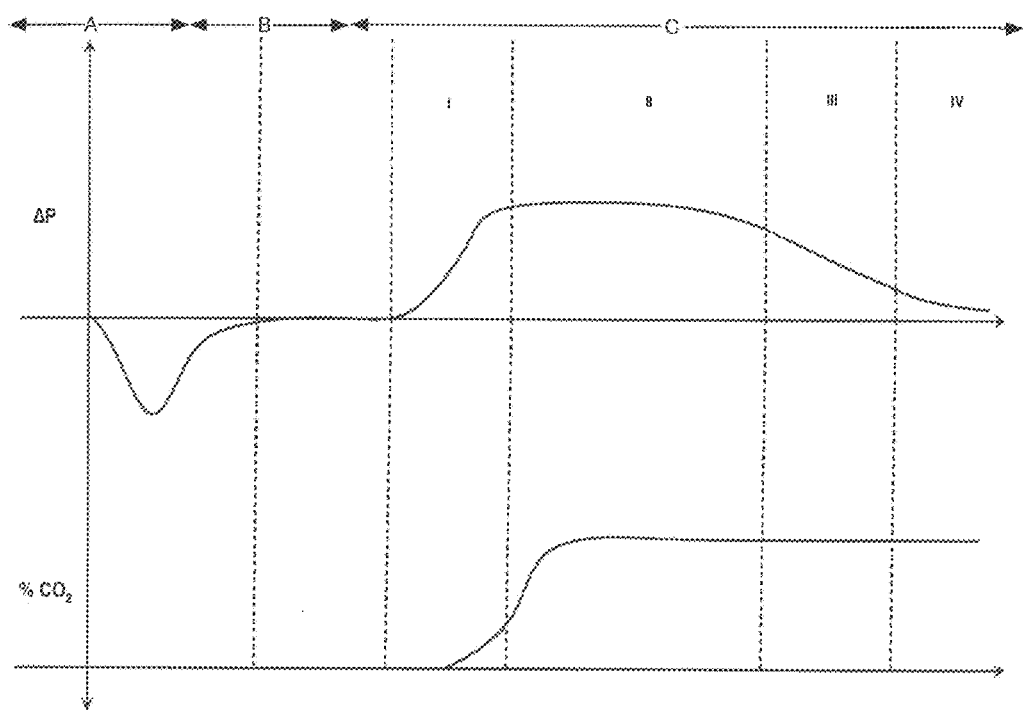
FIG. 10 is another example of a breath profile, with superimposed segmentation.

FIG. 10 shows an illustrative relationship between expired gas concentration (in this case carbon dioxide), as it relates to a given breathing profile, and lung source region. In this figure, the breath profile is characterized by three regions A, B, and C. The x-axis is time, the y-axes are the pressure differential as could be measured with a pneumotachometer and the percentage carbon dioxide in the exhaled air as measured with a real-time capnograph. In this figure, a sampling scheme is presented whereby a subject first takes a deep breath, followed by a period of rest and then a steady exhalation. At a point where the carbon dioxide concentration, as measured using the real-time equipment, crosses a certain threshold, the exhaled air switches its lung sourcing from region I to region II. With continued steady exhalation, the lung sourcing regions pass through regions III and IV.

Figure 11:
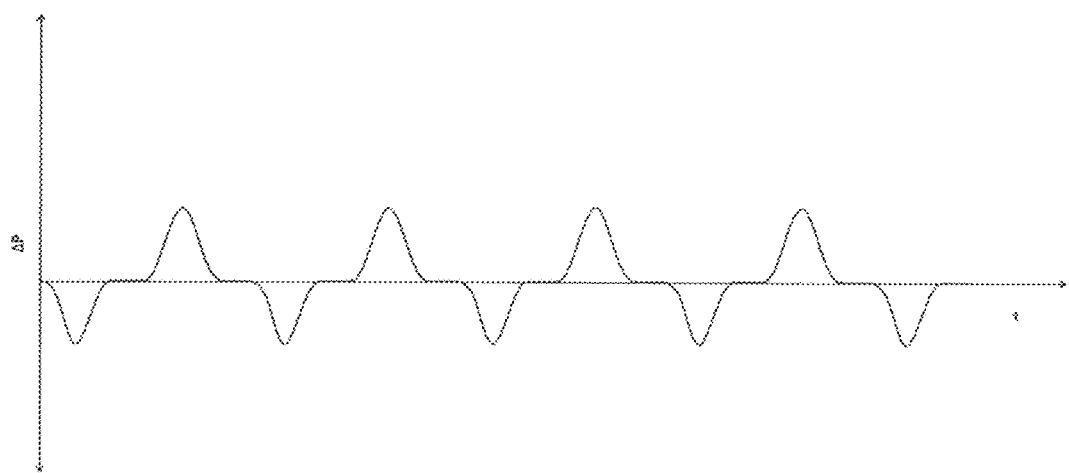
FIG. 11 is another example of a breath profile.

Breath profiles need not be limited to single exhalations. In fact, multiple breaths or continual breathing are very useful sampling techniques. Multiple breaths allow the system and the user's physiology to come to a steady-state. Measurements are not done on dynamic systems and thus repeatability is enhanced. Also, by virtue of a steady-state being achieved, much more information is revealed about the underlying physiology. A continuous breath profile will resemble FIG. 11. In this example, repeated steady breaths are administered. The x-axis is time, the y-axis is the pressure differential as could be measured with a pneumotachometer, with the negative deflections indicating inhalation periods and the positive deflections indicating regions of exhalation.

Breath profiles may intentionally exclude certain behaviors or aspects of a breath. For instance, a breath profile may be solely oral (e.g., the patient is wearing a nose clip to prevent nasal "breathing"). In this example, a nose clip may be used to prevent gases from leaving the body or from entering the body, such as in the event that the patient were in a nail salon and acetone was inhaled (and therefore present in the body and available for exhalation) due to a high ambient concentration of nail polish remover.

These aspects of the invention also comprise using the apparatus to select at least one but less than all of the breath profile segments of each of the breaths of the breath profile to thereby select at least one but less than all of the corresponding anatomical regions.

The process of selecting specific breath profile segments preferably is focused on obtaining the optimal breath sample, e.g., with the highest concentration of the analyte or analytes under study and with the lowest interference or background noise. This can increase the sensitivity and selectivity of the device for the desired analytes. Selection of the specific breath profile segment or segments also can be used to exclude such effects and initial breath fluid flow transients or interferences, e.g., at the beginning or end of the breath sample for subjects breathing directly into the device.

For applications in which the analyte or analytes of interest are small molecules in blood that transmute from the bloodstream into the alveolar space and which have relatively low diffusion rates, for example, one may wish to isolate the breath profile segments to those corresponding to the deep alveolar spaces. Even though the analytes may be present in segments corresponding to the upper alveolar spaces and upper airways, the relatively lower concentrations of the analytes in these segments may adversely dilute the analytes and reduce the ability of the sensor to adequately or optimally detect and measure them.

Alternatively, if the analyte of interest resides primarily in the upper airways, for example, such as nitric oxide buildup resulting from upper airway inflammation, one may select a segment or segments correlated to and isolated to the upper airways.

In sensor designs that are sensitive to fluid flow perturbations, high or low flow rates, or the like, one may wish to select breath profile segments that isolate the sample only to those that have the desired pressure or flow characteristics. One may, for example, exclude initial and terminal breath profile segments where fluid flow rate is changing and focus on a segment or segments that have essentially steady or linear flow rates.

These aspects of the invention further comprise analyzing the selected at least one breath profile segments for the at least one endogenous analyte to obtain information about the analyte, and generating a signal in the apparatus representative of the information.

Segmenting or fractionating a breath may be accomplished in many different ways, including at least mechanically and electronically (e.g., sensor-based). Mechanical fractionation or segmentation of a breath takes advantage of the pressure (whether positive or negative) generated by the patient during exhalation or inhalation. As described below, by fine tuning mechanical parameters (including, for example, component weight and gas flow path diameters), the pressure generated by one or more breaths can drive a mechanical fractionator. By contrast, sensor-based fractionation or segmentation of a breath relies on using a sensor to detect one or more characteristic of the breath (e.g., time, pressure, flow rate, carbon dioxide concentration, oxygen concentration, ammonia concentration, etc.) and actively causing a response by the fractionator (such as movement of a valve or solenoid). Each type of segmentation may have certain advantages over the other. For example, mechanical segmentation systems can be very durable whereas electronic or sensor-based segmentation systems can be more prone to component failure. Electronic or sensor-based segmentation systems can be very sensitive and allow fractionation into two or more segments (e.g., two segments, three segments four segments, or even more segments) whereas mechanical segmentation systems can be difficult to tune for fragmentation into more than two segments. Finally, electronic or sensor-based segmentation systems can easily accept and segment multiple breaths (e.g., can collect various segments of more than one breath) whereas mechanical segmentation systems may require a mechanical or hard "reset" prior a accepting a second breath. Systems and methods for both types of segmentation are discussed below.

Mechanical Segmentation Systems

Figure 29:
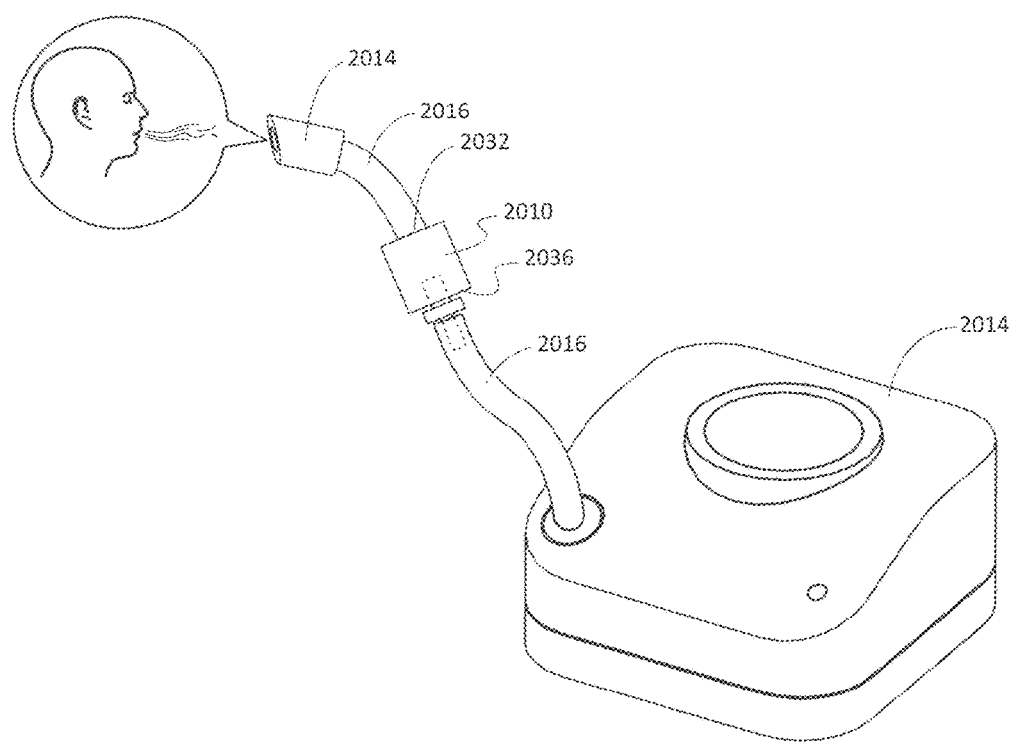
FIG. 29 shows the regulation device of FIGS. 27 and 28 coupled in a breath analysis device with direct breath input from a user.

FIGS. 27 and 28 show an embodiment of a mechanical breath flow regulation device 2010. The regulation device 2010 is shown in these two figures in side cutaway to illustrate the internal components and operation. Regulation device 2010 is designed for use with a portable breath analysis device, for example, such as any of the breath analysis devices shown and described elsewhere herein and/or in the present assignee's U.S. patent application Ser. Nos. 14/206,347 and 13/052,963, the specifications of which are hereby incorporated herein as if fully set forth here. Various sensor designs may be used in breath analyses performed in conjunction with regulation devices according to the invention. Examples include nanoparticle, enzyme-based, thermoelectric, quartz crystal microbalance, optical, colorimetric, metal oxide, semiconductor, magnetoelastic, and gravimetric sensors. Regulation device 2010 may be used as an integral component of such a breath analysis device 2012, an illustration of which is shown in FIG. 29. With continued reference to FIG. 29, the user directly inputs a breath sample into breath analysis device 2012 by exhaling into a mouthpiece 2014 disposed at the distal end of a breath sample input conduit 2016. Regulation device 2010 may be in-line in conduit 2016, which is coupled to the housing of the breath analysis device 2012 at a proximal end of the conduit 2016. In some embodiments, a fluid conditioner, for example, a desiccant, is disposed in the mouthpiece 2014 in addition to or as an alternative to any regulation device 2010, provided, however, that the flow resistance features of conduit 34 are preserved as described herein.

Figure 30:
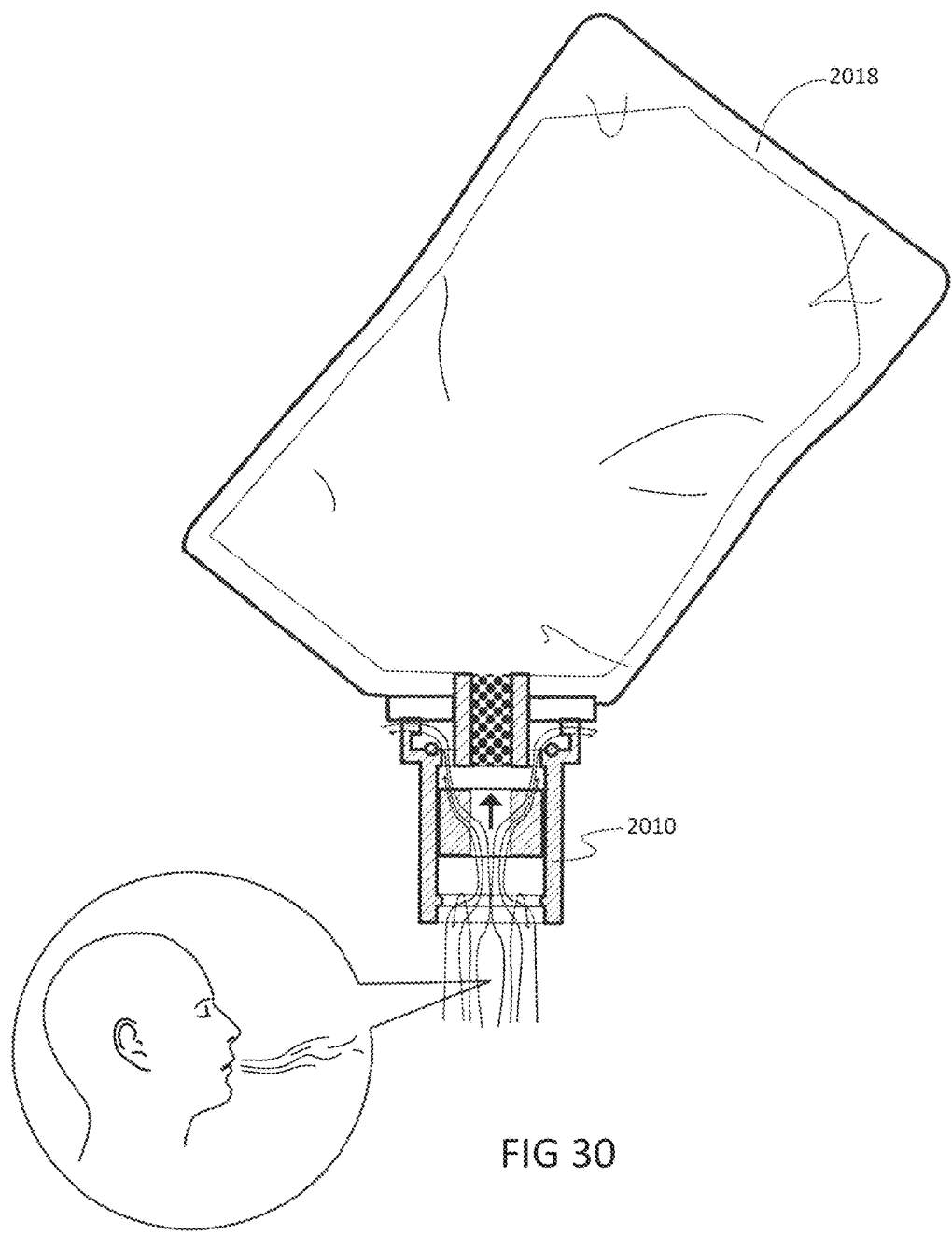
FIG. 30 shows the regulation device of FIGS. 27 and 28 coupled to a breath bag.
Figure 31:
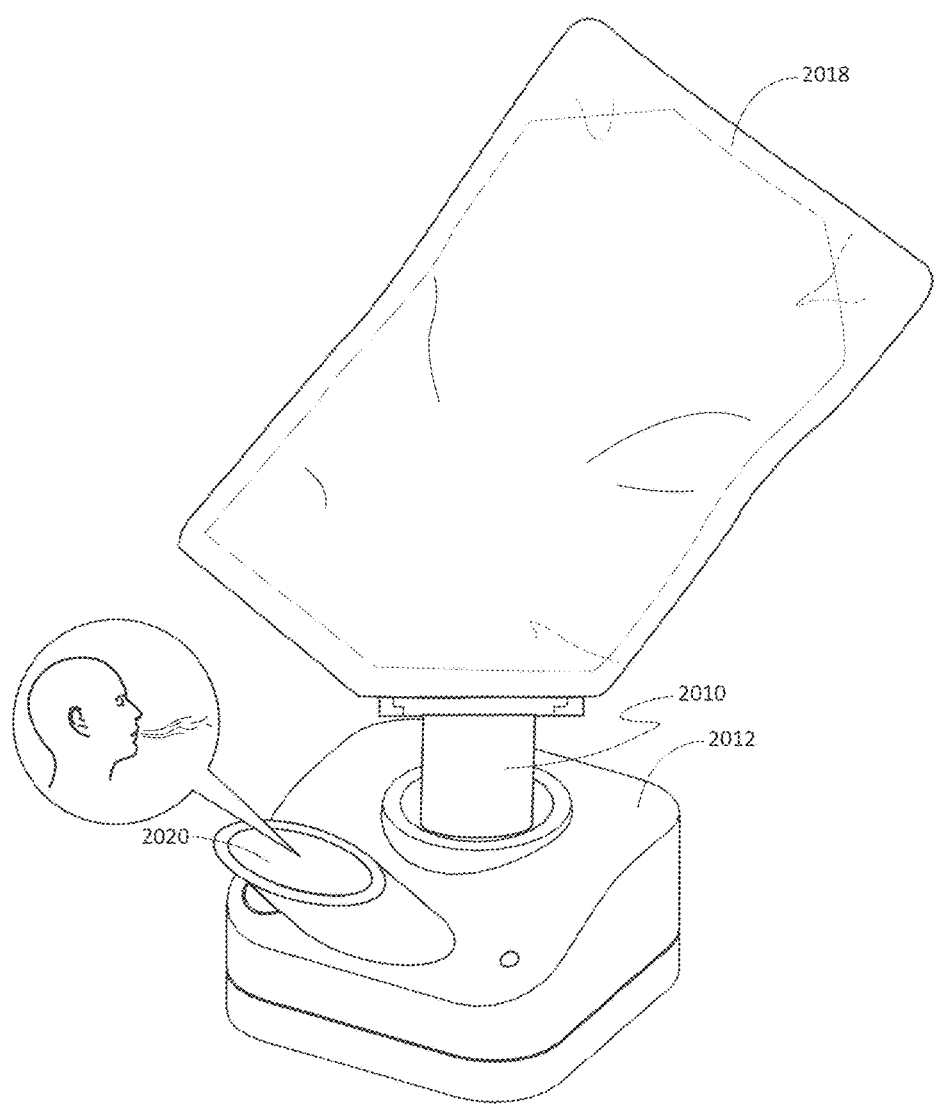
FIG. 31 shows the regulation device and breath bag of FIG. 30 coupled to a breath analysis device.

Other implementations of regulation device 2010 with respect to the breath analysis device, however, are within the scope of the invention. With reference to FIGS. 30 and 31, for example, regulation device 2010 may be incorporated into or made detachably coupled to a stand-alone breath collection apparatus, such as a Tedlar® breath collection bag. In such applications, the user first exhales into the breath collection bag 2018 while it is separate from the breath collection device, e.g., the breath collection device 2012 shown in FIG. 30. The user then detachably couples the bag 2018 to the breath analysis device 2012 (as shown in FIG. 31) so that the breath analysis device 2012 can draw the breath sample from bag 2018 and perform the analyte analysis on it. Alternatively, the breath analysis device 2012 may comprise a mouthpiece 2020, permanently or removably attached to the breath analysis device 2012. The user may exhale through or into the mouthpiece 2020 to inflate the bag 2018 after the bag 2018 has been attached to breath analysis device 2012, as shown in FIG. 31.

There are a number of ways to couple or bond a regulation device (such as regulation device 2010) to a collection bag (such as bag 2018). Examples include detachable couplers, e.g., a bayonet coupler, and more permanent bonding, e.g., such as acoustic or sonic welding, adhesive, and the like. The fitment that unites the breath bag to the rigid valve body may be molded directly into the regulation device body.

With continued reference to FIGS. 27 and 28, regulation device 2010 comprises a hollow and substantially cylindrical housing 2030. The housing 2030 of regulation device 10 has an opening 2032a at its proximal end 2032 that serves as a flow channel through which the breath sample is inputted. A conduit 2034 is disposed at the opposite, distal end 2036 of housing 2030. In describing this and the various other embodiments of the invention, the terms "proximal" and "distal" will be used for reference and direction. Proximal is defined as being nearer to the point(s) at which a breath sample is inputted. By extension, distal is defined as being distant or away from the point(s) at which a breath sample is inputted (i.e., the proximal end). In FIGS. 27 and 28, for example, the proximal end is the end closest to the term "BREATH," i.e., nearer the bottom of the drawing sheet. In FIGS. 27 and 28, for example, the distal direction is the end furthest away from the term "BREATH," i.e., nearer the top of the drawing sheet. Similarly, references to "top" or "bottom" or "up" or "down" are with respect to the devices as shown in the drawing figures, even though the devices may be disposed in directional or geometric configurations other than those shown in the drawing figures, (in which case the directional references would change correspondingly).

Conduit 2034 is the path through which the portion of the breath sample to be analyzed in the breath analysis device 2012 (referred to herein as the "analytical portion" of the breath sample) flows. In the embodiment shown in FIG. 29, conduit 2034 is in fluid communication (e.g., direct communication) with breath analysis device 2012 via conduit 2016. In the embodiment shown in FIG. 30, conduit 2034 is in fluid communication (e.g., direct communication) with the interior of bag 2018. Conduit 2034 may contain (e.g., within its interior) a fluid conditioning material 2038, e.g., a desiccant. This partially-filled conduit 2034 provides a resistance to flow relative to an empty conduit. Alternatively, conduit 2034 may contain any other material or structure that is configured to provide a resistance to flow relative to an empty conduit. As will be readily understood with reference to Poiseuille's equation, as the diameter of a lumen decreases, the resistance to fluid flow through that lumen increases (assuming all other variable are held constant). Therefore, conduit 2034 may restrict fluid flow (e.g., relative to an empty conduit) merely by having a reduced lumen diameter.

At least one aperture 2040 is disposed at end 2036 of housing 2030 as an alternative flow path to conduit 2034. In some embodiments, the at least one aperture 2040 comprises 1 aperture, 2 apertures, 3 apertures 4 apertures, 5 or more apertures, 7 or more apertures, 10 or more apertures, or more than 10 apertures. In some embodiments the at least one apertures 2040 are disposed exteriorly to the wall of conduit 2034. The apertures 2040 allow a gas or fluid within the interior of housing to pass through them, as will be described more fully herein below.

Regulation device 2010 further comprises a flow switching piston 2042 disposed within the interior of housing 2030 and movable or slidable longitudinally within the housing 2030. Piston 2042 comprises an aperture 2044 through its center. In some embodiments, the aperture 2044 is substantially cylindrical and oriented longitudinally through the piston 2042. However, aperture 2044 may be any other shape and have any other orientation that produces the fluid flow patterns and necessary pressure profiles for functioning of the regulation device 2010. For example, aperture may have a cross-section that is elliptical or ovoid, triangular, square, pentagonal or hexagonal, etc. In the same way, the aperture 2044 may be oriented at an angle to, helically about, and/or laterally offset from the longitudinal axis of the piston 2042 or the regulation device 2010. A stop flange 2046 is fixedly disposed within the interior cavity of housing 2030 adjacent to opening 2032 to stop the proximal movement of piston 2042 at its approach to opening 2032 (i.e., provide a proximal most location for the piston 2042).

In some embodiments, regulation device 2010 comprises a coupling collar 2048 and a seal (e.g., an o-ring 2050) to securely couple the regulation device 2010 in air-tight fashion to an associated or mating coupling arrangement on a mating conduit, for example, on conduit 2016 in the embodiment of FIG. 29 or bag 2018 of FIG. 30.

In some embodiments, regulation devices (e.g., mechanical breath segmenters or fractionators) need not have the capability to be reset for multiple breath inputs. They may, for example, be designed for single use. With respect to regulation device 2010, for example, it is not necessary to provide a means for returning piston 2042 to its initial position at proximal end 2032 of housing 2030. However, resetting the device may be useful in some applications.

Figure 32:
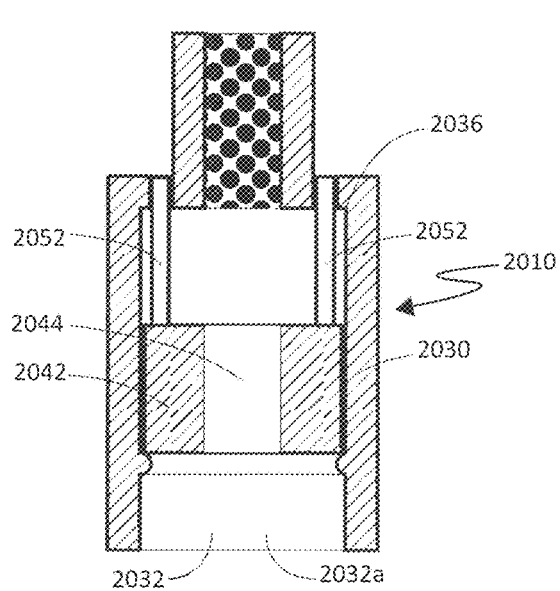
FIG. 32 shows a side cutaway view of the regulation device of FIGS. 27 and 28 in the open position, and with the guides shown in cross section.
Figure 33:
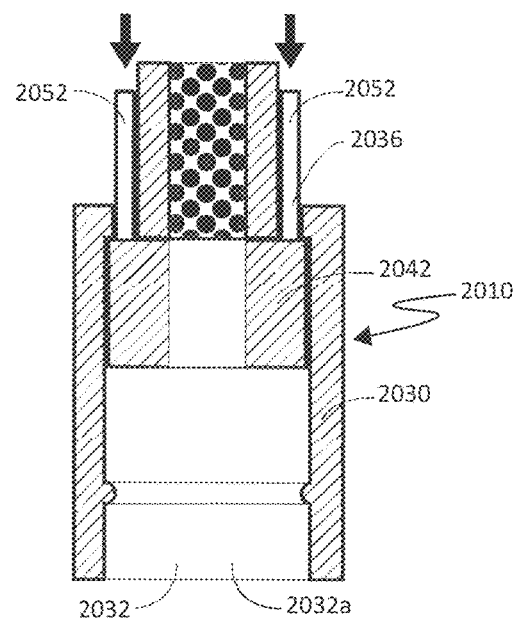
FIG. 33 shows a side cutaway view of the regulation device of FIGS. 27 and 28 in the position directing flow through Flow Path 2, and with the guides extending upwardly from the regulation device housing, (the arrows showing where the user would press to move the piston back down to the initial position and thus reset the regulation device).
Figure 34:
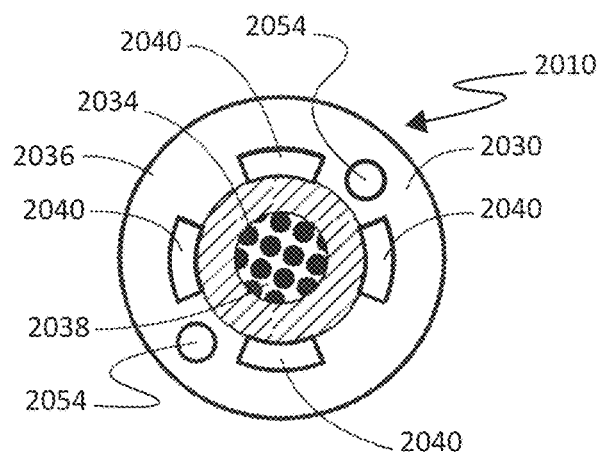
FIG. 34 shows a top or distal view of the regulation device of FIGS. 27 and 28.
Figure 35:
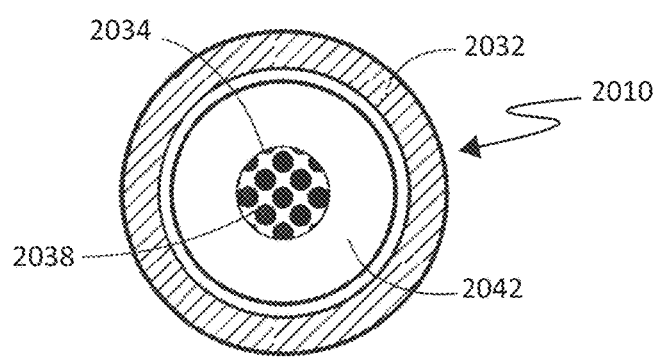
FIG. 35 shows a bottom or proximal view of the regulation device of FIGS. 27 and 28.

Resetting the a mechanical fractionator, such as the regulator device 2010 shown in FIGS. 27 and 28, can occur through a number of different approaches and configurations, including, for example: gravity resets; spring or biasing resets; mechanical or manual resets; and the like. With reference to FIG. 28, a gravity reset may function by simply holding the regulator device 2010 such that its longitudinal axis is approximately vertical to allow the piston 2042 to slide proximally within the regulator device 2010. A gravity reset may be tuned by changing the mass of the piston 2042, and reducing the friction between the interior surface of the housing 2030 and the exterior surface of the piston 2042. Of course, if either the mass of the piston 2042 or the friction between the interior surface of the housing 2030 and the exterior surface of the piston 2042 is changed, it may become necessary to change the size of the 2044 to fine-tune how easy the piston is moved from the proximal end to the distal end of the regulator device 2010. An embodiment of a spring or biasing reset is described with reference to FIGS. 36-38. Finally a mechanical or manual reset may comprise one or more pins, guide posts, or stanchions extending through a surface of the housing. An example of a mechanical or manual reset is described with reference to FIGS. 32-33 in which regulation device 2010 comprises at least a pair of pins, guide posts, or stanchions 2052 disposed on (e.g., extending from) the distal top surface of piston 2042. Each of these posts 2052 extends through a corresponding aperture 2054 at housing end 2036 adjacent to apertures 2040. In this embodiment, the regulator device 2010 may be mechanically reset may be pressing down on one or both of the guide posts 2054, as shown by the arrows in FIG. 33. This downward force on posts 2054 urges piston 2042 downward axially within the housing interior until the downward movement is stopped by abutment with stop flange 2046. Any of a number of other ways of resetting the regulator device may be used.

Regulation device 2010 operates as follows. Prior to receiving a breath sample, piston 2042 is seated in the interior, proximal end of housing 2030, e.g., at or adjacent the opening 2032, held by stop flange 2046. Using the embodiment shown in FIG. 29 or FIG. 30, the user places his or her mouth at mouthpiece 2014 (FIG. 29) or opening 2032 (FIG. 30) and exhales breath into opening 2032a in the end 2032 of housing 2030. A portion of the breath passes directly through aperture 2044 in piston 2042, but a portion also impinges upon the proximal or bottom surface of piston 2042. This creates a relatively higher pressure condition in the cavity at the lower or proximal end of piston 2042 (i.e., the pressure on the proximal end of the piston 2042 is lower than the pressure on the distal end of the piston), which urges the piston 2042 distally in the housing 2030, e.g., toward distal end 2036 of the housing 2030.

As the portion of the breath that has passed through piston aperture 2044 fills the housing cavity above piston 2042 (e.g., in the housing 2030 distal to the piston 2042), it reaches housing distal end 2036. At the distal end 2036 of the housing 2030 are two fluid flow paths by which a fluid may exit the housing 2030. One flow path ("Flow Path 1") is from the distal end 2036 of the housing 2030 and through the apertures 2040. The other flow path ("Flow Path 2") is from the distal end 2036 of the housing 2030 and through conduit 2034.

Flow Path 1 and Flow Path 2 share the total flow as parallel or shunted flow paths according to principles well known in the field of fluid mechanics. The ratio of their resistances will enable one to predict the respective flow rates through them. Similarly, one may set or adjust the respective resistances of the flow paths to achieve a desired relative flow through them. The setting of this ratio may be guided by or determined from various factors, e.g., such as patient or user demographics (e.g., age, sex, etc.), by physiological state (e.g., smoker, non-smoker, hyperventilating, etc.), and so on. In this illustrative embodiment, the flow resistance in Flow Path 1 is essentially zero and, given the characteristics of the fluid conditioning material 2038 in conduit 2034, the resistance through Flow Path 2 is sufficiently high that most, if not all, of the fluid flow exits the housing 2030 through Flow Path 1. In this example, fluid will continue to exit the housing 2030 through Flow Path 1 until piston 2042 has traveled the length of housing 2030 and the distal end of the piston 2042 contacts distal end 2036 of the housing 2030.

When the piston 2042 reaches the distalmost end of its travel in the housing 2030, the distal surface of piston 2042 blocks apertures 2040 and closes Flow Path 1, which leaves Flow Path 2 as the only remaining exit for the pressurized fluid. Once the apertures 2040 have been blocked, the fluid flows into proximal housing end 2032, through piston aperture 2044, into and through and out of conduit 2034 (i.e., along/through Flow Path 2). As explained above, the conduit 2034 may deliver the fluid directly to an analyzing device (e.g., breath analysis device 2012) or to a collection mechanism (e.g., breath collection bag 2018). The portion of a breath sample that passes through conduit 2034 (e.g., along Flow Path 2) is referred to herein as the "analytical portion." All other portions of the breath sample, most notably the portion that is passed through apertures 40 (e.g., exhausted through Flow Path 1), is referred to herein as the "residual portion." The analytical portion of a breath sample may be used for sensing or measurement of the analyte or analytes in that sample. The residual portion of a breath sample is generally exhausted as waste.

After the breath sample has been forcibly exhaled through a regulation device (e.g., regulation device 2010) as described above, if the regulation device is to be re-used the piston (e.g., piston 2042) must be repositioned to its initial or open position at the proximal end 2032 of housing 2030, as shown in FIG. 27. This may be accomplished through a number of different means, as discussed above.

Figures 36, 37, 38:
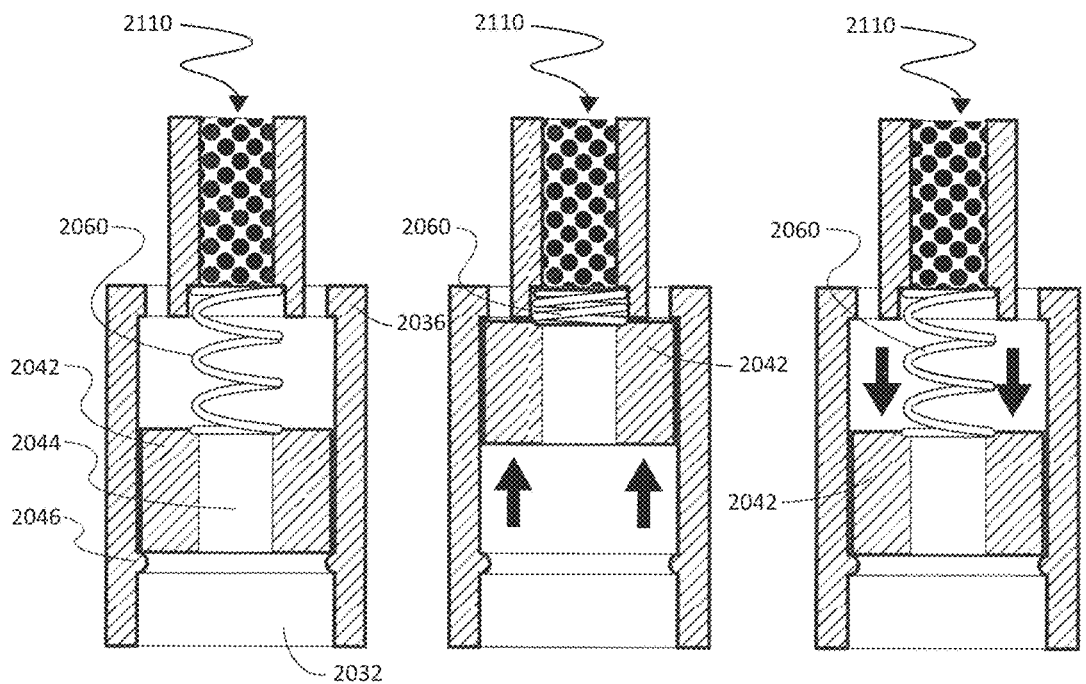
FIG. 36 shows a side cutaway view of a regulation device according to a second embodiment of the invention, wherein the regulation device is in an initial or open position and directs breath through a Flow Path 1.
FIG. 37 shows a side cutaway view of the regulation device of FIG. 36, similar in perspective to FIG. 36, but in which the piston is in the closed position.
FIG. 38 shows a side cutaway view of the regulation device of FIG. 36, similar in perspective to FIGS. 36 and 37, in which the piston has been returned to its initial or open position by the biasing spring.

A regulation device 2110 according to another embodiment, illustrated in FIGS. 36-38, will now be described. This embodiment is similar in some aspects to the embodiment shown in FIGS. 27 and 28 and described herein above, except that in this embodiment the piston 2042 is automatically returned to its initial (proximal) position when the flow of the breath sample ceases, rather than being manually reset using guide posts 2052. In regulation device 2110, the guide posts 2052 and guide post apertures 2054 of regulation device 2010 are omitted. In this embodiment, however, a compression spring 2060 is disposed between the top or distal surface of piston 2042 and the lower surface of conduit 2034 at the interior of the distal end 2036 of the housing 2030 (such as in a cylindrical inset into conduit 2034). As shown in FIG. 36, which illustrates the initial condition of device 2110 prior to receiving the breath sample, the spring 2060 is extended or biased longitudinally to push or secure piston 2042 at its proximalmost position within housing 2030 and against stop flange 2046.

As shown in FIG. 37, when a breath sample is exhaled into proximal end 2032 of the housing 2030, as described herein above, the flow of the breath sample applies a pressure- and drag-induced force on the piston 2042, which pushes it distally along the longitudinal axis of the housing 2030 toward the distal end 2036 of the housing 2030. As piston 2042 moves/translates under this force, the spring 2060 is compressed, which causes it to oppose further piston movement. The compression spring 2060 is selected so that the force of the breath flow that urges piston 2042 distally is greater than the counter-force of the compression spring 2060. Piston 2042 therefore continues its distal movement until it contacts the distal end 2036 of the housing 2030 and blocks Flow Path 1. As the piston 2042 block Flow Path 1, fluid flow will simultaneously shift to Flow Path 2.

As shown in FIG. 38, the breath input flow into proximal end 2032 of housing 2030 attenuates and eventually stops, decreasing and ultimately removing the pressure and drag forces urging piston 2042 distally. Correspondingly, the counterforce of compression spring 2060 urges piston 2042 proximally. As the pressure and drag forces urging piston 2042 distally become less than the counterforce of the compression spring 2060 urging piston 2042 proximally, the piston 2042 moves proximally (e.g. downwardly) until it is stopped by stop flange 2046.

A regulation device 2210 according to another embodiment will now be described with reference to FIGS. 39-42. In this embodiment, which is similar in some aspects to the regulation device 2010 of FIGS. 27-28 and/or 2110 of FIGS. 36-38, the apertures that comprise Flow Path 1 (apertures 2040 in devices 2010 and 2110) are of variable size so that the resistance presented by Flow Path 1 can be set or adjusted.

In devices 2010 and 2110, the distal end 2036 of the housing 2030 is fixedly disposed at the distal end of housing 2030 and includes apertures 2040 comprising the Flow Path 1. Device 2210 also comprises such a distal end 2036 with apertures 2040. However, the device 2210 may also comprise a distal housing cap 2236 rotatably disposed over the distal end 2036. Distal housing cap 2236 comprises apertures 2240 that correspond in number to those of apertures 2040 (i.e., 1 aperture, 2 apertures, 3 apertures 4 apertures, 5 or more apertures, 7 or more apertures, 10 or more apertures, or more than 10 apertures), and which respectively align with such apertures 2040. As the distal housing cap 2236 is rotated, the alignment of apertures 2240 with respect to apertures 2040 is changed, thereby varying (e.g., increasing or decreasing) the axial cross sectional area of Flow Path 1 (e.g., the resultant combined apertures). This rotatable cap 2236 may comprise color coding on its top to facilitate quantification or reproducibility of the flow through the apertures, and similarly may include numbers or a number scale.

A breath flow regulation device 2310 according to another embodiment of the invention will now be described in conjunction with the illustrations of FIGS. 43-48. This embodiment employs a ball valve to selectively provide for, and then close, Flow Path 1.

Figure 48:
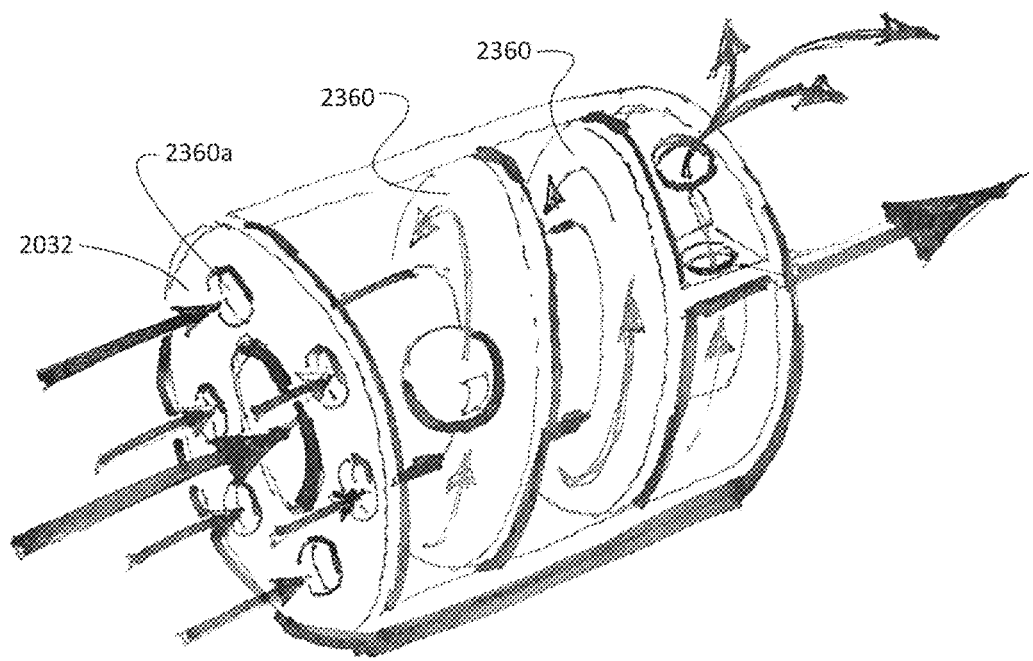
FIG. 48 is a perspective cutaway view of a modification of the device of FIGS. 43-47, illustrating the flow of the breath sample during an open phase and during a closed phase of operation.

An exterior side view of regulation device 2310 is shown in FIG. 43. Corresponding cross-sectional side views of the device 2310 are shown in FIGS. 44 and 45. FIG. 44 shows device 2310 at an initial or open stage prior to receiving a breath sample. FIG. 45 shows device 2310 as Flow Path 1 is shut off and flow is directed through Flow Path 2. FIG. 46 shows a bottom or proximal exterior view of the device 2310, and FIG. 47 shows a top or distal exterior view of the device 2310. FIG. 48 shows a perspective cutaway view of a similar flow regulation device, including specifically the internal mechanisms of the ball valve. It comprises a plurality of apertures 2360a disposed in proximal housing surface 2032 that facilitate input of the breath sample into the device in a way that facilitates the advancement of the ball.

With continued reference to FIGS. 44-47, device 2310 comprises a helical conduit 2360 that starts at aperture 2360a in the proximal end 2032 of the housing 2030, as shown in FIG. 46, and ends at aperture 2360b in the distal end 2036 of the housing 2030, as shown in FIG. 47. A ball 2362 that is sized smaller than the cross-sectional dimensions of the helical conduit 2360 (so that it can travel through the helical conduit 2360), but larger than apertures 2360a and 2360b (so that it cannot exit the helical conduit 2360 through either of the apertures 2360a and/or 2360b), is disposed in helical conduit 2360. Thus, Flow Path 1 extends from proximal aperture 2360a to distal aperture 2360b via helical conduit 2360, and Flow Path 2 extends from proximal opening 2032a through conduit 2034. In some embodiments, the ball 2362 comprises a light weight plastic such as polypropylene. In other embodiments, the ball 2362 comprises steel or another suitable material, Device 2310 is designed to be positioned vertically during normal operation, as shown in FIGS. 43-45. In this way the slope, length and cross-sectional dimensions of the helical conduit 2360 as well as the dimensions and weight of the ball 2362 may be tailored such that the ball 2362 may be pushed up the helical conduit 2360 at a constant velocity by a constant or linear force. Under initial conditions prior to receiving a breath sample, ball 2362 is held at proximal aperture 2360a by gravity. A viscous material like petroleum jelly or a cardboard insert may be used to keep the ball in place prior to use.

When a breath sample is inputted into device 2310 at its proximal end opening 2032a as generally described herein above with respect to the other embodiments, the flow of the breath sample is restricted in Flow Path 2 by the fluid conditioning material 2038 in conduit 2034, and thus flows in Flow Path 1. The flow overcomes the weight of ball 2362 and pushes it up and through helical conduit 2360. When ball 2362 reaches the top of helical conduit 2360 at distal aperture 2360b, the ball 2362 lodges in aperture 2360b and blocks flow through Flow Path 1. When flow is blocked through Flow Path 1, flow is diverted to Flow Path 2, including into, through, and out of conduit 2034 where it may be collected for analysis, such as in a breath analysis device, or for storage device, such as in a breath collection bag.

Figure 49:
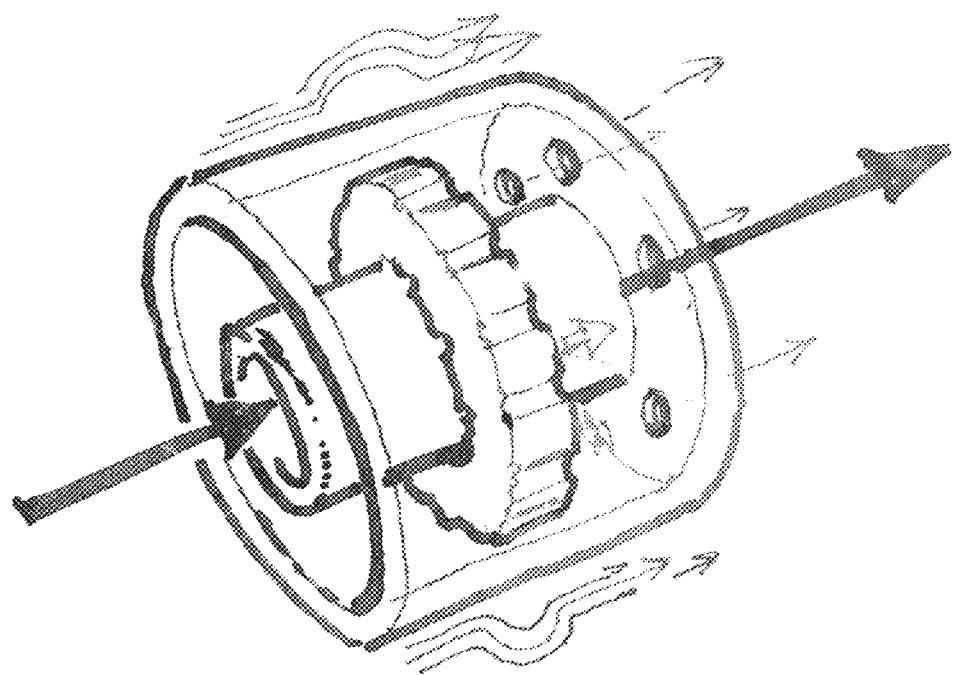
FIG. 49 shows a breath flow regulation device according to still another embodiment of the invention.

Still another embodiment of a mechanical regulation device is shown in FIG. 49. Much like the device illustrated in FIGS. 27 and 28, this device comprises a sliding piston-like ring. However, in the regulation device shown in FIG. 49, the conduit 2034 (e.g., a fixed tube over which the piston-like ring slides) is disposed in the central, axial portion of the piston. Furthermore, the piston comprises at least one cut-out or slot disposed around its periphery (e.g., a plurality of slots). As a breath sample is inputted into the device as shown by the arrows, flow resistance in conduit 2034 causes flow to be directed through the slots at the periphery of the piston (Flow Path 1), and the piston is moved axially in the device housing in the direction shown by the arrows. When the piston contacts the distal end of the housing, it blocks exhaust holes in the distal end of the housing, thereby blocking Flow Path 1 and causing flow to be directed through Flow Path 2 through the central conduit 2034. Movement of the piston may be tailored by increasing the number and or size of the slots. For example, in some embodiments, the piston may include only one slot. In other embodiments, the piston may include 2 slots, three slots, four slots, five slots, five to ten slots ten to fifteen slots, fifteen to twenty slots, more than twenty slots, or any other number of slots that produces the fluid flow patterns and necessary pressure profiles for functioning of the regulation device.

As will be readily understood, each embodiment of a mechanical segmentor/fractionator discussed above may be tailored using principles of fluid dynamics such that the fractionator (regulator device) captures an earlier or later, larger or smaller segment of a breath. Assuming a reproducible breath, representative variables that can be tailored include: resistance to fluid flow past piston (or ball) (this may be altered by increasing/reducing the diameter and/or the length of the aperture through the piston); resistance to fluid flow through conduit 2034 (this may be altered by increasing/reducing the packing fraction of the fluid conditioning material, or increasing/reducing the diameter and/or length of the conduit); and resistance to fluid flow through the apertures in the distal end of the regulator (this may be altered by increasing/reducing the number and diameter and/or length of the apertures in the distal end of the regulator—much as was described with reference to FIGS. 39-42). Each of these variables may be changed so as to change the segment of the breath that is captured.

It is also possible to combine more than one mechanical fractionator to separately capture one than one segment of a breath. For example: a first piston device (such as is shown in FIGS. 28 and 28) could be combined with a second, potentially concentric, piston device; or a piston device (such as is shown in FIGS. 28 and 28) could be combined with a ball and helix (as shown in FIGS. 43-47). Each stage of such a mechanical fractionator could be tailored, as discussed above, so as to capture different segments of a breath. For example: the first stage could exhaust a first, early segment of the breath then deliver the remainder of the breath (comprising a first analytical portion and a second analytical portion) to the second stage; the second stage could then split the remainder of the breath into a first analytical portion and a second analytical portion.

While mechanical fractionators may be particularly durable and easy to use, they may suffer from certain user-derived and analytical limitations. First, mechanical fractionators may require a constant pressure (e.g., a constant exhalation, or at least an exhalation constantly above a minimum flow rate) to move the device. Young or particularly weak individuals may have difficulty maintaining such a constant flow rate, particularly for multi-stage mechanical fractionators. Second mechanical fractionators may suffer from some degree pressure bias. That is to say that a user with particularly strong lungs who is able to exhale with sufficient force to generate a comparatively massive amount of initial pressure may be able to "saturate" the mechanical fractionator and cause it to segment falsely—in this case, the mechanical fractionator will segment the breath too early. By the same token, a user who does not exhale hard enough or exhales for too long a time may experience losses due to fluid leakage which will cause the mechanical fractionator to segment falsely—in this case, the mechanical fractional will segment the breath too late. Only in a lossless mechanical fractionator (including both frictional losses and fluid/pressure leakage/losses) will segmentation be perfectly reproducible. However, it will be easily understood that some variability may be acceptable. Additionally, mechanical fractionators rely only on flow rates and time and are entirely immune to other, potentially more accurate, indicia of breath segmentation. For at least the above-listed reasons, electronic or sensor-based fragmentation systems and methods, including, but not limited to, those described below, may be useful.

Electrical or Sensor-Based Segmentation

Electronic or sensor-based fragmentation systems and methods generally determine how much breath has passed through any part of the system by using any of a number of sensors. For example, sensor-based fragmentation systems may include a timer, a temperature probe, a carbon dioxide sensor, or a flow sensor or a combination of any of these. Each of these sensors outputs a variable that is indicative of one or more portions of a breath. At least one flow controlling element, e.g., a valve or other device, may be included to responds to the sensor outputs.

In one embodiment, a sensor-based fragmentation system includes a time sensor (e.g., simple timer, or a clock). After the system detects the start of the breath input (described elsewhere herein), the system may wait a fixed amount of time before enabling a valve (or other breath direction system) so as to discard a certain segment breath, e.g., the system may discard the entire portion of the breath corresponding to the user's dead space. The time the device waits may be a fixed amount of time (such as a preset amount of time), or may be determined through a calibration step. For example, the device may wait 5 seconds before enabling the valve, thereby allowing the next 5 seconds of breath to flow through Flow Path A. In some embodiments, a time sensor/timer is combined with a table of data stored within the device. The table may be any data set indicative of breath characteristics, such as those several tables presented herein. For example, a tidal volume table having data for sex, age, and height may be incorporated or used. The device may allow a user to input their sex, age, and height (or allow another person to input a patient's sex, age and height, e.g., in the case of a child or hospital patient). Then the device can use the input data to look up and or extrapolate the user's tidal volume. Depending on the breath segment desired to be captured, the theoretical tidal volume can be used to identify a theoretical time corresponding to that breath segment. A processor contained within or associated with the device sets the time sensor/timer to respond at that calculated theoretical time. Thereby, the device can be customized to any given patient with little patient involvement.

In another embodiment, the system may incorporate a flow sensor. The flow sensor measures the amount of air that has passed through the system and activates the valve after a certain volume has passed in order to capture a certain segment of a breath (e.g., alveolar breath). A flow sensor may be ideally suited to capturing a first segment of a breath, e.g., a first 200 ml, 300 ml, etc. However, capturing other segments, such as middle or final segments, may present additional complexity for flow-sensor based systems. It will be readily understood that a system exploiting a flow sensor to identify and capture various segments of a breath can benefit from one or more look up tables containing data corresponding to various breathing parameters for varying segments of the population. As a flow sensor can only measure the volume of a substance, in this case a fluid, that has passed the flow sensor, particularly valuable variables may include a patient's total lung capacity, vital capacity, residual volume, forced vital capacity, and forced expiratory volume. A data table may include only the data relevant to a pre-determined user. For example, a breath analysis device issued or prescribed to a 72 inch tall 30 year old male may have only the data relevant to a 72 inch tall 30 year old male. However A data table may include data for multiple segments of the population, including male and female. Moreover, such data tables may include data for varying heights, e.g., in one in or one half inch increments (or in centimeter increments) and varying ages, e.g., in one month increments or one year increments. By including more data in the look up tables or data tables, the device may increase its accuracy and applicability to multiple users. A device with a comprehensive data table may be able to accept an input from a 75 inch male or from a 61 inch female and identify that the male has a vital capacity of approximately 5.75 liters whereas the female has a vital capacity of approximately 3.12 liters. Using that information, the device may be able to more accurately collect various parts or segments of these user's breaths. This is particularly so when a later-exhaled breath segment is sought to be collected—if the last ⅓ of the patient's volume is desired, a dramatically higher volume of fluid will have to pass for the male than for the female.

Data tables rely on statistical average. However, some users may have aberrant characteristics. For example, it is possible that a given female may have an uncharacteristically high (or low) vital capacity and a given male may have an uncharacteristically low (or high) vital capacity. Merely using data tables for these individuals may well result in false assumptions and miss-collection of breath samples (e.g., collection of an incorrect or undesired breath segment). Therefore, rather than using data tables to customize a device to a given user, the device may be calibrated by/to an individual user so that it can likely (e.g., have a higher likelihood) capture the desired and correct breath sample (e.g., alveolar breath). In some embodiments, the device may be calibrated by sampling a user's exhalations one or more times.

To calibrate a device to a given user using pre-collection exhalation, a user may take a deep breath and exhale for as long as they can one or more times (e.g., two times, three time, four times, five times, 6 times, or even more than 6 times) into the device or cartridge. The cartridge in this example may be a special cartridge designed for calibration. During this calibration step the system will learn certain characteristics of the user (their vital capacity, residual volume, forced vital capacity, forced expiratory volume, their forced expiratory flow 25-75%, or their maximal voluntary ventilation, how long they can exhale, how much volume of air they exhale, the changes in flow of the user's exhalation, the change in pressure when the user exhales, the presence or absence of certain analytes during an exhalation, etc.). The device may use one or more of these characteristics to determine how much breath will pass through the system or to derive the appropriate time to switch from one flow path (e.g., Flow Path B) to another flow path (e.g., Flow Path A). Calibration devices such as those described above may also be used to train a user.

Calibration may advantageously be used to accurately and reproducibly collect a deep lung, or alveolar, sample. For example, a user may use calibrate the collection device to their lung volume or capacity (or any other breath characteristic) and then use that information to control the volume of breath that is vented from the collection device, either automatically or based on user input. The following steps illustrate one embodiment of a method for such calibration and configuration. First, a breath profiling device (which may be separate form or integral to a breath analysis device) measures the lung capacity, and/or other exhalation characteristics of the user, as the user exhales into the breath profiling device. In some embodiments, only one exhalation is required for complete calibration. In other embodiments, more than one exhalation is required for calibration (e.g., 2, 3, 4, 5, or even six exhalations). After exhaling properly into the breath profiling device, the breath profiling device characterizes the exhalation(s). In some embodiments, the breath profiling device includes the ability and functionality to identify and differentiate between proper exhalations capable of calibrating the device (based on volume, flow rate, or other characteristics) and improper exhalations that should be discarded unused for the purposes of calibration). When the breath profiling device detects an improper exhalation, it may take any of a number of actions: it may abort the calibration; it may flag the exhalation as aberrant; or it may assign an aberration index to the exhalation for later use and/or analysis. The breath profiling device then conveys the characteristics, or information derived therefrom, to the breath analysis device. In some embodiments, the characteristics or information derived therefrom are conveyed using Bluetooth, Wi-Fi, or any other appropriate wireless data transfer protocol, or they may be conveyed using a wired connection. Next, a processor of the breath analysis device uses the received information (including at least the characteristics or information derived from the exhalations) to control the timing with which a valve or other type of flow/exhaust control is activated during a sample collection exhalation. For example, if the measured lung capacity/volume is C, the processor may activates the valve once the user has exhaled X % of C, where X is selected to capture an alveolar segment. The breath analysis device may also use the properly calibrated exhalations (e.g., the stored breath profile information received from the breath profiling device) as a standard for any later exhalation intended for analysis. For example, the breath analysis device may compare an exhalation to the user's stored breath profile to determine if the exhalation is proper or aberrant. If the exhalation is proper, the breath analysis device may continue with its analysis of the exhalation. Alternatively, if comparison of the exhalation and the stored breath profile (e.g., previous calibration data) identifies an exhalation as abnormal, aberrant, or improper (e.g., if the exhalation characteristics do not sufficiently match the user's pre-stored breath profile), the breath analysis device may abort the test and analysis of the exhalation or it may flag the resulting test results (e.g., the test results derived from the abnormal exhalation) as being aberrational.

Calibration using a breath profiling device may also prove particularly useful when one breath analysis device is used by more than one individual. In that case, each individual user may calibrate the device using a breath profiling device as described above—in that way, each user will generate a recognizable exhalation pattern, or fingerprint, that the breath analysis device can recognize. The breath analysis device may receive calibration data from a breath profiling device for more than one user, such as two, three, four, or even more users, and store that calibration data relating to each user. Thereafter, these exhalation fingerprints may be used to differentiate between users. For example, a breath analysis device may accept exhalation characteristic data (i.e., the exhalation fingerprint) for four separate individuals. When one of these four exhalation-fingerprinted individuals uses the breath analysis device, the breath analysis device compares one of more metrics associated with the user's exhalation (e.g., volume, flow rate, temperature, carbon dioxide concentration, oxygen concentration, etc.) to the breath analysis device's database of exhalation characteristics (i.e., the four separate exhalation fingerprints) and automatically (i.e., without user involvement) identifies the user based on that comparison.

As different users have different respiratory track anatomies, it may be advantageous for a device to be able to adjust to an individual user (based on such variables as sex, height, and age) so as to adjust a vented or exhausted portion of a breath in relation to the analytical portion. This may be done automatically by using look-up or data tables or user calibration, as discussed above. However, user input may also be accepted to change the volume ratio of exhausted exhalation to analytical portion. In some embodiments, the user adjusts a mechanical setting or portion of the device. In other embodiments, the user inputs a selection or setting into the device (or another peripheral that is in some form of communication with the device, e.g., wired or wireless data communication). Based on that user input, the device responds to vary the volume of the exhalation that is discarded.

"Within User" Variation Problem and Solution

There may be a significant difference in the exhalation characteristics across a population which is primarily driven by sex, age, height, sickness (e.g., the flu) or disease (e.g., chronic emphysema). For example, a normal, healthy adult male in his late 20s and a normal, healthy adult woman in her 70s have difference tidal volumes (571 mL v. 367 mL) and forced vital capacities (4.70 L v. 2.85 L).

Another complicating factor may be that a given individual's exhalation characteristics may change based on changes in health. A common symptom of the flu is difficulty breathing. Nausea or upset stomach may impair diaphragm contraction. Dental work may impact the ability to fully open the mouth (thereby adding flow restriction). Allergies or runny nose may cause shallow breathing. It is still desirable to properly capture an alveolar sample and conduct an analysis of the alveolar breath sample during these times.

A further complicating factor is that breath analysis devices are frequently designed to be small and portable (as discussed elsewhere herein). The mouthpiece is also frequently small. Within a breath analysis device, there are likely sensors, desiccant or flow sensors that contribute to enhanced flow resistance. As such, the actual volume that a user exhales may be substantially less than the user's forced vital capacity (e.g., it is not 2.85 L or 4.70 L from the examples above). In the case of Mylar bags used in the breath collection field, for example, some generally healthy "normal" individuals are unable to fully inflate a 1 L bag. As such, depending on the level of flow restriction, the "dead air" space may be a significant portion of the overall available breath sample.

Yet another complicating factor is that not all users properly exhale into a device. There are instances in which a user may cough, expend submaximal effort, have a "slow start", not be at rest, not have access to total lung capacity (TLC) at the start of the test, etc.

For these reasons, among others, it may be desirable to profile the user periodically in case an adjustment to the measurement is needed. Alternatively or in addition, it may be desirable to associate exhalation characteristics with the breath result so that adjustments can be made based on an atypical relationship between the breath result and the exhalation characteristic. Lastly, it may be desirable to flag certain measurements or display an error message if the user does something that could cause an improper result, such as coughing mid-way through the test. Examples of devices that use these principles are described below.

In one embodiment, a breath analysis device senses one or more real time exhalation characteristic (e.g., flow rate, pressure, exhalation time, temperature, etc.) that may be used to control inflow into the analysis device, for example using a valve. These characteristics are logged in the breath analysis device together with the associated acetone measurements. This logged information could later be used to, for example, discard or discount aberrational analyte measurements (e.g., acetone measurements), or to adjust these measurements to compensate for deviations in how the user exhaled. A learning algorithm could also analyze the log and associated measurements to determine appropriate compensation factors for the user.

In another embodiment, the breath analysis device could use stored breath profile information to determine whether the user exhaled properly into the breath analysis device, and could abort the test (or perhaps flag the result as aberrational) if the exhalation characteristics do not sufficiently match the user's stored breath profile.

In one embodiment, the user is prompted to re-profile based on (a) user suggestion that re-profiling is needed or desirable, (b) information gleaned from the user's location, calendar or other health information suggesting that the user is sick or has made a respiratory impactful change, such as started using an inhaler, or (c) a historical change in certain characteristics such as the duration or rate of exhalation. Re-profiling may occur via an App alone (e.g., the app shown in FIGS. 69A-D), a trainer that is separate from the device, or the device itself.

The user provides an initial breath sample via a capture mechanism. The capture mechanism may be comprised of the device itself, which contains a two flow path system, each containing a flow sensor. As the breath sample passes through the first restrictive path, the flow sensor will indicate various traits regarding the breath sample and create the breath profile for the user. Because a flow sensor is utilized, the mobile interface relationship may be minimal during the profiling process. The interface can instruct the user to breath into the device, and the flow sensor can record the rest of the information, such as the start and end of the test and change in flow rates. During a functional breath analysis test, the breath profile can indicate to the device the time at which the sample should travel through the next flow path. This is achieved by instructing the device to expose another flow channel, creating a new path of less resistance for the sample to travel through (and, possibly, close the first flow channel).

In another embodiment, the device and capture mechanism are separated. The capture mechanism is comprised of a mouthpiece with resistance that is comparable to the device, in order to simulate an actual device test. This capture mechanism, or "trainer," can facilitate the collection of a sample for profiling the user's breath, and is also connected to the mobile interface. The mobile interface can instruct the user on when to start and stop the delivery of a sample through the trainer. The start and stop measurements can help estimate how it long it takes the user to evacuate their entire lung volume, which was be correlated to forced vital capacity, tidal volume, etc.

In another embodiment, the device and capture mechanism are separated. The capture mechanism is comprised of a resistive mouthpiece, which contains both a flow sensor and a clocking feature. The clocking feature can record the time at which a breath began to travel through a flow path, and when it ended. The flow sensor can provide the rate of gas flow. In this embodiment the mobile interface can be minimal during the profiling process. The mobile interface will instruct the user to breathe through the trainer, and the mouthpiece components can generate the rest of the flow characteristics.

Valve Shutoff Problem and Solution

For embodiments that involve closing flow paths at different times during the exhalation, it is important to note the timing constraints of the closing process. For example, a user may comfortably exhale through a medium or high flow resistance device for only 10 seconds. However, if a gear-based linear actuator is used, it may take 2-3 seconds to actually close the flow path. Thus, a significant portion of the sample may be undesirably lost due to a "slow-closing" valve.

The sum of the time (a) to generate the closing signal based on exhalation properties such as temperature, $CO_2$ concentration or other parameters, (b) to communicate the signal to the valve, and (c) to close the path using the valve should be minimized so that an alveolar breath sample can be captured within the duration of a single exhalation by the user. Candidate solutions include solenoid valves or magnetic actuation of a metallic valve.

Another solution may be to know the closing time a priori and thus avoid the time to generate the closing signal or the time to communicate the signal to the valve. A priori determination may be based on known user characteristics (e.g., age, sex, height, weight), medical history or state (e.g., obstructive or restrictive breathing), prior measurement (using a profiling device that looks at exhalation characteristics), or a user setting (e.g., the user selecting a dial or inputting a value setting forth the time to close the valve).

Compensation Challenges

In effect, there are two "volumes" that need to be optimized: (a) the volume of the breath sample that should be vented and not analyzed, and (b) the volume of the breath sample that is necessary for analysis so that the sensor generates an accurate reading.

It may be that the flow resistance through the bypass flow path and the main sensing flow path will be different. While a first set of characteristics are instructive to determine when to switch from the bypass flow path to the main sensing flow path, a second set of characteristics are needed to ensure that the user exhales a sufficient volume through the main sensing flow path. In this regard, if a user can only exhale 1000 mL, the sensor requires 750 mL and the "dead volume" is 450 mL, the device may need to "vent" only the first 250 mL and then be aware that 200 mL of dead volume is being mixed with the 550 mL of alveolar air to generate the 750 mL sample. In this situation, the device may need to compensate by increasing the measured response by 36%. This is further complicated by the fact that the first 250 mL of vented air may be easier for the user to exhale because there is less flow resistance in the bypass valve. Accordingly, the total volume that the user is expected to generate is: $V_{tot}=Q_{bypass}*t_{bypass}+Q_{sensor\_path}*t_{sensor\_path}$, where Q is flow rate, t is time and $V_{tot}$ is the total volume through the device.

Example of Parameter Change by Device

In some embodiments, a particular device can be programmed with certain "breath profile" parameters, based on inputted factors such as age, height, weight, etc. As is discussed elsewhere herein, the breath analysis system may communicate with a mobile interface and accept parameters or other programming from such mobile interface. The breath profile can help determine total expired volume of a user, as well as what volume of air needs to be vented, in order to receive a deep alveolar lung sample.

As an example, consider two users, referred to as User A and User B. User A is a 70 year old female, and User B is a 25 year old male. User A's breath profile indicates a total expired volume of about 1.5 L and a subsequent dead space of about 100 mL that requires venting. Due to age, user A exhales with less force and pressure. This translates into a slower flow rate. User B is a healthy athlete with a breath profile indicating a total expired volume of about 4.0 L and a subsequent dead space of 750 mL that requires venting. User B expel their total expiratory volume in about 1-2 seconds.

In the case of User A, user A's device would utilize a solenoid valve that is controlled by a processor. This valve would be instructed by the processor to pivot and create a completely open flow path. This path would remain open for about 5 seconds, which would translate to the evacuation of the user's dead space. After about 5 seconds, the solenoid valve would close and allow the breath sample to flow through a secondary flow path which contains the disposable cartridge. The valve would then remain closed for the duration of the sample collection. Alternatively, the valve can be activated by the user using a button mechanism that when pushed, exposes the first flow path. Due to the user's lower expiration rates, the device likely has enough time to accurately switch between flow paths during the test.

In the case of User B, expelled air can be hard to control in an automated device due to their higher expiration rates. If User B is known to expel their total expiratory volume in 1-2 seconds, their flow path may need to be restricted in order to create a longer dwell time that is manageable by the device. User B's device could use the same solenoid valve used in User A's example, however the processor would instruct the valve to pivot at a lower angle and create a flow path that is "halfway" open. Such a restrictive path would allow less air to travel through (i.e., would force a lower flow rate). Therefore, the valve could remain open for about 3 seconds (longer than it would take User B to fully exhale in the absence of any flow restriction) to evacuate the dead space volume. After about 3 seconds, the solenoid valve would close and deliver the rest of the breath sample to the disposable via a secondary flow path. The remaining volume (e.g., the analytical volume) may be delivered to the disposable without flow restriction, or while maintaining the "halfway" open flow path.

Figure 70:
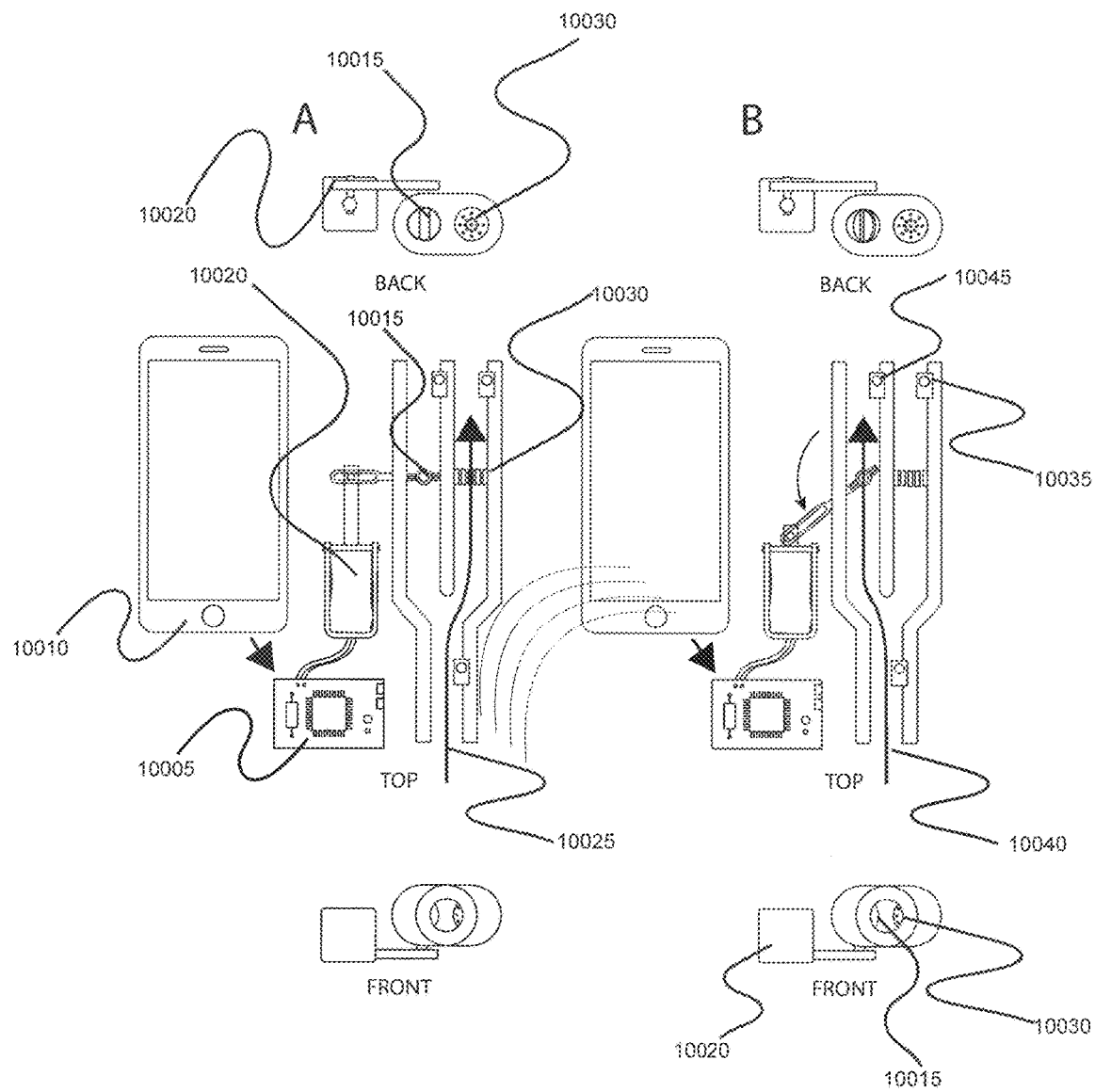
FIGS. 70A-B show an embodiment of a breath capture device that communicates with a processor that may be configured to control a solenoid valve.

FIG. 70 shows a breath capture device (e.g., a device such as might be used in the example immediately above) that communicates with a processor 10005. The processor controls a solenoid valve 10015, which is manipulated through the use of an actuating mechanism, e.g., a linear actuator 10020. The processor receives various inputs from the processor in order to perform an analysis.

When in an unactivated mode (A), the solenoid valve blocks one of two flow paths within the device. Following the path of least resistance, the breath sample will first flow through the second flow path 10025. The second flow path is comprised of a porous barrier 10030 that provides less resistance then the closed butterfly solenoid valve, as well as flow sensor 10035. The flow sensor 10035 measures how much air is going through the second flow path 10025 and communicates this to the processor, which then causes the solenoid valve to close the flow path when the desired vented volume has been evacuated.

After the evacuation of the desired vented volume, the device is in a different mode (B). In this mode, the processor 10005 instructs the linear actuator 10020 to retract, thus pivoting the solenoid valve 10015, and opening up the first flow path 10040. This first flow path 10040 now provides less resistance than the original porous barrier found in the second flow path. This flow path is coupled to a sensing element, such as colorimetric breath acetone analyzer. The first flow path also contains a flow sensor 10045 that determines when the gas delivery to the disposable cartridge is sufficient. The top and bottom of sections A and B contain perspective drawings of the device from the front and back, respectively.

Figure 71:
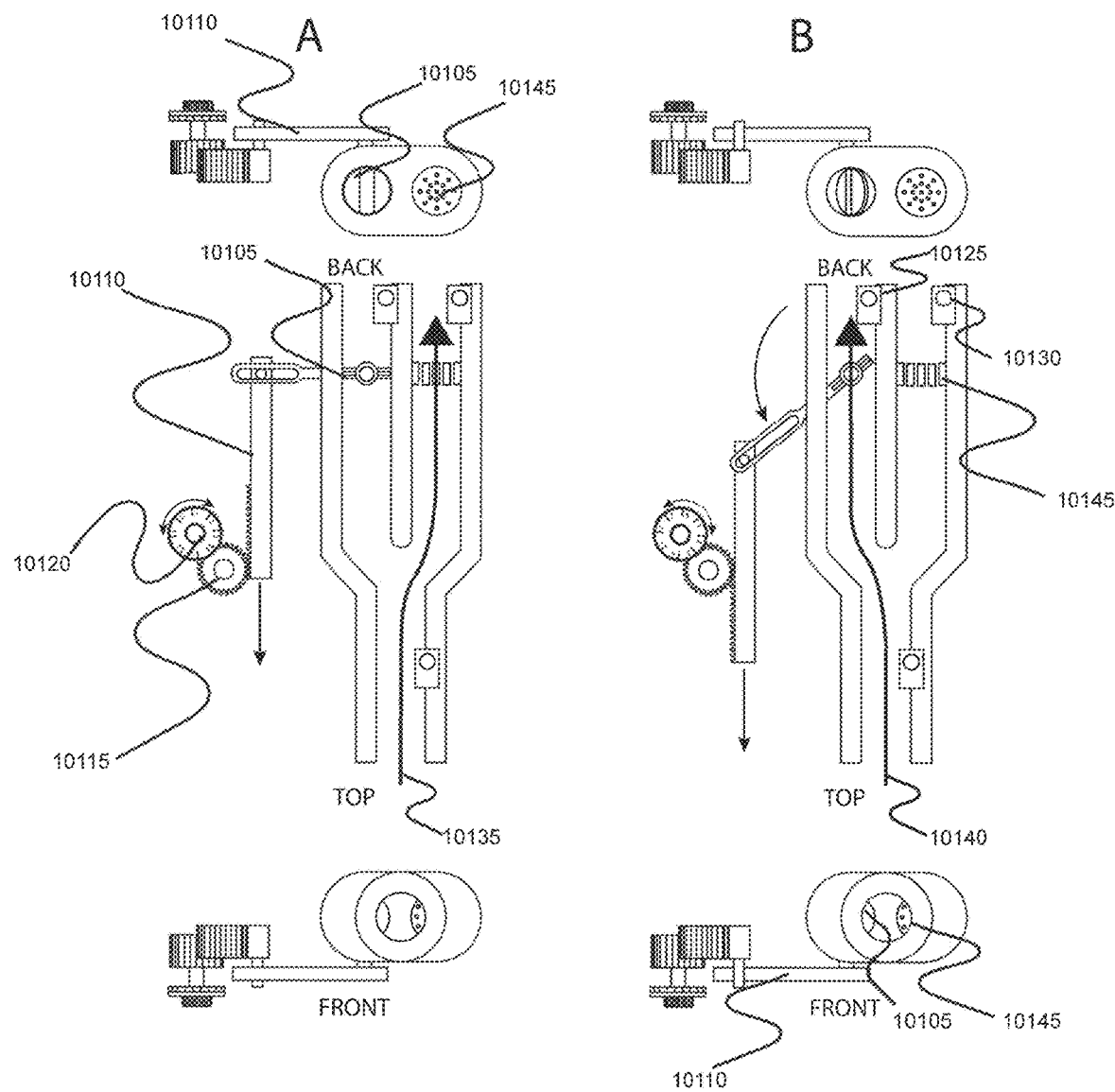
FIGS. 71A-B show an embodiment of a breath capture device that operates using mechanical principles.

FIG. 71 shows a breath capture device that operates using mechanical principles. In this embodiment, the solenoid valve 10105 is attached to a linear actuator 10110 that is controlled by a dial 10115. This dial is attached to gear 10120 that can be manipulated by the user. The gear 10120 contains various levels or notches that the user can set. The rotation of the gear directly influences the pivot angle of the solenoid valve 10105, which can provide variations in between the open and closed scenario identified in FIG. 70. As an example, if a particular user only required half the normal sample volume in order to complete the test, the solenoid valve could open "half-way" to lead to a semi-restrictive flow path. Similar to the embodiment illustrated in FIG. 70, this embodiment utilizes flow sensors 10125, 10130 in both flow paths 10135, 10140 to determine when the desired vented volume has been evacuated, when to switch flow paths, and when a test has been completed. The top and bottom of sections A and B contain perspective drawings of the device from the front and back, respectively.

User training and or preparation for exhalation may be accomplished in any of a number of ways. Some types of user training function simply to prepare the user for their ultimate exhalation. For example, a collection device or cartridge may be a bi-directional "whistle" that can accept exhalation into either end. In such devices one end may be a "dummy" end, while the other end is the analysis end. In some embodiments, the dummy end does nothing but accept exhalation. Such a featureless dummy end can simply allow the user to get in the mind-set of exhalation, e.g., thinking about how to properly exhale to satisfy the analytical portion's requirements). In other embodiments, the dummy end senses one or more characteristics of the user's exhalation. For example, the dummy end senses that the user has actually performed at least one practice exhalation. In some embodiments, the analysis end includes a valve that prevents the user from exhaling into the analysis end until the dummy end has detected at least one practice exhalation. In much the same way, the dummy end may respond (e.g., signal the user or allow exhalation into the analysis end) once the user has performed a number (e.g., 1, 2, 3, 4, or more) of correct exhalations (e.g., exhalations that satisfy the exhalation required by the testing parameters). Such a user training system may help to ensure that each and every test cartridge is used to the fullest of its potential and that no cartridges are wasted or false results produced due to improper exhalation by the user.

To more effectively separate different breath segments (e.g., I, II, III and IV, or combinations thereof, from FIG. 4), a system can utilize different potential triggers. In one embodiment, the system analyzes the volume of breath passing through the device. The first portion of breath that is exhaled is "dead space"—e.g., air from the mouth and upper trachea. In some embodiments, it is desirable to capture breath that is deeper in the respiratory tract as that air has been in more direct contact with the blood from which volatile organics will evaporate. In this case, the device could utilize a timer to determine how much volume of breath has passed through the device. A timer would be used if the user's flow rate is constant or above a certain level. If that flow rate is known, then it need only be multiplied by time to determine how much breath has passed through the device. In general, for an adult, an alveolar breath sample occurs after about 230 ml of breath. In another embodiment, the system would begin to take an alveolar breath sample after about 300 ml of breath have been passed through the device. This would insure that an alveolar sample is collected, but may reduce the precision of the device.

In another embodiment, the system measures temperature to determine when an alveolar breath sample has been obtained. A device can measure temperature with a thermistor or any other appropriate temperature measuring device. Systems based on temperature sensors may require ambient temperature as a reference. Breath that is close to the blood (e.g., breath that is in the lungs) will be at about body temperature (roughly 37° C.). Atmospheric gas (e.g., air), on the other hand, should be close to or at the ambient temperature. In one embodiment, the device directs breath to a reactive chamber only after or when it detects that the breath's temperature is about 90% closer to the body temperature than the ambient air temperature. For example, if the outside temperature is 25° C. and the individual is at 37° C., designate the sample at 0.9*(37° C.−25° C.)+25° C.=35.8° C. This should help to ensure that substantially only alveolar breath is collected.

In another embodiment, the system measures the carbon dioxide concentration to determine when an alveolar breath sample should be obtained. FIG. 58 shows a graph of the general relationship between carbon dioxide concentration as a function of the amount of air expired. Around about the exhalation of 250 ml to 300 ml of breath, the concentration of carbon dioxide increases rapidly and then remains approximately constant, regardless of the volume of expired air. As shown in FIG. 59, carbon dioxide concentration is significantly higher in alveolar air than atmospheric or expired air—this is because carbon dioxide is produced as the body metabolizes fuel substrates. In fact, as shown in FIG. 59, atmospheric air comprises only about 0.04% carbon dioxide, well below half a percent. By contrast, expired air comprises between about 3.6 and 5.3% carbon dioxide. Using these approximations, it can be seen that expired air has between about 7 and 130 times the concentration of carbon dioxide as does atmospheric air. In one embodiment, the system may include a carbon dioxide sensor in line with the exhalation pathway. In one embodiment, the device directs breath to the reactive chamber only after or when it detects that the carbon dioxide concentration is a concentration indicative of the desired breath segment (e.g., for alveolar air it is between about 3.6% or 5.3%). This should help to ensure that substantially only alveolar breath is collected.

In another embodiment, the system measures the oxygen concentration to determine when an alveolar breath sample should be obtained. With continued reference to FIGS. 58 & 59, oxygen concentration is significantly lower in alveolar air than atmospheric or expired air because oxygen is consumed as the body metabolizes fuel substrates. In addition to showing the relationship between carbon dioxide and volume of air expired, FIG. 58 shows a graph of the general relationship between oxygen concentration as a function of the amount of air expired. Around about the exhalation of 250 ml to 300 ml of breath, the concentration of carbon dioxide decreases rapidly and then remains approximately constant, regardless of the volume of expired air. This is because oxygen is absorbed at higher rates the deeper into the respiratory tract—the trachea absorbs dramatically less oxygen from inspired air than do the alveoli. As shown in FIG. 59, oxygen concentration is lower in both alveolar and expired air than in atmospheric—this is because oxygen is consumed as the body metabolizes fuel substrates. In fact, as shown in FIG. 59, alveolar air comprises only about 13.6% oxygen. By contrast, expired and atmospheric air comprise about 15.7% and 20.84% oxygen, respectively While not as a dramatic difference in concentrations as is observed with carbon dioxide, this change in concentration may also be used to segment or fractionate a breath. In one embodiment, the system may include an oxygen sensor in line with the exhalation pathway. In one embodiment, the device would direct alveolar breath to the reactive chamber only when or after it detects that the oxygen concentration is around less than about 15.7% or 13.6%.

In yet another embodiment, the system measures another analyte to determine when to collect any given breath sample, e.g., when an alveolar breath sample should be obtained. For example, certain analytes may be predominantly present in alveolar breath segments. Alternatively, other analytes may be predominantly present in tracheal breath segments. The presence or absence of such analytes can be used to determine if a breath segment from the alveoli or the trachea is being analyzed. FIG. 59 lists the relative amounts of various analytes at different segments of breath. This information can be used to by a sensor in line with the exhalation pathway.

In another embodiment, the system may aggregate information over time of through calibration of a user's history. Once a user is trained to properly exhale through the device, the user's prior history may be used to determine if an alveolar sample (or other desired sample) has been collected. As one simple example, that data or user history may include when that user's exhalation begins to include alveolar breath based on any of the preceding methods done over many uses. In one embodiment, the system includes a process that stores or can access data, e.g., a user history log. In some embodiments, the device may compare a present data variable(s) (e.g., one or more of temperature, carbon dioxide concentration, oxygen concentration, time, flow rate/volume, etc.) to the user's history: if the present data variable(s) falls within an acceptable margin of error (e.g., a previously determined acceptable margin of error), the device accepts the test as valid; if the present data variable(s) fall outside the acceptable margin of error, the device discards the test as invalid (e.g., stamps a chip associated with that test) so that the test is not ultimately used. Of course, validating a user's test based on an increasing number of variables may tend to improve the likelihood a test identified as valid is, indeed, valid. In that case, it is likely that the number of false positive test results will decrease. However, as the number of variables increases, the number of valid test results will likely decrease because one or more of the multiple variables being compared may be outside of an acceptable range. In this case, it is likely that the number of false negative test results will increase. Acceptable values may be tailored to the user an application by varying the number of compared variables (i.e., increasing or decreasing the number of variables) as well as the acceptable margins of error (i.e., increasing or decreasing the acceptable margins of error).

In another embodiment, the system may use user input to determine when an alveolar sample has been collected or when alveolar breath should be directed to the reactive chamber. Information such a population data or data from other equipment, e.g., spirometry, can be inputted by the user to assist. In another embodiment, the user may input the time (e.g., 2 seconds) as the time when alveolar breath should be directed to the reactive chamber.

In some embodiments, the system monitors the user's exhalation and signals the user when to capture a sample, e.g., a deep lung sample. For example, a user may simply being exhaling into the system at which time the system registers the commencement of the user's breath. The user may be trained to continue exhaling into the device. Based on factors, parameters, and data discussed elsewhere herein (e.g., time, volume, temperature, carbon dioxide concentration, oxygen concentration, or a combination of any of these), the system identifies the segment of interest of the user's breath and signals the user when that segment is reached or ready for collection. In some embodiments, the system signals the user minimally in advance of when the sample is ready for collection so that none of the sample is accidentally discarded as exhaust gas. For example, the system may signal the user in advance of sample collection by a time of about 0.25 seconds, 0.5 seconds, 0.75 seconds, 1 second, or more than 1 second, depending on the user and the desired sample. The signal provided or given by the device to the user may be any of a visual, auditor, or haptic signal. For example, for a visual signal the device may have an LED (or any other type of light) that changes color (e.g., from red to green), blinks, turns off, gets brighter, or dims. Alternatively, for an auditory signal the device may have a speaker that beeps, makes a tone, increases in volume, decreases in volume, increases in pitch, or decreases in pitch. Finally, for a tactile signal the device may have a buzzer that vibrates, buzzes, or shakes. Once the device has signaled the user that they have reached the appropriate time to collect the desired sample or segment, the user may interact with the device to take the sample. For example, in some embodiments, the device has an analysis end and a dummy end (as discussed above): when the device signals the user, the user stops exhaling into the dummy end and begins exhaling into the analysis end (e.g., substantially immediately, or as quickly as possible). Alternatively, the user may push a button or flip a switch that changes the flow path from an exhaust route to an analysis route.

Figure 72:
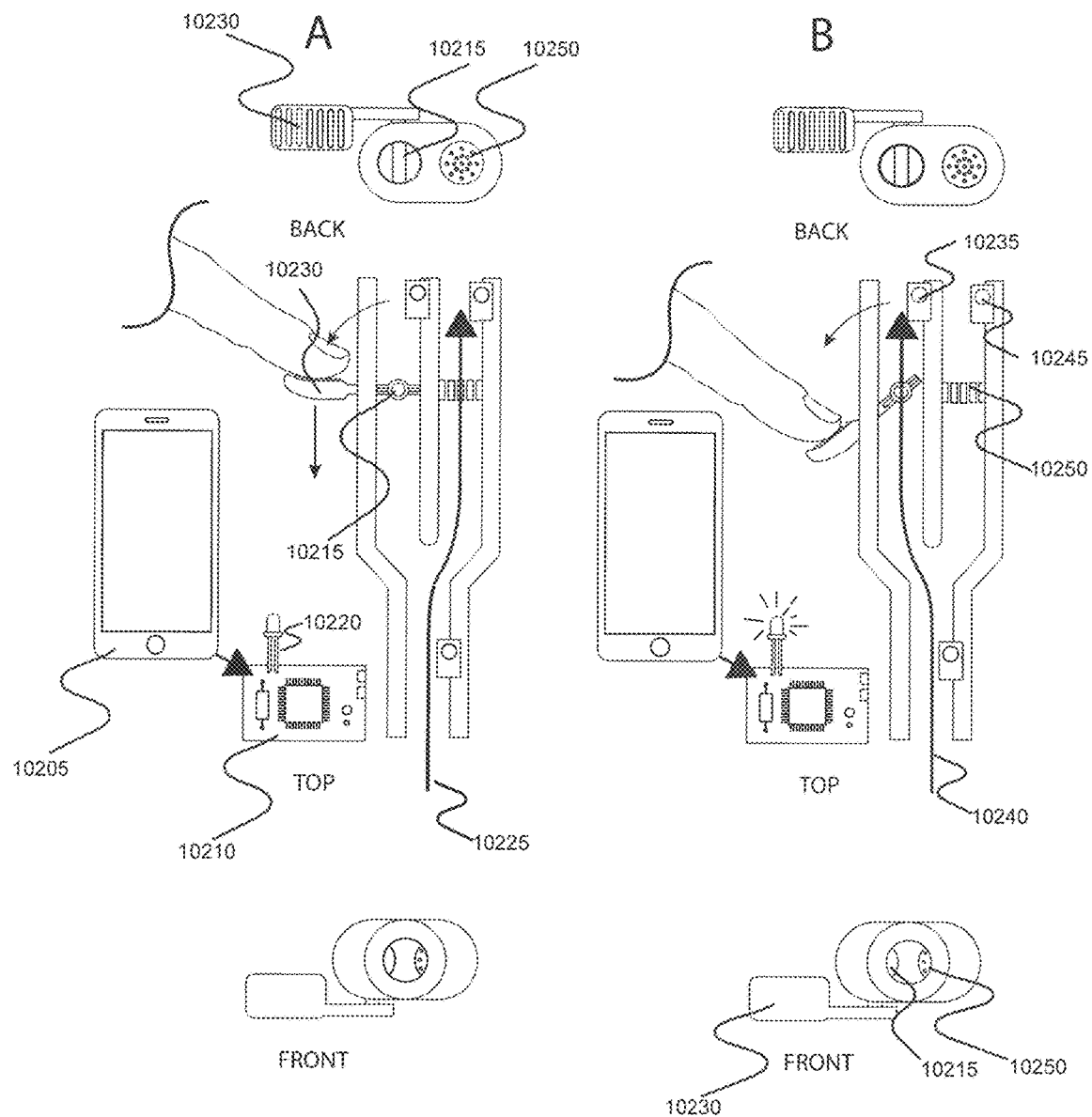
FIGS. 72A-B & 73A-B show various embodiments of a breath capture device that involves interaction with the user to switch the flow path.

FIG. 72 shows an embodiment of a breath capture device that involves interaction with the user to switch the flow path. In this embodiment, the processor 10210 does not directly attach to the solenoid valve 10215, and instead contains an indicator 10220. As discussed above, this indicator 10220 can be in the form of an LED light or other visual notification, or can also be a speaker that emits an audio indicator for the user. The first flow path 10225 in this embodiment is comprised of a butterfly valve attached to a finger pedal 10230 or lever, and a mass flow sensor 10235. In an unactivated mode (A), the breath sample travels through the second flow path until the indicator is activated. This indicator serves the purpose of notifying the user to push the level, thus exposing the first flow path. This indicator remains active, to let the user know to keep the first flow path open until the test is over, symbolized by the turning off or inactivation of the indicator. This embodiment does not allow for any variations in the resistance of the first flow path. The top and bottom of sections A and B contain perspective drawings of the device from the front and back, respectively.

Figure 73:
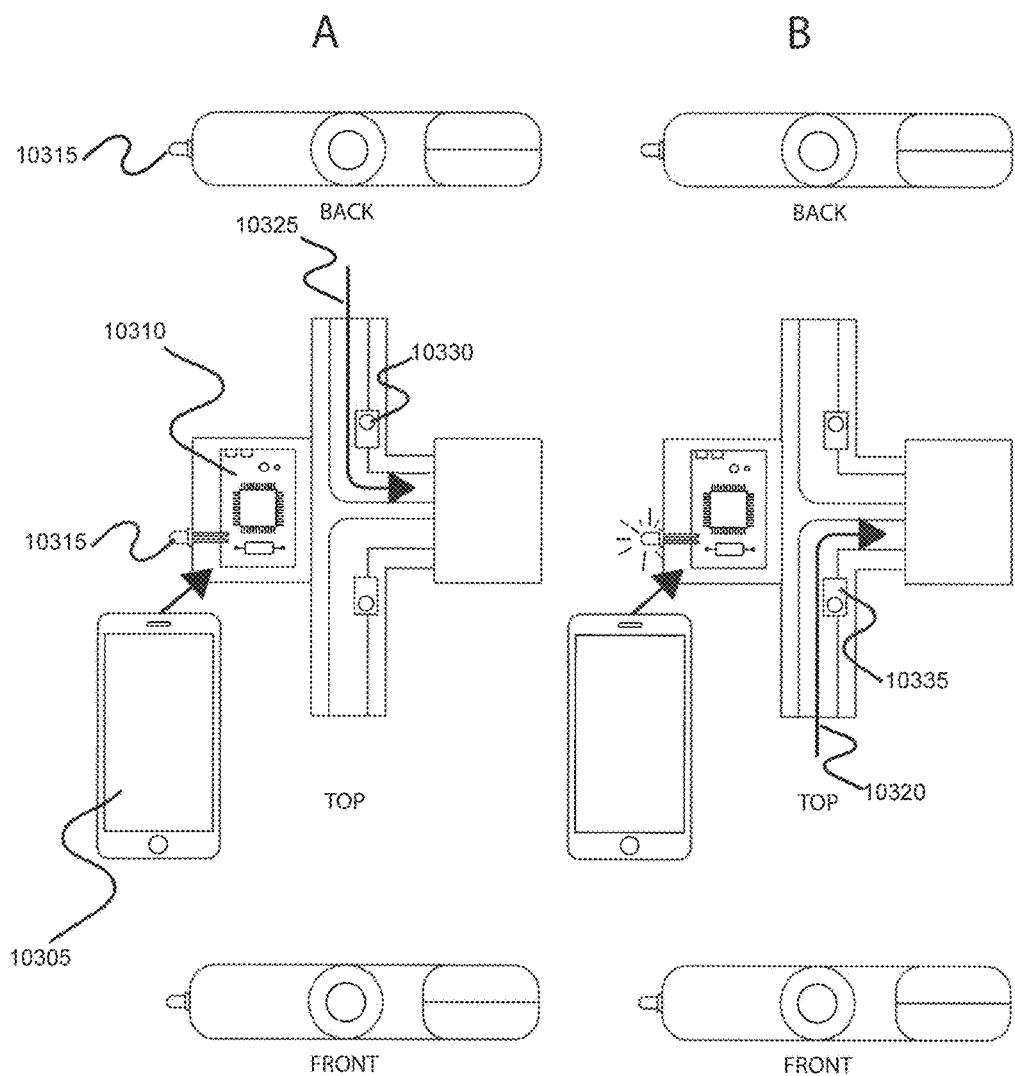

FIG. 73 shows another breath capture device that involves interaction with the user to switch the flow path. Here, the system includes a mobile interface and processor. Similar to the example in FIG. 72, this embodiment also utilizes an indicator. In this embodiment, however, there are two flow paths that are identical, with the exception that one flow path would be attached to the disposable cartridge. Both flow paths remain open at all times. Flow paths are alternated by physically rotating the device, and breathing into the alternative flow path. In an unactivated mode (A), the sample will travel through the flow path that does not contain the disposable cartridge until the flow sensor indicates that the dead space has been evacuated. At this time, the flow sensor input will be received by the processor. The processor activates or turns on the indicator. This will notify the user to rotate the device and deliver sample through the second flow path, and through the disposable cartridge. The indicator turns off at the end of the test, notifying the user to discontinue breathing into the device. The top and bottom of sections A and B contain perspective drawings of the device from the front and back, respectively.

In addition to separating the desired vented volume from a desired alveolar volume, the separate flow paths can be utilized in other applications. As an example, two users can operate from the same device. When a flow path has been switched or rotated, the processor can operate under a different breath profile. Under this application, each separate flow path may end in a cartridge. The flow sensor and indicator can be utilized to tell the user when to attach and remove the disposable cartridge. The cartridge would be attached after the desired vented volume and removed at the end of a test.

Alternatively, the two separate flow paths can facilitate two different tests for a single user. Under this application, each separate flow path may end in two different cartridges, for example, one (1) acetone cartridge and one (1) ammonia cartridge. The flow sensor and indicator would be utilized to instruct the user when to attach and move the disposable cartridge. Different variations of the indicator (for example, differently colored lights) can be utilized to determine when switch to rotate the device and begin a new test.

The breath analysis system preferably comprises an air fractionator that separates the breath sample into different segments or fractions of interest. Exemplary apparatus and methods to achieve this are disclosed elsewhere herein as well as in U.S. Patent Application Ser. No. 62/247,778, which is hereby incorporated herein by express reference as if fully set forth herein.

Signal generation can be accomplished using a wide variety of known transduction techniques in conjunction with appropriate sensors. Examples include, but are not limited to: colorimetric analysis of chemical reactions measured by reflectance, colorimetric analysis of chemical reactions measured by absorbance, fluorescence analysis of chemical reactions measured by lifetime analysis, analyte-nanoparticle interactions measured by resistance/impedance analysis, electrochemical analysis of chemical reactions measured by chronoamperometry, gas concentration analysis by laser absorbance, and many others.

The manner in which the breath sample is obtained and the profile segment definitions and demarcations can have a significant impact on the quantity and quality of information that can be obtained.

There are a plethora of different breath profiles. Breath is also rich with different analytes. In addition to selecting chemistry, transducers, environmental controls, etc. to facilitate the analysis of a particular analyte, it is also important to select a breath profile that is of significance to the analyte of interest.

Selecting the appropriate breath profile for a particular analyte renders more meaningful information than analyzing all analytes using a generic breath profile. For example, nitric oxide may be present in the bloodstream and thus in alveolar air as equilibrium is achieved between the breath and blood. However, nitric oxide may also be generated in the bronchial tubes in the event of airway constriction due to conditions like asthma.

The breath profile may be the natural result of the breathing characteristics of the patient, for example, as when a patient is asked to merely breath normally into the device. Alternatively, in some instances it is desirable or necessary for the patient to be instructed on what breathing profile he or she is to use. For example, it may be desirable for the patient to inhale maximally before a breath is delivered to the breath analysis device. Other examples of patient instructions or user-modified breathing profiles include rapid exhalations, slow and steady exhalations, shallow inhalations, deep exhalations with shallow inhalations, etc.

In light of this, it may be advantageous in some instances to provide a patient assist device, which may be any apparatus that aids the patient in conforming to a breath profile. For instance, a patient assist device may be a flow restrictor that is designed to help the patient breath in a consistent manner. Patient assist devices are increasingly significant if the breath profile is complex or if the patient has a hard time following directions.

Preferably breath profiles are used in conjunction with a plurality of breaths (e.g., multi-breath analysis), whether rebreathing or non-rebreathing.

Under certain circumstances, it may be useful to display information to the user regarding the status of the analysis, e.g., breath profile. This information may be provided during the analysis process, e.g., a graph showing the user what to do next, or at the end of the analysis, e.g., providing instruction to the user that he or she did not perform the test correctly for one or more of the breath profiles.

The breath analyzers may and preferably will also include an interface by which the device may instruct the user what to do next. This is particularly significant if a complex breath profile is required, such as the breath profile described in FIG. 15. The device may, and preferably will, position sequential breath profiles in the order of hardest to easiest or requiring the most to least concentration to account for diminishing attention or reduced compliance over time by the patient. In other words, if breath profile A is the most difficult as it involves multiple re-breaths and it also provides the most critical information, the software incorporated within the device may provide instruction such that breath profile A is performed prior to breath profile B, C, and D. Yet another ordering scheme has to do with ordering the tests such that one test does not interfere with the next. For instance, forced expiration may cause error to computation of the respiratory quotient (RQ). Accordingly, if forced expiration is useful for measurement of a particular analyte, this may be performed after the more relaxed breathing for RQ.

Example of Detection of Diabetes Onset Using Breath Acetone Concentration

To illustrate certain aspects of at least one embodiment of the invention, consider the following example. A physician suspects a patient is suffering from the onset of diabetes. Acetone in breath has been correlated with fat metabolism, and can be used to identify metabolic issues associated with the onset of diabetes. The physician therefore seeks to use a breath analysis device to analyze the patient's breath for this analyte using apparatus (4) appropriately configured for this test, as described elsewhere herein.

A suitable test for breath acetone is a normal, single breath exhalation, such as that shown in FIG. 3. This breath profile is selected and/or preprogrammed into processor 38 of apparatus (4).

Breath acetone appears in the breath endogenously through fat metabolism. The acetone, being a volatile organic chemical, travels through the vascular system into the lungs, where it permeates the lung tissue and enters the deep alveolar spaces. As it accumulates in the deep alveoli, it diffuses into the general alveolar space, but typically does not infiltrate into the upper airways, at least not in significant concentrations. Accordingly, the processor of apparatus (4) has been previously programmed and configured to segregate the breath profile into four segments (roman numerals I through IV), corresponding to the upper airways (post tracheal airways (I) and bronchial spaces (II)), general alveolar spaces (III) and deep alveolar spaces (IV). The processor is also preprogrammed to select segments III and IV as those of interest based on the expectation of their relatively higher concentrations of acetone. Note that, instead of preprogramming, apparatus (4) may be configured to allow the user to select these inputs, e.g., using a user input such as a key pad, keyboard, or the like.

Acetone in the selected gas fraction can be measured through a variety of means. Preferably, an acetone sensor is comprised of a disposable reactive volume of chemically-coupled silica gel particles housed in a hand-held cartridge. Acetone in a gas sample flowing over the silica particles adheres to the silica gel and reacts to form a colored product when in the presence of a reaction-promoting solution. A color camera or other light-sensing device, preferentially with spatial resolution, can be used to quantitate the color change and to correlate that change to acetone concentration.

The subject is then asked to exhale into the mouthpiece. In its initial state, the valving device is in its closed position. As the subject exhales into the device, pneumotachometer or alternative flow measurement device 18 provides pressure and velocity information to the processor. As pressure increases from its initial value, the processor causes the valving device to move from its initial closed position to the second open position, whereupon the initial portion of the breath sample is vented via the conduit and the exhaust conduit out of the apparatus. As the breath sample input proceeds, the processor traces out the breath profile and divides it into the four segments noted above.

When the processor identifies the transition from segment II to segment III, it causes the valving device to move to the first open position, whereupon the breath sample is directed via the conduit to the reaction cavity and the sensor. Acetone present in the breath sample contacts the reactive surface or component of the sensor, where it reacts and a signal representative of the concentration of the acetone is generated. This signal is communicated to the processor, which then generates a corresponding output of this sensed information on the display. In some embodiments, the device (e.g., breath analysis device) senses one or more real time exhalation characteristics (flow rate, pressure, exhalation time, temperature, etc.) that are used to control the valve. Such characteristics may be logged in the breath analysis device together with any associated acetone measurements. Logged information may later be used to, for example, discard or discount aberrational acetone measurements, or to adjust these measurements to compensate for deviations in the users exhalation pattern. Additionally, the device may also incorporate a processor that runs a learning algorithm to analyze the log and associated measurements to determine appropriate compensation factors for the user. Examples of various compensation factors are described in U.S. patent application Ser. No. 14/690,756, filed Apr. 20, 2015, now U.S. Pat. No. 9,486,169, which is hereby incorporated by express reference as if fully set forth herein, As the exhalation attenuates and the flow velocity reduces below a threshold level as detected by pneumotachometer or a flow measurement device, the processor causes the valving device to return to the second open position, thus stopping the flow into the reaction cavity and causing it to be vented via the conduits. When flow stops, the processor causes the valving device to close to avoid backflowing ambient air into the apparatus (4) if the subject then inhales through it.

Figure 25:
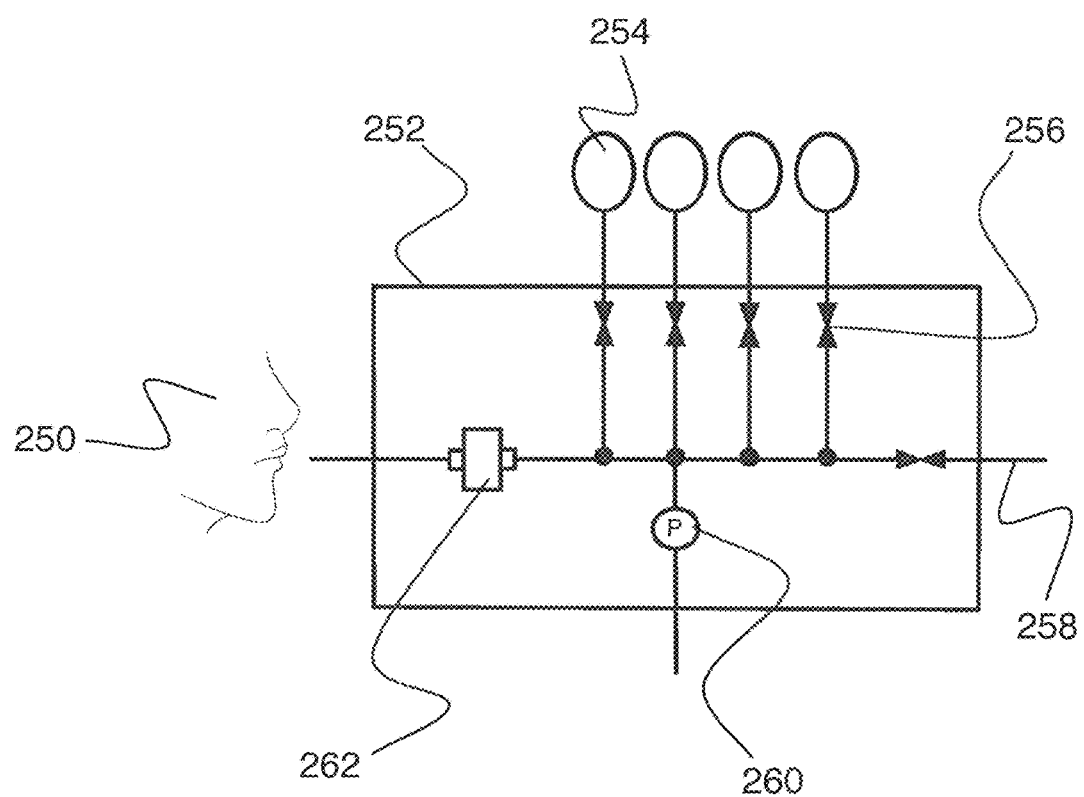
FIG. 25 is an embodiment of a breath analysis device that utilizes breath profiles.

Example of Fractionation of a Breath to Detect Analytes in Separate Breath Segments Multiple analytes in a single exhalation can be quantified in a manner similar to that described herein. In this case, however, provisions must be made so that a gas sample, sufficient to be split amongst the multiple sensors, can be directed to those sensors in sequence or in parallel. In some cases, a sampling protocol may require the collection of gas fractions from different anatomical regions; in other cases, the anatomical region to source the samples can be the same. An example of a flexible system capable of measuring 4 different analytes from four physiological regions in a single breath is shown in FIG. 25. In this example, a user breathes into a breath input device and the exhaled pressure is measured using a pressure transducer. The exhaled volume and flow rate are also measured using a pneumotachometer or alternative flow measurement device. At the required time, the first valve in a valve array is opened, allowing the first bag of a bag array to fill with gas corresponding to physiological region I. The other bags are filled in sequence until all bags are filled with samples from distinct regions. Each bag can then be evacuated in sequence and directed to sensors for a single analyte or multiple analytes, depending on the needs of the measurement and the available hardware. Some embodiments make use of multiple and/or separate sensors, e.g., a sensor for acetone and a sensor for ammonia. The gas from a particular region is evacuated from the bag and the contents are passed over a chemically reactive column first for acetone and the resultant color change (in response to analyte concentration) is measured with a camera. A second portion of gas is sent to an ammonia column. Up to four different analytes (or the same analyte from four separate regions) can be measured from a single breath in this manner.

As the volumetric capacity of the human lung will vary from individual to individual, more significant results may be obtained by first measuring the maximum exhaled volume of an individual and dividing the exhaled air into fractions by the percentage of maximum volume that has been exhaled.

Example of Analysis of Complex Combination of Other Breath Profiles

Figure 12:
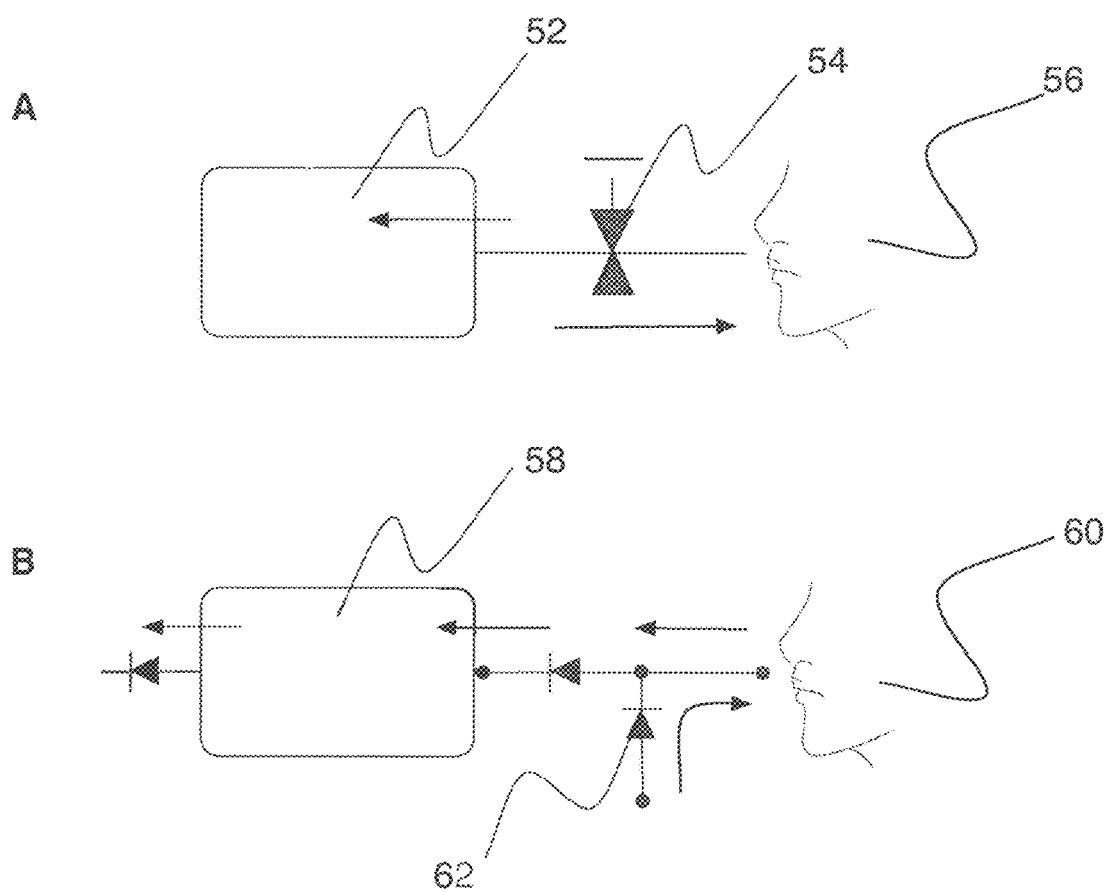
FIGS. 12A-B demonstrate two valving systems used for rebreathing and non-rebreathing applications.

Multiple breath profiles include rebreathing and non-rebreathing modalities. These are illustrated in FIG. 12. In panel A, a valve is used to assist in the capture and containment of breath samples. With the valve open, the subject can re-breath the air in the bag, thus accumulating volatile compounds and allowing the individual to breath in a natural fashion. When the sampling is completed, the valve is shut. In panel B, a non-rebreathing sampling scheme is depicted. In this case, two one-way valves combine to form a non-rebreathing valve such that inhalations of the subject draw air from the ambient, whereas exhalations push air into the collection bag. An optional valve at the outlet of the bag allows breathing to continue indefinitely to assure contamination-free concentrations of exhaled breath.

A breath profile may also be a complex combination of other breath profiles. See FIG. 15. In this figure, the complete breath profile comprises a normal single exhalation, followed by multiple re-breaths, followed by a single exhalation where the user is instructed to maintain a steady flow.

The above method is preferably repeated for a plurality of analytes.

FIG. 3 is a flow chart demonstrating a method for operating a breath analysis device using multiple breath profiles. Step 1 prompts for the user to identify an analyte of interest. Step 2 prompts the user to specify a breath profile. Step 3 prompts the user to input whether further analyte-breath profile combinations are desired.

FIG. 1 is a breath analysis device that comprises feedback to the patient regarding compliance with a breath profile. A patient configures a breath analyzer by using the keyboard to input the desired analyte of interest and the desired breath input. The display appears to provide feedback to the patient as to whether the patient is complying with the desired breath profile. Once the patient has configured the device, the patient exhales through the breath input and the breath is directed to the analysis portion of the device. The analysis portion may comprise a valving system and/or a sensor.

Preferably, the analyzer is conducive to field analysis, or otherwise to make such assessment without a requirement for expensive and cumbersome support equipment such as would be available in a hospital, laboratory or test facility. It is often desirable to do so in some cases with a largely self-contained device, preferably portable, and often preferably easy to use. It also is necessary or desirable in some instances to have the capability to sense the analyte in the fluid stream in real time or near real time. In addition, and as a general matter, it is highly desirable to accomplish such sensing accurately and reliably.

Figure 13:
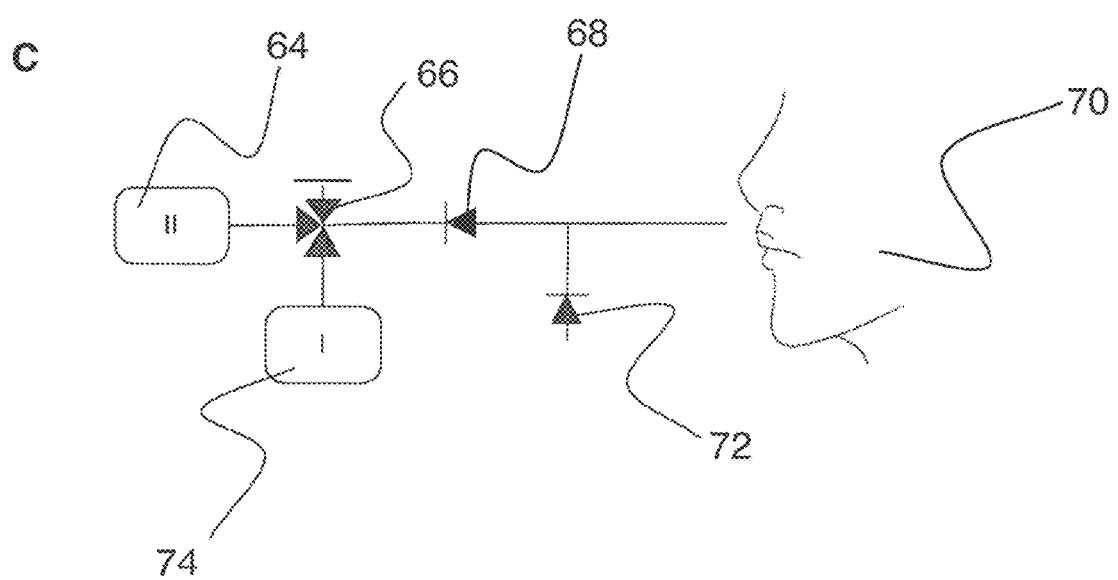
FIG. 13 is an example of a valving system used to fractionate exhaled breath.

FIG. 13 depicts a system that could be used to automatically fractionate the expired air into samples I and II (not necessarily corresponding to the theoretical regions I and II as discussed earlier). An automatic three-way valve directs expired air to either bag I or II. Note that for this to be successful, the dead volume of the apparatus from the patient mouth to the outlets of the three-way valve must be sufficiently small. This may require an automated 4-way valve, where the patient draws air from one port, and then the valve can be automatically switched between outlet port A and outlet port B. An idea for an automated 4-way valve uses a single actuator to control stops on a rod to provide mechanical hindrance to the passive opening of the standard non-rebreathing valves.

Figure 14:
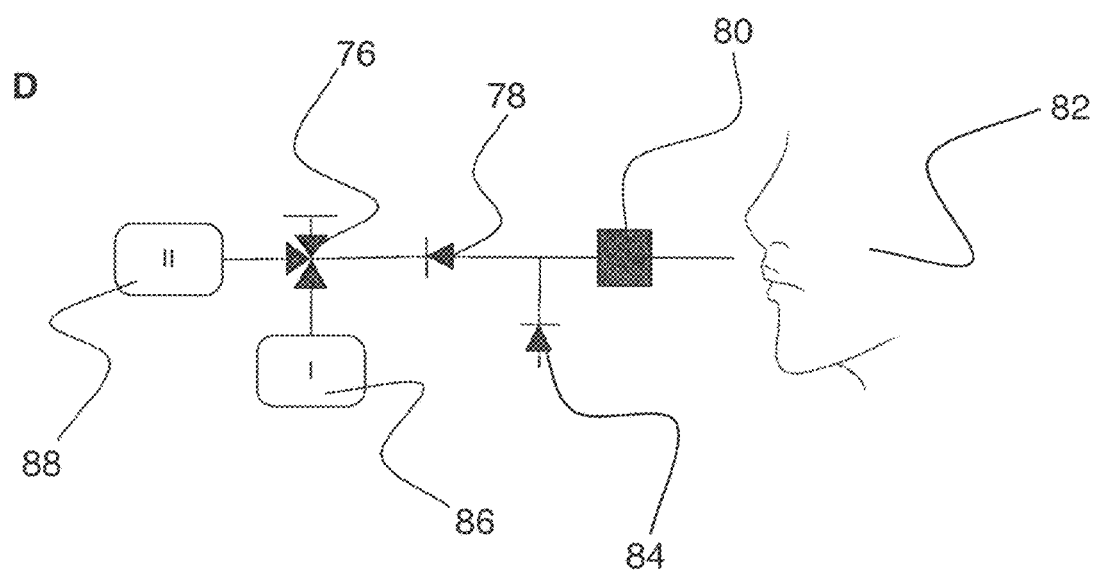
FIG. 14 is another example of a valving system used to fractionate exhaled breath.

A further refinement of this idea is shown in FIG. 14. In this figure, the ability of the system to make closed-loop decisions on valve switch times is afforded by a high-speed sensor for a gas (carbon dioxide in the example). When the carbon dioxide concentration in a breathing cycle crosses a certain threshold, then the automated non-rebreathing valve is actuated. In this way, a patient can sit at the instrument and breath repeatedly and comfortably. With no intervention from the user, the system can fractionate the breath into two components. The contents of the bags, in light of both their analytes and the information regarding their physiological source, can be of interest.

In certain cases it may be important to control the inhalation depth of a patient before a breath is expired in order to control the breath profile. Measuring the pressure at the mouth can be an objective means to determine when a certain inhalation (or exhalation) volume has been achieved.

Figure 26:
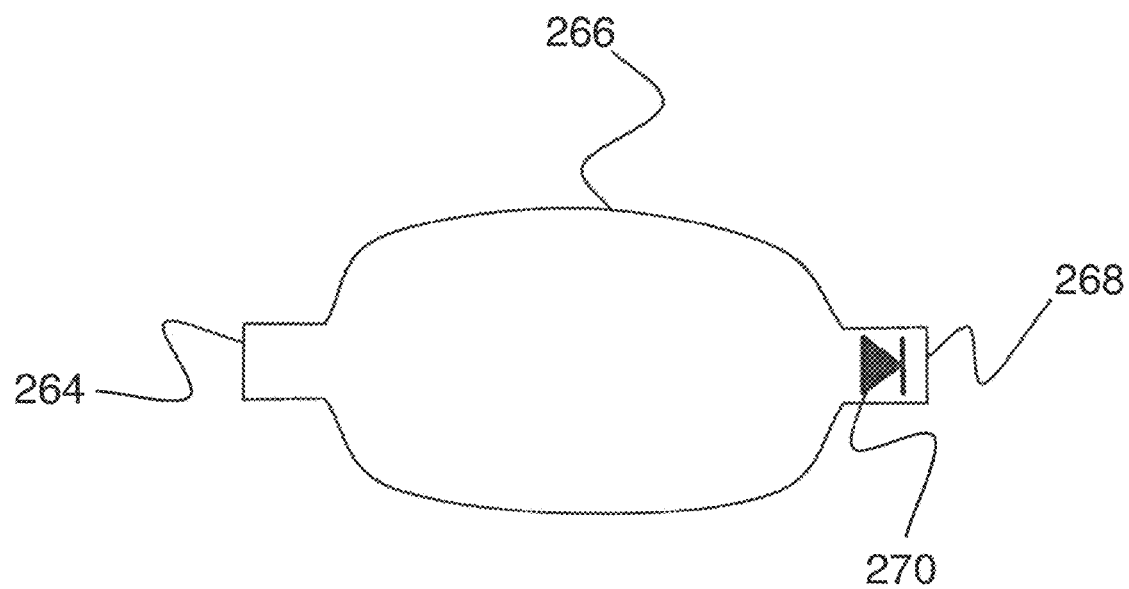
FIG. 26 is an example of a valved breath bag.

A bag for passively collecting breath fractions from either the upper airways or deep alveolar region is presented in FIG. 26. With this apparatus, a breath bag is fitted at one end with a breath inlet and at the other a one-way valve. The breath inlet contains a spring-loaded ball valve, or suitable alternative, such that compression of the mouthpiece opens the breath inlet to accept exhaled air and the bag can be inflated. The one-way valve contains a threaded lock disk such that the valve can be configured to open against small amounts of pressure or to be permanently closed. If a deep alveolar sample is desired (or prompted by device software), then the one-way valve lock disk is turned to allow the valve to crack. A user pinches to release to spring-loaded ball valve in the inlet and breathes to inflate the bag. The first portion of breath is largely displaced by successive portions as the exit valve allows the early breath samples to exit the bag. At the end of an exhalation, the bag is filled primarily with deep alveolar air. Releasing the spring-loaded ball valve traps the sample in the bag until the bag is evacuated through the suction of an external pump. If an upper airways fraction is desired, the user turns the lock ring on the one-way valve to close the valve. The user inflates the bag until the bag is filled. The bag is thus filled with upper airway air. The lock-ring is turned to allow cracking of the one-way valve to enable evacuation of the bag contents through the suction of an external pump.

In accordance with another aspect of the invention, a method is provided for analyzing an analyte in breath of a patient, wherein the method comprises inputting a first sample of the breath from the patient into an apparatus as a first breath profile, segregating the first breath profile into a plurality of breath profile segments corresponding to anatomical regions of the patient, inputting a second sample of the breath from the patient having characteristics substantially similar to the first profile into the apparatus as a second breath profile, and using the first breath profile to analyze the second breath profile during at least one portion but less than all portions of the second breath profile.

In certain circumstances, it may be desirable to establish a baseline with a breath profile. Establishing a baseline can be important for a number of reasons. In the event of expensive reagents, the first breath sample may be obtained to prime the device and the user for the second breath sample, which is the one actually analyzed. This may help minimize unnecessary reagent waste and reduce the overall cost.

In instances of complex analysis, e.g., analysis requiring high selectivity or sensitivity, inputting a first breath sample may enable the apparatus to lock in certain parameters and limit the subsequent analysis to those parameters of increased complexity.

Additionally, in the event of an inexperienced, non-compliant, or distressed patient, the first breath profile may be used to help determine if the user needs further instructions so as to streamline the measurement process.

Breath analyzers employing the breath profile approach preferably include a volume measurement apparatus. The volume measurement apparatus allows for the breath profile to be studied and allows the device to provide feedback to the user if the user did not perform the measurement correctly. The volume measurement apparatus may be any device or system that can determine the flow profile, e.g., a pressure transducer.

The breath analyzers may and preferably will also include an interface by which the device may instruct the user what to do next. This is particularly significant if a complex breath profile is required, such as the breath profile described in FIG. 15. The device may, and preferably will, position sequential breath profiles in the order of hardest to easiest or requiring the most to least concentration to account for diminishing attention or reduced compliance over time by the patient. In other words, if breath profile A is the most difficult as it involves multiple re-breaths and it also provides the most critical information, the software incorporated within the device may provide instruction such that breath profile A is performed prior to breath profile B, C, and D. Yet another ordering scheme has to do with ordering the tests such that one test does not interfere with the next. For instance, forced expiration may cause error to computation of the respiratory quotient (RQ). Accordingly, if forced expiration is useful for measurement of a particular analyte, this may be performed after the more relaxed breathing for RQ.

Production Rate

In accordance with another aspect of the invention, a method is provided for obtaining information about a physiological production rate of an endogenous analyte from a breath sample of a patient. The method comprises providing an apparatus that comprises a breath input portion and an analysis portion, and inputting the breath sample into the breath input portion. The breath sample comprises a breath profile comprising at least one breath, wherein each of the at least one breaths comprising a plurality of segments, and each of the segments of a given breath corresponds to an anatomical region of the patient that is non-identical to the anatomical regions for others of the segments. The method also comprises analyzing at least one but less than all of the breath profile segments of each of the breaths of the breath profile to sense the analyte within the anatomical region or regions corresponding to the at least one breath profile segments to obtain the information about the physiological production rate of the analyte, and generating a signal in the apparatus representative of the information.

Example of Detecting Production Rate of Endogenous Volatile Organic Compound

In the case of using an apparatus to determine the production rate of an endogenous volatile organic compounds, the manner in which the analysis is conducted and the sample is collected can have profound impact on the significance of the information obtained.

Figure 23:
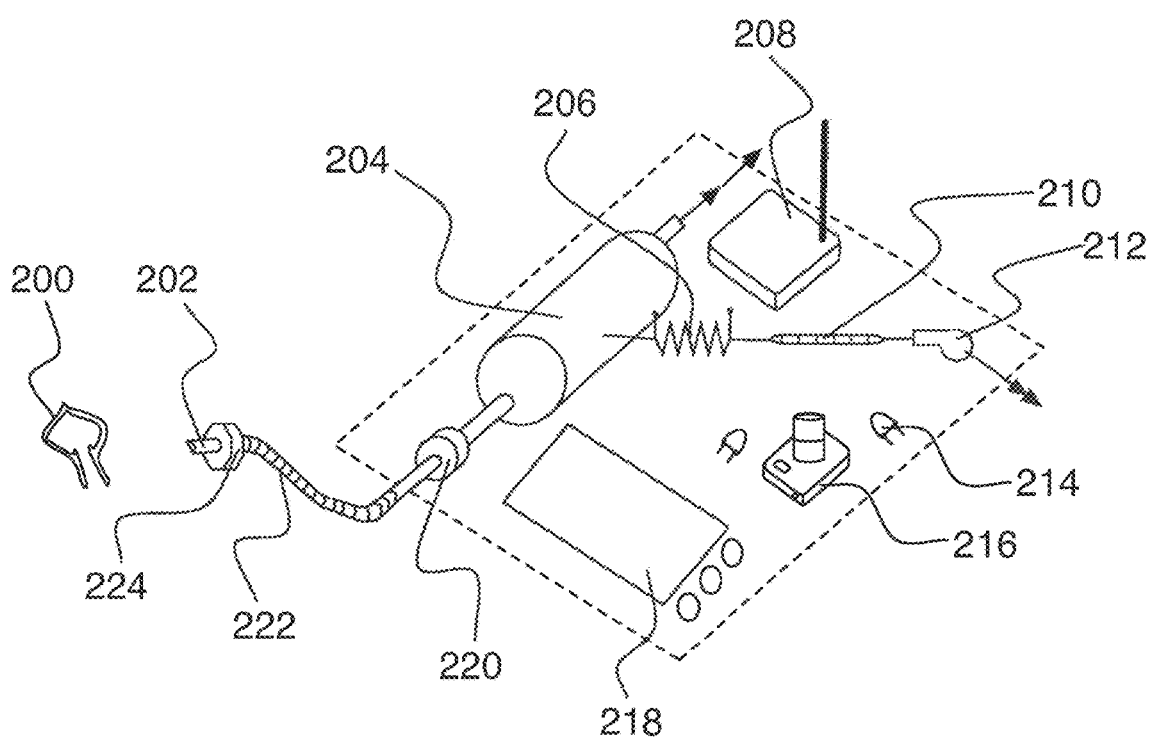
FIG. 23 is an apparatus for determining production rate.
Figure 24:
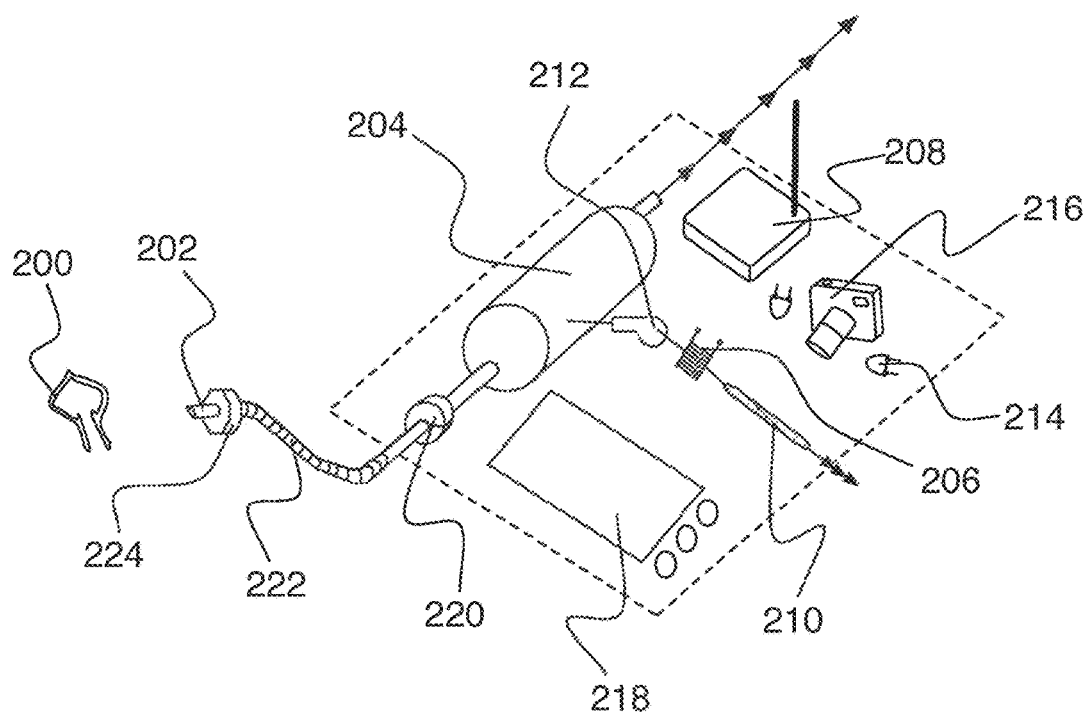
FIG. 24 is an apparatus for determining production rate.

FIG. 23 and FIG. 24 present examples of apparatuses that can measure the production rate of acetone in the human body, as measured through breath. The devices in both figures are the same except for the positioning and components of the sensor element (items 206, 210, and 212 in both figures). Component (202) is a mouthpiece, representing a sterile interface to breath collection whereby a user can physically interact with the instrument. Component (224) is an anti-viral/bacterial filter, which provides protection from cross-contamination between the user and the instrument. Component (222) is a breathing hose, presenting a gas line between the user and the instrument without imposing a significant breathing resistance onto the user. Component (220) is a flow measurement device that imposes a low breathing resistance to the user. Item (220) can be any device that measures flow and that imposes minimal obstruction to breathing. For resting measurements, the flow is preferably in the range of 5-20 L/min. Examples of candidate devices include: heated Fleisch pneumotachometer, a Lilly-style tachometer, an ultrasonic flow transducer, and a turbine flow meter. Component (204) is a mixing chamber, a vessel that allows a sufficient store of mixed exhalation gases to accumulate so as to allow accurate sampling of the gas measurement equipment, described next. Components (206, 210, and 212) comprise a gas sampling line, whereby a pump (212) removes gas from the mixing chamber (204) and pushes it through a flow measurement element (206) and a sensor element (210). A separate gas sampling line, with its own motive force (pump), is desirable to divorce sensor gas sampling from user breath input. In certain sensor configurations, particularly packed bed columns, a significant restriction to breathing is imposed by the sensor element. It is desirable to maintain breathing resistance as low as possible for user comfort, and thus a separate sample line allows the breath collection to be designed for optimal user interface, completely independent of sensor requirements which include, in general, known and steady flow rates and constant gas line pressures.

FIG. 23 and FIG. 24 differ in the placement and constituency of the gas sample line components. In FIG. 23, a flow restrictor and differential pressure transducer (206) is placed upstream of the sensor element and the sampling pump. In FIG. 24, the pump (212) is upstream of a flow sensing element (206) and the sensor element (210). The significance of this is that in FIG. 24, the sensor element requires a leak-free connection at both ends. The benefit of this placement is that the sensor element, in certain configurations, namely packed bed columns, provides a pulse-dampening effect and flow laminarization from the sampling pump allowing a simple flow restrictor and differential pressure transducer to effectively measure sampled gas flow rates without a flow laminarization device.

In FIG. 23, the sensor element does not require a leak-free connection on the downstream end, at the expense of the flow measurement device (206) requiring, in addition to a known resistance and differential pressure sensor, a flow laminarization device. Component (216) is a camera for imaging the sensor response, as can be applied to colorimetric packed-bed column reactors, but that component can be any signal transducer appropriate to the applied sensor. Note that there are numerous optical transducer approaches that apply to colorimetric packed-bed columns, for example scanning reflectance measurements (such as a barcode scanner or compact disk/DVD optical head) or bulk reflectance such as from a simple Light Emitting Diode ("LED") excitation/Photodetector detection scheme. If a camera is used for (206), then a suitable lighting scheme (214) may be necessary. Any lighting scheme that provides even illumination may be suitable, but usage of LEDs as lighting elements is especially useful for many reasons, not the least of which is the availability of numerous wavelengths. Appropriately selected illumination wavelengths can reduce background noise in reflectance measurements and improve system signal to noise ratio. Component (218) illustrates a user interface, comprised of a screen and interface buttons. Associated with (218) is a set of electronics and computational power capable of driving the user interface and system components, as well as implementing various computational algorithms and otherwise facilitating data processing. Component (208) illustrates an automated data uplink device, whereby measurement results, in electronic form, are automatically sent to locations external to the breath analysis unit for implementation into databases, support groups, etc., as described elsewhere. Component (200) is a nosepiece, used to constrain user breathing into the device through the mouth and to also eliminate leakage of breath gases through the nose.

An illustrative implementation for obtaining information about a physiological production rate of an endogenous volatile organic analyte from a breath sample of a patient is as follows. First, an apparatus is provided that comprises a breath input portion and an analysis portion. The breath sample is input into the breath input portion and directed to the analysis portion. The breath sample is analyzed to sense the analyte and obtain the information about the physiological production rate of the analyte. A signal is generated in the apparatus that is representative of this information. In some implementations, the endogenous volatile organic analyte is in near-zero concentration in the ambient atmosphere and, preferably, in concentration ranges less than or equal to low ppm.

Taking advantage of the breath profile subject matter presented herein, in some implementations, the analysis of the breath comprises segmenting the breath into a plurality of breath profile segments, wherein each of the breath profile segments corresponds to an anatomical region of the patient that is non-identical to the anatomical regions for others of the segments. The breath profile segments are then analyzed to sense the analyte within the anatomical region or regions corresponding to the at least one breath profile segments to obtain the information about the physiological production rate of the analyte. This approach, using breath profiles and anatomical segmentation, enables the most accurate measurement of production rate for volatile organic compounds, which is likely a superior analysis parameter than concentration alone.

Although the nature of some measurement phenomena is sensitive to the quantity of volatile organic compounds (moles of acetone, for instance) and not to the concentration in the sample per se, reporting of volatile organic compounds measurements is almost universally in ppm. However, knowing the ppm of an analyte of interest in a given sample is not the same as knowing the amount (in moles) of gas produced by the body in a particular span of time. For many applications, the rate of volatile organic compound production in an individual has greater utility than knowing the concentration measured in a sample. There are many reasons for this, including the following.

Production time may not be the same as exhalation time. Although the volume of breath in a single exhalation can be measured, the amount of time associated with the production of the analyte in the breath sample may not be accurately estimated (the amount of time associated with the production of analyte in the sample may and likely is not the same as the duration of the breath exhalation.

Depending on the analyte, purpose of the test, and condition of the patient, the concentration of the analyte in a single breath may not be the same as the concentration of the analyte over a series of breaths. Furthermore, the concentration may vary significantly depending on the particular breathing maneuver performed (see breath profile definition).

For the vast majority of use conditions, physiological steady-state cannot be assumed for a single breath, and thus the extrapolation of single breath data into production rates is tenuous.

As such, a more useful metric of volatile organic compounds in breath is moles per unit time (as compared to just moles). Further, this new metric has particular utility when used in conjunction with our breath profile embodiments and implementations.

Mathematical Model

The ensuing example uses acetone as the analyte. The analysis, however, can be broadened to various other analytes described herein.

If the partition coefficient at steady-state is known for an individual, then the concentration of acetone in the breath can be used to accurately estimate the concentration of acetone in the blood under the particular steady-state conditions. Furthermore, the rate of acetone removal from the body (through the breath) can be used to accurately estimate the rate of acetone production due to metabolic processes.

The following is an illustration of the application of mass balance principles in the case of endogenously produced acetone. First, the amount of acetone produced per unit time (per minute in this example) needs to be measured. The amount of breath exhaled over a minute is multiplied into the average concentration of acetone in the breath during that time to yield the total acetone excretion:

$$VAc = \frac{PV}{RT} Ve \cdot FeAc \quad \text{(Eqn. 1)}$$

The variable VAc is the production rate of acetone per minute time, in moles, Ve is the volume of breath exhaled per unit time with units of liters per minute, and FeAc is the average fraction of acetone in the exhaled breath with units of liters of acetone per million liters of breath. The liters of acetone can be converted to moles using the Ideal Gas Law under the associated pressure and temperature (using n=PV/RT, where n is the moles of acetone, P is the pressure in kPa, V is the volume in liters, R is the universal gas constant in units 1-kPa/mol-K (with value 8.314 in these units), and T is the temperature in Kelvin at the time of measurement).

A specific example of an apparatus that utilizes different profiles to analyze different analytes is presented. The ensuing apparatus senses oxygen, carbon dioxide, and acetone, which can provide a metabolism assessment.

Oxygen and carbon dioxide can be used to determine the respiratory quotient ("RQ"), which is generally, the ratio of the carbon dioxide produced to the oxygen consumed. The RQ varies from about 0.7 to 1.1. Among normal subjects, the RQ value is approximately 0.85. Those who are consuming strictly carbohydrates have RQ values close to or about 1 (assuming the intake is sufficient to meet the caloric needs of the individual). When fats are predominately the source of energy, the RQ approaches 0.7.

Breath acetone, on the other hand, correlates to blood acetone, which correlates to fat metabolism. However, the acetone concentration relates to the magnitude of fat consumption in the individual, and as such has been correlated to fat loss rate. The two measurands, though linked, do not provide the same information. Consider that RQ can be higher than 0.85, for instance, while acetone levels are elevated, in individuals burning lots of fuel which is predominately carbohydrate. In this case, although most of the fuels consumed are carbohydrates, the individual is still burning elevated amounts of fat. Thus, RQ and acetone combined provide significant information that neither provides alone.

In this embodiment, oxygen and carbon dioxide are measured using repeated non-rebreathing with tidal volumes. Acetone is measured via single-exhalation of the alveolar air.

An instrument that can measure both measurands in one sitting and that can sample for both using the analyte-specific optimal breath profile will offer considerable analytical information that is not currently available using commercially available instruments or techniques.

Figure 16:
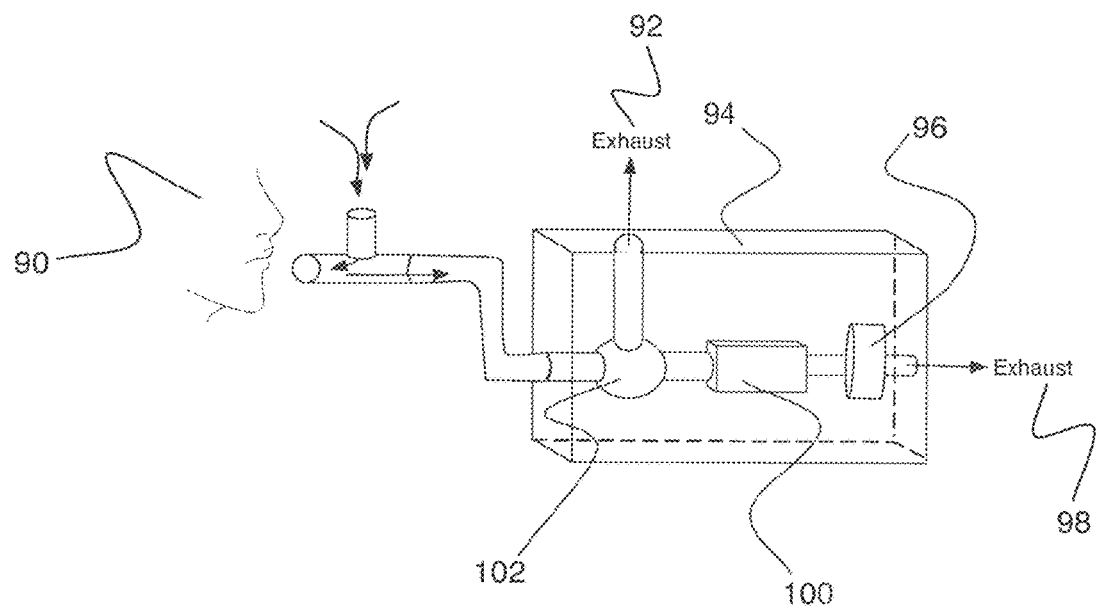
FIG. 16 is an apparatus that uses breath profiles to analyze analytes in breath.

A method and instrument for sampling and measuring RQ and acetone in human breath is shown in FIG. 16. A breath profile for optimal sampling of the two measurands is shown in FIG. 9.

Figure 15:
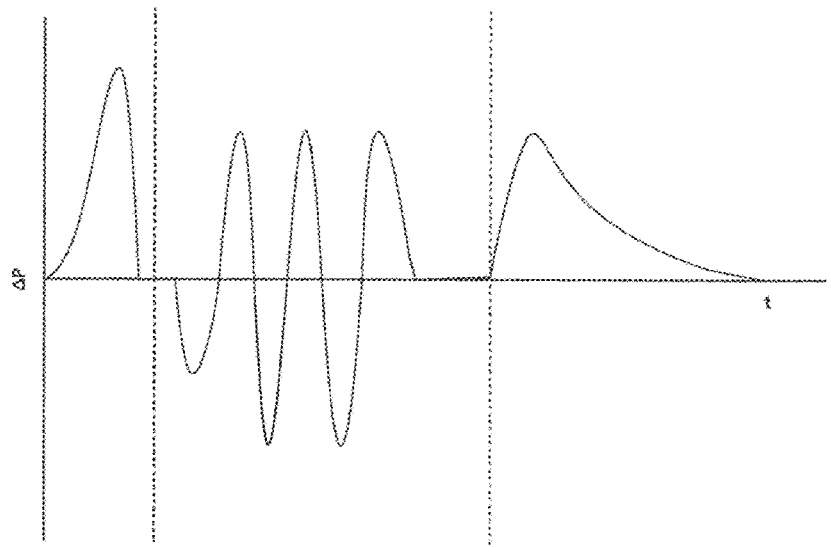
FIG. 15 is a method for using a complex breath profile.

FIG. 15 depicts a system comprised of: a three-way non-rebreathing valve; a section of breathing hose; an automatic 3-way valve; a sensor block containing sensors and fixtures for $O_2$, carbon dioxide, acetone, relative humidity, ambient pressure, and temperature sensors; and a pneumotachometer.

In certain apparatuses, heating of the sensor block enables the sensors to operate more reliably, both from the perspective of protection from breath condensation and from the perspective of eliminated temperature effects on sensor performance. Two 5 watt silicone PSA heaters are sufficient to keep a block of aluminum (3.5"×2"×2") at 38° C. using either commercial temperature controllers or simple analog setpoint circuits. Likewise, heating of the pneumotachometer screens (a Lilly-style pneumotachometer was used in the development described here) provides resistance to breath condensation buildup and thus alteration of the pressure vs. flow rate waveform.

In this embodiment, the apparatus first measures the RQ and then measures the acetone concentration. RQ is measured first since its optimal breath profile is a set of tidal volume breaths for an extended period of time. This type of breathing is in fact the same as normal breathing inasmuch as the sampling equipment does not impose a greater burden on the user. The RQ measurement thus does not affect downstream measurements. After the RQ measurement is complete, the user is instructed to exhale normally (perhaps with a visual or audio indicator from the device) and then to wait for a given period of time. After the set time (again as perhaps indicated with a visual or audio cue), the user is instructed to exhale the air from the deeper portions of the lungs as much as is possible.

Once the final exhalation is complete (sensed by the apparatus using a device like a pneumotachometer), the three-way valve is closed. The "closed" 3-way valve allows the user to continue to breathe through the instrument's non-rebreathing valve, but the exhaled breath is then directed to exhaust directly outside the instrument while the instrument proceeds with and finalizes the acetone analysis on the deep exhalation. With the three-way valve, the user does not need to disconnect from the device and it is not possible to contaminate the breath sample with more (upper airway diluted) gases. With the three-way valve, breathing after the acetone sample can allow the user to recover in preparation for another breath test, as necessary.

In making ergonomic assessments (which will be specific for a particular application), one consideration is the dilutive effect of the design. Computing the amount of residual volume in the pneumatic system is a factor to consider. For instance, if using a 24" length, 22 mm diameter tube, the system will include approximately 200 ml of residual gas. Assume that the instrument is intended to measure an analyte in alveolar air space. Once the initial (approximately) 500 ml of "dead-air" space is evacuated, to sample the alveolar air, 200 ml will be required to force the sample through. This 200 ml may be critical if the patient is only able to exhale 250 ml of alveolar air (e.g., a young child or an elderly patient with COPD). Another approach would be to allow external air to "push" any residual gas from the tubing. Such considerations should be adequately addressed in the design.

The patient's breath, in its entirety, may pass through the breath input or the breath may be side-sampled, e.g., a fraction of the breath is analyzed.

Depending on the sensors used, especially for low-level volatile organic compounds, sidestream sampling may be beneficial. In this case, small bore tubing can be attached to hose taps through the side of the sensor block and miniature sampling pumps can withdraw samples through any requisite conditioning stages and into the volatile organic compound sensor space.

The pneumotachometer, in the configuration described, is beneficial for both attenuating mass transfer via diffusion at the outlet of the sensor block (and, thus, no exit valve is required) and also for measuring the volume of air breathed through the sensor setup. Note that the pressure waveforms created by breathing through the pneumotachometer occur only on subject exhalations (and, only then when the 3-way valve is set towards the sensor block). Still, the pneumotachometer is capable of seeing when the user exhales, including when the user has finished a deep lung exhalation. This sight enables the system to smartly deal with quality control issues and to provide data for useful feedback during system operation (including measuring the breath rate of the individual, the tidal volume, and the total volume of breath in a sample or series of samples).

Advantages of this system include: optimal analyte sampling; appropriate analyte sampling sequencing (it would be less appropriate to sample RQ after the acetone exhalation, since the acetone exhalation is considerably more physiologically perturbing); low breath resistance (pressure drops occur only over the non-rebreathing valve, the large-bore tubing, the large-bore sensor block, and the low-resistance pneumotachometer), specifically there is no need for an antibacterial filter stage; and the ability to cascade longer and more complex breath sampling routines since the 3-way valve enables subject recovery after deep exhalations without removing the breathing valve.

Figure 17:
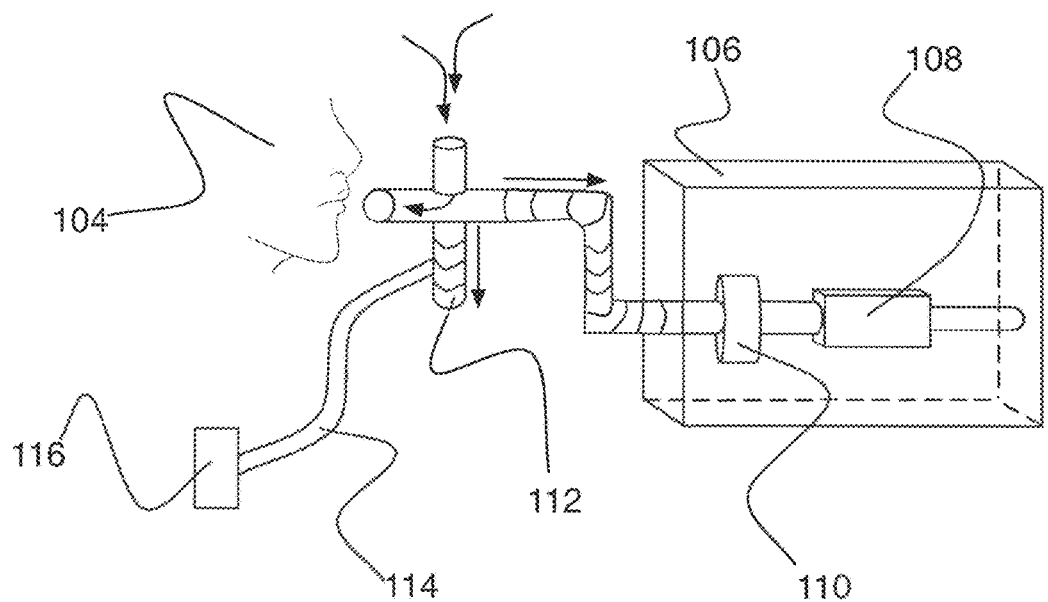
FIG. 17 is another apparatus that uses breath profiles to analyze analytes in breath.
Figure 18:
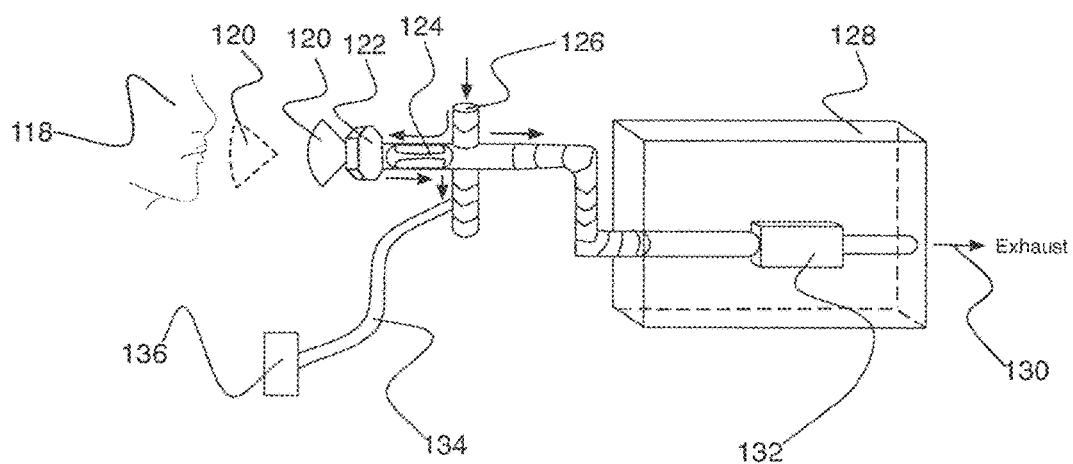
FIG. 18 is another apparatus that uses breath profiles to analyze analytes in breath.
Figure 19:
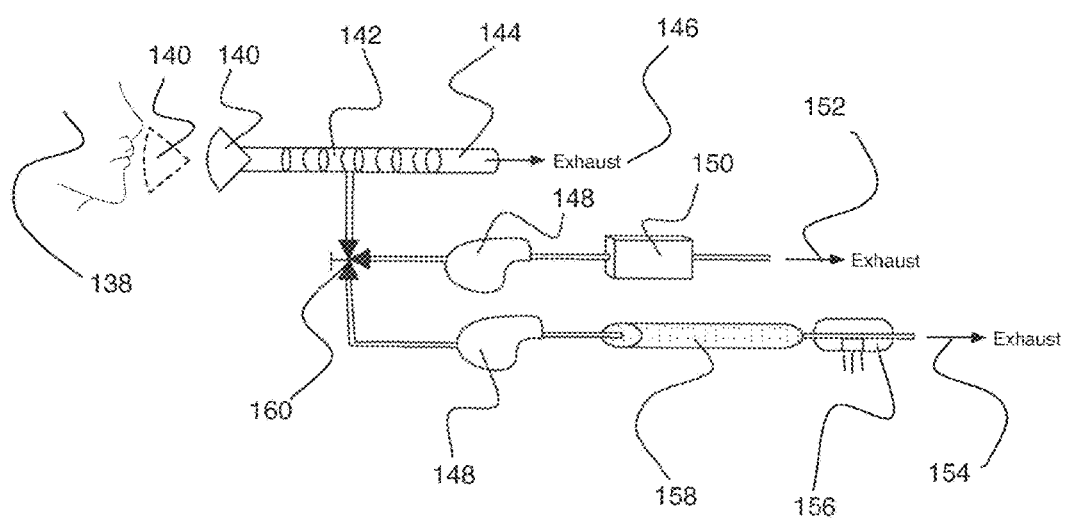
FIG. 19 is another apparatus that uses breath profiles to analyze analytes in breath.
Figure 20:
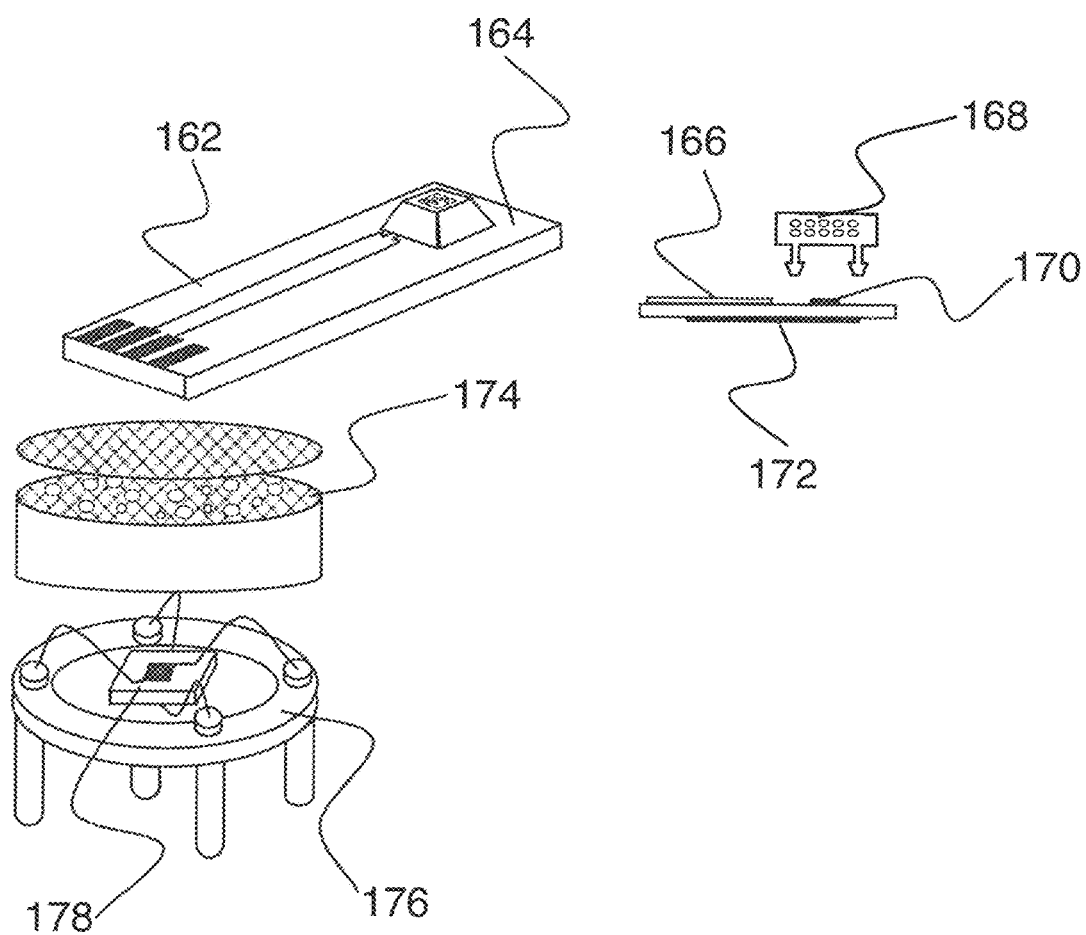
FIG. 20 is a sensor that utilizes nanoparticle principles.
Figure 21:
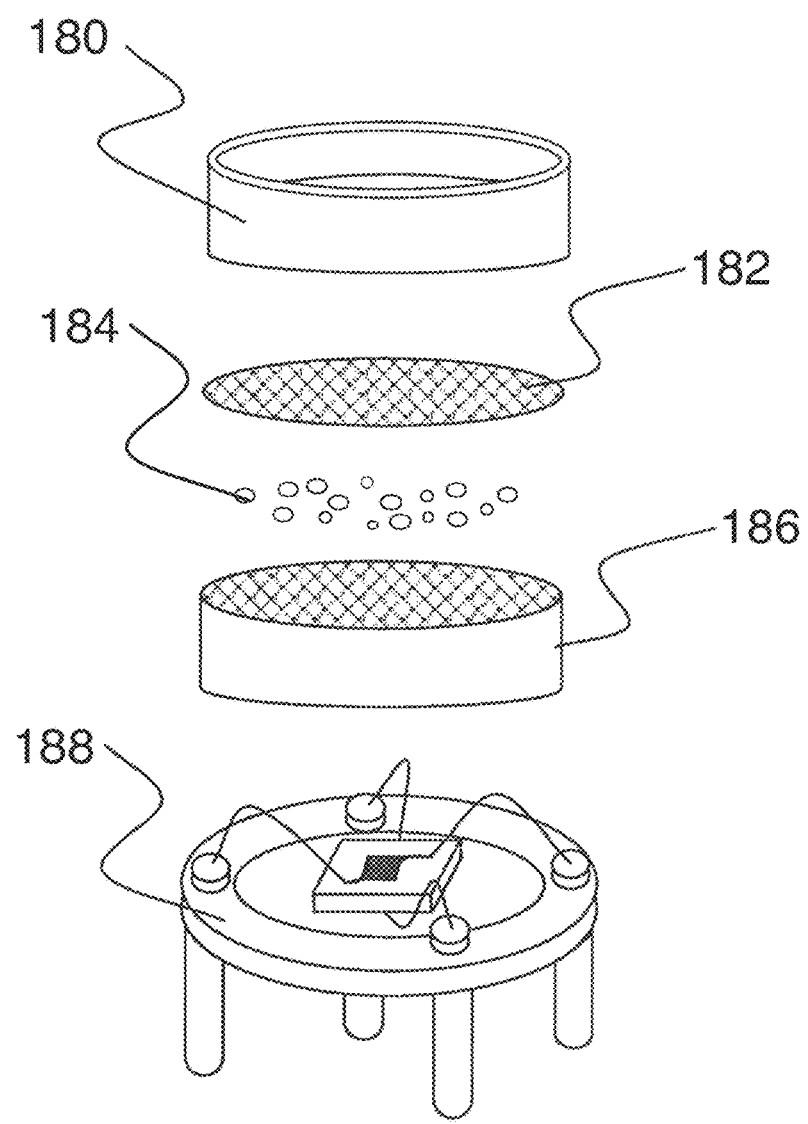
FIG. 21 is a sensor that utilizes nanoparticle principles.
Figure 22:
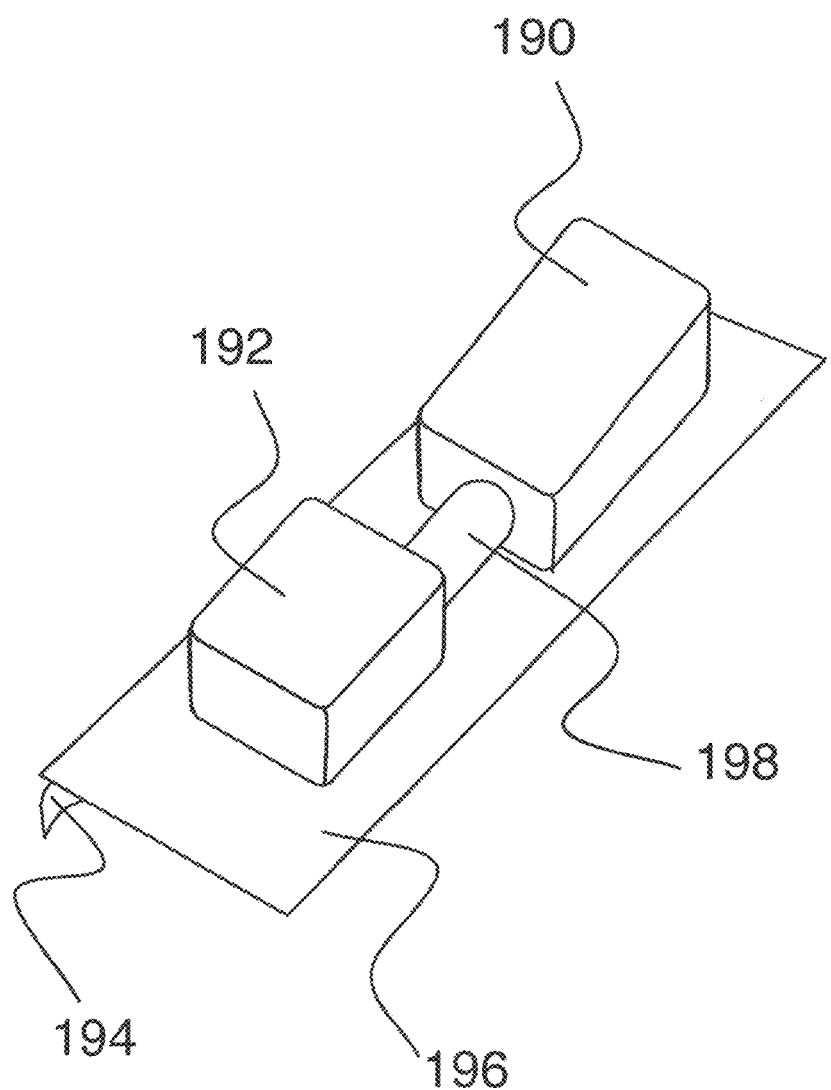
FIG. 22 is an enzymatic sensor that utilizes optical, or electrochemical, principles.

Alternate embodiments are shown in FIG. 17, FIG. 18, and FIG. 19. The embodiment shown in FIG. 18 can be further described by FIG. 20, FIG. 21, and FIG. 22.

A variety of breath inputs may be used. When designing the instrument for the specific application of interest, it is desirable to account for certain ergonomics. For instance, many patients find it uncomfortable to breathe through devices with a high level of flow restriction. This is particularly significant for young users, elderly users, and individuals with pulmonary disorders. However, also, if the patient is breathing multiple breaths into a device, it may be uncomfortable for the patient to be manually holding the device for extended (e.g., 3-10 minutes) of time. To account for this, certain ergonomic additions (e.g., a strap to attach the device to the face) may be employed. The device may also be designed as a portable bench-top system, where the user may sit next to the device and breathe through a hose for the extended period of time.

Figure 50:
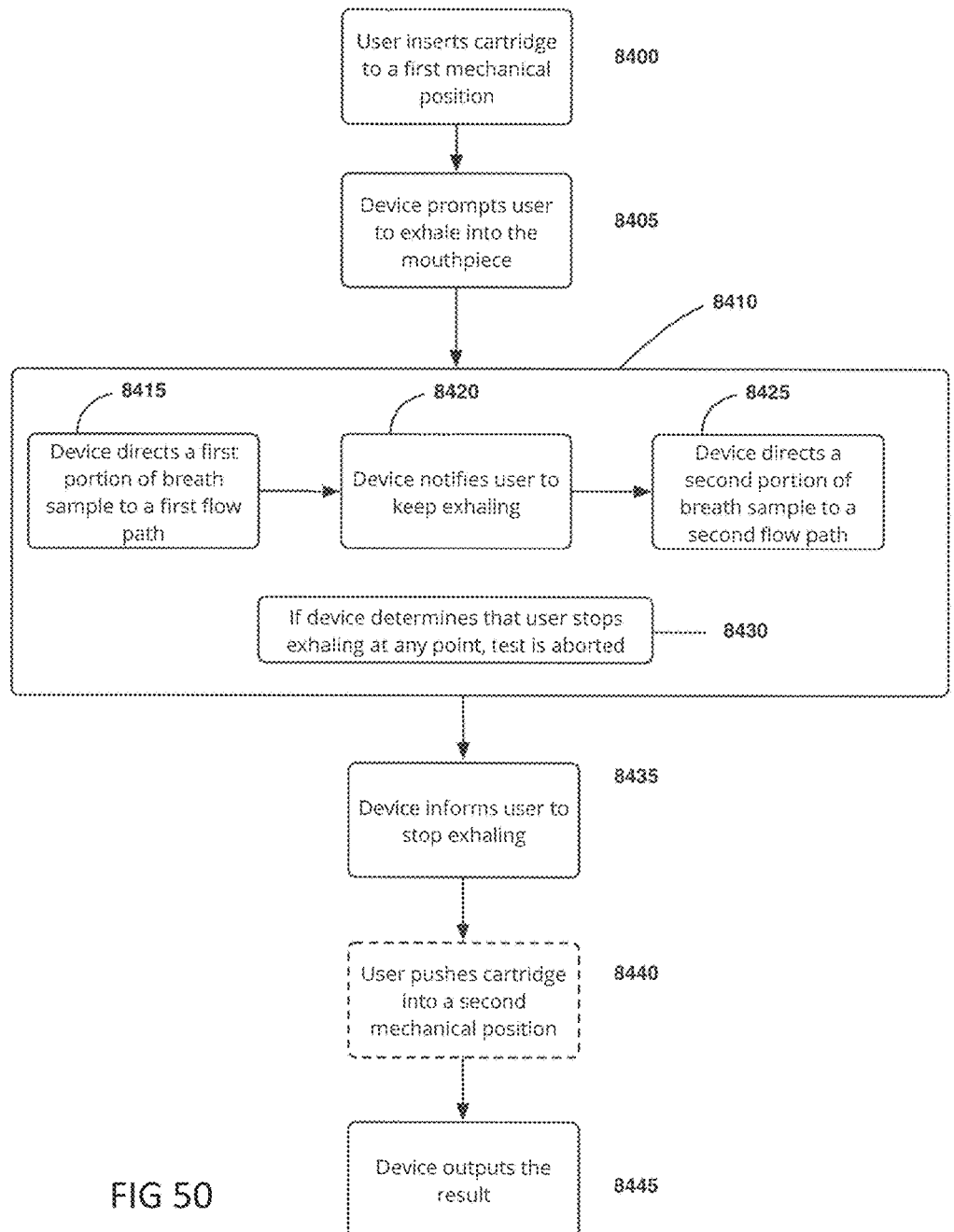
FIG. 50 is a flow chart of the user-device interaction for one embodiment of a breath analysis system.

FIG. 50 is an exemplary flow chart of the user-device interaction for one embodiment of a breath analysis system as disclosed herein. In the first step 8400 in the user-device interaction for one embodiment of a breath analysis system, a user inserts a cartridge (e.g., a test cartridge, as is described elsewhere herein) into the device. In some embodiments, the cartridge is inserted by the user until the cartridge reaches a mechanical stop position. For example, the user may insert the cartridge to a first position where part of the cartridge remains outside of the device. Alternatively, the user may insert the cartridge to be fully inside the device as the first position. In other embodiments, the user inserts the cartridge only a small portion after which the device automatically accepts the cartridge to the correct depth (the device may have any of a number of sensors to determine how deep the cartridge should be inserted, including, but not limited to, a click-type sensor, a photo sensor, a displacement sensor, or a processor that communicates with a chip in the cartridge).

After insertion of the cartridge, in step 8405, the user begins to exhale into the mouthpiece of the cartridge. In one embodiment, the user is prompted to begin exhaling by the device. In another embodiment, the user is not prompted to begin exhaling and merely begins exhaling whenever the user is ready. In either embodiment, the device may include a sensor to detect the beginning of the user's exhalation. The sensor may be a flow sensor, pressure sensor, or other sensor described below. In some embodiments, the user may be notified that the device has sensed the beginning of the breath sample by an LED, or other audio/visual or haptic indication. Next, in step 8410, the device obtains an alveolar breath sample. In step 8415, the device directs a first portion of the breath sample that the user is exhaling to a first flow path. The first flow path may be in the device or in the cartridge. This portion of the breath most likely does not contain any alveolar breath as it includes mostly breath from the mouth. After this step, the user receives a notification to continue exhaling in step 8240. The notification in step 8420 may coincide with step 8425 where the device directs a second portion of the breath sample to a second flow path. The second flow path is in the cartridge. The second portion of the breath preferably includes alveolar breath from the lungs. Step 8420 may also occur immediately after step 8425. When this transition from the first flow part to second flow path occurs, the user may notice a change in the resistance to the user's breath or in the flow of the breath. The notification to the user to keep exhaling may prevent the user from stop breathing when the transition occurs. The notification may also assure the user that the device is operating correctly. This notification may be audio, visual and/or haptic and any combination of these. In one embodiment, the device is monitoring the flow of breath being exhaled into the device by means discussed elsewhere in this specification. If the device determines that the user has stopped exhaling at any point prior to the device obtaining an alveolar sample, the user will get an indication that the device has abandoned the test as shown in step 8430. The indication may be audio, visual or haptic or some combination. If the device successfully obtains an alveolar breath sample, the device informs the user by audio, visual and/or haptic feedback that the user may stop breathing into the cartridge or device as shown in step 8435. In one embodiment, the next step is step 8440, and the user pushes the cartridge into a second position inside the device for the analysis to begin. In one embodiment, the device prompts the user to push the cartridge into a second mechanical position in the device as in step 8440. In another embodiment, the device may begin the processing of the breath sample without further intervention by the user. In either embodiment, in step 8445, the device outputs the result of its analysis of the breath sample. The output of the device may be audio or visual or the device may communicate the output to another device, such as a smartphone or tablet.

Figure 51A:
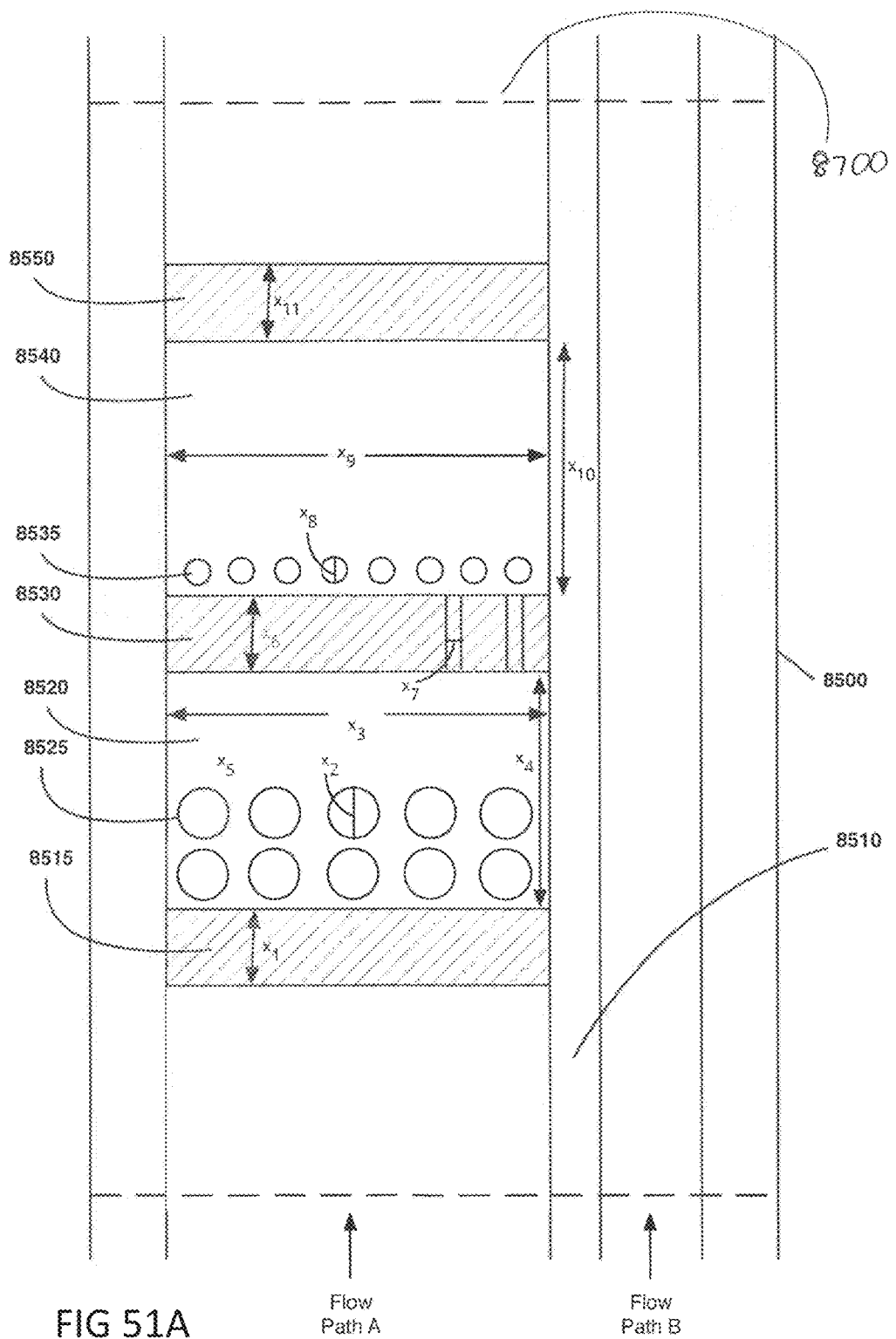
FIGS. 51A-B show an exemplary cartridge design identifying features and variables that have been optimized for certain applications described in this disclosure.
Figure 51B:
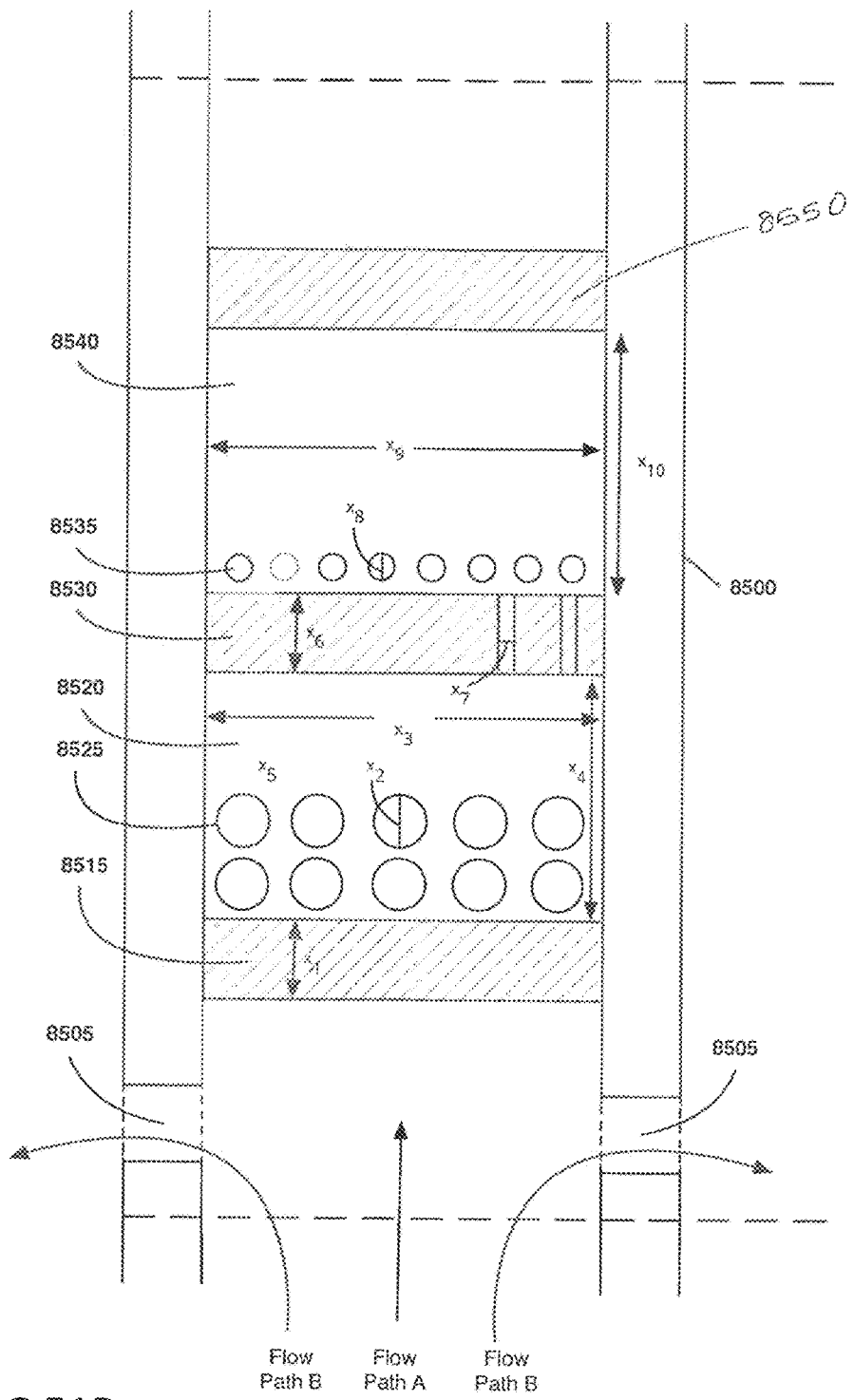

FIGS. 51A-B show exemplary cartridge designs identifying features and variables that can be optimized for certain applications described in this disclosure. For certain applications, it may be desirable for a user to be able to exhale directly into a cartridge. This type of design may eliminate the need for a breath bag and/or a pump. If not pump or breath bag is used, then the cartridge will be configured to operate with pressure generated by the human respiratory system.

Expiratory pressure varies based on a user's sex, age, smoking status and other variables, such as whether the individual has asthma, COPD or other respiratory conditions. Typically, expiratory pressure is determined empirically using spirometry. General ranges of maximum expiratory pressure (MEP or PEmax) are provided in the below chart (Wilson 1984):

TABLE 2

Significance of the sex differences in mean maximum respiratory pressures in adults and in children (values are means with standard deviation in parentheses)

| Group (n) | Age (y) | Height (cm) | Weight (kg) | $PE_{max}$ (cm $H_2O$) | $PI_{max}$ (cm $H_2O$) |
|---|---|---|---|---|---|
| Men (48) | 34 · 7 (14) | 179 (6) | 74.5 (8.5) | 148 (34) | 106 (31) |
| Women (87) | 36 · 8 (13) | 163 (7) | 61.4 (9) | 93 (17) | 73 (22) |
| Significance of t | NS | p < 0.01 | p < 0.01 | p < 0.001 | p < 0.001 |
| Boys (137) | 11 · 1 (2 · 2) | 149 (15) | 41 (12) | 96 (23) | 75 (23) |
| Girls (98) | 11 · 6 (2 · 5) | 147 (16) | 40.5 (12) | 80 (21) | 63 (21) |
| Significance of t | NS | NS | NS | p < 0.001 | p < 0.001 |

Using the equations in the above chart, the predicted maximal respiratory pressure in adults and children can be estimated (Wilson 1984):

TABLE 3

Prediction equations for maximal respiratory pressures in adults (over 18 years) and children (7-17 years)

| Group | $PI_{max}$ (cm $H_2O$) | $PE_{max}$ (cm $H_2O$) |
|---|---|---|
| Mens | 142 − (1.03 × Age*) | 180 − (0.91 × Age*) |
| Women | −43 + (0.71 × Hi†) | 3.5 + (0.55 × Hi†) |
| Boys | 44.5 + (0.75 × Wt‡) | 35 + (5.5 × Age*) |
| Girls | 40 + (0.57 × Wt‡) | 24 + (4.8 × Age*) |

*Age in years.
†Height in centimeters.
‡Weight in kilograms.

Other reports show slightly lower ranges. In one study, men generate MEP from 62 to 97 cmH$_2$O and women generate levels from 38 to 62 cmH$_2$O. The same study shows an age dependence with a decrease in MEP in men from 106 to 68 cmH$_2$O between the ages of 20 to 60 and a decrease in women from 65 to 49 cmH$_2$O between the same ages.

As such, if a device is to have broad applicability across children, adult men and elderly women, the device should support expiratory pressures as low as 40 cmH$_2$O (=29.4 mmHg or 0.569 psi) and this assumes that all users are capable of and chose to exhale at their MEP for the duration of a measurement cycle.

If the device is designed primarily for healthy adults, such as for adult athletes, a higher expiratory pressure may be supported. For example, an expiratory pressure of 90 cmH$_2$O may be used.

Instead of evaluating this from the perspective of human capability, another way of evaluating the desired flow resistance of a cartridge are the flow requirements to obtain a measurable colorimetric signal. In the case of breath acetone in a cartridge, such as the one described in FIG. 51A, it is desirable that 400 ml of breath at 3 ppm be directed through the cartridge over a period of 10 seconds. These characteristics impose a certain maximum flow resistance that can be contained within the cartridge.

Variables Involved in Cartridge Flow Resistance

In view of the foregoing, it is desirable that the cartridge flow resistance be optimized such that the desired user can exhale through it.

FIG. 51A shows a cross section of a cartridge 8700. The cartridge 8700 has two outer walls 8500. Within the cartridge 8700, an inner wall 8510 creates a gap that defines Flow Path B on one side and Flow Path A on the other side. In this embodiment, Flow Paths A and B are used by the user to exhale directly into the cartridge 8700. In such an embodiment, a pump or breath bag may not be required. In another embodiment, Flow Path B is configured to be part of the device and is outside the cartridge 8700 while Flow Path A remains in the cartridge 8700. In theory, these two flow paths will share the total flow as parallel or shunted flow paths according to principles known in the field of fluid mechanics. The ratio of their resistances will enable one to predict the respective flow rates through them. Similarly, one may set or adjust the respective resistances of the flow paths to achieve a desired relative flow through them. The setting of this ratio may be guided by or determined from various factors, e.g., such as patient or user demographics (e.g., age, sex, etc.), by physiological state (e.g., smoker, non-smoker, hyperventilating, etc.), and so on. In this illustrative embodiment, the flow resistance in Flow Path B is essentially zero and the resistance in Flow Path A is sufficiently high that the flow is directed through Flow Path B. This continues until a solenoid blocks Flow Path B, thus forcing the user to exhale through Flow Path A.

In FIG. 51A, Flow Path B is an unobstructed, separate flow path from Flow Path A. In another embodiment, as shown in FIG. 51B, Flow Path B could be an opening or openings 8505 on the side or sides of Flow Path A. Other arrangements could also be used with other embodiments.

With regards to both FIGS. 51 A and B, Flow Path A includes a lower disk 8515, a bed of desiccant 8525, a middle disk 8530, the bed of reactive beads 8535, and an upper disk 8550. The low disk 8515 may be a porous polyethylene disk with a thickness of X1. The bed of desiccant beads includes beads 8525 with a diameter of X2. The desiccant chamber width is X3 and height is X4. X5 is the void factor in the reactive chamber and is defined as the void volume divided by the total volume. The middle disk 8530 may be a porous polyethylene disk with a thickness of X6 with a disk porosity of X7. The reactive beads 8535 have a diameter of X8. The reactive bead chamber width is X9 and height is X10. The reactive bead chamber may also include a void 8540. And, the reactive chamber may include an upper disk 8550. All of these structures with their various dimensions will impact the flow resistance.

For example, an increase in the thickness of the lower disk, X1, will increase the flow resistance of Flow Path A. A decrease in the X1 will lower the mechanical rigidity of the lower disk on the other hand. If the lower disk is too thin, then particles may not be properly contained in the lower disk area 8520. A thin lower disk will also be harder to manage in an assembly process. As the size of the pores of the lower disk increases, the flow resistance decreases. As the pore size of the disk increases, the diameter of the beads that can be contained by the disk has to increase. This decreases the surface area available for reaction. The same will be true for the middle disk and the upper disk.

The porosity of the permeable, or porous discs (as discussed herein) which maintain the support beads within the reaction chamber and the flow rate permitted through the support beads may be configured to enable a flow rate of breath of at least about 100 cc's and in some implementations at least about 200 cc's or 300 cc's or more in no more than about 2 minutes and optimally no more than about 120 seconds or 60 seconds or less, under a reference pressure of 1 psi. That reference pressure is within the range of pressures that can normally be generated exhaling from a healthy lung, which exhaling pressure may be as high as 2 psi in a healthy adult. This enables the test to be run directly on exhaled volume of breath, without the need for a breath container such as an inflatable bag, and without the need for a pump to generate enough pressure to drive the sample through the analytical pathway.

The flow rate can also be adjusted by adjusting the total support volume relative to the reaction chamber volume. Total support volume represents the smallest volume that the support will occupy when snugly packed but without deformation of the support structures. Thus for example where the support comprises beads, the total support volume equals the sum of the volumes of the individual beads plus the total volume of interstitial spaces in between the beads. Total support volumes of between about 10% and about 70%, and in some implementations between about 20% and about 50% of the reaction chamber volume may be desirable. Low packing volumes such as on the order of 20% or 10% or less of the reaction chamber volume, depending upon bead size, may allow beads to pack tightly against the effluent filter and increase the pressure required to maintain a desired flow rate.

In any of the foregoing constructs, it may be desirable to provide a wick for facilitating the flow of liquid from the ampoule to the beads. The wick can comprise any of a variety of surface structures for facilitating liquid flow, such as a porous strip of a material such as polyethylene or other material having suitable stability in the intended use environment. Further embodiments including wicks are discussed elsewhere herein.

An increase in the desiccant particle diameter, X2, will decrease the flow resistance of Flow Path A as long as the number of desiccant particles is reduced over all. An increase in the desiccant particle diameter will also decrease the surface area that is available to dry the breath sample. The desiccant may be unnecessary altogether if the chemistry is not moisture-sensitive (e.g., color is not attenuated in the presence of water) or if the intended use expects very high concentrations of the analyte of interest such that any attenuation is not expected to impact efficacy. The same is generally true for the reactive bead diameter, X8.

In addition, increasing the desiccant chamber width, X3, increases the chamber size which should decrease the flow resistance. Of course, this assumes that there is not a proportional increase in the number of desiccant particles. Similarly, increasing the desiccant chamber height, X4, will also increase the chamber size and decrease the flow resistance. As with the desiccant chamber width, X3, a proportional increase in desiccant particles could nullify any increase in chamber height. So, if a larger chamber is packed with a certain % of beads, the benefit of the larger chamber dimensions may be overtaken by the increased overall flow restriction from the beads. The same is true for the reactive bead chamber width, X9, and reactive bead chamber height, X10.

Also, if the void factor, X5 increases, the flow resistance will decrease. However, as the number of desiccant beads decreases, the surface area available for the reaction also decreases.

One of skill in the art could evaluate different cartridge configurations by considering the following relationships. Generally, the resistance through a tube is given by:

$$v = \frac{Q}{A}$$

where v is the velocity, Q is the flow rate, and A is the cross sectional area of the tube. Furthermore, Q can be defined as $$Q = \frac{P_2 - P_1}{R}$$

where Q is the flow rate, P is the pressure at one of two points (1, 2) and R is the flow resistance. R can be defined by the following relationship $$R \propto \frac{n \cdot L}{r^4}$$

where R is the flow resistance, n is a set of physical properties pertaining to the fluid, L is the length of the column and r is the radium of the column. Of course, hydraulic radii may be used if applicable and appropriate.

For packed beds, the Kozeny-Carman relationship may be used.

$$\frac{\Delta P}{L} = \frac{180 \cdot \mu}{\phi_s^2 \cdot D_p^2} \cdot \frac{(1-\varepsilon)^2}{\varepsilon} \cdot v_s$$

where viscosity, sphericity of the beads, particle diameter and void factor are all considered. This version of the equation only applies to laminar flow.

One cartridge embodiment that may be useful for applications such as monitoring adherence to ketogenic diets involves the following parameters. Using a cartridge with an internal diameter of approximately 0.7 cm, disks that are ⅛" are used (50 to 90 micron pore size). Approximately 5 mg of reactive silica beads (140-170 mesh) are used in a reactive chamber that is 30% full. Approximately 190 mg of calcium chloride beads (12-18 mesh) are used in a loosely packed chamber. One of skill in the art would be able to use the foregoing relationships and examples to determine other dimensions for use in embodiments.

FIG. 53, FIG. 54, FIG. 55 and FIG. 56 show embodiments of a breath analysis system that is configured to generate a rapid response using alveolar breath. Like other breath analysis systems described herein, the system is comprised of a device 8705 and a disposable cartridge 8700. This embodiment may operate without a breath bag or breath container. It further may operate without a pump, at least in the most basic configurations. However, in certain embodiments, a pump may be used. In other embodiments, a breath bag or breath container can be used.

Figure 53:
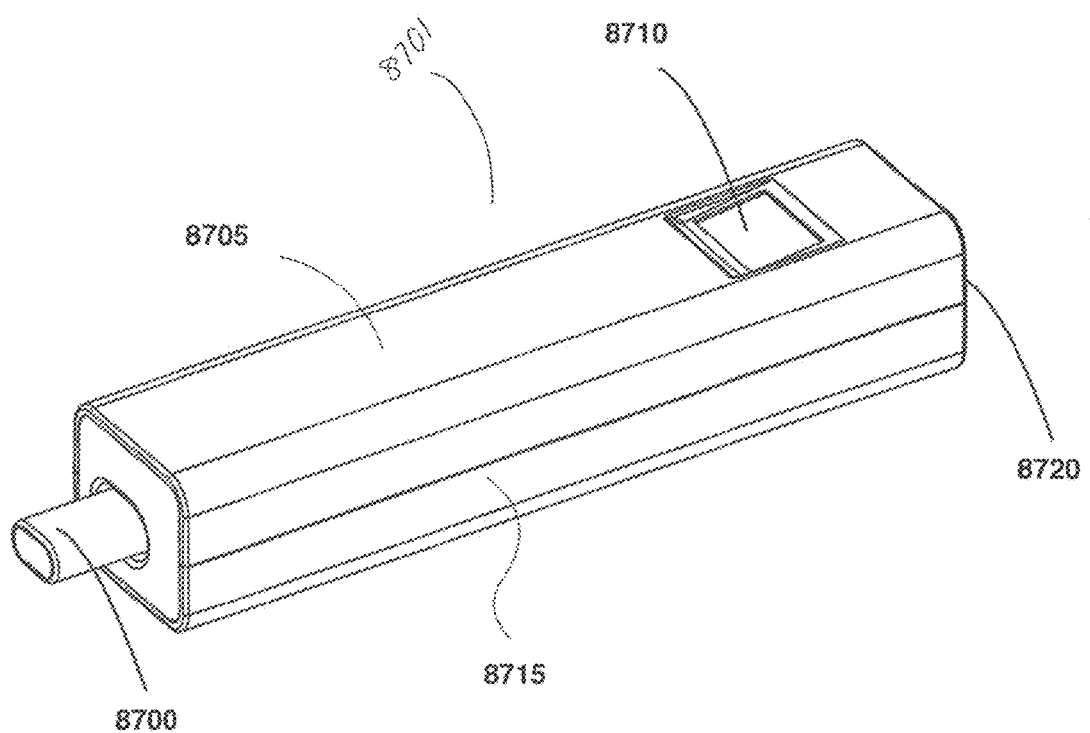
FIG. 53 shows an embodiment of a breath analysis device that works in conjunction with the cartridge shown in FIG. 54.

FIG. 53 shows a view of the device 8701 with a lower housing 8715 and upper housing 8705 with a cartridge 8700 inserted. The device may include a display 8710. The display 8710 may include a touch screen. The device 8705 may be rectangular with side wall 8715 and a back 8720.

Figure 54:
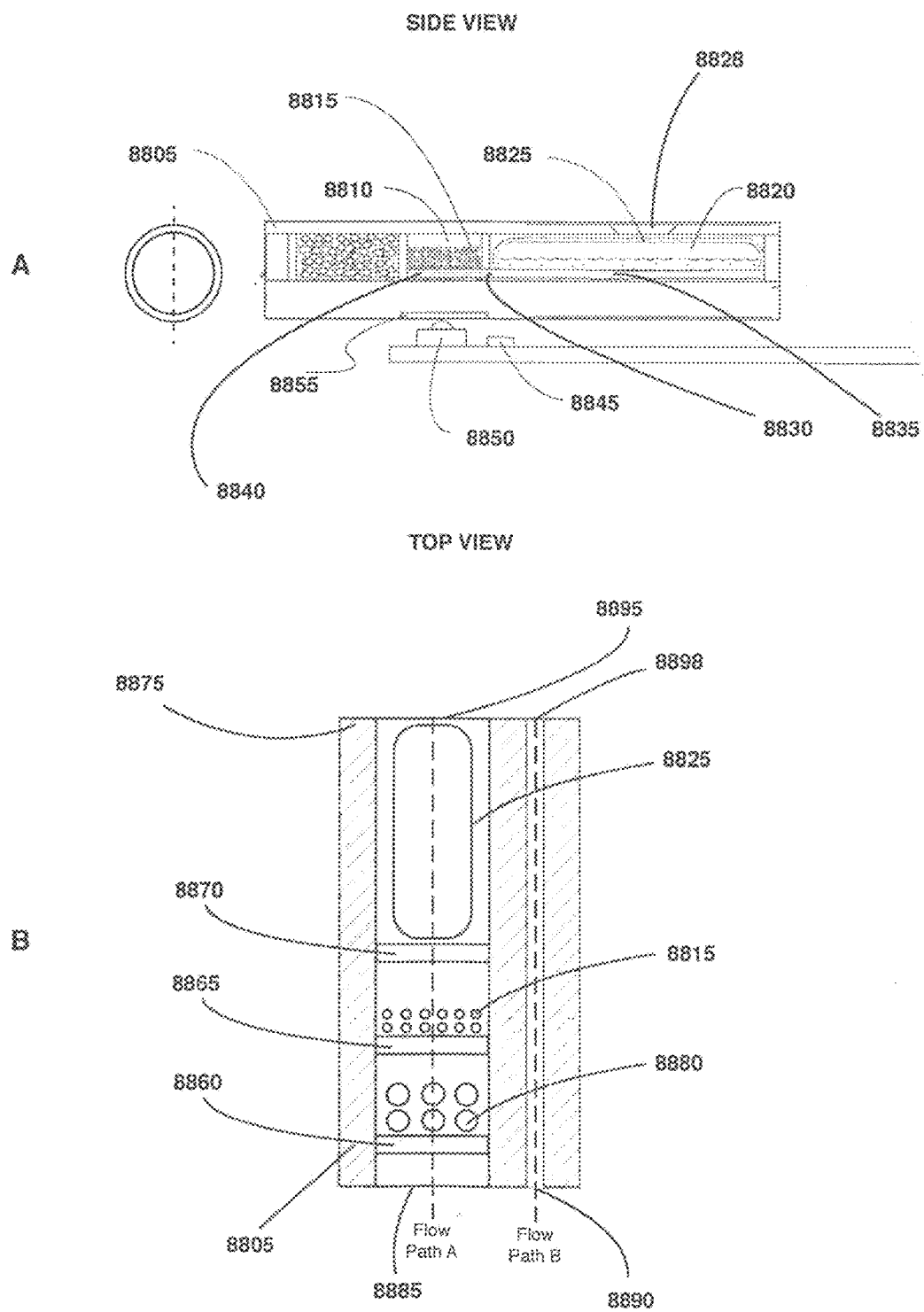
FIGS. 54A-B show an embodiment of a cartridge with a partially packed reactive chamber.

FIG. 54 shows a cross sectional side-view of the cartridge 8700 and a top view of the cartridge 8700. In the side-view, the cartridge includes an inlet 8800, with a mouthpiece 8805, a reactant bead chamber 8810 with reactive beads 8815, an ampule 8825 including a chemical reactant 8820, and a wick 8830 with a lower portion 8840, a middle and an upper portion 8835. The cartridge 8700 also includes a hammer access opening 8828 which allows a hammer to contact the ampule as discussed elsewhere in the specification. A viewing window 8855 is arranged next to the reactive bead chamber 8810 to allow a color sensor 8850 on the device to sense the color in the reactive bead. An LED 8845 may illuminate the treated material through the window 8855.

In the top view in FIG. 54 the cartridge 8700 is shown along the dashed line from the side-view. The cartridge includes Flow Path A which includes a lower disk 8860, a bed of desiccant 8800, a middle disk 8865, the bed of reactive beads 8815, an upper disk 8870, and an ampule 8825. Flow Path A has an inlet 8885 and wall 8805 and outlet 8895. Flow Path B includes 8890 and outlet 8898.

Figure 55:
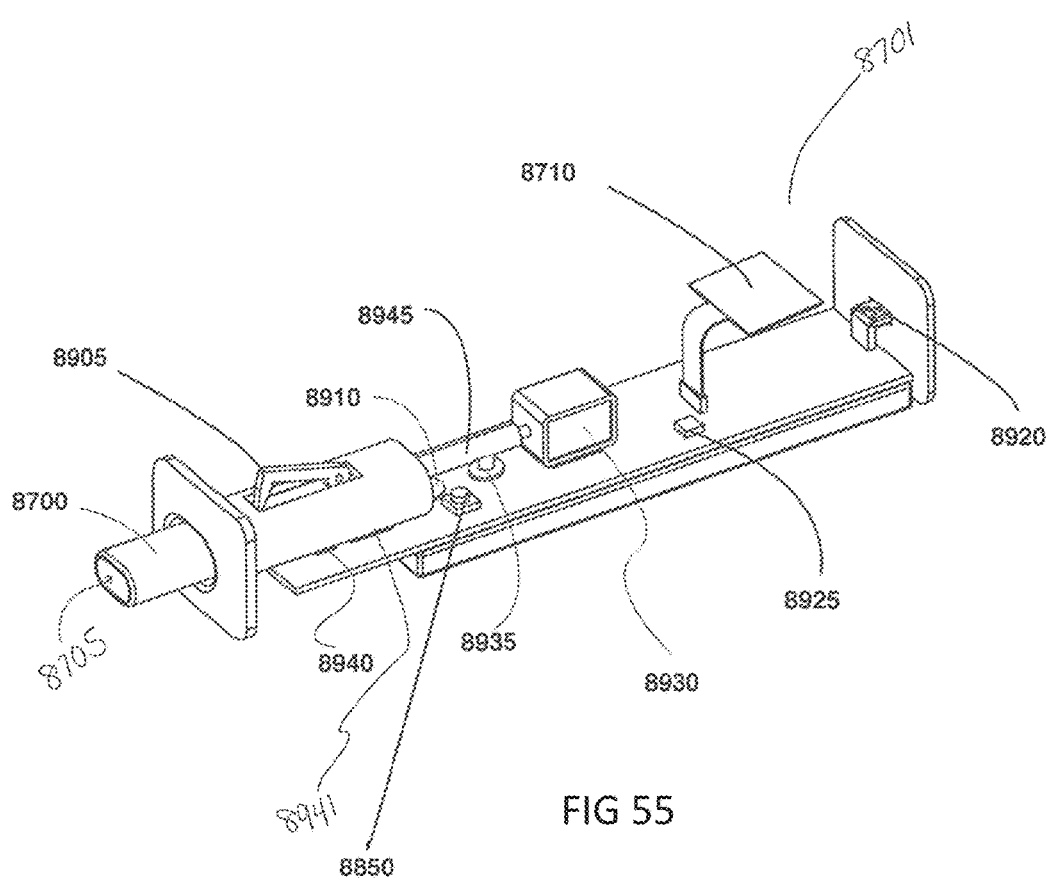
FIG. 55 shows certain internal components of the breath analysis device shown in FIG. 53.

FIG. 55 shows the insides of the device 8701 with an inserted cartridge 8700. The device 8701 includes a hammer 8905, a first mass flow sensor 8910, an outlet flow path 8945, a second mass flow sensor 8935, a solenoid valve 8930, a display 8710, a microprocessor 8925, a USB port 8920, a color sensor 8940, and an LED light 8941.

Figure 56:
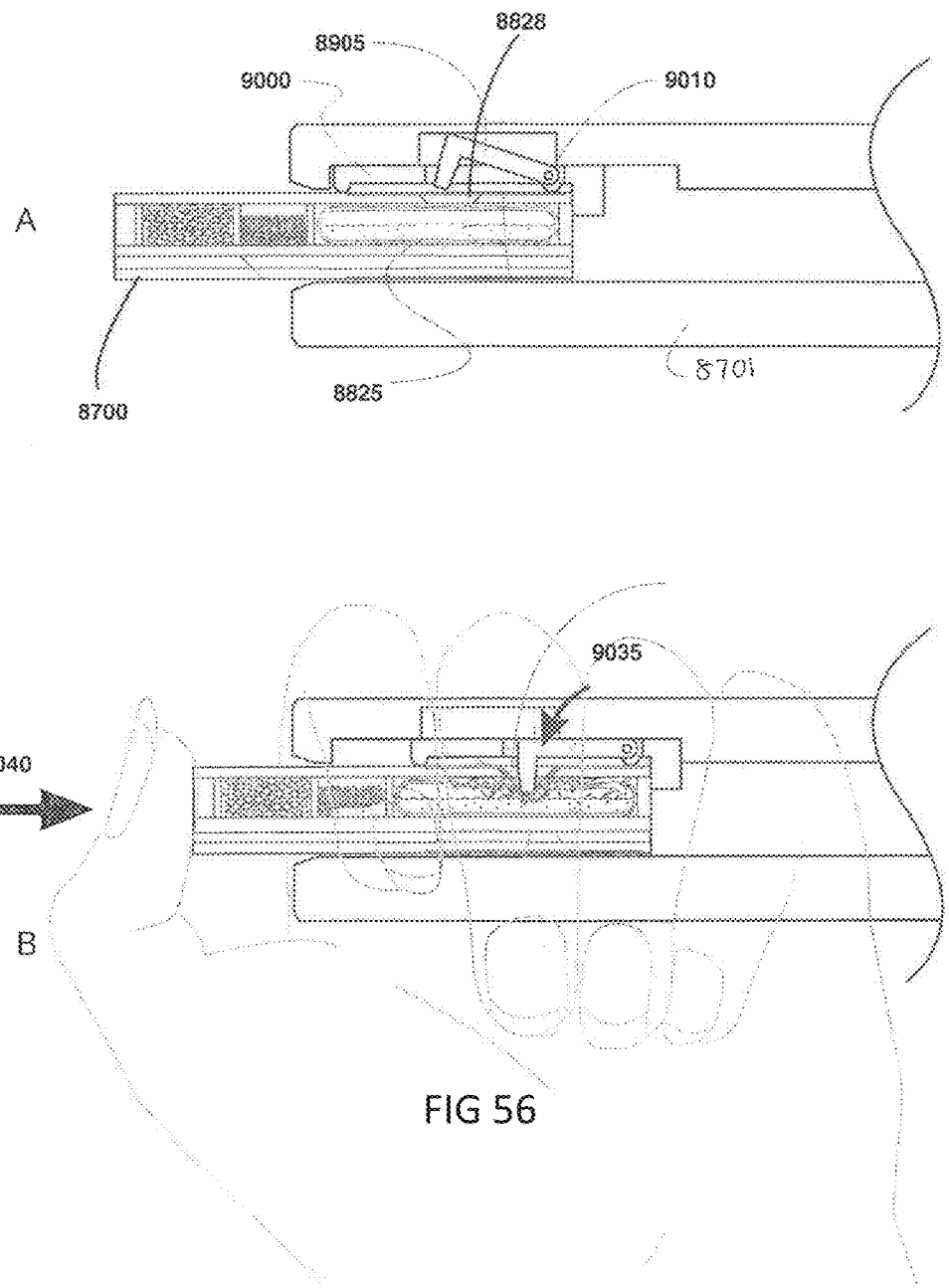
FIGS. 56A-B show the two-step insertion of the cartridge shown in FIG. 54 with the device shown in FIG. 55.
Figure 56A:
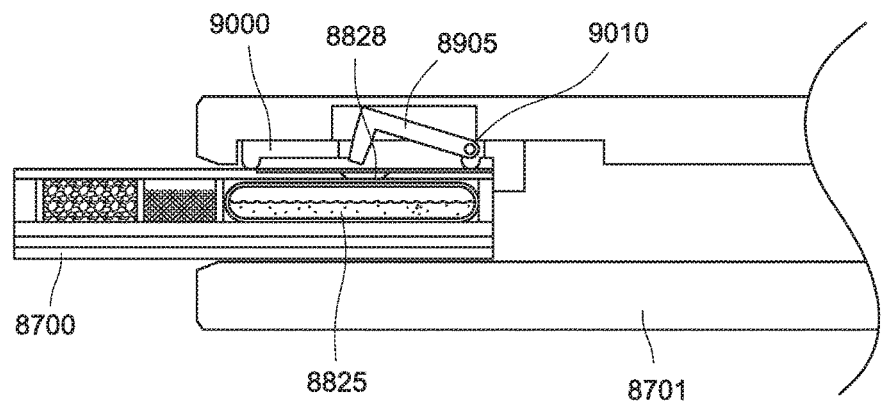
Figure 56B:
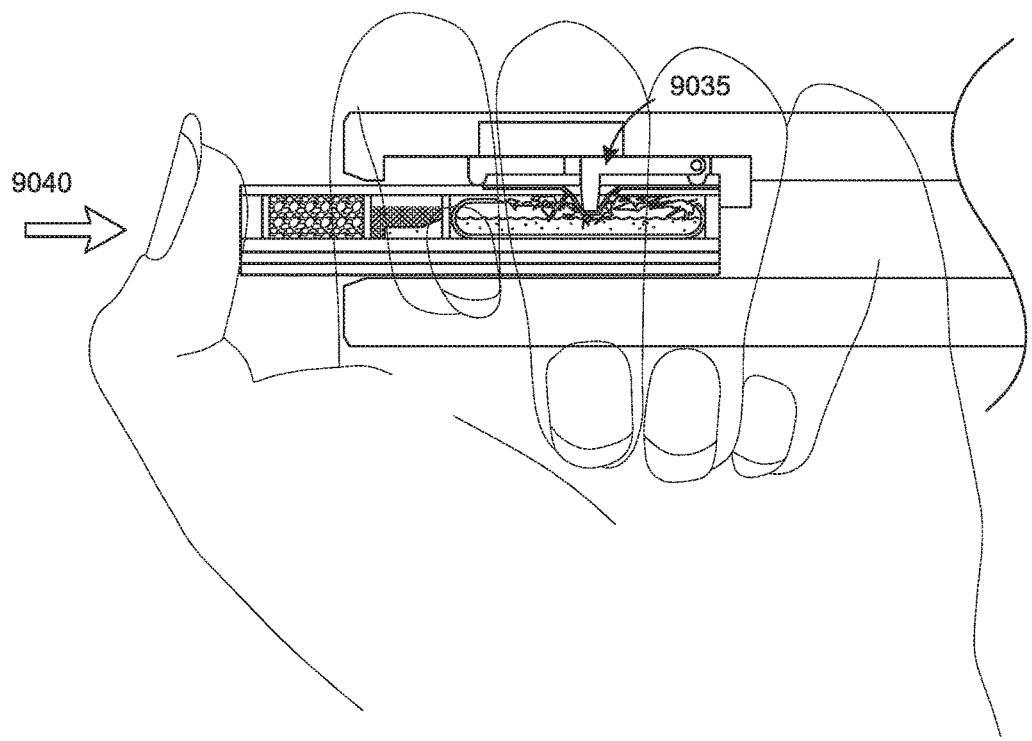

FIG. 56 shows a cross sectional side view of the device 8701 with an inserted cartridge 8700. The hammer 8905 of the device 8701 is mounted on a pivot point 9010. The hammer 8905 is positioned so that its head is directly above an hammer access opening 8825. A hammer sled 9000 keeps the cartridge 8700 from moving laterally and acts as a first mechanical stop as the cartridge 8700 is inserted into the device 8701. As the cartridge is further inserted with some force 9040 such as a thumb, the hammer sled 9000 moves further into the device 8701 until a second stop is reached in the divide 8701. At that point, the hammer 8905 is pivoted down by its contact with a ledge, forcing the hammer 8905 to piece the crushable glass ampule 8825. A rubber band wrap 9035 surrounds the ampoule.

This system is described in terms of the steps described in FIG. 86: (a) directing alveolar breath to the reactive chamber, (b) releasing the liquid, (c) wicking the liquid through the reactive chamber, (d) detecting color via a color sensor and (e) displaying the output.

Starting the Test

Figure 52:
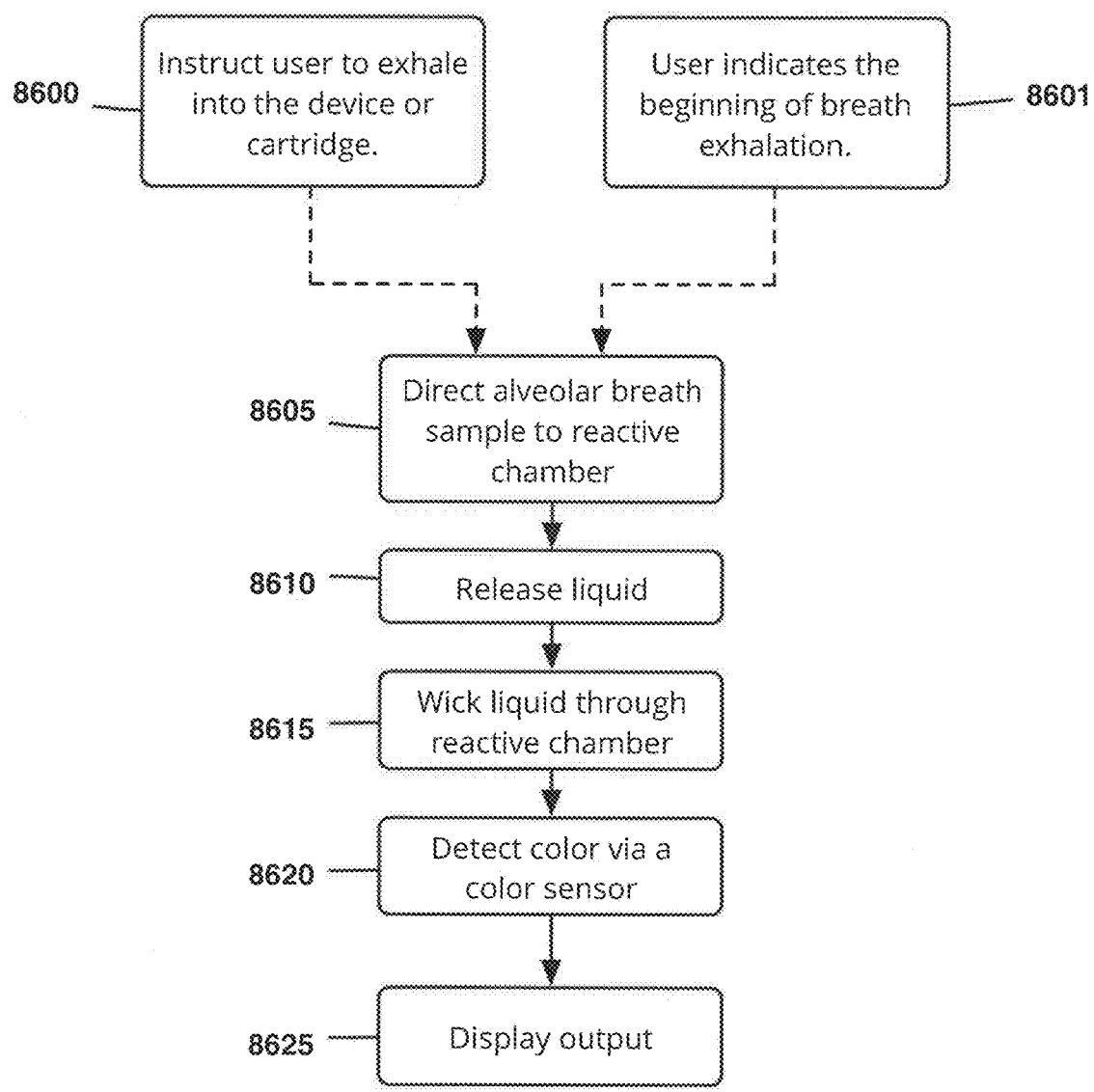
FIG. 52 is a flow chart of the operating steps of one embodiment of a breath analysis system.

With respect to FIG. 52, a first step 8600 may be to instruct the user to exhale into the cartridge or device. The device may instruct the user to exhale into the cartridge by means of an audio, visual and/or haptic indication. A visual screen 8710, for example, may be part of the device 8705. Alternatively, as in step 8601, the user may indicate to the device that breath exhalation has begun. The user may indicate the onset of exhalation by various means to the device, such as by pressing a button, voice recognition, etc. The mechanism for the device to determine the start of the breath input may incorporate one or more of a push button, a pressure sensor, a flow sensor, humidity sensor, temperature, and a photodiode. In one embodiment, the user may depress a physical button close to the time in which the user will start to breath into the cartridge and/or device. If the button is pressed again it may be assumed that the first press was in error and the second press signals the true start of the breath input. In another embodiment, the button is on a touch screen of the device or on a mobile device wirelessly connected to the device to controlling the device.

In another embodiment, in step 8602, the deep lung system may determine that the user has begun to exhale. In one embodiment, the device includes a photodiode near the mouth piece. When the user places the use's mouth on the mouth piece (in preparation to exhale), the user's mouth will cover the photodiode. Accordingly, the ambient lighting conditions will become dark (because it is in the user's mouth) and the photodiode can detect the lighting change. Once the photodiode detects that it is in a dark environment, it outputs a signal that can indicate the start of the breath input. In another embodiment, similar to the previous, the deep lung feature may incorporate a humidity or temperature sensor to augment or replace the photodiode. The human mouth is typically more humid and hot that the ambient environment. Thus, a humidity or temperature sensor may also be able to determine that the user has place their mouth on the mouth piece and signal the start of the breath input. In another embodiment, the deep lung feature may incorporate some form of a flow sensor. When the user begins to exhale, the flow sensor detects the flow of air and signals the start of the breath input. A flow sensor may operate by including a turbine that is attached to an electrical generator. When the turbine spins it generates an electric current which indicates air flow. In another embodiment, the deep lung feature may incorporate some form of a pressure sensor. When the user begins to exhale they will exert a certain amount of pressure which the pressure sensor detects and signals the start of the breath input. Valve? The pressure sensor may operate by including a piezoelectric material which experiences a change in its resistivity once pressure is applied.

Directing Alveolar Breath to the Reaction Chamber

In the next step 8605, the device or cartridge or both together, direct the alveolar breath sample to the reactive chamber of the cartridge. In one embodiment, the user exhales through the mouthpiece 8805 of a cartridge 8700. The cartridge contains two flow paths, Flow Path A and Flow Path B. Flow Path A leads to various chambers in the cartridge. Flow Path B can be the route instead of Flow Path A for a breath sample that does not contain alveolar breath. Flow Path B thus serves to route the breath sample out of the cartridge. In one embodiment, Flow Path B may be a separate flow channel from Flow Path A. In another embodiment, Flow Path B may be a detour from Flow Path A. In either design, by default, the breath sample travels the path of least resistance, which is initially Flow Path B.

Flow Path B directs the breath sample from the inlet 8890 to the exit 8898. When the cartridge 8700 is inserted into the base unit 8720, an airtight seal is made between the exit 8898 of Flow Path B and a path (8945) to a solenoid valve 8930 that is in the open position when the user first exhales. As the breath sample traverses this flow path, it passes by a mass flow sensor 8935 before it is discarded to the outside environment. The breath will continue to take this detour until the processor (8925) instructs the solenoid valve to switch to a closed position. With the valve closed, the path of least resistance will become Flow Path A. At this point, a user's breath should contain alveolar breath. As such, the device directs alveolar breath to the reactive chamber in step 8605 by the switch of the flow path from Flow Path B to Flow Path A.

Flow Path A directs the breath sample from the inlet 8885 through a desiccant chamber 8880, a reactive chamber 8815, a liquid developer chamber 8825 and an exit 8895. As the breath exits the cartridge, it travels past a second mass flow sensor 8910, and then out of the device, back to the outside environment.

The form factor of the base unit is not intended to be limiting. For example, the base unit may be substantially smaller than the base units shown in the figures, but it may still work with the same disposable components. In some embodiments, the base unit is portable, such as less than about 250 cubic inches, or less than about 125 cubic inches (or 5 inches cubed). In other embodiments, the base unit is between 27 and 125 cubic inches. For example, in at least one embodiment, the base unit is approximately 27 cubic inches (3 inches cubed). In other embodiments, the base unit is between 8 cubic inches and 27 cubic inches. For example, in at least one embodiment, the base unit is approximately 8 cubic inches (2 inches cubed). In other yet embodiments, the base unit is less than 8 cubic inches. Of course, the cuboidal shape is not limiting, e.g., the base unit may be other shapes.

In some embodiments, the cartridge is compact. For example, the cartridge may be less than about 8 cm in length. In other embodiments, the cartridge is less than about 6 cm in length. For example, in some embodiments, the cartridge is about 5.3 cm, including the length of the handle. In other embodiments, the cartridge is between about 4 cm and 6 cm. In certain configurations, the cartridge is less than 4 cm. The width of the cartridge is typically no more than about 33% of the height, and often is no more than about 20 to 25% of the height.

In some embodiments, the height of the reactive chamber of the cartridge is short. In certain embodiments, it is less than about 3 cm. In certain embodiments, it is less than about 2 cm. In other embodiments, it is less than about 1 cm. In still other embodiments, it is less than 0.5 cm or between 0.25 cm and 0.5 cm. In other embodiments, it is less than 0.25 cm. The ratio of the height of the reactive column to the height of the column overall is often less than 25% and is preferably less than 10%.

In some embodiments, the breath bag volume is less than about 1 L. In certain embodiments, it is between about 500 ml and 1 L. In other embodiments, it is between about 250 ml and 500 ml.

The system may include a fractionator or venting system to determine how much breath has passed through a give part of the system. Any of the number of fractionators and/or venting systems discussed herein may be used, including user-initiated, device initiated (automatic), mechanical, or sensor-based based fractionators.

Releasing the Liquid

In this embodiment, after the user's breath has been run through the system, the disposable cartridge is activated and the reactive material 8815 is saturated with a developer solution. The solution is stored in a sealed ampoule 8825 made from crushable glass. It may be resistant to ultraviolet ("UV") light (or covered by a UV light shield) and is in the shape of a cylinder with spherical ends. It is approximately 1.5" long and 0.25" in diameter. When the ampoule is broken open by the actuation mechanism, the solution floods the cartridge cavity that the ampoule 8825 is housed inside.

In this embodiment, the actuation mechanism is comprised of the following components: glass crush hammer 8905, hammer sled, crushable glass ampoule, developer solution, and microprocessor. They work together to release and distribute developer solution in a controlled way that ensures full saturation of the reactive material. When the user is prompted by the microprocessor to push the cartridge into the device as far as it will travel, the ampoule is broken open by the hammer which is made of rigid plastic or metal. This hammer is on a pivot and is pivoted downward onto the ampoule by interference with other plastic features on the inside of the base unit housing as the sled moves deeper into the base unit. A torsion or coil spring returns the hammer to its original position when the cartridge sled is restored to its original position and the cartridge is removed. In this embodiment, the hammer is attached to the sled at the pivot point. The hammer tip is designed to have very little surface area which increases the force applied to the ampoule during actuation. The cartridge has mating features that interlock with the sled and the two become one as the cartridge drags the sled along to a new, deeper position inside the base unit. The cylindrical glass ampoule is supported by features inside the cartridge that promote breakage. One support at each end of the ampoule's length so that the hammer applies force directly in between the two supports. The shards of crushable glass stay inside the cartridge and do not come in direct contact with the user. An elastomeric membrane covers the opening in the cartridge that the hammer tip travels through. The hammer never punctures the membrane that flexes and takes on the temporary shape of the hammer tip. This keeps glass shards and liquid solution inside the cartridge. For this embodiment, the membrane can be installed as a wide rubber band that wraps around an entire end of the cartridge and covers the hammer tip opening. This opaque, wide rubber band also serves as a UV light shield for the sensitive developer solution contained inside the glass ampoule. The glass ampoule is either an amber glass or a near opaque glass.

Wicking Liquid Through the Reactive Chamber

Referring to the same embodiment, within the ampoule cavity is a strip of wicking material 8830 that is comprised of an optional portion that is within the ampoule cavity 8835 and a portion that is within the reactive bead cavity 8855. The wick runs the entire length of the ampoule and continues on into the neighboring reactive chamber where it comes into direct contact with the reactive material (loosely packed silica beads). In this instance, the wick strip is comprised of a porous, hydrophilic polyethylene material and it is approximately 2" long by 0.25" wide, by 0.0625" thick, but other materials and sizes can be used as well including those described herein. The solution is wicked from one cavity to the other until the reactive material is fully saturated.

Detecting Color Using a Color Sensor

Figure 63:
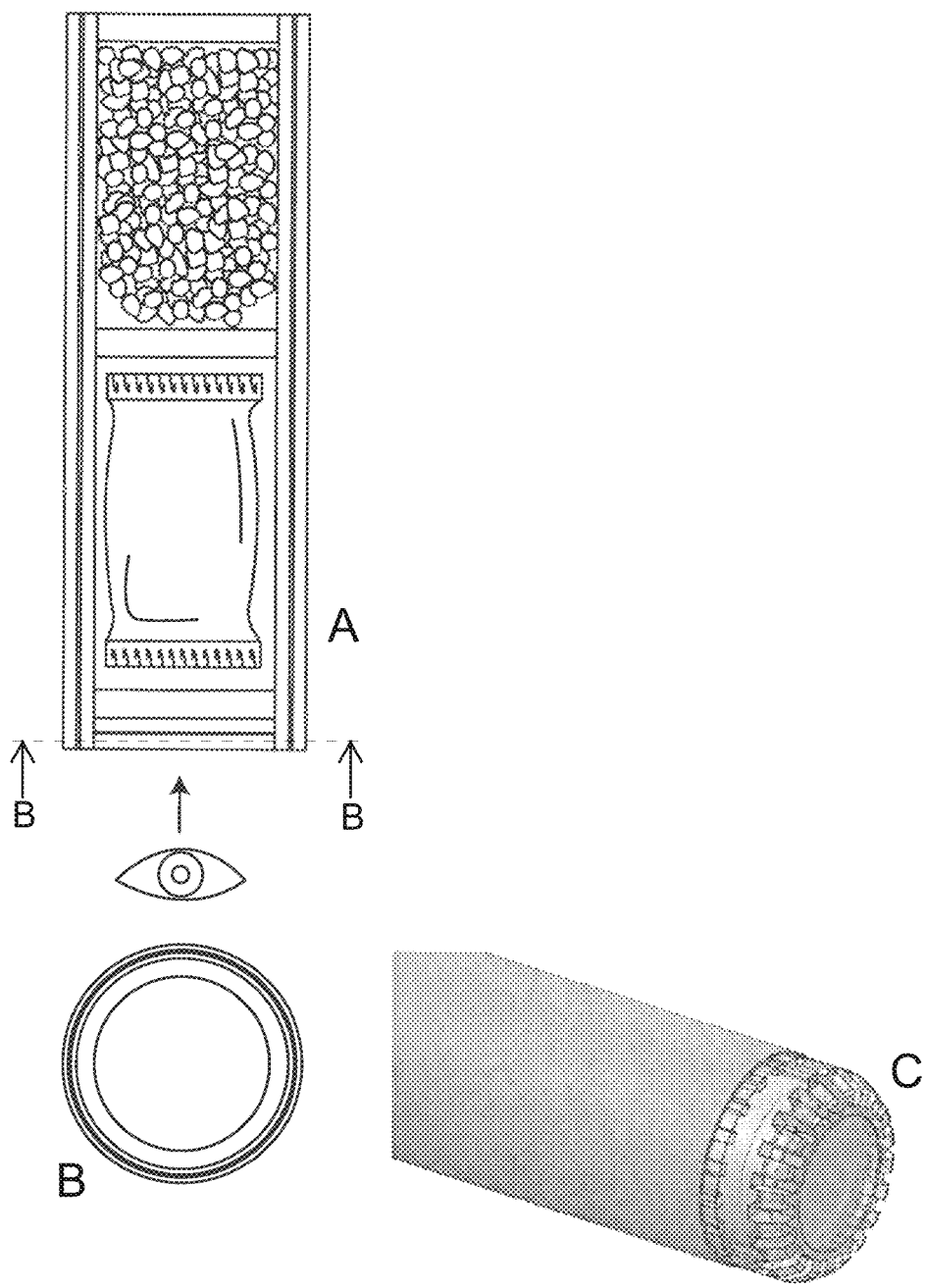
FIGS. 63A-C show an embodiment of a cartridge that utilizes a different packing strategy.

A color is formed when the reactive material interacts with a developer solution. One of the reactive chamber walls serves as a viewing window to the exterior of the cartridge. This window is transparent and gives a full view of the reactive material. In FIG. 63, a different design is shown in which the reactive chamber is viewed perpendicular (instead of parallel) to the initial flow direction of the breath sample. In either case, when the cartridge is inserted into the base unit, the cartridge is lined up in such as a way that the viewing window is in direct view of an optical sensor.

In certain embodiments the system incorporates a sensor which exhibits a phenomenological color change. For example, depending on the concentration of an analyte in a gas sample, the sensor may induce a color change between light blue and dark blue. In such embodiments, the system should incorporate some mechanism to capture this color. The mechanism to capture the color may incorporate one or more of a photodiode, color sensor, image sensor, lens, light filter, illumination source, and light pipes.

In one embodiment the system incorporates an LED illumination source that emits a light with a phenomenologically specific wavelength to induce a desired spectral response. The light from the LED is optionally directed at a light pipe constructed from plastic or glass that redirects the light to the region of color change. The light passes through the region of the color change such that the exiting or reflected light is a different color. The exiting light is optionally routed through a second light pipe for a sensing region. A photodiode if positioned such that the exit light that arrives at the sensing region will enter into the photodiode. The photodiode may optionally be equipped with a lens and a filter to focus the light and filter out phenomenologically irrelevant signals. The photodiode may be connected to an analog to digital converter to convert the color response into a digital output. In some embodiments there may be multiple photo diodes and those photodiodes may contain different filters. For example, one embodiment may call for three photodiodes specific to red, green, and blue light respectively.

Figure 57:
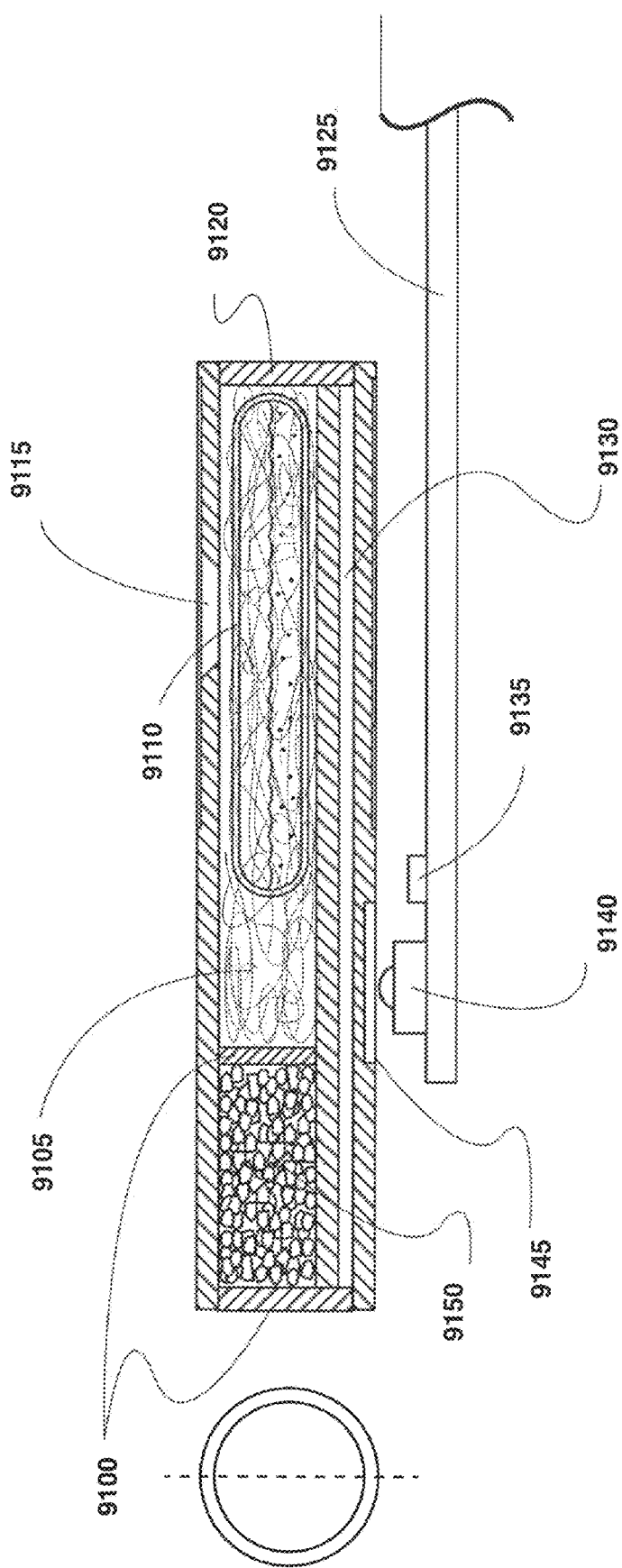
FIG. 57 shows another embodiment of a cartridge that utilizes reactive material other than beads.

FIG. 57 illustrates another embodiment that includes glass/quartz wool 9105 for its chemistry. In FIG. 57, a cartridge includes porous disks 9100, desiccant 9150, glass/quartz wool 9105, a crushable glass ampoule 9110, a hammer access opening 911 a hydrophobic permeable disk 9120, a detour pathway 9130, and a viewing window. The device into which the cartridge is inserted may include a color sensor 9140, and LED light 9135 and a PCB 9125.

Color Sensing Algorithms

In certain embodiments the system incorporates a sensor which exhibits a phenomenological color change. For example, depending on the concentration of an analyte in a gas sample, the sensor may induce a color change from light blue to dark blue. A color sensing algorithm may be used to quantify this color change. The color sensing algorithm may incorporate one or more of the following pieces of information (1) a scalar or vector representation of the input color (2) a reference color (3) a calibration curve or lookup table.

In one embodiment, the sensing algorithm accepts a single scalar color value. This color value is compared against the reference color to determine a difference. This difference may involve one or more of a simple arithmetic subtraction, Euclidean distance of an RGB value, or a color space distance computation. In the event that a color space distance is used, the specific algorithm may use a perceptual color distance computation that mimics how humans perceive color differences, often called Delta E. An example of a perceptual color difference equation is CIEDE2000 published in 2005 by Sharma et al. Once the comparison value between the reference color and input color is known it is compared again a calibration curve or look up table to determine the corresponding analyte concentration.

In another embodiment, the sensing algorithm accepts multiple color values in the form of a pixel map or image representation. The sensing algorithm may compute an average or some other aggregate metric on these values. Or, alternatively, the sensing algorithm may use the multiple values to simply ensure that all values are sufficiently similar to one another indicating that an error likely did not take place.

In another embodiment, the sensing algorithm accepts multiple color values but these color values may have been taken at different times. This is useful in cases in which not only is the color change phenomenologically significant, but the rate at which it changes is significant as well. Additionally, this is useful in cases in which the time needed for a full color change is not known and must be determined dynamically by the system by continually checking until the color stops changing.

Orientation Check

In certain embodiments the system incorporates the use of a developer solution and an activation mechanism by which the developer solution is operatively used. In such embodiments the system may further incorporate a tracking mechanism to track when, if, and how much of the developer solution has been used. The tracking mechanism will be primarily used to determine that a reading was performed correctly and fully.

In one embodiment, the activation mechanism incorporates action on behalf of the user in which they shake, rotate, or otherwise orient the device in a certain position which allows the developer solution to be dispensed. For example, the user may push a button to open a valve and then rotate the device by about 90 degrees so that gravity may cause the developer solution to pass through the valve and into a cartridge. In such an embodiment, the tracking mechanism may incorporate the use of one or more of a magnetometer, accelerator, gyroscope, and microprocessor. Using these components, the tracking mechanism will determine that the device was in its "normal" position during the initial phase of a reading (i.e., the developer solution was not released early) and then rotated between two threshold angles (for example, 75 degrees and 105 degrees) for a certain amount of time (for example, 10 seconds). Moreover, the tracking mechanism may ensure that the device is not violently shaken before activation in a manner that runs the risk of the developer solution being released accidentally. Likewise, the tracking mechanism may ensure that the device is held steady and does not move during the time it is rotated.

In another embodiment, the activation mechanism is similar to the previous embodiment, but the tracking mechanism may be augmented by or replaced with a mechanism that incorporates a mass flow sensor in-line with the cartridge and measures how much of the developer solution pass into the cartridge. The tracking mechanism ensures that no developer solution is dispensed until the appropriate time and then further ensures that when the time comes, an appropriate amount of developer solution is dispensed in a certain time range.

In another embodiment, the activation mechanism is similar to the previous embodiment, but the tracking mechanism may be augmented by or replaced with a mechanism that incorporates a fluid volume sensor which measures the amount of unused developer solution. The fluid volume sensor may incorporate one or more of a photodiode, camera, or other optical sensors to visually determine how much solution remains and ensures that the developer solution is dispensed only at the appropriate times. Alternatively, the fluid volume sensor may incorporate the use of electrode to measure the resistance across the developer solution. As the developer solution is used the resistance across the developer solution changes and thus the device is able to determine that the developer solution is dispensed appropriately.

In another embodiment, the activation mechanism is similar to the previous embodiment, but the tracking mechanism may be augmented by or replaced with a mechanism that incorporates one or more of an altimeter, pressure sensor, temperature sensor, and Global Positioning System ("GPS") module as the tracking mechanism may need to operate differently depending on the environmental conditions. For example, if the ambient environment is very cold the device may need to be rotated and kept still for a longer period of time.

In another embodiment, the activation mechanism is similar to the previous embodiment, but does not require explicit user input. For example, instead of the user pressing a button to open a valve, the valve is programmatically opened by microprocessor based on input from the tracking mechanism. For example, the tracking mechanism may incorporate an accelerometer and when the accelerometer determines that the device is being shaken it causes the microprocessor to automatically open the valve.

Figure 65A:
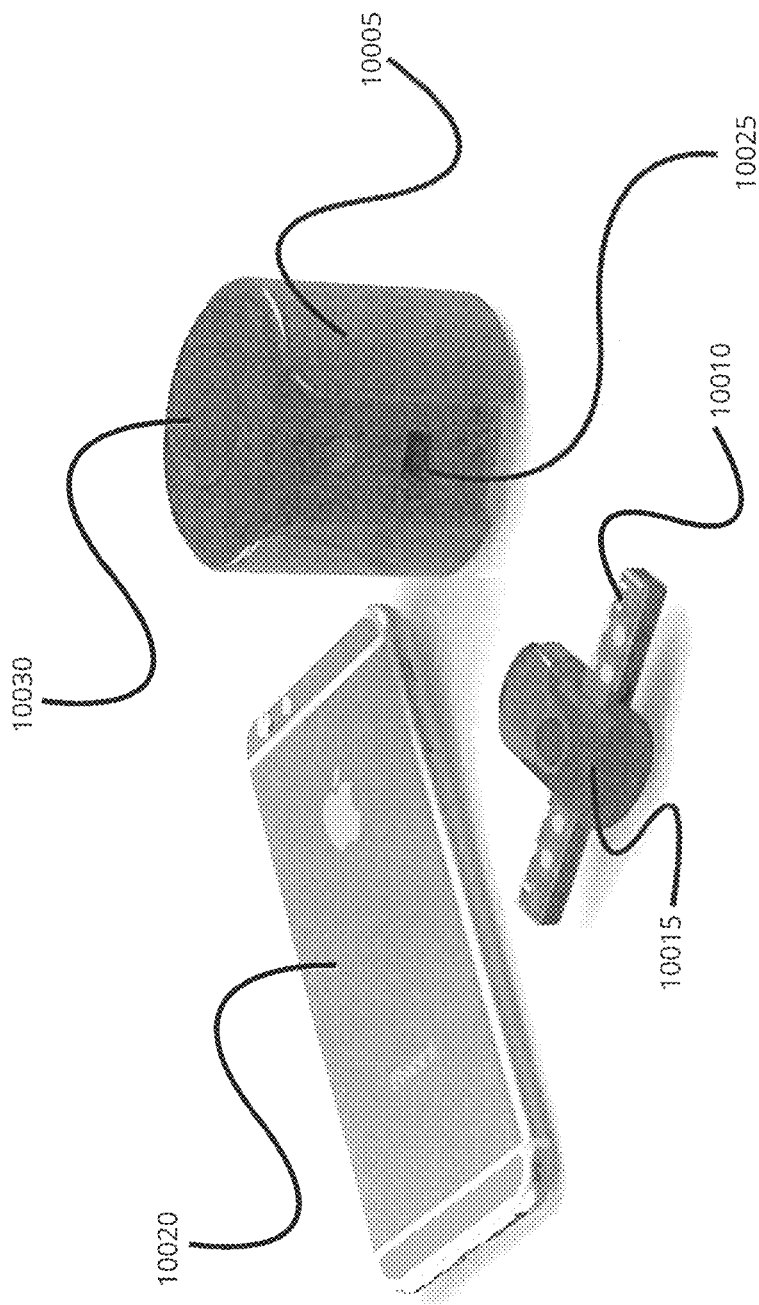
FIGS. 65A-C show various embodiments of a breath analysis system.

FIG. 65A shows another embodiment of a breath analysis subsystem in which the time of breath sampling and the time of breath analysis may be substantially different and are thus decoupled.

The embodiment is comprised of a base unit 10005, a cartridge 10010, an integrated mouthpiece 10015, and a mobile device 10020. The base unit 10005 is comprised of a color sensor (not shown in FIG. 65A), a detachable liquid container 10030, a ROM chip reader, and a cartridge insertion port 10025. The cartridge insertion port is configured to receive a cartridge 10010. When the cartridge is inserted, it can move bidirectionally, although the primary output is on the backside of the unit shown in FIG. 65B (implying that, at least for a 7 day cartridge, a preferred direction of movement is "through" the device and out the other end).

Figure 66A:
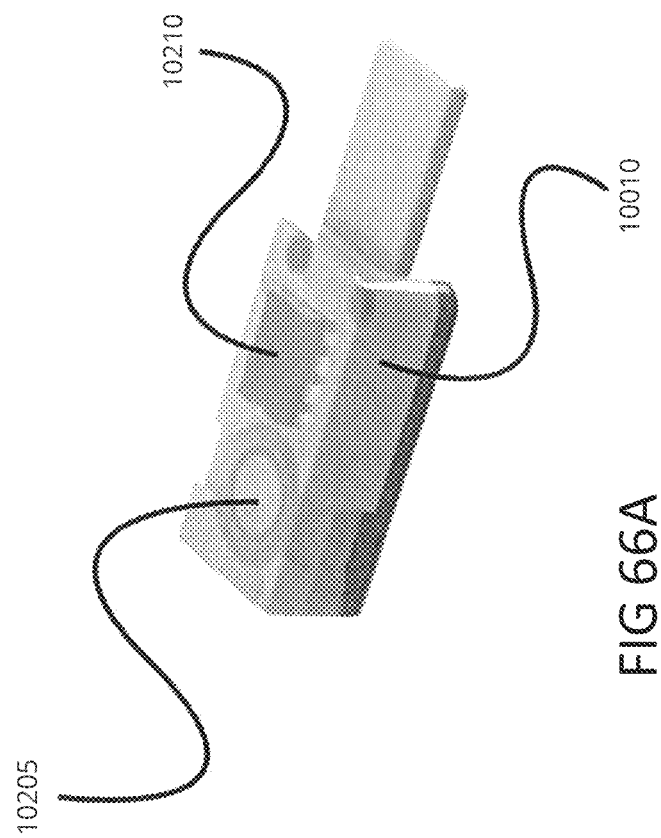
FIGS. 66A-C show various embodiments of cartridges for a breath analysis system, such as the breath analysis system of FIGS. 65A-C.
Figure 66B:
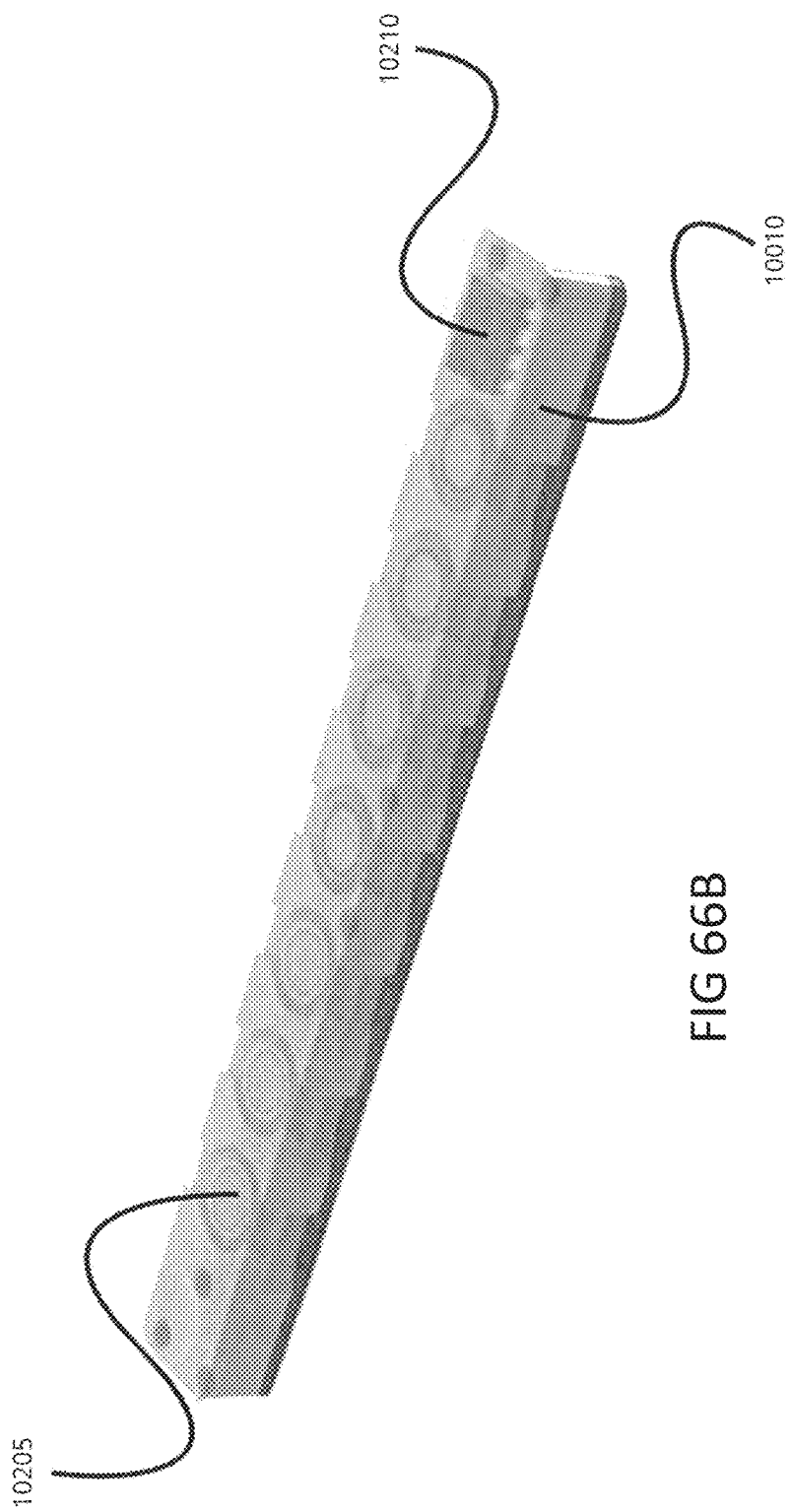
Figure 66C:
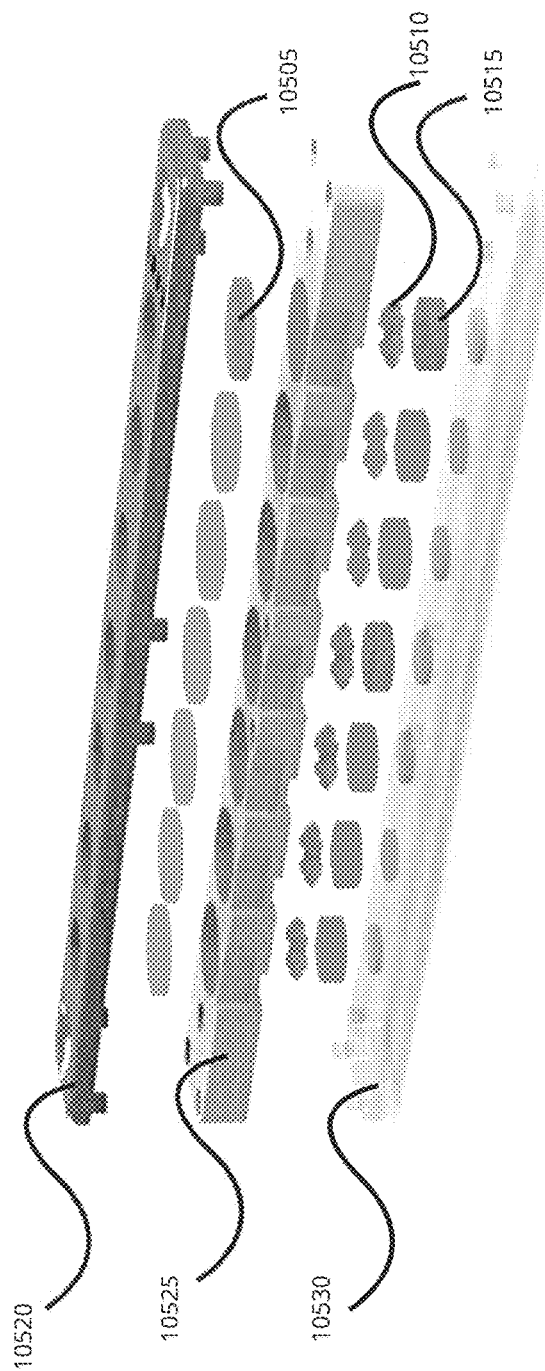

The cartridge may contain a plurality of test chambers as shown in FIG. 66B or it may comprise a single test chamber as shown in FIG. 66A. In this design, the cartridge is comprised of three barriers 10520, 10525 and 10530 that separate chemical reagents, such as desiccant and reactive beads. The cartridge also comprises an EEPROM chip, such as a read only memory chip or similar memory storage device 10210.

Figure 65B:
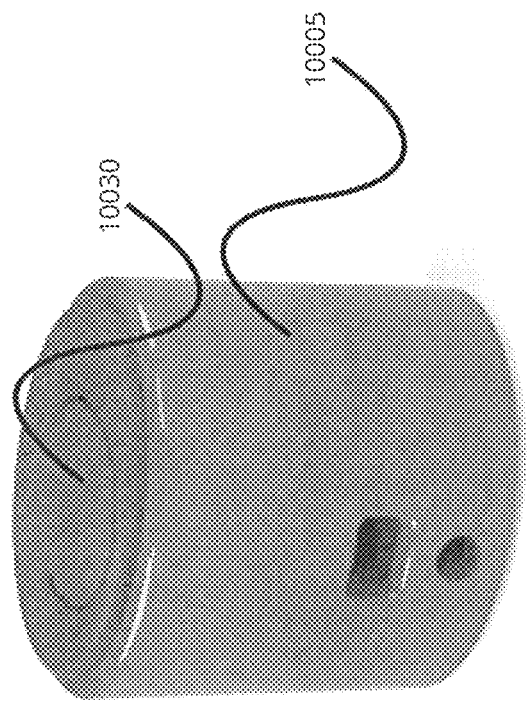
Figure 65C:
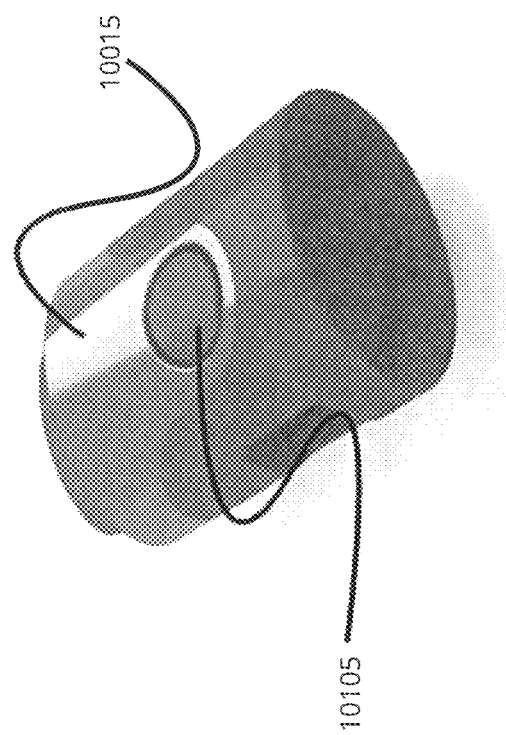
Figure 67A:
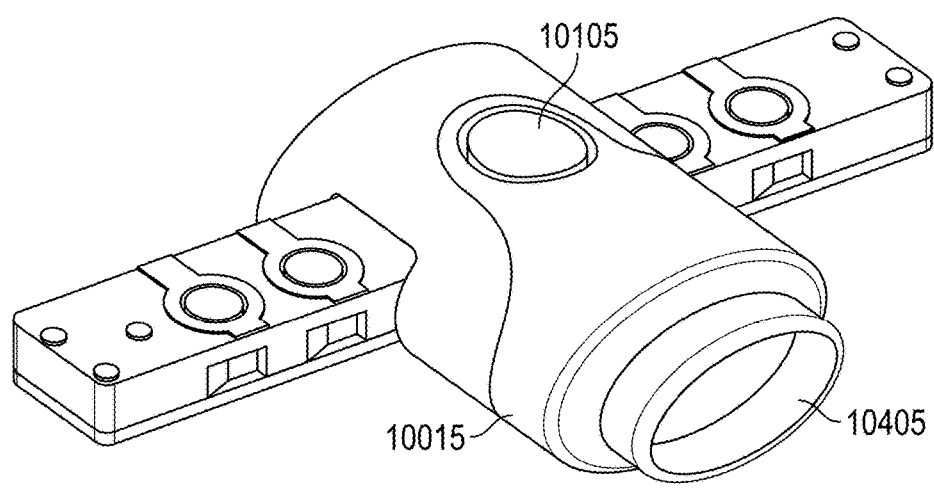
Figure 68A:
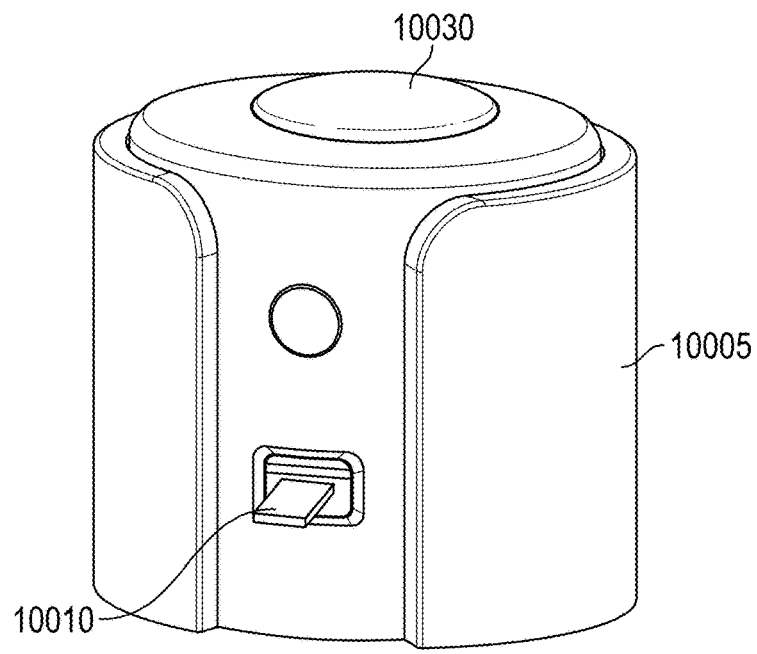
FIGS. 68A-B show an embodiment of a base unit of a breath analysis system mating with various embodiments of a cartridge.
Figure 68B:
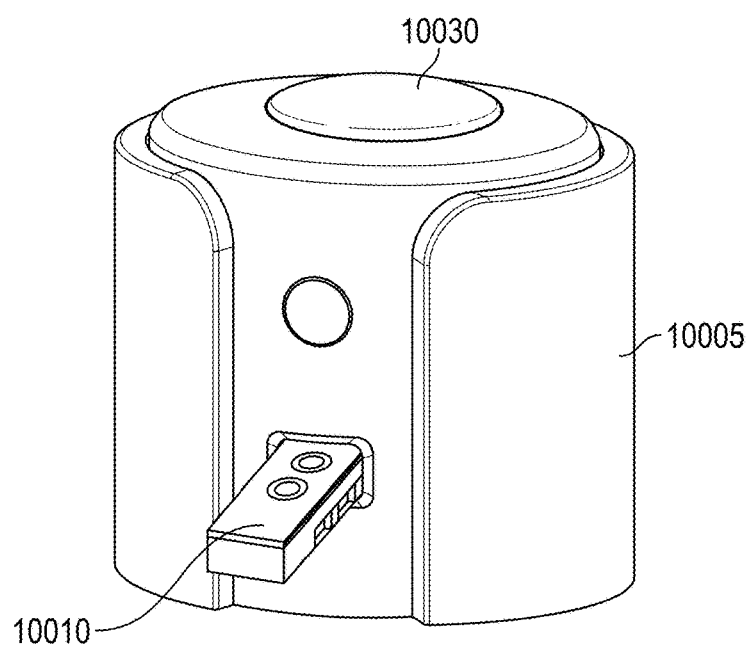
Figure 69A:
FIGS. 69A-D show screen shots of a mobile application that works in conjunction with the breath analysis device or otherwise with ketone results generated from the breath analysis device.
Figure 69B:
Figure 69C:
Figure 69D:

The integrated mouthpiece 10015 is comprised of a button 10105, an LED indicator light (shown in FIG. 67B), a sample collection valve (not shown), a clock (not shown), and a cartridge receiving port through which the cartridge may be inserted (as shown in FIGS. 65B-C).

In this system, cartridge is first inserted into the integrated mouthpiece and aligned with a specific test chamber within the cartridge. The user exhales through the mouthpiece at timing specified by the LEDs shown in FIG. 67B so that a breath sample is delivered to the test chamber. At this time, the first two steps of the chemical reaction take place: the sample is dried by the desiccant and it is also reacted with the reactive beads. The cartridge is then inserted into the base unit. The base unit analyzes each test chamber individual using a sensor. The sensor generates a raw signal, which is computed and processed to create a result. The result is transmitted wirelessly from the base unit, such as to the user's mobile device or directly to a remote server.

In the above embodiment, the base unit serves as the primary mode of analysis, as it is comprised of the processing mechanism, in this case a color sensor. Upon insertion of a cartridge, the base unit provides bidirectional movement of the cartridge in order to read the ROM chip, as well as analyze individual test chambers within a cartridge. The base unit also comprises a developer solution container. This container is optimized to require replacement at a less frequent rate than the cartridge use. Ideally, this container would hold enough developer solution for roughly 100 tests, and would be able to dispense enough solution to react with an additional reactant or chemistry, and create a reaction product, or response. A useful range of developer solution would be approximately 100 microliters. In another embodiment, it is between about 60-100 microliters. In another embodiment, it is between about 40-60 microliters. In another embodiment, it is between about 20-40 microliters. In another embodiment, it is between about 10-20 microliters.

In the above embodiment, the integrated mouthpiece serves two purposes. First, the mouthpiece acts as a trainer, and assists the user in creating a desirable breath profile. U.S. Patent Application Ser. No. 62/247,778 describes different profiles and is incorporated by reference herein. As an example, the LEDs on the mouthpiece may instruct the user to begin to exhale into the room when the LED is green and then through the mouthpiece when the LED is red and to stop when the LED is blue. The mouthpiece may also block flow paths using a solenoid as described elsewhere in this disclosure.

Second, the mouthpiece comprises a clock or time-stamping mechanism. As an example, this mechanism can place a time stamp on each individual test chamber within the cartridge. In one application of this system, the user would collect samples every day for a week. The cartridge would contain only one test chamber for one breath sample. The cartridge would be inserted into the base unit every day for analysis. The base unit would analyze only one test chamber on a daily basis. In another application of the system, the cartridge would be comprised of multiple test chambers. In this example, the base unit comprises a mechanism for bidirectional movement, which allows the base unit to ignore previously analyzed chambers and move onto the test chamber collected on that specific day. In another application of the subsystem, the user may user multiple test chambers over the course of a day. The base unit would recognize the time stamps that were assigned to each cartridge test chamber by the integrated mouthpiece.

The cartridge can be comprised of either one or multiple test chambers. The multi-chambered cartridge can utilize both multiple tests using a single analyte, as well as multiple test using multiple analytes. Each test chamber is comprised of small quantities of reactant.

The inventors have learned that small quantities of desiccant can be used when the flow characteristics and geometries of the system are optimized. As an example, calcium chloride readily absorbs moisture, and can be placed into a loosely-packed bed of roughly 5 or 6 granules, amounting to substantially less than 380 mg, potentially less than 200 mg, less than 100 mg, and even as low as 10 mg. These small quantities of both reactant and desiccant lend itself to a smaller form factor. The small quantities also allow only a small volume of developer solution to be dispensed for each test. As an example, for roughly 400 mg and silica and 5-6 granules of calcium chloride, a sodium nitroprusside solution would only need to be combined in quantities of 40 to 50 microliters in order to complete the reaction.

The cartridge reactant would be packed into a disk shape that resides on top of the desiccant. In another embodiment, the cartridge reactant can be loosely packed into the test chamber. The reactant would only use about 50% of the normal volume. This loose packing of the reactant bed provides less restriction of air flow, making the test chamber easier to breathe through for the user. This reactant would be facing upward and directly contact the developer solution.

The base unit comprises a liquid delivery system that dispenses a precise amount of liquid solution atop the cartridge, for example, the 7-day cartridge. In one example, the delivery system applies lateral energy to a plastic dropper that generates a precise "bead" of liquid when the energy is applied. The head of the dropper is immediately atop the cartridge so that the drop immediately wicks through the layers of the cartridge. Once the solution has been dispensed and the chemical reaction has been initiated, the sensor within the base unit would view the top of the reactant from an aerial perspective in order to measure the response.

The breath analysis system shown in FIG. 65A is designed to separate breath sample capture from breath sample analysis.

The separation of the capture of the breath sample from the analysis of the breath sample is achieved by the integrated mouthpiece. Each cartridge test chamber is comprised of chemistry that allows the sample to be collected separately from the base unit. The chemistry within the test chamber is such that it can hold the absorbed analyte for a prolonged period of time. The cartridge could, as an example, record multiple samples over the course of the day, and maintain the sample until the end of the day, when it is connected to the base unit and analysis is performed. Table 5, below, highlights the time sequence for obtaining a response in a de-coupled system. Even when the actual base unit coupling is delayed by two hours, the response is still generated, and the total test time from the perspective of the user is 60 seconds.

TABLE 5

| Time (t = #:##:##: h:m:s) | Step |
| --- | --- |
| t = 0:00:00 to t = 0:00:10 | Deliver breath sample to cartridge |
| t = 0:00:10 to t = 2:00:10 | User travels with the cartridge only (e.g., at a gym, on a hike, at school, etc.) Analyte is absorbed into the cartridge reactant and remains intact |
| t = 2:00:10 | Insert cartridge into base unit |
| t = 2:01:00 | Receive base unit response |

Additionally, the separation of the sampling and analysis process is achieved by separation of the analyte chemistry. In this embodiment, the base unit is comprised of a developer solution container. The developer solution within the container is meant to react with the reactant within the cartridge. When the cartridge is inserted into the base unit and a test chamber is aligned with the container, developer solution is dispensed onto the test chamber. This solution is meant to react with the analyte that has been absorbed and captured in the cartridge chemistry. An example of this embodiment could be functionalized silica gel that readily absorbs acetone in the breath. The developer solution would be a liquid nitroprusside that, when in contact with the silica gel, reacts with the captured acetone and produces a color response.

In designs in which sample capture is separated from sample analysis, the time that the sample was captured is preferably documented. The identification of a specific test chamber relies on the relationship between the cartridge and the integrated mouthpiece. The cartridge is comprised of a ROM chip, which serves the purpose of storing information. This information can be stamped onto the chip, and can also be read off of the chip. The integrated mouthpiece is comprised of a clock mechanism that, when aligned with a cartridge, stamps information onto its respective ROM chip. This information can include: test chamber, type of analyte within chamber, date and time of sample collected within chamber, etc. Once the cartridge is inserted into the base unit, the unit comprises a ROM chip reader that will read the information stored within the cartridge's chip. This information will be associated with a test result at the end of analysis. Once a test is complete, all information will be provided to the user via the mobile device application. This information can also help determine whether or not certain base unit components are required for that specific test. As an example, if the test chamber chemistry is for a particular analyte that does not require a developer solution, the detachable liquid container may not be utilized for that specific test.

Example of Breath Analysis Device Used to Monitor Success of Ketogenic Diet

This particular system embodiment can be applicable to individuals suffering from epilepsy, specifically children. Ketogenic diets have been proven to reduce seizures in certain forms of epilepsy. For this use case, if test results need to be continuous, but not in real-time, the integrated mouthpiece would stamp the ROM chip with each date and time that a sample was collected throughout the day. The cartridge would be inserted into the base unit at the end of the day, and the test results generated monitored would be provided to an individual that is not the patient, in this case a parent or nurse. The test results would provide feedback regarding the efficacy of the ketogenic diet for the child. This design would allow a child to simply take a "whistle" (the integrated mouthpiece) and a cartridge to the classroom instead of a more expensive base unit.

If test results needed to be continuous and provided in real time, the cartridge serves as a carrier for the child in order to easily provide breath samples. The actual analysis could be done by a nurse or aide at school throughout the day to ensure that the child does not require medication at that time.

Example of Breath Analysis Device Used to Monitor Efficacy of Exercise/Diet

This particular system embodiment can be applicable in the case of athletes, and can be optimized to measure ammonia levels in the breath. In this example, the primary chemistry would be a functionalized silica gel that can absorb ammonia when passed through via breath sample. The silica would be accompanied by a desiccant, such as a sodium hydroxide coated silica. The liquid within the developer solution container would not need to react with this chemistry in order to produce a result. The user would provide samples before a work out, after a work, and at other critical points within their day if applicable. Once the cartridge is inserted into the base unit, the ROM chip would indicate that the cartridge involved ammonia chemistry, prompting the base unit to withhold the developer solution from the test reaction.

In this embodiment, the base unit would comprise a processor that assists in the transfer of information between the base unit and other devices. This processor would allow an interaction between the base unit and the user's mobile device using either Wi-Fi capability, tethering capability, or a network broadcasting capability. These three capabilities work either separately or in certain combinations to produce different user "modes". These modes are utilized depending on the use case that the user finds themselves in. As an example, this embodiment could use the Wi-Fi capability and the tethering capability for a basic home use mode. In the event the user is traveling, the broadcasting capability could utilize a generated network to create a travel mode; this mode would be used to connect to the base unit and get data onto the user's mobile device. The base unit would also be powered via USB charging. This USB charging port could also be utilized in an internal mode, where troubleshooting personnel can access the device via USB and pull data that would not be accessibly to a general user. Lastly, the Wi-Fi capability can also be utilized in a customer support mode, where data from the base unit is generated and sent to a customer support specialist in the form of reports.

FIG. 69 shows screen shots of a mobile application that is configured to "coach" a user through the process of ketone monitoring. This application is integrated with diet journals, such as MyFitnessPal. Using this information, the App looks for patterns and provides a simple tip to help the user make behavioral changes. One example is: identify the highest carbohydrate content in any one food that the user consumed. Suggest that the user stop consuming that food. A second example is: identify a food that the user consumed repeatedly over the past 3 days that contains a decent number of carbohydrates. Suggest that the user stop consuming that food. In some instances, the messages that are provided may be directed to the user himself or herself. But in other instances, the messages may be provided to the user's parent or coach, such as in the case of a parent of an epileptic 3-year old.

Figure 74:
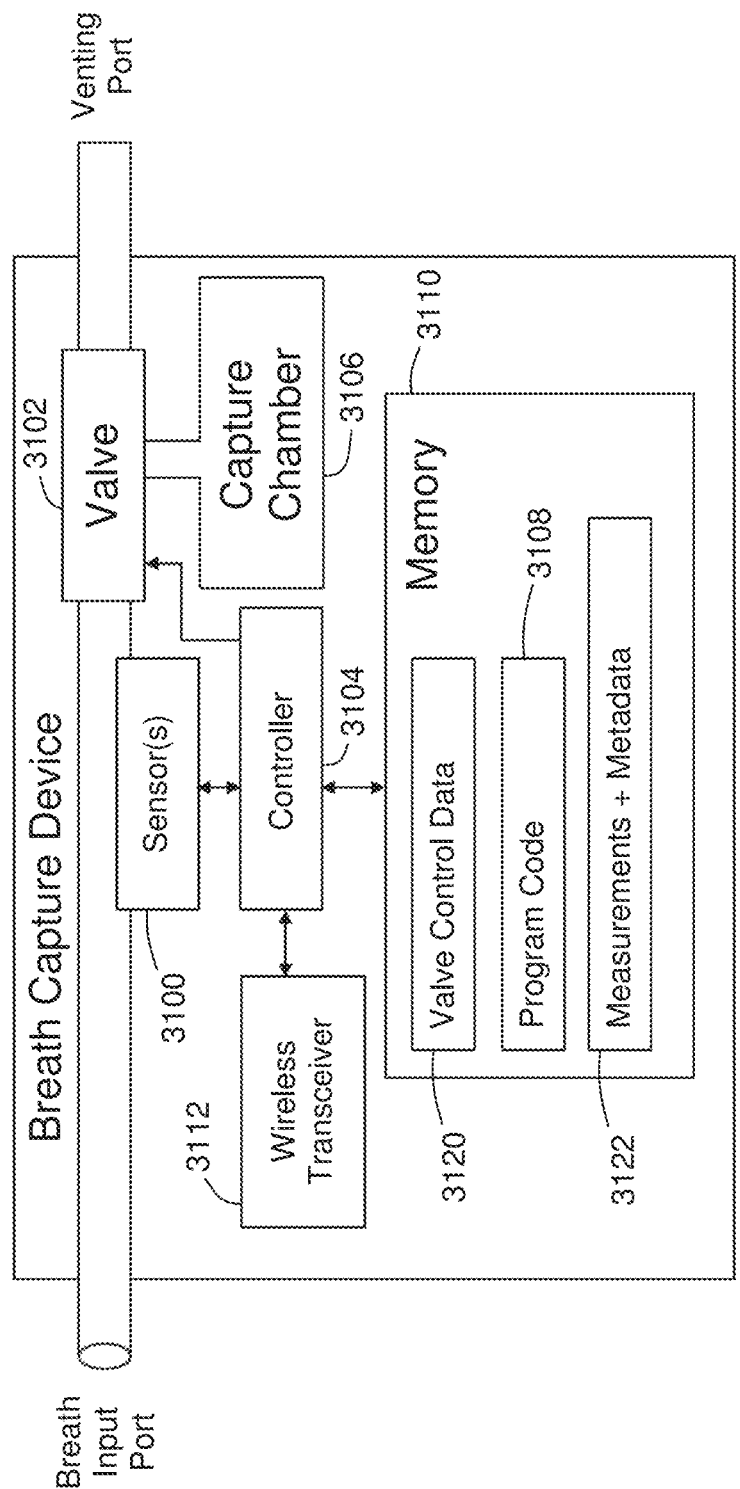
FIG. 74 shows a block diagram of an embodiment of breath capture device.

FIG. 74 illustrates a breath capture device that implements some of the above-mentioned features. In the illustrated embodiment, one or more sensors 3100 are positioned along an influent flow path between the breath input port and the valve 3102 to measure one or more exhalation characteristics of the user. As explained below, these exhalation characteristics may, in some embodiments, be used to configure or personalize the device for the user. In one embodiment, the only sensor 3100 that is provided is a flow rate sensor or a pressure sensor, although various other types of sensors (such as a temperature sensor, a carbon dioxide sensor, or another type of gas sensor) may additionally or alternatively be provided. Although the sensor(s) 3100 are shown along the influent conduit, upstream from the valve, they may additionally or alternatively be positioned downstream from the valve, such as along the venting conduit and/or the conduit leading to the capture chamber 3106.

As illustrated in FIG. 74, the device includes a controller 3104 that controls the state of the valve 3102 during the exhalation process to effectively select the portion of the breath sample to be routed into the capture chamber 3106. The controller may, for example, be a microcontroller or microprocessor that executes program code stored in a non-transitory memory 3110. (All of the functions described below in connection with FIG. 74 may be performed under the control of this program code.) The device also includes a wireless transceiver 3112, such as a Bluetooth or WIFI transceiver, that enables the breath capture device to communicate with a smartphone or other mobile device (not shown) of the user. In some cases the mobile device may execute a mobile application that enables the user to configure and otherwise control the breath capture device.

As illustrated, the memory 3110 persistently stores valve control data 3120 that is used by the controller to control the timing with which the valve state is changed during the capture process. (The valve 3102 in the illustrated embodiment is a 2-way valve that routes the incoming breath either to a venting port or to the capture chamber, depending on the valve's state.) The valve control data is preferably generated or selected programmatically based on one or more characteristics of the user, so that the operation of the valve is customized for the particular user. This advantageously enables the breath capture device to account for the above-described variations in the breathing characteristics of individuals.

The valve control data may take on various forms, and may depend upon the type or types of sensors included in the device. The table below illustrates specific examples.

| Sensor(s) | Valve control data |
| --- | --- |
| Flow rate | The valve control data specifies the volume threshold at which the valve should be activated during exhalation to cause the remaining portion of the breath sample to be routed to the capture chamber. This volume threshold is approximately equal to the "dead space" volume for the particular user, and may be determined by, for example, measuring the user's total exhalation volume and multiplying this value by a constant such as __. The volume threshold may alternatively be calculated based on other characteristics of the user, such as height and weight. |
| Pressure | The valve control data specifies the amount of time after exhalation begins (as detected by the pressure sensor) before the valve is activated to cause the remaining portion of the breath sample to be routed to the capture chamber. This time threshold may be selected by measuring the user's total exhalation time as the user exhales into the device or a separate breath profiling device, and by multiplying this time value by a constant such as ___. |
| None | Same as for pressure, except that the user indicates the initiation of exhalation using either a switch on the device or a user interface element of the mobile application. |

The valve control data 3120 may alternatively be in the form of a mode identifier or user type identifier. For example, the breath capture device may support 3, 4 or 5 different modes (or user types), each of which is associated with a different set of one more valve control parameters for controlling the valve. In these embodiments, the currently selected mode (or user type) may either be recorded in the memory 3110, or it may be selected by the user via a dial, switch, touch screen, or other interface of the breath capture device.

The valve control data 3120 may be generated by the breath capture device, by an external source, or by a combination thereof. The following are examples of how the valve control data 3120 may be generated:

Breath Capture Device Implements Breath Profiling Mode

In this embodiment, the breath capture device can be placed by the user into a breath profiling mode via, for example, the mobile application or a switch on the breath capture device. When the user exhales into the breath input port while the device is in this mode, the device measures one or more exhalation characteristics of the user (such as those mentioned in the table above), and the controller 3104 uses this information to generate the valve control data. (Any past valve control data may be overwritten.) During this profiling process, the valve state may remain unchanged so that the entire breath sample is vented from the device. At the end of the profiling process, the breath capture device may automatically transition into capture mode, and the user may exhale into the device a second time to enable the device to capture an alveolar or other desired breath sample using the newly-generated valve control data 3120. In some embodiments, the breath capture device may enter into the breath profiling mode automatically after being used to capture a breath sample (or after some default time period following capture), in which case the user may be expected to perform the profiling process before each new breath sample is captured.

Breath Capture Device Determines Breath Profile from Prior Capture Cycle(s)

In this embodiment, the breath capture device determines the user's breath profile (and generates the associated valve control data) based on measurements taken during one or more breath capture cycles. The valve control data may thus be generated using the same process as described in #1 above, but without the need to implement a separate breath profiling mode. For example, if the breath capture device includes a flow rate sensor, the controller 3104 may measure the total exhalation volume the first time the device is used to capture a breath sample, and may use this measurement to generate valve control data in the form of a volume threshold. The next time the device is used to capture a breath sample, this valve control data will be used to control the timing with which the valve state is changed. With each capture cycle thereafter, the device may use valve control data that is based on the immediately preceding N breath capture cycles, where N may, for example, be 1, 2, 3, 4, or 5 (optionally with more weight given to the most recent measurements); for example, if the user has used the device to capture 3 breath samples, a weighted average of the three associated total exhalation volume measurements may be used to determine the volume threshold for controlling the valve during the next capture cycle.

Use of Separate Breath Profiling Device

In some embodiments, the user may be asked to exhale into a separate breath profiling device that measures one or more exhalation characteristics of the user as described above. This breath profiling device may then wirelessly communicate the measurement(s), or valve control data derived therefrom, to the breath capture device.

Configuration Via Mobile Application ("App")

In some embodiments, the user may configure the breath capture device using the mobile application. For example, the mobile application may prompt the user to enter one or more items of user data such as weight, height, gender, and age. The mobile application may then use this information to generate the valve control data using one or more look up tables that map specific user attributes (such as weight and height) to specific breathing characteristics such as lung capacity, and may wirelessly communicate this valve control data to the breath capture device. Alternatively, the mobile application may convey the user information to the breath capture device, which would then use this information to generate the valve control data.

Hybrids of the Above

Any two or more of the four methods described above may be used in combination. As one example, the user may initially use a mobile application to configure/personalize the breath capture device as in #4 above. Thereafter, the device may use method 1 and/or method 2 to automatically adjust the valve control data over time.

Referring again to FIG. 74, the capture chamber 3106 may, in some embodiments, be a reaction chamber that contains a reactant (typically in the form of reactive beads) that reacts to the breath sample. In such embodiments, the breath capture device may also include a color sensor (not shown) for sensing a resulting color change representing an acetone or other ketone concentration in the captured breath sample. In these embodiments in which the breath capture device is also a breath analysis device, the controller 3104 may record each ketone measurement in the memory 3110 with associated metadata 3122 descriptive of the breath capture cycle. Depending upon the type(s) of sensors 3100 (if any) provided, this metadata may include, for example, total exhalation volume, average flow rate, maximum flow rate, exhalation time, pressure, exhalation volume prior to valve actuation, exhalation volume following valve actuation, valve actuation time relative to start of exhalation, time of day, etc. As explained above, these any other types of measurement metadata may be useful for a variety of purposes, such as explaining aberrational ketone measurements and improving the operation of the device.

During the breath capture process, the controller 3104 may, in some embodiments, determine whether the user's exhalation satisfies one or more requirements, and may notify the user when it does not (e.g., via an audible tone or by causing the mobile application to display an error message). The exhalation requirements may, in some cases, be based on one or more measurements taken during the above-described breath profiling process. For example, during capture, the controller may compare one or more exhalation characteristics (such as total exhalation time, total exhalation volume, maximum flow rate, maximum pressure, etc.) to like measurements taken during the profiling process. If the comparison yields a significant difference (e.g., a difference in time or volume exceeding 20%), the controller may generate an error message.

Accounting for Valve Actuation Times

As explained above, the valve actuation time can be significant, especially if a gear-based linear actuator is used. To account for the valve actuation time, the controller 3104 may be programmed to predictively or preemptively generate the signal for actuating the valve 3102. For example, if the desired time threshold for actuating the valve is four seconds after exhalation begins, and the valve takes two seconds to change state, the controller may send a valve actuation signal two seconds after exhalation begins. This may be accomplished either by using valve control data that accounts for the valve actuation time, or by accounting for the delay via the executable program code 3108. Where the device uses flow volume to actuate the valve, the controller may use the flow rate to determine how far in advance to actuate the valve such that the valve state will change at the desired volume threshold.

The description herein has largely been explained with respect to a patent or subject, terms used herein according to their common meanings and used largely interchangeably. The description also has been focused on application to human subjects, but this is not necessarily limiting. The principles of the invention also may be applied in veterinary applications.

It will be appreciated that the invention is not limited to the specific embodiments and method implementations described herein. The description herein has largely been explained with respect to human patients or subjects, but this is not necessarily limiting. The principles of the invention also may be applied in veterinary applications.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A breath analyte capture and analysis system for determining a concentration of an analyte in a breath sample from a user, comprising:
    a cartridge having a chamber containing an interactant material;
    a mouthpiece device configured to receive and fluidly connect to the cartridge, the mouthpiece device configured to enable the user to exhale a portion of the breath sample through the chamber such that the portion passes through the interactant material under an exhalation force created by the user, causing the interactant material to absorb the analyte, the mouthpiece device comprising:
        an influent flow port into which the user exhales the breath sample;
        a first flow path coupled to the influent flow port, the first flow path extending into the chamber when the cartridge is positioned in the mouthpiece device;
        a second flow path coupled to the influent flow port; and
        a valve that is manually switchable by the user, by application of a depressive force by the user, between a first orientation in which breath entering the influent port travels through the second flow path and a second orientation in which breath entering the influent port travels through the first flow path, the valve enabling the user to manually route the portion of the breath sample exhaled into the mouthpiece device through the chamber of the cartridge to cause the portion to be exposed to the interactant material; and
    a base unit configured to receive and analyze the cartridge after the portion of the breath sample has been routed through the chamber of the cartridge using the mouthpiece device, the base unit comprising a sensor that senses the concentration of the analyte in the portion of the breath sample, wherein the base unit is physically separate from the mouthpiece device such that the user can exhale the portion of the breath sample into the mouthpiece device and cartridge at a location that is remote from the base unit.

2. The system of claim 1, wherein the valve is manually switchable by the user by depression of a button.

3. The system of claim 1, further comprising a signal generation device that provides a signal to the user during exhalation, the signal indicating to the user when to apply the depressive force.

4. The system of claim 3, wherein the signal generation device is configured to provide the signal a selected time interval prior to a desired valve actuation time to account for human delay in applying the depressive force.

5. The system of claim 3, further comprising a timer that controls a timing with which the signal generation device generates the signal relative to initiation of exhalation.

6. The system of claim 1, wherein the base unit is configured to dispense a developer solution into the cartridge.

7. The system of claim 1, wherein the second flow path is an exhaust path that exhausts from the mouthpiece device a second portion of the breath sample.

8. The system of claim 1, wherein the cartridge comprises multiple chambers for receiving multiple breath samples, each chamber containing an interactant material, the cartridge being movable between multiple inserted positions in the mouthpiece device, each of the multiple positions corresponding to a different respective one of the chambers.

9. The system of claim 1, wherein the cartridge comprises a memory, and the mouthpiece device is configured to store in the memory a timestamp corresponding to a time at which a breath sample was exhaled into the cartridge.

10. The system of claim 1, wherein the sensor senses the concentration by sensing a color change produced in the chamber by a chemical reaction.

11. A method of analyzing breath, comprising:
    with a portable mouthpiece device configured to receive a cartridge having a chamber containing an interactant material, routing a selected portion of a breath sample of a user through the chamber of the cartridge as the user exhales the breath sample into the mouthpiece device such that an exhalation force created by the user forces the selected portion of the breath sample through the chamber, causing the interactant material to absorb an analyte in the selected portion of the breath sample, wherein routing the selected portion comprises actuating a valve of the mouthpiece device; and
    subsequently, after the cartridge has been removed from the mouthpiece device and inserted into a base unit that is physically separate from the mouthpiece device, generating a measurement of a concentration of the analyte in the selected portion of the breath sample, wherein generating the measurement comprises analyzing the cartridge with a sensor of the base unit.

12. The method of claim 11, wherein the valve is actuated in response to application of a depressive force by the user.

13. The method of claim 12, further comprising, by the mouthpiece device, generating a signal that notifies the user of a timing with which to apply the depressive force.

14. The method of claim 11, wherein the valve is actuated by a programmed controller.

15. The method of claim 14, wherein actuating the valve comprises, by the programmed controller, using valve control data to control a timing of valve actuation, the valve control data being based on one or more characteristics of the user such that operation of the valve is customized for the user.

16. The method of claim 15, further comprising generating the valve control data based on one or more measured breathing characteristics of the user.

17. The method of claim 14, wherein actuating the valve comprises, by the programmed controller, determining when to actuate the valve based on one or more sensed characteristics of the exhaled breath sample.

18. The method of claim 11, further comprising, by a controller of the mouthpiece device, storing in a memory of the cartridge a timestamp corresponding to a time at which the breath sample was exhaled into the mouthpiece.

19. The method of claim 11, wherein generating the measurement comprises measuring, with the sensor of the base unit, a color produced by a chemical reaction in the cartridge.

20. The method of claim 11, further comprising, by the base unit, dispensing a developer solution into the cartridge.

21. A breath analyte capture and analysis system capable of determining a concentration of an analyte in breath of a user, the system comprising:

a disposable cartridge having a test chamber containing an interactant material;

a portable mouthpiece device configured to receive and fluidly connect to the disposable cartridge, the portable mouthpiece device configured to route a portion of a breath sample, exhaled into the portable mouthpiece device by the user, through the test chamber such that the portion passes through the test chamber and interactant material under an exhalation force created by the user, causing the interactant material to absorb the analyte, the portable mouthpiece device further configured to route an additional portion of the breath sample out of the portable mouthpiece device such that the additional portion does not pass through the test chamber; and a base unit configured to receive and analyze the disposable cartridge after the portion of the breath sample has been routed through the test chamber of the disposable cartridge using the portable mouthpiece device, the base unit comprising a sensor that senses a color change produced by a reaction in the test chamber, the color change indicative of a concentration level of the analyte;

wherein the base unit is physically separate from the portable mouthpiece device such that the user can exhale the portion of the breath sample into the portable mouthpiece device and disposable cartridge while located remotely from the base unit.

22. The system of claim 21, wherein the base unit is configured to dispense, into the disposable cartridge, a developer solution that reacts with the analyte to produce the color change.

23. The system of claim 21, wherein the disposable cartridge additionally includes a desiccant.

24. The system of claim 21, wherein the mouthpiece device comprises a valve that is manually switchable by the user by depression of a button of the mouthpiece device, wherein a position of the valve controls a routing of breath exhaled into the mouthpiece device.

25. The system of claim 21, wherein the portable mouthpiece device is a handheld device.

* * * * *